US009023820B2

(12) United States Patent
MacDonald et al.

(10) Patent No.: US 9,023,820 B2

(45) Date of Patent: May 5, 2015

(54) COMPOSITIONS AND METHODS FOR SILENCING APOLIPOPROTEIN C-III EXPRESSION

(75) Inventors: Marcia MacDonald, Vancouver (CA); Amy C. H. Lee, Burnaby (CA); Ian MacLachlan, Mission (CA)

(73) Assignee: Protiva Biotherapeutics, Inc., Burnaby, BC (CA)

(*) Notice: Subject to any disclaimer, the term of this patent is extended or adjusted under 35 U.S.C. 154(b) by 0 days.

(21) Appl. No.: 13/146,394

(22) PCT Filed: Jan. 26, 2010

(86) PCT No.: PCT/CA2010/000120

§ 371 (c)(1), (2), (4) Date: Dec. 12, 2011

(87) PCT Pub. No.: WO2010/083615

PCT Pub. Date: Jul. 29, 2010

(65) Prior Publication Data

US 2012/0184595 A1 Jul. 19, 2012

Related U.S. Application Data

(60) Provisional application No. 61/147,235, filed on Jan. 26, 2009, provisional application No. 61/293,452, filed on Jan. 8, 2010.

(51) Int. Cl.

*A61K 48/00* (2006.01)

*C07H 21/02* (2006.01)

(Continued)

(52) U.S. Cl.

CPC ............ *C12N 15/113* (2013.01); *A61K 9/1272* (2013.01); *A61K 9/1617* (2013.01); *A61K 31/713* (2013.01); *A61K 47/48215* (2013.01); *A61K 47/488* (2013.01);

(Continued)

(58) Field of Classification Search

USPC ................................................ 536/24.1, 24.5

See application file for complete search history.

(56) References Cited

U.S. PATENT DOCUMENTS 5,334,761 A 8/1994 Gebeyehu et al.
5,578,475 A 11/1996 Jessee (Continued)

FOREIGN PATENT DOCUMENTS

WO WO 2004/093783 A2 11/2004
WO WO 2004/097429 A2 11/2004

(Continued)

OTHER PUBLICATIONS

Vickers et al. (Journal of Biological Chemistry, 2003 vol. 278: 7108-7118, Epub date Dec. 23, 2002).*

(Continued)

*Primary Examiner* — Terra Cotta Gibbs

(74) *Attorney, Agent, or Firm* — Viksnins Harris & Padys PLLP

(57) ABSTRACT

The present invention provides compositions comprising therapeutic nucleic acids such as interfering RNA that target apolipoprotein C-III (APOC3) gene expression, lipid particles comprising one or more (e.g., a cocktail) of the therapeutic nucleic acids, methods of making the lipid particles, and methods of delivering and/or administering the lipid particles (e.g., for the treatment of lipid diseases or disorders such as atherosclerosis or a dyslipidemia such as hypertriglyceridemia or hypercholesterolemia).

12 Claims, 8 Drawing Sheets

(51) Int. Cl.
*C07H 21/04* (2006.01)
*A61K 9/127* (2006.01)
*A61K 9/16* (2006.01)
*A61K 31/713* (2006.01)
*A61K 47/48* (2006.01)
*B82Y 5/00* (2011.01)
*C12N 15/113* (2010.01)

(52) U.S. Cl.
CPC ............ *A61K 47/48853* (2013.01); *B82Y 5/00* (2013.01); *C12N 2310/14* (2013.01); *C12N 2310/321* (2013.01); *C12N 2310/3515* (2013.01); *C12N 2310/3521* (2013.01)

(56) References Cited

U.S. PATENT DOCUMENTS

| | | | |
|---|---|---|---|
| 5,627,159 | A | 5/1997 | Shih et al. |
| 5,674,908 | A | 10/1997 | Haces et al. |
| 5,736,392 | A | 4/1998 | Hawley-Nelson et al. |
| 5,877,220 | A | 3/1999 | Schwartz et al. |
| 5,958,901 | A | 9/1999 | Dwyer et al. |
| 6,020,202 | A | 2/2000 | Jessee |
| 6,020,526 | A | 2/2000 | Schwartz et al. |
| 6,034,135 | A | 3/2000 | Schwartz et al. |
| 6,051,429 | A | 4/2000 | Hawley-Nelson et al. |
| 6,075,012 | A | 6/2000 | Gebeyehu et al. |
| 6,172,049 | B1 | 1/2001 | Dwyer et al. |
| 6,251,939 | B1 | 6/2001 | Schwartz et al. |
| 6,339,173 | B1 | 1/2002 | Schwartz et al. |
| 6,376,248 | B1 | 4/2002 | Hawley-Nelson et al. |
| 6,638,529 | B2 | 10/2003 | Schwartz et al. |
| 6,671,393 | B2 | 12/2003 | Hays et al. |
| 7,166,745 | B1 | 1/2007 | Chu et al. |
| 7,479,573 | B2 | 1/2009 | Chu et al. |
| 7,601,872 | B2 | 10/2009 | Chu et al. |
| 7,687,070 | B2 | 3/2010 | Gebeyehu et al. |
| 7,915,450 | B2 | 3/2011 | Chu et al. |
| 8,058,068 | B2 | 11/2011 | Hawley-Nelson et al. |
| 8,158,827 | B2 | 4/2012 | Chu et al. |
| 2003/0069173 | A1 | 4/2003 | Hawley-Nelson et al. |
| 2003/0143732 | A1 | 7/2003 | Fosnaugh et al. |
| 2004/0259247 | A1 | 12/2004 | Tuschl et al. |
| 2005/0260757 | A1 | 11/2005 | Gebeyehu et al. |
| 2005/0282188 | A1 | 12/2005 | Haeberli et al. |
| 2006/0147514 | A1 | 7/2006 | Gebeyehu et al. |
| 2006/0228406 | A1 | 10/2006 | Chiou et al. |
| 2006/0264395 | A1 | 11/2006 | Crooke et al. |
| 2007/0135372 | A1 | 6/2007 | MacLachlan et al. |
| 2007/0202598 | A1 | 8/2007 | Chu et al. |
| 2007/0202600 | A1 | 8/2007 | Chu et al. |
| 2009/0143583 | A1 | 6/2009 | Chu et al. |
| 2010/0159593 | A1 | 6/2010 | Chu et al. |
| 2012/0136073 | A1 | 5/2012 | Yang et al. |
| 2012/0238747 | A1 | 9/2012 | Chu et al. |

FOREIGN PATENT DOCUMENTS

| | | | |
|---|---|---|---|
| WO | WO 2005/007196 | A2 | 1/2005 |
| WO | WO 2006/074546 | A1 | 7/2006 |
| WO | WO 2007/051303 | A1 | 5/2007 |
| WO | WO 2008/043561 | A2 | 4/2008 |
| WO | WO 2011/038031 | A1 | 3/2011 |

OTHER PUBLICATIONS

Subramaniam, A. et al., "ApoC-III antisense oligonucleotides reduce liver mRNA and serum triglyceride levels in hypertriglyceridemic rats," Diabetes vol. 54, No. Supp.1, 2005, ISSN 0012-1797, p. A233.

Pollin, T.I. et al., "A null mutation in human APOC3 confers a favorable plasma lipid profile and apparent cardioprotection," Science, 2008, 322(5908), pp. 1702-1705.

Van Der Ham, R.L. et al., "Plasma apolipoprotein CI and CIII levels are associated with increased plasma triglyceride levels and decreased fat mass in men with the metabolic syndrome," Diabetes Care, Jan. 2009, 32(1):184-186.

Carlson, L.A. and Ballantyne, D., "Changing relative proportions of apolipoproteins CII and CIII of very low density lipoproteins in hypertriglyceridaemia," Atherosclerosis, May-Jun. 1976, 23(3):563-568.

Schonfeld, G. et al., "Apolipoprotein C-II and C-III levels in hyperlipoproteinemia, "Metabolism, Oct. 28, 1979 (10):1001-1010.

Le, N. A. et al., "Independent regulation of plasma apolipoprotein C-II and C-III concentrations in very low density and high density lipoproteins: implications for the regulation of the catabolism of these lipoproteins," Journal Lipid Res, May 1988, 29(5):669-677.

Kawakami, A. et al., "Apolipoprotein CIII induces expression of vascular cell adhesion molecule-1 in vascular endothelial cells and increases adhesion of monocytic cells," Circulation, Aug. 15, 2006, 114(7):681-687.

Kawakami, A. et al., "Apolipoprotein CIII links hyperlipidemia with vascular endothelial cell dysfunction," , Circulation, Aug. 12, 2008, 118(7):731-742.

Khvorova, A. et al., "Functional siRNAs and miRNAs exhibit strand bias," Cell, Oct. 17, 2003,115(2):209-216.

Elbashir, S.M. et al., "RNA interference is mediated by 21- and 22-nucleotide RNAs," Genes Dev, Jan 15, 2001, 15(2):188-200.

Schwarz, D.S. et al., "Asymmetry in the assembly of the RNAi enzyme complex," Cell, Oct. 17, 2003, 115(2):199-208.

Su, A.I. et al., "A gene atlas of the mouse and human protein-encoding transcriptomes," Proc Natl Acad Sci USA, 2004, 101(16):6062-6067.

Thompson, J.D. et al., "The CLUSTAL_X windows interface: flexible strategies for multiple sequence alignment aided by quality analysis tools," Nucleic Acids Res, 1997, 25(24):4876-4882.

Vickers, A. et al., "Efficient Reduction of Target RNAs by Small Interfering RNA and RNase H-dependent Antisense Agents," The Journal of Biological Chemistry, vol. 278, No. 9, Issue of Feb. 28, pp. 7108-7118, 2003.

Xu, Yunhe et al., "Effective small interfering RNAs and phosphorothioate antisense DNAs have different preferences for target sites in the luciferase mRNAs," Biochemical and Biophysical Research Communications 306 (2003) 712-717.

Sætrom, Pål, "Predicting the efficacy of short oligonucleotides in antisense and RNAi experiments with boosted genetic programming," Bioinformatics, 2004, vol. 20 issue 17, pp. 3055-3063.

Lee, Li Kim et al., "Cellular Dynamics of Antisense Oligonucleotides and Short Interfering RNAs," Ann. N.Y. Acad. Sci. 1082: 47-51 (2006).

Beale, Gary et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, Aug. 2003 vol. 11 (7), pp. 449-456.

Miyagishi, Makoto et al., "Comparison of the Suppressive Effects of Antisense Oligonucleotides and siRNAs Directed Against the Same Targets in Mammalian Cells," Antisense and Nucleic Acid Drug Dev, 13:1-7 (2003).

Lou, Tzu-Fang et al., "The Reduction of Raf-1 Protein by Phosphorothioate ODNs and siRNAs Targeted to the Same Two mRNA Sequences," Oligonucleotides 13:313-324 (2003).

Lu, Zhi John et al., "Fundamental differences in the equilibrium considerations for siRNA and antisense oligodeoxynucleotide design," Nucleic Acids Research, 2008, vol. 36, No. 11, pp. 3738-3745.

Far, R.K-K et al., "The activity of siRNA in mammalian cells is related to structural target accessibility: a comparison with antisense oligonucleotides," Nucleic Acids Research, 2003, vol. 31, No. 15, pp. 4417-4424.

Fang, Huafeng et al., "Native mRNA antisense-accessible sites library for the selection of antisense oligonucleotides, PNAs, and siRNAs," RNA (2010), 16:1429-1435.

(56) References Cited

OTHER PUBLICATIONS

Holen, Torgeir et al., "Similar behaviour of single-strand and double-strand siRNAs suggests they act through a common RNAi pathway," Nucleic Acids Research, 2003, vol. 31, No. 9, pp. 2401-2407.

Jekerle, Veronika et al., "Functional comparison of singleand double-stranded mdr1 antisense oligodeoxynucleotides in human ovarian cancer cell lines," J Pharm Pharmaceut Sci, 8(3):516-527, 2005.

Reynolds, A. et al., "Rational siRNA design for RNA interference," Nature Biotech., 2004, vol. 22, pp. 326-330.

Crooke, "Antisense oligonucleotides as therapeutics for hyperlipidaemias", *Expert Opinion on Biological Therapy*, vol. 5 (7), 907-917 (2005).

Huard et al., "Apolipoproteins C-II and C-III inhibit selective uptake of low- and high-density lipoprotein cholesteryl esters in HepG2 cells", *International Journal of Biochemistry and Cell Biology*, vol. 37, 1308-1318 (2005).

Maeda et al., "Targeted disruption of the apolipoprotein C-III gene in mice results in hypotriglyceridemia and protection from postprandial hypertriglyceridemia", *Journal of Biological Chemistry*, vol. 269 (38), 23610-23616 (1994).

* cited by examiner

COMPOSITIONS AND METHODS FOR SILENCING APOLIPOPROTEIN C-III EXPRESSION

CROSS-REFERENCE TO RELATED APPLICATIONS

This application is related to U.S. Provisional Application Nos. 61/147,235, filed Jan. 26, 2009, and 61/293,452, filed Jan. 8, 2010, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The sequence Listing written in file -88-2,TXT, created on Mar. 12, 2012, 356,352 bytes, machine format IBM-PC, MS-Windows operating system, is hereby incorporated by reference in its entirety for all purposes.

BACKGROUND OF THE INVENTION

Lipoproteins are globular, micelle-like particles that consist of a non-polar core of acylglycerols and cholesteryl esters surrounded by an amphiphilic coating of protein, phospholipid, and cholesterol. Lipoproteins have been classified into five broad categories on the basis of their functional and physical properties: chylomicrons, which transport dietary lipids from intestine to tissues; very low density lipoproteins (VLDL), intermediate density lipoproteins (IDL), and low density lipoproteins (LDL), all of which transport triacylglycerols and cholesterol from the liver to tissues; and high density lipoproteins (HDL), which transport endogenous cholesterol from tissues to the liver.

Lipoprotein particles undergo continuous metabolic processing and have variable properties and compositions. Lipoprotein densities increase without decreasing particle diameter because the density of their outer coatings is less than that of the inner core. The protein components of lipoproteins are known as apolipoproteins. At least nine apolipoproteins are distributed in significant amounts among the various human lipoproteins.

Apolipoprotein C-III is a constituent of HDL and triglyceride-rich lipoproteins and has a role in hypertriglyceridemia, a risk factor for coronary artery disease. Apolipoprotein C-III slows the clearance of triglyceride-rich lipoproteins by inhibiting lipolysis, both through inhibition of lipoprotein lipase and by interfering with lipoprotein binding to the cell-surface glycosaminoglycan matrix (see, Shachter, *Curr. Opin. Lipidol.,* 12:297-304 (2001)).

The gene encoding human apolipoprotein C-III (also called APOC3 and apoC-III) was cloned in 1984 (see, Levy-Wilson et al., *DNA,* 3:359-364 (1984); Protter et al., *DNA,* 3:449-456 (1984); Sharpe et al., *Nucleic Acids Res.,* 12:3917-3932 (1984)). The coding sequence is interrupted by three introns (see, Protter et al., supra). The human APOC3 gene is located approximately 2.6 kilobases to the 3' direction of the apolipoprotein A-1 gene and these two genes are convergently transcribed (see, Karathanasis, *Proc. Natl. Acad. Sci. U.S.A.,* 82:6374-6378 (1985)). Also cloned was a variant of the human APOC3 gene resulting in a Thr74 to Ala74 mutation from a patient with unusually high levels of serum apoC-III protein. As the Thr74 is O-glycosylated, the Ala74 mutant therefore resulted in increased levels of serum apoC-III protein lacking the carbohydrate moiety (see, Maeda et al., *J. Lipid Res.,* 28:1405-1409 (1987)).

Five polymorphisms have been identified in the promoter region of the APOC3 gene: C(−641) to A; G(−630) to A; T(−625) to deletion; C(−482) to T; and T(−455) to C. All of these polymorphisms are in linkage disequilibrium with the SstI polymorphism in the 3' untranslated region. The SstI site distinguishes the S1 and S2 alleles and the S2 allele has been associated with elevated plasma triglyceride levels (see, Dammerman et al., *Proc. Natl. Acad. Sci. U.S.A.,* 90:4562-4566 (1993)). The APOC3 promoter is downregulated by insulin and this polymorphic site abolishes insulin regulation. Thus, the potential overexpression of apoC-III resulting from the loss of insulin regulation may be a contributing factor to the development of hypertriglyceridemia associated with the S2 allele (see, Li et al., *J. Clin. Invest.,* 96:2601-2605 (1995)). The T(-455) to C polymorphism has been associated with an increased risk of coronary artery disease (see, Olivieri et al., *J. Lipid Res.,* 43:1450-1457 2002)).

In addition to insulin, other regulators of APOC3 gene expression have been identified. A response element for the nuclear orphan receptor rev-erb alpha has been located at positions −23/−18 in the APOC3 promoter region and rev-erb alpha decreases APOC3 promoter activity (see, Raspe et al., *J. Lipid Res.,* 43:2172-2179 (2002)). The APOC3 promoter region −86 to −74 is recognized by two nuclear factors, CIIIb1 and CIIIB2 (see, Ogami et al., *J. Biol. Chem.,* 266:9640-9646 (1991)). APOC3 expression is also upregulated by retinoids acting via the retinoid X receptor, and alterations in retinoid X receptor abundance affects APOC3 transcription (see, Vu-Dac et al., *J. Clin. Invest.,* 102:625-632 (1998)). Specificity protein 1 (Sp1) and hepatocyte nuclear factor-4 (HNF-4) have been shown to work synergistically to transactivate the APOC3 promoter via the HNF-4 binding site (see, Kardassis et al., *Biochemistry,* 41:1217-1228 (2002)). HNF-4 also works in conjunction with SMAD3-SMAD4 to transactivate the APOC3 promoter (see, Kardassis et al., *J. Biol. Chem.,* 275:41405-41414 (2000)).

Transgenic and knockout mice have further defined the role of apoC-III in lipolysis. Overexpression of APOC3 in transgenic mice leads to hypertriglyceridemia and impaired clearance of VLDL-triglycerides (see, de Silva et al., *J. Biol. Chem.,* 269:2324-2335 (1994); Ito et al., *Science,* 249:790-793 (1990)). Knockout mice with a total absence of apoC-III protein exhibited significantly reduced plasma cholesterol and triglyceride levels compared with wild-type mice and were protected from postprandial hypertriglyceridemia (see, Maeda et al., *J. Biol. Chem.,* 269:23610-23616 (1994)).

Recently, it was discovered that about 5% of the Lancaster Amish are heterozygous carriers of a null mutation in exon 3 of the APOC3 gene consisting of a C to T transition at nucleotide 55, resulting in an Arg19 to Ter (R19X) substitution (see, Pollin et al., *Science,* 322:1702-1705 (2008)). As the mutation occurs in the signal peptide of the protein, a complete lack of production of apoC-III from alleles carrying the mutation was predicted. Carriers of the R19X null mutation expressed half the amount of apoC-III present in noncarriers. Mutation carriers compared with noncarriers had lower fasting and postprandial serum triglycerides, higher levels of HDL cholesterol, and lower levels of LDL cholesterol. Subclinical atherosclerosis, as measured by coronary artery calcification, was less common in carriers than noncarriers, which suggested that lifelong deficiency of apoC-III protein has a cardioprotective effect.

In view of the foregoing, there is a need for therapeutic agents capable of effectively inhibiting APOC3 function and methods for their in vivo delivery to target tissues such as the liver. The present invention addresses these and other needs.

BRIEF SUMMARY OF THE INVENTION

The present invention provides compositions comprising therapeutic nucleic acids such as interfering RNA that target apolipoprotein C-III (APOC3) gene expression, lipid particles comprising one or more (e.g., a cocktail) of the therapeutic nucleic acids, methods of making the lipid particles, and methods of delivering and/or administering the lipid particles (e.g., for the treatment of lipid diseases or disorders such as atherosclerosis or a dyslipidemia such as hypertriglyceridemia or hypercholesterolemia).

More particularly, the invention provides compositions comprising unmodified and chemically modified interfering RNA (e.g., siRNA) molecules which silence APOC3 gene expression. The present invention also provides serum-stable nucleic acid-lipid particles (e.g., SNALP) and formulations thereof comprising one or more (e.g., a cocktail) of the interfering RNA (e.g., siRNA) described herein, a cationic lipid, and a non-cationic lipid, which can further comprise a conjugated lipid that inhibits aggregation of particles.

In one aspect, the present invention provides an siRNA that targets APOC3 gene expression, wherein the siRNA comprises a sense strand and a complementary antisense strand, and wherein the siRNA comprises a double-stranded region of about 15 to about 60 nucleotides in length. In certain embodiments, the present invention provides compositions comprising a combination (e.g., a cocktail) of siRNAs that target APOC3 and at least 1, 2, 3, 4, 5, 6, 7, or 8 additional genes associated with metabolic diseases and disorders. The siRNA molecules of the present invention are capable of silencing APOC3 gene expression, reducing triglyceride levels, and/or reducing cholesterol levels in vivo.

Human APOC3 sequences are set forth in Genbank Accession No. NG_008949 REGION: 5001..8164 (SEQ ID NO:1), which corresponds to the human APOC3 genomic sequence, and Genbank Accession No. NM_000040.1 (SEQ ID NO:2), which corresponds to the human APOC3 mRNA sequence. Mouse Apoc3 sequences are set forth in Genbank Accession No. NC_000075 REGION: complement (46041134..46043380), which corresponds to the mouse Apoc3 genomic sequence, and Genbank Accession No. NM_023114.3, which corresponds to the mouse Apoc3 mRNA sequence.

Each of the siRNA sequences present in the compositions of the invention may independently comprise at least one, two, three, four, five, six, seven, eight, nine, ten, or more modified nucleotides such as 2'OMe nucleotides, e.g., in the sense and/or antisense strand of the double-stranded region. Preferably, uridine and/or guanosine nucleotides are modified with 2'OMe nucleotides. In particular embodiments, each of the siRNA sequences present in the compositions of the invention comprises at least one 2'OMe-uridine nucleotide and at least one 2'OMe-guanosine nucleotide in the sense and/or antisense strands.

In some embodiments, each of the siRNA sequences present in the compositions of the invention may independently comprise a 3' overhang of 1, 2, 3, or 4 nucleotides in one or both strands of the siRNA or may comprise at least one blunt end. In certain instances, the 3' overhangs in one or both strands of the siRNA each independently comprise 1, 2, 3, or 4 of any combination of modified and unmodified deoxythymidine (dT) nucleotides, 1, 2, 3, or 4 of any combination of modified (e.g., 2'OMe) and unmodified uridine (U) ribonucleotides, or 1, 2, 3, or 4 of any combination of modified (e.g., 2'OMe) and unmodified ribonucleotides having complementarity to the target sequence (3' overhang in the antisense strand) or the complementary strand thereof (3' overhang in the sense strand).

In further embodiments, the present invention provides a composition comprising at least one or a cocktail (e.g., at least two, three, four, five, six, seven, eight, nine, ten, or more) of the unmodified and/or modified siRNA sequences set forth in Tables 1-10. In particular embodiments, the invention provides a composition comprising at least one or a cocktail of the siRNA sequences set forth in Table 7. In these embodiments, each siRNA sequence set forth in Table 7 may comprise a modified (e.g., 2'OMe) and/or unmodified 3' overhang of 1, 2, 3, or 4 nucleotides in one or both strands of the siRNA. In other particular embodiments, the composition comprises at least one or a cocktail of the siRNA sequences set forth in Table 10, and each siRNA sequence present in the composition comprises nucleotides 1-19 of one of the sense and/or antisense strand sequences set forth in Table 10. In certain embodiments, the composition comprises at least one or a cocktail of the siRNA sequences set forth in Table 10, and each siRNA sequence present in the composition consists of one of the sense and/or antisense strand sequences set forth in Table 10. In preferred embodiments, the present invention provides a composition comprising at least one or a cocktail of the modified siRNA sequences set forth in Tables 1-6. In these embodiments, each sequence set forth in Tables 1-6 may comprise a modified (e.g., 2'OMe) and/or unmodified 3' overhang of 1, 2, 3, or 4 nucleotides. In other preferred embodiments, at least 1, 2, 3, 4, 5, 6, 7, 8, 9, 10, or more (e.g., all) of the siRNA sequences present in the composition comprises at least 1, 2, 3, 4, 5, 6, 7, 8, 9, 10, or more modified nucleotides such as 2'OMe nucleotides, e.g., in the double-stranded region.

The present invention also provides a pharmaceutical composition comprising one or a cocktail of interfering RNA (e.g., siRNA) molecules that target APOC3 gene expression and a pharmaceutically acceptable carrier.

In another aspect, the present invention provides a nucleic acid-lipid particle that targets APOC3 gene expression. The nucleic acid-lipid particle typically comprises one or more unmodified and/or modified siRNA that silence APOC3 gene expression, a cationic lipid, and a non-cationic lipid. In certain instances, the nucleic acid-lipid particle further comprises a conjugated lipid that inhibits aggregation of particles. Preferably, the nucleic acid-lipid particle comprises one or more unmodified and/or modified siRNA that silence APOC3 gene expression, a cationic lipid, a non-cationic lipid, and a conjugated lipid that inhibits aggregation of particles.

In some embodiments, the nucleic acid-lipid particle comprises 1, 2, 3, 4, 5, 6, 7, 8, 9, 10, or more of the unmodified or modified sequences set forth in Tables 1-10. In particular embodiments, the nucleic acid-lipid particle comprises one or a cocktail (e.g., at least 2, 3, 4, 5, 6, 7, 8, 9, 10, or more) of the siRNA sequences set forth in Table 7. In these embodiments, each siRNA sequence present in the nucleic acid-lipid particle composition may comprise a modified (e.g., 2'OMe) and/or unmodified 3' overhang of 1, 2, 3, or 4 nucleotides in one or both strands of the siRNA. In other particular embodiments, the nucleic acid-lipid particle comprises one or a cocktail (e.g., at least 2, 3, 4, 5, 6, 7, 8, 9, 10, or more) of the siRNA sequences set forth in Table 10, and each siRNA sequence present in the nucleic acid-lipid particle composition comprises nucleotides 1-19 of one of the sense and/or antisense strand sequences set forth in Table 10. In certain embodiments, the nucleic acid-lipid particle comprises one or a cocktail (e.g., at least 2, 3, 4, 5, 6, 7, 8, 9, 10, or more) of the siRNA sequences set forth in Table 10, and each siRNA sequence present in the nucleic acid-lipid particle composition consists of one of the sense and/or antisense strand sequences set forth in Table 10. In preferred embodiments, the nucleic acid-lipid particle comprises at least one or a cocktail of the modified siRNA sequences set forth in Tables 1-6. In these embodiments, each sequence present in the nucleic acid-lipid particle composition may comprise a modified (e.g., 2'OMe) and/or unmodified 3' overhang of 1, 2, 3, or 4 nucleotides. In other preferred embodiments, at least 1, 2, 3, 4, 5, 6, 7, 8, 9, 10, or more (e.g., all) of the siRNA sequences present in the nucleic acid-lipid particle formulation comprises at least 1, 2, 3, 4, 5, 6, 7, 8, 9, 10, or more modified nucleotides such as 2'OMe nucleotides, e.g., in the double-stranded region.

In other embodiments, the siRNA molecules of the invention are fully encapsulated in the nucleic acid-lipid particle (e.g., SNALP). With respect to formulations comprising an siRNA cocktail, the different types of siRNAs may be co-encapsulated in the same nucleic acid-lipid particle, or each type of siRNA species present in the cocktail may be encapsulated in its own nucleic acid-lipid particle.

The present invention also provides pharmaceutical compositions comprising a nucleic acid-lipid particle and a pharmaceutically acceptable carrier.

The nucleic acid-lipid particles of the invention are useful for the prophylactic or therapeutic delivery of interfering RNA (e.g., siRNA) molecules that silence APOC3 gene expression. In some embodiments, one or more of the siRNA molecules described herein are formulated into nucleic acid-lipid particles, and the particles are administered to a mammal (e.g., a rodent such as a mouse or a primate such as a human, chimpanzee, or monkey) requiring such treatment. In certain instances, a therapeutically effective amount of the nucleic acid-lipid particle can be administered to the mammal, e.g., for reducing apoC-III protein levels to prevent morbidity and/or mortality associated with cardiac-related disorders. The nucleic acid-lipid particles of the invention are particularly useful for reducing plasma and/or serum levels of triglycerides, cholesterol, and/or glucose and find utility in preventing, treating, or reducing susceptibility to a lipid disorder such as atherosclerosis or a dyslipidemia such as hypertriglyceridemia or hypercholesterolemia. The nucleic acid-lipid particles of the invention (e.g., SNALP) find utility in targeting cells, tissues, and/or organs associated with metabolic diseases and disorders, such as hepatocytes as well as other cell types of the liver. Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal. In particular embodiments, the nucleic acid-lipid particle is administered systemically, e.g., via enteral or parenteral routes of administration.

In some embodiments, downregulation of APOC3 gene expression is determined by detecting APOC3 mRNA or apoC-III protein levels in a biological sample from a mammal after nucleic acid-lipid particle administration. In other embodiments, downregulation of APOC3 gene expression is determined by measuring triglyceride, cholesterol, and/or glucose levels in a biological sample from a mammal after nucleic acid-lipid particle administration.

In certain embodiments, the present invention provides a method for treating a mammal having hyperlipidemia comprising administering to a mammal suffering from hyperlipidemia an siRNA that silences APOC3 expression (e.g., encapsulated in a nucleic acid-lipid particle such as SNALP), thereby reducing hyperlipidemia in the mammal. In certain other embodiments, the present invention provides a method for delaying the onset of hyperlipidemia in a mammal comprising administering to a mammal at risk for developing hyperlipidemia an siRNA that silences APOC3 expression (e.g., encapsulated in a nucleic acid-lipid particle such as SNALP), thereby delaying the onset of hyperlipidemia. In further embodiments, the present invention provides a method for lowering triglyceride levels in a mammal comprising administering to a mammal in need of a reduction in triglyceride levels an siRNA that silences APOC3 expression (e.g., encapsulated in a nucleic acid-lipid particle such as SNALP), wherein the administering results in reduced triglyceride levels in the mammal. In other embodiments, the present invention provides a method for lowering cholesterol levels in a mammal comprising administering to a mammal in need of a reduction in cholesterol levels an siRNA that silences APOC3 expression (e.g., encapsulated in a nucleic acid-lipid particle such as SNALP), wherein the administering results in reduced cholesterol levels in the mammal.

In a further aspect, the present invention provides compositions comprising at least one siRNA that silences APOC3 expression and at least one siRNA that silences APOB expression. In certain instances, the siRNA targeting APOC3 and the siRNA targeting APOB are formulated in the same nucleic acid-lipid particle (e.g., SNALP). As a non-limiting example, the cocktail of APOC3 and APOB siRNA molecules may be co-encapsulated in the same nucleic acid-lipid particle. In certain other instances, the APOC3 and APOB siRNA molecules are formulated in separate nucleic acid-lipid particles. In these instances, one formulation may be administered before, during, or after the administration of the other formulation to a mammal in need thereof. Exemplary siRNA sequences targeting APOB that are suitable for use in the present invention are described in, e.g., U.S. Patent Publication Nos. 20060134189 and 20070135372.

In a related aspect, the present invention provides compositions comprising at least one siRNA that silences APOC3 expression (e.g., encapsulated in a nucleic acid-lipid particle such as SNALP) and at least one lipid-lowering agent which decreases apoC-III levels but does not mediate RNA interference. Such lipid-lowering agents include, but are not limited to, statins, fibrates, thiazolidinediones, ezetimibe, niacin, beta-blockers, nitroglycerin, calcium antagonists, and fish oil. One skilled in the art will appreciate that one or more APOC3 siRNA molecules (e.g., encapsulated in a nucleic acid-lipid particle such as SNALP) may be administered before, during, or after the administration of one or more lipid-lowering agents to a mammal in need thereof.

Other objects, features, and advantages of the present invention will be apparent to one of skill in the art from the following detailed description and figures.

DETAILED DESCRIPTION OF THE INVENTION

I. Introduction

Figure 1:
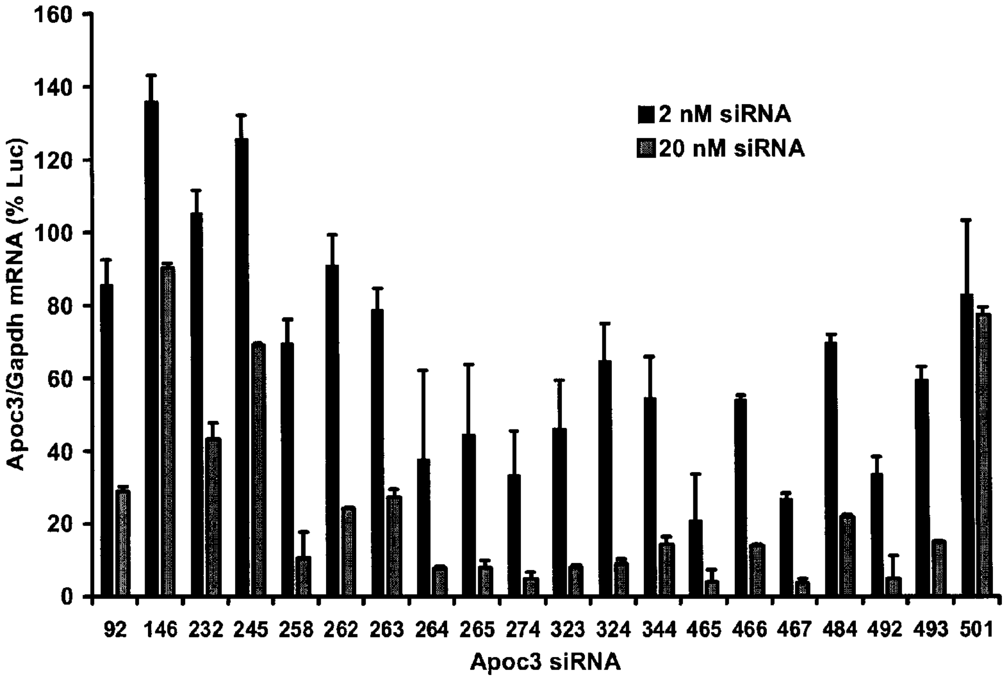
FIG. 1 illustrates data demonstrating that Apoc3 siRNAs display dose-dependent activity in vitro. A panel of siRNAs targeting mouse Apoc3 mRNA and a firefly luciferase (Luc) control siRNA were transfected into mouse primary hepatocytes and silencing activity was assessed by QuantiGene Assay 24 h post-treatment. Cells were treated with SNALP-formulated Apoc3 siRNA at 2 nM (black bars) and 20 nM (gray bars). Sequence numbers represent the nucleotide position of mouse Apoc3 mRNA (Genbank Accession No. NM_023114.3) that is complementary to the 3' end of the antisense strand of the siRNA.

Coronary artery disease (CAD) or atherosclerotic cardiovascular disease (CVD) is the leading cause of illness and death worldwide. The risk of developing CAD is closely associated with alterations in blood lipids (i.e., dyslipidemias), particularly elevated plasma cholesterol (i.e., hypercholesterolemia). While the symptoms and signs of CAD are noted in the advanced state of disease, most individuals with CAD show no evidence of disease for decades as the disease progresses before the first onset of symptoms, often a "sudden" heart attack, finally arises. After decades of progression, some of the atheromatous plaques that develop may rupture and (along with the activation of the blood clotting system) start limiting blood flow to the heart muscle. CAD is the most common cause of sudden death, and is also the most common reason for death of men and women over 20 years of age. According to present trends in the United States, half of healthy 40-year-old males will develop CAD in the future, and one in three healthy 40-year-old women. As the degree of CAD progresses, there may be near-complete obstruction of the lumen of the coronary artery, severely restricting the flow of oxygen-carrying blood to the myocardium. Individuals with this degree of CAD typically have suffered from one or more myocardial infarctions (heart attacks), and may have signs and symptoms of chronic coronary ischemia, including symptoms of angina at rest and flash pulmonary edema. It is therefore clear that CAD and other diseases associated with elevated blood cholesterol, triglyceride, and/or glucose levels represent a significant unmet medical need that requires the development of novel therapeutic agents for more effective treatment options.

Apolipoprotein C-III (APOC3) is an important regulator of lipoprotein metabolism that has been implicated in the progression of atherosclerosis through its association with hypertriglyceridemia and its direct induction of endothelial dysfunction. Example 2 below describes the preclinical development of chemically modified siRNA targeting Apoc3 in mice. Apoc3-targeting siRNA formulated in stable nucleic acid-lipid particles (SNALP) were administered by intravenous injection to female C57BL/6 mice at doses of 0.5 and 5 mg/kg. Both doses demonstrated potent efficacy, reducing hepatic Apoc3 mRNA by more than 90% and reducing plasma triglycerides by 35-45%, without an increase in hepatic triglycerides. No measurable immune response was induced with these formulations, minimizing the potential for nonspecific effects in models of chronic inflammatory disease, such as atherosclerosis. In addition, Example 3 below illustrates the identification of human APOC3 siRNA sequences which demonstrated potent silencing activity. As such, these Examples demonstrate the clinically relevant effects and benefits of siRNA-based silencing of APOC3 in mammals, e.g., the utility of Apoc3-targeting SNALP in animal models of dyslipidemia and atherosclerosis, as well as the utility of SNALP-formulated siRNA targeting the human APOC3 gene for treating, preventing, reducing the risk of developing, or delaying the onset of a lipid disorder such as atherosclerosis or a dyslipidemia, e.g., a hyperlipidemia such as elevated triglyceride levels (hypertriglyceridemia) and/or elevated cholesterol levels (hypercholesterolemia).

II. Definitions

As used herein, the following terms have the meanings ascribed to them unless specified otherwise.

The term "interfering RNA" or "RNAi" or "interfering RNA sequence" as used herein includes single-stranded RNA (e.g., mature miRNA, ssRNAi oligonucleotides, ssDNAi oligonucleotides) or double-stranded RNA (i.e., duplex RNA such as siRNA, Dicer-substrate dsRNA, shRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA,* 99:9942-9947 (2002); Calegari et al., *Proc. Natl. Acad. Sci. USA,* 99:14236 (2002); Byrom et al., *Ambion TechNotes,* 10(1):4-6 (2003); Kawasaki et al., *Nucleic Acids Res.,* 31:981-987 (2003); Knight et al., *Science,* 293:2269-2271 (2001); and Robertson et al., *J. Biol. Chem.,* 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of an interfering RNA (e.g., siRNA) of the present invention to silence, reduce, or inhibit the expression of a target gene (e.g., APOC3 and/or other genes associated with metabolic diseases and disorders). To examine the extent of gene silencing, a test sample (e.g., a biological sample from an organism of interest expressing the target gene or a sample of cells in culture expressing the target gene) is contacted with an interfering RNA (e.g., siRNA) that silences, reduces, or inhibits expression of the target gene. Expression of the target gene in the test sample is compared to expression of the target gene in a control sample (e.g., a biological sample from an organism of interest expressing the target gene or a sample of cells in culture expressing the target gene) that is not contacted with the interfering RNA (e.g., siRNA). Control samples (e.g., samples expressing the target gene) may be assigned a value of 100%. In particular embodiments, silencing, inhibition, or reduction of expression of a target gene is achieved when the value of the test sample relative to the control sample is about 95%, 90%, 85%, 80%, 75%, 70%, 65%, 60%, 55%, 50%, 45%, 40%, 35%, 30%, 25%, 20%, 10%, 5%, or 0%. Suitable assays include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of a therapeutic nucleic acid such as an interfering RNA is an amount sufficient to produce the desired effect, e.g., an inhibition of expression of a target sequence in comparison to the normal expression level detected in the absence of an interfering RNA. In particular embodiments, inhibition of expression of a target gene or target sequence is achieved when the value obtained with an interfering RNA relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring the expression of a target gene or target sequence include, but are not limited to, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-10, IL-12, IL-13, TGF, and combinations thereof Detectable immune responses also include, e.g., induction of interferon-induced protein with tetratricopeptide repeats 1 (IFIT1) mRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.,* 2:482 (1981), by the homology alignment algorithm of Needleman and Wunsch, *J. Mol. Biol.,* 48:443 (1970), by the search for similarity method of Pearson and Lipman, *Proc. Natl. Acad. Sci. USA,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.,* 25:3389-3402 (1977) and Altschul et al., *J. Mol. Biol.,* 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Another example is a global alignment algorithm for determining percent sequence identity such as the Needleman-Wunsch algorithm for aligning protein or nucleotide (e.g., mRNA) sequences.

The BLAST algorithm also performs a statistical analysis of the similarity between two sequences (see, e.g., Karlin and Altschul, *Proc. Natl. Acad. Sci. USA,* 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.,* 19:5081 (1991); Ohtsuka et al., *J. Biol. Chem.,* 260: 2605-2608 (1985); Rossolini et al., *Mol. Cell. Probes,* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., interfering RNA) to a target site of interest (e.g., cell, tissue, organ, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the therapeutic nucleic acid (e.g., interfering RNA) may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid such as an interfering RNA (e.g., siRNA), with full encapsulation, partial encapsulation, or both. In a preferred embodiment, the nucleic acid (e.g., interfering RNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, polyamide oligomers (e.g., ATTA-lipid conjugates), PEG-lipid conjugates, such as PEG coupled to dialkyloxypropyls, PEG coupled to diacylglycerols, PEG coupled to cholesterol, PEG coupled to phosphatidylethanolamines, PEG conjugated to ceramides (see, e.g., U.S. Pat. No. 5,885,613, the disclosure of which is herein incorporated by reference in its entirety for all purposes), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In preferred embodiments, non-ester containing linker moieties are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N-N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 double bonds; and ether or ketal linkages between the head group and alkyl chains. Such lipids include, but are not limited to, DSDMA, DODMA, DLinDMA, DLenDMA, DLin-K-DMA, DLin-K-C2-DMA (also known as DLin-C2K-DMA, XTC2, and C2K), DLin-K-C3-DMA, and DLin-K-C4-DMA.

The term "salts" includes any anionic and cationic complex, such as the complex formed between a cationic lipid and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(═O)alkyl, —C(═O)alkenyl, and —C(═O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (═O), two hydrogen atoms are replaced. In this regard, substituents include, but are not limited to, oxo, halogen, heterocycle, —CN, —$OR^x$, —$NR^xR^y$, —$NR^xC$(═O)$R^y$, —$NR^xSO_2R^y$, —C(═O)$R^x$, —C(═O)$OR^x$, —C(═O)$NR^xR^y$, —$SO_nR^x$, and —$SO_nNR^xR^y$, wherein n is 0, 1, or 2, $R^x$ and $R^y$ are the same or different and are independently hydrogen, alkyl, or heterocycle, and each of the alkyl and heterocycle substituents may be further substituted with one or more of oxo, halogen, —OH, —CN, alkyl, —$OR^x$, heterocycle, —$NR^xR^y$, —$NR^xC(=O)R^y$, —$NR^xSO_2R^y$, —$C(=O)R^x$, —$C(=O)OR^x$, —$C(=O)NR^xR^y$, —$SO_nR^x$, and —$SO_n$-$NR^xR^y$. The term "optionally substituted," when used before a list of substituents, means that each of the substituents in the list may be optionally substituted as described herein.

The term "halogen" includes fluoro, chloro, bromo, and iodo.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

III. Description of the Embodiments

The present invention provides therapeutic nucleic acids such as interfering RNA that target APOC3 gene expression, lipid particles comprising one or more (e.g., a cocktail) of the therapeutic nucleic acids, methods of making the lipid particles, and methods of delivering and/or administering the lipid particles (e.g., for the prevention or treatment of dyslipidemia and/or atherosclerosis).

In one aspect, the present invention provides interfering RNA molecules that target APOC3 expression. Non-limiting examples of interfering RNA molecules include siRNA, Dicer-substrate dsRNA, shRNA, aiRNA, miRNA, and mixtures thereof. In certain instances, the present invention provides compositions comprising a combination (e.g., a cocktail, pool, or mixture) of siRNAs that target different regions of the APOC3 gene and/or multiple genes (e.g., a cocktail of siRNAs that silence APOC3 and APOB expression). The interfering RNA (e.g., siRNA) molecules of the present invention are capable of reducing APOC3 mRNA in vitro (e.g., in primary hepatocytes) or in vivo (e.g., in liver tissue).

In particular embodiments, the present invention provides an siRNA that silences APOC3 gene expression, wherein the siRNA comprises a sense strand and a complementary antisense strand, and wherein the siRNA comprises a double-stranded region of about 15 to about 60 nucleotides in length (e.g., about 15-60, 15-30, 15-25, 19-30, or 19-25 nucleotides in length, or about 15, 16, 17, 18, 19, 20, 21, 22, 23, 24, or 25 nucleotides in length).

In some embodiments, the antisense strand comprises one of the antisense strand sequences set forth in Tables 1-10. In related embodiments, the antisense strand comprises at least 15 contiguous nucleotides (e.g., at least 15, 16, 17, 18, or 19 contiguous nucleotides) of one of the antisense strand sequences set forth in Tables 1-10. In one particular embodiment, the antisense strand comprises nucleotides 1-19 of one of the antisense strand sequences set forth in Tables 1-10. In further embodiments, the sense strand comprises one of the sense strand sequences set forth in Tables 1-10. In related embodiments, the sense strand comprises at least 15 contiguous nucleotides (e.g., at least 15, 16, 17, 18, or 19 contiguous nucleotides) of one of the sense strand sequences set forth in Tables 1-10. In one particular embodiment, the sense strand comprises nucleotides 1-19 of one of the sense strand sequences set forth in Tables 1-10. In other embodiments, the antisense strand specifically hybridizes to one of the target sequences set forth in Tables 1-10. In additional embodiments, the APOC3 siRNA targets one of the target sequences set forth in Tables 7-10.

In certain embodiments, the APOC3 siRNA of the invention may comprise at least one, two, three, four, five, six, seven, eight, nine, ten, or more modified nucleotides such as 2'OMe nucleotides, e.g., in the sense and/or antisense strand of the double-stranded region of the siRNA. Preferably, uridine and/or guanosine nucleotides in the siRNA are modified with 2'OMe nucleotides. In certain instances, the siRNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the siRNA may further comprise modified (e.g., 2'OMe-modified) adenosine and/or modified (e.g., 2'OMe-modified) cytosine nucleotides, e.g., in the double-stranded region of the siRNA.

In one embodiment, the antisense strand of the APOC3 siRNA comprises one of the 2'OMe-modified sequences set forth in Table 1. The antisense strand sequence of APOC3 siRNA "262" shown in Table 7 sets forth the unmodified version of the 2'OMe-modified sequences set forth in Table 1. Nucleotides 1-19 of the antisense strand sequence of the hAPOC3_260 siRNA shown in Table 10 also correspond to the unmodified version of the 2'OMe-modified sequences set forth in Table 1.

TABLE 1

| | SEQ ID NO. | | SEQ ID NO. |
|---|---|---|---|
| 5'-CUUAACGG**U**GC**U**CCAG**U**AG-3' | 3 | 5'-C**U**UAACGGU**G**C**U**CCAG**U**AG-3' | 31 |
| 5'-C**U**UAACGG**U**GC**U**CCAG**U**AG-3' | 4 | 5'-C**U**UAAC**G**GU**G**C**U**CCAG**U**AG-3' | 32 |
| 5'-CU**U**AACGG**U**GC**U**CCAG**U**AG-3' | 5 | 5'-C**U**UAAC**G**GU**G**C**U**CCAG**U**A**G**-3' | 33 |
| 5'-C**UU**AACGG**U**GC**U**CCAG**U**AG-3' | 6 | 5'-CU**U**AACGG**U**GC**U**CCAG**U**A**G**-3' | 34 |
| 5'-CUUAACGGU**G**CUCCA**G**UA**G**-3' | 7 | 5'-CU**U**AAC**G**G**U**GC**U**CCAG**U**AG-3' | 35 |
| 5'-CUUAAC**G**GUGCUCCA**G**UA**G**-3' | 8 | 5'-CU**U**AACG**GU**GC**U**CCAG**U**A**G**-3' | 36 |
| 5'-CUUAAC**G**GU**G**CUCCA**G**UA**G**-3' | 9 | 5'-CU**U**AACG**GU**GC**U**CCAG**U**AG-3' | 37 |
| 5'-CUUAACG**G**U**G**CUCCA**G**UA**G**-3' | 10 | 5'-CU**U**AACGG**UG**C**U**CCAG**U**A**G**-3' | 38 |
| 5'-CUUAAC**GG**U**G**CUCCA**G**UA**G**-3' | 11 | 5'-CU**U**AACGG**UG**C**U**CCAG**U**AG-3' | 39 |
| 5'-CUUAAC**G**G**U**GC**U**CCAG**U**AG-3' | 12 | 5'-CU**U**AAC**G**G**U**GC**U**CCA**GU**A**G**-3' | 40 |
| 5'-CUUAACGG**U**GC**U**CCAG**U**A**G**-3' | 13 | 5'-CU**U**AAC**G**G**U**GC**U**CCA**GU**AG-3' | 41 |
| 5'-CUUAAC**G**G**U**GC**U**CCAG**U**A**G**-3' | 14 | 5'-CU**U**AACGG**U**GC**U**CCA**GU**AG-3' | 42 |
| 5'-C**U**UAAC**G**G**U**GC**U**CCAG**U**A**G**-3' | 15 | 5'-CU**U**AACG**GU**GC**U**CCA**GU**AG-3' | 43 |
| 5'-CU**U**AAC**G**G**U**GC**U**CCAG**U**A**G**-3' | 16 | 5'-CU**U**AACGG**UG**C**U**CCA**GU**AG-3' | 44 |
| 5'-CUUAAC**G**G**U**GC**U**CCA**GU**AG-3' | 17 | 5'-CUUAACG**GU**GC**U**CCAG**U**AG-3' | 45 |
| 5'-CUUAAC**G**G**UG**C**U**CCAG**U**A**G**-3' | 18 | 5'-CUUAACG**GU**GC**U**CCAG**U**A**G**-3' | 46 |
| 5'-C**U**UAAC**G**GUGC**U**CCAG**U**AG-3' | 19 | 5'-CUUAACGG**UG**C**U**CCAG**U**AG-3' | 47 |
| 5'-C**UU**AAC**G**GUGC**U**CCAG**U**AG-3' | 20 | 5'-CUUAACGG**UG**C**U**CCAG**U**A**G**-3' | 48 |
| 5'-C**UU**AACG**G**UGC**U**CCAG**U**AG-3' | 21 | 5'-CUUAACGG**U**GC**U**CCA**GU**A**G**-3' | 49 |
| 5'-C**UU**AACG**G**UGC**U**CCAG**U**A**G**-3' | 22 | 5'-CUUAAC**G**G**UG**C**U**CCAG**U**A**G**-3' | 50 |
| 5'-C**U**UAAC**G**G**U**GC**U**CCA**GU**A**G**-3' | 23 | 5'-CUUAAC**G**G**UG**C**U**CCA**GU**A**G**-3' | 51 |
| 5'-CUUAACG**G**U**G**C**U**CCAG**U**A**G**-3' | 24 | 5'-CUUAACG**G**U**G**C**U**CCAG**U**AG-3' | 52 |
| 5'-CUUAACG**G**UGC**U**CCAG**U**A**G**-3' | 25 | 5'-CUUAACG**G**U**G**C**U**CCA**GU**AG-3' | 53 |
| 5'-CUUAACG**G**U**G**C**U**CCA**GU**A**G**-3' | 26 | 5'-CU**U**AACG**G**U**G**C**U**CCAG**U**AG-3' | 54 |
| 5'-CU**U**AACG**G**UGC**U**CCAG**U**A**G**-3' | 27 | 5'-CU**U**AACG**G**U**G**C**U**CCAG**U**A**G**-3' | 55 |
| 5'-CUUAAC**GG**UGC**U**CCAG**U**A**G**-3' | 28 | 5'-CUUAAC**GG**U**G**C**U**CCAG**U**AG-3' | 56 |
| 5'-CUUAAC**GG**U**G**C**U**CCA**GU**AG-3' | 29 | 5'-CU**U**AAC**GG**U**G**C**U**CCAG**U**AG-3' | 57 |
| 5'-CUUAAC**GG**U**G**C**U**CCAG**U**A**G**-3' | 30 | 5'-CUUAAC**GG**UGC**U**CCAG**U**A**G**-3' | 58 |

2'OMe nucleotides are indicated in bold and underlined.

In particular embodiments, the 2'OMe-modified sequence set forth in Table 1 corresponds to the antisense strand sequence present in the double-stranded region of the siRNA. In some embodiments, the 2'OMe-modified sequence set forth in Table 1 comprises a modified (e.g., 2'OMe) and/or unmodified 3' overhang of 1, 2, 3, or 4 nucleotides. In other embodiments, the 2'OMe-modified sequence set forth in Table 1 further comprises at least one, two, three, four, five, six, or more 2'OMe-modified adenosine and/or modified 2'OMe-modified cytosine nucleotides. Each of the 2'OMe-modified antisense strand sequences set forth in Table 1 may comprise the complementary strand of any of the 2'OMe-modified sense strand sequences set forth in Table 2 or the unmodified APOC3 siRNA "262" sense strand sequence shown in Table 7.

In another embodiment, the sense strand of the APOC3 siRNA comprises one of the 2'OMe-modified sequences set forth in Table 2. The sense strand sequence of APOC3 siRNA "262" shown in Table 7 sets forth the unmodified version of the 2'OMe-modified sequences set forth in Table 2. Nucleotides 1-19 of the sense strand sequence of the hAPOC3_260 siRNA shown in Table 10 also correspond to the unmodified version of the 2'OMe-modified sequences set forth in Table 2.

TABLE 2

| | SEQ ID NO. | | SEQ ID NO. |
|---|---|---|---|
| 5'-C**U**AC**U**GGAGCACCG**U**UAAG-3' | 59 | 5'-C**U**AC**U**G**G**A**G**CACCG**U**UAA**G**-3' | 85 |
| 5'-C**U**AC**U**GGAGCACCGU**U**AAG-3' | 60 | 5'-C**U**AC**U**G**G**AGCACCGU**U**AAG-3' | 86 |
| 5'-C**U**AC**U**GGAGCACCG**UU**AAG-3' | 61 | 5'-C**U**AC**U**GGA**G**CACCGU**U**AAG-3' | 87 |
| 5'-CUAC**U**GGAGCACCG**U**UAAG-3' | 62 | 5'-C**U**AC**U**GGAGCACCGU**U**AA**G**-3' | 88 |
| 5'-CUAC**U**GGAGCACCGU**U**AAG-3' | 63 | 5'-C**U**AC**U**G**G**A**G**CACCGU**U**AAG-3' | 89 |
| 5'-CUACU**G**GA**G**CACC**G**UUAAG-3' | 64 | 5'-C**U**AC**U**G**G**AGCACCGU**U**AA**G**-3' | 90 |
| 5'-CUACU**G**GA**G**CACCGUUAA**G**-3' | 65 | 5'-C**U**AC**U**GGA**G**CACCGU**U**AA**G**-3' | 91 |
| 5'-CUACUG**G**A**G**CACC**G**UUAAG-3' | 66 | 5'-C**U**AC**U**G**G**A**G**CACCGU**U**AA**G**-3' | 92 |
| 5'-CUACUG**G**A**G**CACCGUUAA**G**-3' | 67 | 5'-CUAC**U**G**G**A**G**CACCG**U**UAAG-3' | 93 |
| 5'-CUACU**G**GA**G**CACC**G**UUAA**G**-3' | 68 | 5'-CUAC**U**G**G**AGCACCG**U**UAA**G**-3' | 94 |
| 5'-CUACUG**G**A**G**CACC**G**UUAA**G**-3' | 69 | 5'-CUAC**U**GGA**G**CACCG**U**UAA**G**-3' | 95 |
| 5'-CUACU**GG**A**G**CACC**G**UUAA**G**-3' | 70 | 5'-CUAC**U**G**G**A**G**CACCG**U**UAA**G**-3' | 96 |
| 5'-C**U**AC**U**G**G**AGCACCG**U**UAAG-3' | 71 | 5'-CUAC**U**G**G**A**G**CACC**GU**UAA**G**-3' | 97 |
| 5'-C**U**AC**U**GGA**G**CACCG**U**UAAG-3' | 72 | 5'-CUAC**U**G**G**A**G**CACCG**UU**AA**G**-3' | 98 |
| 5'-C**U**AC**U**GGAGCACCG**U**UAA**G**-3' | 73 | 5'-CUAC**UG**GA**G**CACCG**U**UAA**G**-3' | 99 |
| 5'-C**U**AC**U**G**G**A**G**CACCG**U**UAAG-3' | 74 | 5'-CUAC**U**G**G**A**G**CACCGU**U**AAG-3' | 100 |
| 5'-C**U**AC**U**G**G**AGCACCG**U**UAA**G**-3' | 75 | 5'-CUAC**U**G**G**AGCACCGU**U**AA**G**-3' | 101 |
| 5'-C**U**AC**U**GGA**G**CACCG**U**UAA**G**-3' | 76 | 5'-CUAC**U**GGA**G**CACCGU**U**AA**G**-3' | 102 |
| 5'-C**U**AC**U**GGA**G**CACCG**UU**AA**G**-3' | 77 | 5'-CUAC**U**G**G**A**G**CACCGU**U**AA**G**-3' | 103 |
| 5'-C**U**ACU**G**GA**G**CACCG**U**UAAG-3' | 78 | 5'-C**U**ACU**G**GA**G**CACCG**U**UAA**G**-3' | 104 |
| 5'-C**U**ACU**G**GA**G**CACCGU**U**AAG-3' | 79 | 5'-C**U**ACU**G**GA**G**CACCGU**U**AA**G**-3' | 105 |
| 5'-C**U**AC**U**G**G**AGCACC**G**U**U**AAG-3' | 80 | 5'-C**U**AC**U**G**G**AGCACC**G**U**U**AA**G**-3' | 106 |
| 5'-C**U**AC**U**GGA**G**CACC**G**U**U**AAG-3' | 81 | 5'-C**U**AC**U**G**G**AGCACC**G**U**U**AA**G**-3' | 107 |
| 5'-C**U**AC**U**GGAGCACC**G**U**U**AA**G**-3' | 82 | 5'-C**U**AC**U**G**G**A**G**CACC**G**U**U**AA**G**-3' | 108 |
| 5'-C**U**AC**U**G**G**A**G**CACC**G**U**U**AAG-3' | 83 | 5'-CUAC**U**G**G**AGCACC**GU**UAAG-3' | 109 |
| 5'-C**U**AC**U**G**G**A**G**CACC**GU**UAAG-3' | 84 | 5'-CUAC**U**G**G**A**G**CACC**GU**UAAG-3' | 110 |

2'OMe nucleotides are indicated in bold and underlined.

In particular embodiments, the 2'OMe-modified sequence set forth in Table 2 corresponds to the sense strand sequence present in the double-stranded region of the siRNA. In some embodiments, the 2'OMe-modified sequence set forth in Table 2 comprises a modified (e.g., 2'OMe) and/or unmodified 3' overhang of 1, 2, 3, or 4 nucleotides. In other embodiments, the 2'OMe-modified sequence set forth in Table 2 further comprises at least one, two, three, four, five, six, or more 2'OMe-modified adenosine and/or modified 2'OMe-modified cytosine nucleotides. Each of the 2'OMe-modified sense strand sequences set forth in Table 2 may comprise the complementary strand of any of the 2'OMe-modified antisense strand sequences set forth in Table 1 or the unmodified APOC3 siRNA "262" antisense strand sequence shown in Table 7.

In yet another embodiment, the antisense strand of the APOC3 siRNA comprises one of the 2'OMe-modified sequences set forth in Table 3. The antisense strand sequence of APOC3 siRNA "314" shown in Table 7 sets forth the unmodified version of the 2'OMe-modified sequences set forth in Table 3. Nucleotides 1-19 of the antisense strand sequence of the hAPOC3_312 siRNA shown in Table 10 also correspond to the unmodified version of the 2'OMe-modified sequences set forth in Table 3.

TABLE 3

| | SEQ ID NO. | | SEQ ID NO. |
|---|---|---|---|
| 5'-C**U**GAAG**U**UGG**U**CUGACCUC-3' | 111 | 5'-C**U**GAAG**U**U**G**G**U**CU**G**ACCUC-3' | 131 |
| 5'-C**U**GAAGU**U**GG**U**CUGACCUC-3' | 112 | 5'-CU**G**AAG**U**UGG**U**C**U**GACC**U**C-3' | 132 |

TABLE 3-continued

| | SEQ ID NO. | | SEQ ID NO. |
|---|---|---|---|
| 5'-CUGAAGUUGGUCUGACCUC-3' | 113 | 5'-CUGAAGUUGGUCUGACCUC-3' | 133 |
| 5'-CUGAAGUUGGUCUGACCUC-3' | 114 | 5'-CUGAAGUUGGUCUGACCUC-3' | 134 |
| 5'-CUGAAGUUGGUCUGACCUC-3' | 115 | 5'-CUGAAGUUGGUCUGACCUC-3' | 135 |
| 5'-CUGAAGUUGGUCUGACCUC-3' | 116 | 5'-CUGAAGUUGGUCUGACCUC-3' | 136 |
| 5'-CUGAAGUUGGUCUGACCUC-3' | 117 | 5'-CUGAAGUUGGUCUGACCUC-3' | 137 |
| 5'-CUGAAGUUGGUCUGACCUC-3' | 118 | 5'-CUGAAGUUGGUCUGACCUC-3' | 138 |
| 5'-CUGAAGUUGGUCUGACCUC-3' | 119 | 5'-CUGAAGUUGGUCUGACCUC-3' | 139 |
| 5'-CUGAAGUUGGUCUGACCUC-3' | 120 | 5'-CUGAAGUUGGUCUGACCUC-3' | 140 |
| 5'-CUGAAGUUGGUCUGACCUC-3' | 121 | 5'-CUGAAGUUGGUCUGACCUC-3' | 141 |
| 5'-CUGAAGUUGGUCUGACCUC-3' | 122 | 5'-CUGAAGUUGGUCUGACCUC-3' | 142 |
| 5'-CUGAAGUUGGUCUGACCUC-3' | 123 | 5'-CUGAAGUUGGUCUGACCUC-3' | 143 |
| 5'-CUGAAGUUGGUCUGACCUC-3' | 124 | 5'-CUGAAGUUGGUCUGACCUC-3' | 144 |
| 5'-CUGAAGUUGGUCUGACCUC-3' | 125 | 5'-CUGAAGUUGGUCUGACCUC-3' | 145 |
| 5'-CUGAAGUUGGUCUGACCUC-3' | 126 | 5'-CUGAAGUUGGUCUGACCUC-3' | 146 |
| 5'-CUGAAGUUGGUCUGACCUC-3' | 127 | 5'-CUGAAGUUGGUCUGACCUC-3' | 147 |
| 5'-CUGAAGUUGGUCUGACCUC-3' | 128 | 5'-CUGAAGUUGGUCUGACCUC-3' | 148 |
| 5'-CUGAAGUUGGUCUGACCUC-3' | 129 | 5'-CUGAAGUUGGUCUGACCUC-3' | 149 |
| 5'-CUGAAGUUGGUCUGACCUC-3' | 130 | 5'-CUGAAGUUGGUCUGACCUC-3' | 150 |

2'OMe nucleotides are indicated in bold and underlined.

In particular embodiments, the 2'OMe-modified sequence set forth in Table 3 corresponds to the antisense strand sequence present in the double-stranded region of the siRNA. In some embodiments, the 2'OMe-modified sequence set forth in Table 3 comprises a modified (e.g., 2'OMe) and/or unmodified 3' overhang of 1, 2, 3, or 4 nucleotides. In other embodiments, the 2'OMe-modified sequence set forth in Table 3 further comprises at least one, two, three, four, five, six, or more 2'OMe-modified adenosine and/or modified 2'OMe-modified cytosine nucleotides. Each of the 2'OMe-modified antisense strand sequences set forth in Table 3 may comprise the complementary strand of any of the 2'OMe-modified sense strand sequences set forth in Table 4 or the unmodified APOC3 siRNA "314" sense strand sequence shown in Table 7.

In still yet another embodiment, the sense strand of the APOC3 siRNA comprises one of the 2'OMe-modified sequences set forth in Table 4. The sense strand sequence of APOC3 siRNA "314" shown in Table 7 sets forth the unmodified version of the 2'OMe-modified sequences set forth in Table 4. Nucleotides 1-19 of the sense strand sequence of the hAPOC3_312 siRNA shown in Table 10 also correspond to the unmodified version of the 2'OMe-modified sequences set forth in Table 4.

TABLE 4

| | SEQ ID NO. | | SEQ ID NO. |
|---|---|---|---|
| 5'-GAGGUCAGACCAACUUCAG-3' | 151 | 5'-GAGGUCAGACCAACUUCAG-3' | 172 |
| 5'-GAGGUCAGACCAACUUCAG-3' | 152 | 5'-GAGGUCAGACCAACUUCAG-3' | 173 |
| 5'-GAGGUCAGACCAACUUCAG-3' | 153 | 5'-GAGGUCAGACCAACUUCAG-3' | 174 |
| 5'-GAGGUCAGACCAACUUCAG-3' | 154 | 5'-GAGGUCAGACCAACUUCAG-3' | 175 |
| 5'-GAGGUCAGACCAACUUCAG-3' | 155 | 5'-GAGGUCAGACCAACUUCAG-3' | 176 |
| 5'-GAGGUCAGACCAACUUCAG-3' | 156 | 5'-GAGGUCAGACCAACUUCAG-3' | 177 |
| 5'-GAGGUCAGACCAACUUCAG-3' | 157 | 5'-GAGGUCAGACCAACUUCAG-3' | 178 |
| 5'-GAGGUCAGACCAACUUCAG-3' | 158 | 5'-GAGGUCAGACCAACUUCAG-3' | 179 |
| 5'-GAGGUCAGACCAACUUCAG-3' | 159 | 5'-GAGGUCAGACCAACUUCAG-3' | 180 |

TABLE 4-continued

| | SEQ ID NO. | | SEQ ID NO. |
|---|---|---|---|
| 5'-GAGGUCAGACCAACUUCAG-3' | 160 | 5'-GAGGUCAGACCAACUUCAG-3' | 181 |
| 5'-GAGGUCAGACCAACUUCAG-3' | 161 | 5'-GAGGUCAGACCAACUUCAG-3' | 182 |
| 5'-GAGGUCAGACCAACUUCAG-3' | 162 | 5'-GAGGUCAGACCAACUUCAG-3' | 183 |
| 5'-GAGGUCAGACCAACUUCAG-3' | 163 | 5'-GAGGUCAGACCAACUUCAG-3' | 184 |
| 5'-GAGGUCAGACCAACUUCAG-3' | 164 | 5'-GAGGUCAGACCAACUUCAG-3' | 185 |
| 5'-GAGGUCAGACCAACUUCAG-3' | 165 | 5'-GAGGUCAGACCAACUUCAG-3' | 186 |
| 5'-GAGGUCAGACCAACUUCAG-3' | 166 | 5'-GAGGUCAGACCAACUUCAG-3' | 187 |
| 5'-GAGGUCAGACCAACUUCAG-3' | 167 | 5'-GAGGUCAGACCAACUUCAG-3' | 188 |
| 5'-GAGGUCAGACCAACUUCAG-3' | 168 | 5'-GAGGUCAGACCAACUUCAG-3' | 189 |
| 5'-GAGGUCAGACCAACUUCAG-3' | 169 | 5'-GAGGUCAGACCAACUUCAG-3' | 190 |
| 5'-GAGGUCAGACCAACUUCAG-3' | 170 | 5'-GAGGUCAGACCAACUUCAG-3' | 191 |
| 5'-GAGGUCAGACCAACUUCAG-3' | 171 | 5'-GAGGUCAGACCAACUUCAG-3' | 192 |

2'OMe nucleotides are indicated in bold and underlined.

In particular embodiments, the 2'OMe-modified sequence set forth in Table 4 corresponds to the sense strand sequence present in the double-stranded region of the siRNA. In some embodiments, the 2'OMe-modified sequence set forth in Table 4 comprises a modified (e.g., 2'OMe) and/or unmodified 3' overhang of 1, 2, 3, or 4 nucleotides. In other embodiments, the 2'OMe-modified sequence set forth in Table 4 further comprises at least one, two, three, four, five, six, or more 2'OMe-modified adenosine and/or modified 2'OMe-modified cytosine nucleotides. Each of the 2'OMe-modified sense strand sequences set forth in Table 4 may comprise the complementary strand of any of the 2'OMe-modified antisense strand sequences set forth in Table 3 or the unmodified APOC3 siRNA "314" antisense strand sequence shown in Table 7.

In yet another embodiment, the antisense strand of the APOC3 siRNA comprises one of the 2'OMe-modified sequences set forth in Table 5. The antisense strand sequence of APOC3 siRNA "268" shown in Table 7 sets forth the unmodified version of the 2'OMe-modified sequences set forth in Table 5. Nucleotides 1-19 of the antisense strand sequence of the hAPOC3_266 siRNA shown in Table 10 also correspond to the unmodified version of the 2'OMe-modified sequences set forth in Table 5.

TABLE 5

| | SEQ ID NO. | | SEQ ID NO. |
|---|---|---|---|
| 5'-CUUGUCCUUAACGGUGCUC-3' | 193 | 5'-CUUGUCCUUAACGGUGCUC-3' | 216 |
| 5'-CUUGUCCUUAACGGUGCUC-3' | 194 | 5'-CUUGUCCUUAACGGUGCUC-3' | 217 |
| 5'-CUUGUCCUUAACGGUGCUC-3' | 195 | 5'-CUUGUCCUUAACGGUGCUC-3' | 218 |
| 5'-CUUGUCCUUAACGGUGCUC-3' | 196 | 5'-CUUGUCCUUAACGGUGCUC-3' | 219 |
| 5'-CUUGUCCUUAACGGUGCUC-3' | 197 | 5'-CUUGUCCUUAACGGUGCUC-3' | 220 |
| 5'-CUUGUCCUUAACGGUGCUC-3' | 198 | 5'-CUUGUCCUUAACGGUGCUC-3' | 221 |
| 5'-CUUGUCCUUAACGGUGCUC-3' | 199 | 5'-CUUGUCCUUAACGGUGCUC-3' | 222 |
| 5'-CUUGUCCUUAACGGUGCUC-3' | 200 | 5'-CUUGUCCUUAACGGUGCUC-3' | 223 |
| 5'-CUUGUCCUUAACGGUGCUC-3' | 201 | 5'-CUUGUCCUUAACGGUGCUC-3' | 224 |
| 5'-CUUGUCCUUAACGGUGCUC-3' | 202 | 5'-CUUGUCCUUAACGGUGCUC-3' | 225 |
| 5'-CUUGUCCUUAACGGUGCUC-3' | 203 | 5'-CUUGUCCUUAACGGUGCUC-3' | 226 |
| 5'-CUUGUCCUUAACGGUGCUC-3' | 204 | 5'-CUUGUCCUUAACGGUGCUC-3' | 227 |
| 5'-CUUGUCCUUAACGGUGCUC-3' | 205 | 5'-CUUGUCCUUAACGGUGCUC-3' | 228 |
| 5'-CUUGUCCUUAACGGUGCUC-3' | 206 | 5'-CUUGUCCUUAACGGUGCUC-3' | 229 |
| 5'-CUUGUCCUUAACGGUGCUC-3' | 207 | 5'-CUUGUCCUUAACGGUGCUC-3' | 230 |

TABLE 5-continued

| | SEQ ID NO. | | SEQ ID NO. |
|---|---|---|---|
| 5'-CUU**G**UCCUUAACG**G**U**G**CUC-3' | 208 | 5'-CUUG**U**CC**U**UAACG**GU**GC**U**C-3' | 231 |
| 5'-CUUGUCCUUAAC**GG**U**G**CUC-3' | 209 | 5'-CUUG**U**CC**U**UAACGG**UG**C**U**C-3' | 232 |
| 5'-CUU**G**UCCUUAAC**GG**U**G**CUC-3' | 210 | 5'-CUUG**U**CC**UU**AACGG**U**GC**U**C-3' | 233 |
| 5'-CU**U**GUCC**U**UAAC**G**G**U**GCUC-3' | 211 | 5'-CUUG**U**CC**UU**AAC**G**G**U**GC**U**C-3' | 234 |
| 5'-CU**U**GUCCU**U**AAC**G**G**U**GCUC-3' | 212 | 5'-CUUG**U**CC**UU**AAC**G**G**U**GCUC-3' | 235 |
| 5'-CU**U**GUCC**U**UAAC**G**GUGC**U**C-3' | 213 | 5'-CUUG**U**CC**UU**AAC**G**GU**G**C**U**C-3' | 236 |
| 5'-CUU**G**UCC**U**UAACGG**U**GC**U**C-3' | 214 | 5'-CUU**GU**CC**U**UAACGG**U**GC**U**C-3' | 237 |
| 5'-CUU**G**UCC**U**UAAC**G**G**U**GC**U**C-3' | 215 | 5'-CUU**GU**CCU**U**AACGG**U**GC**U**C-3' | 238 |

2'OMe nucleotides are indicated in bold and underlined.

In particular embodiments, the 2'OMe-modified sequence set forth in Table 5 corresponds to the antisense strand sequence present in the double-stranded region of the siRNA. In some embodiments, the 2'OMe-modified sequence set forth in Table 5 comprises a modified (e.g., 2'OMe) and/or unmodified 3' overhang of 1, 2, 3, or 4 nucleotides. In other embodiments, the 2'OMe-modified sequence set forth in Table 5 further comprises at least one, two, three, four, five, six, or more 2'OMe-modified adenosine and/or modified 2'OMe-modified cytosine nucleotides. Each of the 2'OMe-modified antisense strand sequences set forth in Table 5 may comprise the complementary strand of any of the 2'OMe-modified sense strand sequences set forth in Table 6 or the unmodified APOC3 siRNA "268" sense strand sequence shown in Table 7.

In still yet another embodiment, the sense strand of the APOC3 siRNA comprises one of the 2'OMe-modified sequences set forth in Table 6. The sense strand sequence of APOC3 siRNA "268" shown in Table 7 sets forth the unmodified version of the 2'OMe-modified sequences set forth in Table 6. Nucleotides 1-19 of the sense strand sequence of the hAPOC3_266 siRNA shown in Table 10 also correspond to the unmodified version of the 2'OMe-modified sequences set forth in Table 6.

TABLE 6

| | SEQ ID NO. | | SEQ ID NO. |
|---|---|---|---|
| 5'-GAGCACCG**UU**AAGGACAAG-3' | 239 | 5'-**G**A**G**CACCGU**U**AA**G**GACAAG-3' | 262 |
| 5'-**G**A**G**CACC**G**UUAA**G**GACAA**G**-3' | 240 | 5'-**G**A**G**CACCGU**U**AAG**G**ACAAG-3' | 263 |
| 5'-**G**A**G**CACC**G**UUAAG**G**ACAA**G**-3' | 241 | 5'-GA**G**CACCGU**U**AA**G**GACAA**G**-3' | 264 |
| 5'-GA**G**CACC**G**UUAA**G**GACAA**G**-3' | 242 | 5'-GA**G**CACCGU**U**AAG**G**ACAA**G**-3' | 265 |
| 5'-GA**G**CACC**G**UUAAG**G**ACAA**G**-3' | 243 | 5'-**G**A**G**CACCGU**U**AA**G**GACAA**G**-3' | 266 |
| 5'-GA**G**CACC**G**UUAA**GG**ACAAG-3' | 244 | 5'-**G**A**G**CACCGU**U**AAG**G**ACAA**G**-3' | 267 |
| 5'-**G**A**G**CACC**G**UUAA**GG**ACAAG-3' | 245 | 5'-**G**A**G**CACCGU**U**AA**GG**ACAA**G**-3' | 268 |
| 5'-**G**A**G**CACCG**U**UAA**G**GACAAG-3' | 246 | 5'-GA**G**CACC**G**U**U**AAG**G**ACAAG-3' | 269 |
| 5'-**G**A**G**CACCG**U**UAAG**G**ACAAG-3' | 247 | 5'-GA**G**CACC**G**U**U**AAG**G**ACAA**G**-3' | 270 |
| 5'-GA**G**CACCG**U**UAAG**G**ACAA**G**-3' | 248 | 5'-**G**AGCACCG**U**UAA**G**GACAA**G**-3' | 271 |
| 5'-GA**G**CACCG**U**UAAG**G**ACAA**G**-3' | 249 | 5'-**G**AGCACCG**U**UAAG**G**ACAA**G**-3' | 272 |
| 5'-**G**A**G**CACCG**U**UAA**G**GACAA**G**-3' | 250 | 5'-**G**AGCACCG**U**UAA**GG**ACAAG-3' | 273 |
| 5'-**G**A**G**CACCG**U**UAAG**G**ACAA**G**-3' | 251 | 5'-**G**AGCACCG**U**UAA**GG**ACAA**G**-3' | 274 |
| 5'-**G**A**G**CACCG**U**UAA**GG**ACAA**G**-3' | 252 | 5'-**G**AGCACC**GU**UAA**G**GACAA**G**-3' | 275 |
| 5'-GA**G**CACC**GU**UAAG**G**ACAAG-3' | 253 | 5'-**G**AGCACC**GU**UAAG**G**ACAA**G**-3' | 276 |
| 5'-GA**G**CACC**GU**UAAG**G**ACAA**G**-3' | 254 | 5'-GAGCACC**G**U**U**AA**G**GACAA**G**-3' | 277 |
| 5'-**G**A**G**CACCG**UU**AA**G**GACAAG-3' | 255 | 5'-GAGCACC**G**U**U**AAG**G**ACAA**G**-3' | 278 |
| 5'-**G**A**G**CACCG**UU**AAG**G**ACAAG-3' | 256 | 5'-GAGCACC**G**U**U**AA**GG**ACAAG-3' | 279 |
| 5'-GA**G**CACCG**UU**AA**G**GACAA**G**-3' | 257 | 5'-GAGCACC**G**U**U**AA**GG**ACAA**G**-3' | 280 |
| 5'-GA**G**CACCG**UU**AAG**G**ACAA**G**-3' | 258 | 5'-GAGCACCG**UU**AA**G**GACAA**G**-3' | 281 |

TABLE 6-continued

| | SEQ ID NO. | | SEQ ID NO. |
|---|---|---|---|
| 5'-**G**A**G**CACCG**UU**AA**G**GACAA**G**-3' | 259 | 5'-GAGCACCG**UU**AAGG**G**CAA**G**-3' | 282 |
| 5'-**G**A**G**CACCG**UU**AAG**G**ACAA**G**-3' | 260 | 5'-**G**A**G**CACC**GUU**AA**GG**ACAA**G**-3' | 283 |
| 5'-**G**A**G**CACCG**UU**AA**GG**ACAA**G**-3' | 261 | 5'-GA**G**CACCGU**U**AA**GG**ACAA**G**-3' | 284 |

2'OMe nucleotides are indicated in bold and underlined.

In particular embodiments, the 2'OMe-modified sequence set forth in Table 6 corresponds to the sense strand sequence present in the double-stranded region of the siRNA. In some embodiments, the 2'OMe-modified sequence set forth in Table 6 comprises a modified (e.g., 2'OMe) and/or unmodified 3' overhang of 1, 2, 3, or 4 nucleotides. In other embodiments, the 2'OMe-modified sequence set forth in Table 6 further comprises at least one, two, three, four, five, six, or more 2'OMe-modified adenosine and/or modified 2'OMe-modified cytosine nucleotides. Each of the 2'OMe-modified sense strand sequences set forth in Table 6 may comprise the complementary strand of any of the 2'OMe-modified antisense strand sequences set forth in Table 5 or the unmodified APOC3 siRNA "268" antisense strand sequence shown in Table 7.

One of skill in the art will understand that the sequences set forth in Tables 1-6 can also be modified in accordance with the selective modification patterns described herein (e.g., at alternative uridine and/or guanosine nucleotides, and optionally at adenosine and/or cytosine nucleotides, within the siRNA duplex), and screened for RNAi activity as well as immune stimulation, such that the degree of chemical modifications introduced into the siRNA molecule strikes a balance between reduction or abrogation of the immunostimulatory properties of the siRNA and retention of RNAi activity. Similarly, one of skill in the art will understand that the sequences set forth in Tables 7-10 can be modified in accordance with the selective modification patterns described herein (e.g., at uridine and/or guanosine nucleotides, and optionally at adenosine and/or cytosine nucleotides, within the siRNA duplex), and screened for RNAi activity as well as immune stimulation, such that the degree of chemical modifications introduced into the siRNA molecule strikes a balance between reduction or abrogation of the immunostimulatory properties of the siRNA and retention of RNAi activity.

In preferred embodiments, the APOC3 siRNA of the present invention (e.g., siRNA comprising nucleotides 1-19 of one of the sense and/or antisense strand sequences set forth in Tables 1-10) comprises a 3' overhang of 1, 2, 3, or 4 nucleotides in one or both strands of the siRNA. In certain instances, the siRNA may contain at least one blunt end. In particular embodiments, the 3' overhangs in one or both strands of the siRNA molecule may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target APOC3 sequence (3' overhang in antisense strand) or the complementary strand thereof (3' overhang in sense strand).

In another embodiment, the present invention provides a composition comprising a cocktail (e.g., at least 2, 3, 4, 5, 6, 7, 8, 9, 10, 11, 12, 13, 14, 15, 16, 17, 18, 19, 20, or more) of the unmodified and/or modified siRNA sequences set forth in Tables 1-10. In particular embodiments, the present invention provides a composition comprising one or more of the siRNA sequences set forth in Tables 1-10 in combination with one or more siRNAs that target one or more other genes (e.g., additional genes associated with liver diseases or disorders such as dyslipidemia or atherosclerosis). In certain embodiments, at least 1, 2, 3, 4, 5, 6, 7, 8, 9, 10, or more (e.g., all) of these siRNA sequences are chemically modified (e.g., 2'OMe-modified) as described herein.

The present invention also provides a pharmaceutical composition comprising one or more (e.g., a cocktail) of the siRNA molecules described herein and a pharmaceutically acceptable carrier.

In another aspect, the present invention provides a nucleic acid-lipid particle (e.g., SNALP) that targets APOC3 gene expression. The nucleic acid-lipid particles (e.g., SNALP) typically comprise one or more (e.g., a cocktail) of the siRNAs described herein, a cationic lipid, and a non-cationic lipid. In certain instances, the nucleic acid-lipid particles (e.g., SNALP) further comprise a conjugated lipid that inhibits aggregation of particles. Preferably, the nucleic acid-lipid particles (e.g., SNALP) comprise one or more (e.g., a cocktail) of the siRNAs described herein, a cationic lipid, a non-cationic lipid, and a conjugated lipid that inhibits aggregation of particles. In particular embodiments, the nucleic acid-lipid particles (e.g., SNALP) of the invention comprise 1, 2, 3, 4, 5, 6, 7, 8, or more unmodified and/or modified siRNAs that silence 1, 2, 3, 4, 5, 6, 7, 8, or more different genes associated with liver diseases or disorders (e.g., APOC3, alone or in combination with other genes expressed in the liver), a cationic lipid, a non-cationic lipid, and a conjugated lipid that inhibits aggregation of particles.

In some embodiments, the siRNA molecules of the invention are fully encapsulated in the nucleic acid-lipid particle (e.g., SNALP). With respect to formulations comprising an siRNA cocktail, the different types of siRNA species present in the cocktail (e.g., siRNA compounds with different sequences) may be co-encapsulated in the same particle, or each type of siRNA species present in the cocktail may be encapsulated in a separate particle. The siRNA cocktail may be formulated in the particles described herein using a mixture of two or more individual siRNAs (each having a unique sequence) at identical, similar, or different concentrations or molar ratios. In one embodiment, a cocktail of siRNAs (corresponding to a plurality of siRNAs with different sequences) is formulated using identical, similar, or different concentrations or molar ratios of each siRNA species, and the different types of siRNAs are co-encapsulated in the same particle. In another embodiment, each type of siRNA species present in the cocktail is encapsulated in different particles at identical, similar, or different siRNA concentrations or molar ratios, and the particles thus formed (each containing a different siRNA payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

The cationic lipid in the nucleic acid-lipid particles of the present invention (e.g., SNALP) may comprise, e.g., one or more cationic lipids of Formula I-II or any other cationic lipid species. In one particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), salts thereof, and mixtures thereof.

The non-cationic lipid in the nucleic acid-lipid particles of the present invention (e.g., SNALP) may comprise, e.g., one or more anionic lipids and/or neutral lipids. In some embodiments, the non-cationic lipid comprises one of the following neutral lipid components:

(1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a particularly preferred embodiment, the non-cationic lipid is a mixture of DPPC and cholesterol.

The lipid conjugate in the nucleic acid-lipid particles of the invention (e.g., SNALP) inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof.

In some embodiments, the present invention provides nucleic acid-lipid particles (e.g., SNALP) comprising: (a) one or more (e.g., a cocktail) siRNA molecules that target APOC3 gene expression; (b) one or more cationic lipids or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more (e.g., a cocktail) siRNA molecules that target APOC3 gene expression; (b) a cationic lipid or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:57" formulation. In one particular embodiment, the 1:57 formulation is a four-component system comprising about 1.4 mol % PEG-lipid conjugate (e.g., PEG2000-C-DMA), about 57.1 mol % cationic lipid (e.g., DLinDMA) or a salt thereof, about 7.1 mol % DPPC (or DSPC), and about 34.3 mol % cholesterol (or derivative thereof).

In another aspect of this embodiment, the nucleic acid-lipid particle comprises: (a) one or more (e.g., a cocktail) siRNA molecules that target APOC3 gene expression; (b) a cationic lipid or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-C-DMA), about 61.5 mol % cationic lipid (e.g., DLinDMA) or a salt thereof, and about 36.9 mol % cholesterol (or derivative thereof).

Additional embodiments related to the 1:57 and 1:62 formulations are described in PCT Publication No. WO 09/127060 and U.S. Provisional Application No. 61/184,652, filed Jun. 5, 2009, the disclosures of which are herein incorporated by reference in their entirety for all purposes.

In other embodiments, the present invention provides nucleic acid-lipid particles (e.g., SNALP) comprising: (a) one or more (e.g., a cocktail) siRNA molecules that target APOC3 gene expression; (b) one or more cationic lipids or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more (e.g., a cocktail) siRNA molecules that target APOC3 gene expression; (b) a cationic lipid or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid (e.g., DLinDMA) or a salt thereof, about 10 mol % DPPC (or DSPC), and about 48 mol % cholesterol (or derivative thereof).

The present invention also provides pharmaceutical compositions comprising a nucleic acid-lipid particle such as a SNALP and a pharmaceutically acceptable carrier.

The nucleic acid-lipid particles of the invention are useful for the therapeutic delivery of interfering RNA (e.g., siRNA) molecules that silence the expression of one or more genes associated with liver diseases or disorders (e.g., APOC3). In some embodiments, a cocktail of siRNAs that target one or more genes expressed in the liver is formulated into the same or different nucleic acid-lipid particles, and the particles are administered to a mammal (e.g., a human) requiring such treatment. In certain instances, a therapeutically effective amount of the nucleic acid-lipid particles can be administered to the mammal, e.g., for treating, preventing, reducing the risk of developing, or delaying the onset of a lipid disorder such as dyslipidemia (e.g., elevated triglyceride and/or cholesterol levels) or atherosclerosis. In particular embodiments, administration of the nucleic acid-lipid particles of the invention does not alter (e.g., reduce) hepatic triglyceride levels, e.g., liver triglyceride levels are not significantly changed upon particle administration.

Non-limiting examples of lipid disorders suitable for prevention and/or treatment with the nucleic acid-lipid particles of the invention (e.g., SNALP) include dyslipidemia (e.g., hyperlipidemias such as elevated triglyceride levels (hypertriglyceridemia) and/or elevated cholesterol levels (hypercholesterolemia)), atherosclerosis, low HDL-cholesterol, high LDL-cholesterol, coronary heart disease, coronary artery disease, atherosclerotic cardiovascular disease (CVD), fatty liver disease (hepatic steatosis), abnormal lipid metabolism, abnormal cholesterol metabolism, pancreatitis (e.g., acute pancreatitis associated with severe hypertriglyceridemia), diabetes (including Type 2 diabetes), obesity, cardiovascular disease, and other disorders relating to abnormal metabolism.

In some embodiments, the interfering RNA (e.g., siRNA) molecules described herein are used in methods for silencing APOC3 gene expression, e.g., in a cell such as a liver cell. In particular, it is an object of the invention to provide methods for treating, preventing, reducing the risk of developing, or delaying the onset of a lipid disorder in a mammal by downregulating or silencing the transcription and/or translation of the APOC3 gene. In certain embodiments, the present invention provides a method for introducing one or more interfering RNA (e.g., siRNA) molecules described herein into a cell by contacting the cell with a nucleic acid-lipid particle described herein (e.g., a SNALP formulation). In one particular embodiment, the cell is a liver cell such as, e.g., a hepatocyte present in the liver tissue of a mammal (e.g., a human). In another embodiment, the present invention provides a method for the in vivo delivery of one or more interfering RNA (e.g., siRNA) molecules described herein to a liver cell (e.g., hepatocyte) by administering to a mammal (e.g., human) a nucleic acid-lipid particle described herein (e.g., a SNALP formulation).

In some embodiments, the nucleic acid-lipid particles described herein (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In particular embodiments, the nucleic acid-lipid particles of the invention (e.g., SNALP) can preferentially deliver a payload such as an interfering RNA (e.g., siRNA) to the liver as compared to other tissues, e.g., for the treatment of a liver disease or disorder such as dyslipidemia or atherosclerosis.

In certain aspects, the present invention provides methods for silencing APOC3 gene expression in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting the APOC3 gene). In some embodiments, administration of nucleic acid-lipid particles comprising one or more APOC3-targeting siRNAs reduces liver APOC3 mRNA levels by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to liver APOC3 mRNA levels detected in the absence of the siRNA (e.g., buffer control or irrelevant non-APOC3 targeting siRNA control). In other embodiments, administration of nucleic acid-lipid particles comprising one or more APOC3-targeting siRNAs reduces liver APOC3 mRNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-APOC3 targeting siRNA control. The APOC3-targeting siRNAs may comprise at least one of the sequences set forth in Tables 1-10 in unmodified or modified (e.g., 2'OMe-modified) form.

In certain other aspects, the present invention provides methods for treating, preventing, reducing the risk or likelihood of developing (e.g., reducing the susceptibility to), delaying the onset of, and/or ameliorating one or more symptoms associated with a lipid disorder in a mammal (e.g., human) in need thereof, the method comprising administering to the mammal a therapeutically effective amount of a nucleic acid-lipid particle (e.g., a SNALP formulation) comprising one or more interfering RNA molecules (e.g., siRNAs) described herein (e.g., one or more siRNAs targeting the APOC3 gene). Non-limiting examples of lipid disorders are described above and include dyslipidemia and atherosclerosis. The APOC3-targeting siRNAs may comprise at least one of the sequences set forth in Tables 1-10 in unmodified or modified (e.g., 2'OMe-modified) form.

In a related aspect, the present invention provides a method for treating and/or ameliorating one or more symptoms associated with atherosclerosis or a dyslipidemia such as hyperlipidemia (e.g., elevated levels of triglycerides and/or cholesterol) in a mammal (e.g., human) in need thereof (e.g., a mammal with atheromatous plaques, elevated triglyceride levels, and/or elevated cholesterol levels), the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting the APOC3 gene). In some embodiments, administration of nucleic acid-lipid particles comprising one or more APOC3-targeting siRNA molecules reduces the level of atherosclerosis (e.g., decreases the size and/or number of atheromatous plaques or lesions) or blood (e.g., serum and/or plasma) triglyceride and/or cholesterol levels by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the level of atherosclerosis, blood triglyceride levels, or blood cholesterol levels detected in the absence of the siRNA (e.g., buffer control or irrelevant non-APOC3 targeting siRNA control). The APOC3-targeting siRNAs may comprise at least one of the sequences set forth in Tables 1-10 in unmodified or modified (e.g., 2'OMe-modified) form.

In another related aspect, the present invention provides a method for reducing the risk or likelihood of developing (e.g., reducing the susceptibility to) atherosclerosis or a dyslipidemia such as hyperlipidemia (e.g., elevated levels of triglycerides and/or cholesterol) in a mammal (e.g., human) at risk of developing atherosclerosis or dyslipidemia, the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting the APOC3 gene). In some embodiments, administration of nucleic acid-lipid particles comprising one or more APOC3-targeting siRNAs reduces the risk or likelihood of developing atherosclerosis or dyslipidemia by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the risk or likelihood of developing atherosclerosis or dyslipidemia in the absence of the siRNA (e.g., buffer control or irrelevant non-APOC3 targeting siRNA control). The APOC3-targeting siRNAs may comprise at least one of the sequences set forth in Tables 1-10 in unmodified or modified (e.g., 2'OMe-modified) form.

In yet another related aspect, the present invention provides a method for preventing or delaying the onset of atherosclerosis or a dyslipidemia such as hyperlipidemia (e.g., elevated levels of triglycerides and/or cholesterol) in a mammal (e.g., human) at risk of developing atherosclerosis or dyslipidemia, the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting the APOC3 gene). The APOC3-targeting siRNA molecules may comprise at least one of the sequences set forth in Tables 1-10 in unmodified or modified (e.g., 2'OMe-modified) form.

In a further related aspect, the present invention provides a method for lowering or reducing cholesterol levels in a mammal (e.g., human) in need thereof (e.g., a mammal with elevated blood cholesterol levels), the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting the APOC3 gene). In particular embodiments, administration of nucleic acid-lipid particles (e.g., SNALP) comprising one or more APOC3-targeting siRNA molecules lowers or reduces blood (e.g., serum and/or plasma) cholesterol levels. In some embodiments, administration of nucleic acid-lipid particles (e.g., SNALP) comprising one or more APOC3-targeting siRNA reduces blood cholesterol levels by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to blood cholesterol levels detected in the absence of the siRNA (e.g., buffer control or irrelevant non-APOC3 targeting siRNA control). In certain instances, administration of nucleic acid-lipid particles (e.g., SNALP) comprising one or more APOC3-targeting siRNA molecules elevates HDL-cholesterol levels and/or reduces LDL-cholesterol levels. The APOC3-targeting siRNAs may comprise at least one of the sequences set forth in Tables 1-10 in unmodified or modified (e.g., 2'OMe-modified) form.

In another related aspect, the present invention provides a method for lowering or reducing triglyceride levels in a mammal (e.g., human) in need thereof (e.g., a mammal with elevated blood triglyceride levels), the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting the APOC3 gene). In particular embodiments, administration of nucleic acid-lipid particles (e.g., SNALP) comprising one or more APOC3-targeting siRNA molecules lowers or reduces blood (e.g., serum and/or plasma) triglyceride levels. In certain embodiments, administration of nucleic acid-lipid particles comprising one or more APOC3-targeting siRNA reduces blood triglyceride levels by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to blood triglyceride levels detected in the absence of the siRNA (e.g., buffer control or irrelevant non-APOC3 targeting siRNA control). In other embodiments, administration of nucleic acid-lipid particles of the invention lowers or reduces hepatic (i.e., liver) triglyceride levels. The APOC3-targeting siRNAs may comprise at least one of the sequences set forth in Tables 1-10 in unmodified or modified (e.g., 2'OMe-modified) form.

In an additional related aspect, the present invention provides a method for lowering or reducing glucose levels in a mammal (e.g., human) in need thereof (e.g., a mammal with elevated blood glucose levels), the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting the APOC3 gene). In particular embodiments, administration of nucleic acid-lipid particles (e.g., SNALP) comprising one or more APOC3-targeting siRNA lowers or reduces blood (e.g., serum and/or plasma) glucose levels. In some embodiments, administration of nucleic acid-lipid particles comprising one or more APOC3-targeting siRNA reduces blood glucose levels by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to blood glucose levels detected in the absence of the siRNA (e.g., buffer control or irrelevant non-APOC3 targeting siRNA control). The APOC3-targeting siRNAs may comprise at least one of the sequences set forth in Tables 1-10 in unmodified or modified (e.g., 2'OMe-modified) form.

IV. Therapeutic Nucleic Acids

The term "nucleic acid" includes any oligonucleotide or polynucleotide, with fragments containing up to 60 nucleotides generally termed oligonucleotides, and longer fragments termed polynucleotides. In particular embodiments, oligonucletoides of the invention are from about 15 to about 60 nucleotides in length. In some embodiments, nucleic acid is associated with a carrier system such as the lipid particles described herein. In certain embodiments, the nucleic acid is fully encapsulated in the lipid particle. Nucleic acid may be administered alone in the lipid particles of the present invention, or in combination (e.g., co-administered) with lipid particles comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid can be single-stranded DNA or RNA, or double-stranded DNA or RNA, or DNA-RNA hybrids. In preferred embodiments, the nucleic acid is double-stranded RNA. Examples of double-stranded RNA are described herein and include, e.g., siRNA and other RNAi agents such as Dicer-substrate dsRNA, shRNA, aiRNA, and pre-miRNA. In other embodiments, the nucleic acid is single-stranded.

Single-stranded nucleic acids include, e.g., antisense oligonucleotides, ribozymes, mature miRNA, and triplex-forming oligonucleotides.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

A. siRNA

The unmodified and modified siRNA molecules of the invention are capable of silencing APOC3 gene expression, e.g., to reduce plasma triglyceride levels and/or plasma cholesterol levels. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. The siRNA sequences may have overhangs (e.g., 3' or 5' overhangs as described in Elbashir et al., *Genes Dev.,* 15:188 (2001) or Nykänen et al., *Cell,* 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the APOC3 siRNA reduces or completely abrogates the immune response to that siRNA molecule. In certain instances, the immunostimulatory properties of APOC3 siRNA sequences and their ability to silence APOC3 gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide).

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

Additional ranges, percentages, and patterns of modifications that may be introduced into siRNA are described in U.S. Patent Publication No. 20070135372, the disclosure of which is herein incorporated by reference in its entirety for all purposes.

1. Selection of siRNA Sequences

Suitable siRNA sequences can be identified using any means known in the art. Typically, the methods described in Elbashir et al., *Nature,* 411:494-498 (2001) and Elbashir et al., *EMBO J.,* 20:6877-6888 (2001) are combined with rational design rules set forth in Reynolds et al., *Nature Biotech.,* 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO J.,* 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell,* 115:209-216 (2003); and Schwarz et al., *Cell,* 115:199-208 (2003). In other embodiments, potential siRNA sequences may be further analyzed based on secondary structure at the target site as described in, e.g., Luo et al., *Biophys. Res. Commun.,* 318: 303-310 (2004). For example, secondary structure at the target site can be modeled using the Mfold algorithm (available at http://mfold.burnet.edu.au/ma_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3', 5'-UGU-3', 5'-GUGU-3', 5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.,* 255:4980-4983 (1980)); enzyme-linked immunosorbent assays (ELISA) as described, for example, by Raines et al., *J. Biol. Chem.,* 257:5154-5160 (1982); immunocytochemical techniques, including the use of fluorochromes (Brooks et al., *Clin. Exp. Immunol.,* 39:477 (1980)); and neutralization of activity (Bowen-Pope et al., *Proc. Natl. Acad. Sci. USA,* 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.,* 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature,* 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

2. Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occuring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

3. Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.,* 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.,* 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholine, amidate, carbamate, carboxymethyl, acetamidate, polyamide, sulfonate, sulfonamide, sulfamate, formacetal, thioformacetal, and alkylsilyl substitutions (see, e.g., Hunziker et al., Nucleic Acid Analogues: Synthesis and Properties, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

4. Target Genes

The siRNA molecules of the invention can be used to downregulate or silence the translation (i.e., expression) of the APOC3 gene, alone or in combination with one or more additional genes associated with metabolic diseases and disorders (e.g., liver diseases and disorders). In certain embodiments, the invention provides a cocktail of siRNA molecules that silences the expression of the APOC3 gene, wherein each siRNA present in the cocktail is complementary to a different part of the APOC3 mRNA sequence. Each APOC3 siRNA present in the cocktail may target a distinct region of the APOC3 mRNA sequence, or there may be some degree of overlap between two or more APOC3 siRNAs present in the cocktail. In certain other embodiments, the present invention provides a cocktail of siRNA molecules that silences the expression of the APOC3 gene and one or more additional genes associated with metabolic diseases and disorders (e.g., liver diseases and disorders). In some instances, the cocktail of siRNA molecules is fully encapsulated in a lipid particle such as a nucleic acid-lipid particle (e.g., SNALP). The siRNA molecules present in the cocktail may be co-encapsulated in the same lipid particle, or each siRNA species present in the cocktail may be formulated in separate particles.

Examples of additional genes associated with metabolic diseases and disorders (e.g., disorders in which the liver is the target and liver diseases and disorders) include, but are not limited to, genes expressed in dyslipidemia, such as, e.g., apolipoprotein B (ApoB) (Genbank Accession No. NM_000384), apolipoprotein E (ApoE) (Genbank Accession Nos. NM_000041 and NG_007084 REGION: 5001..8612), proprotein convertase subtilisin/kexin type 9 (PCSK9) (Genbank Accession No. NM_174936), diacylglycerol O-acyltransferase type 1 (DGAT1) (Genbank Accession No. NM_012079), diacylglyerol O-acyltransferase type 2 (DGAT2) (Genbank Accession No. NM_032564), liver X receptors such as LXRα (Genbank Accession Nos. NM_001130101, NM_001130102, and NM_005693) and LXRβ (Genback Accession No. NM_007121), farnesoid X receptors (FXR) (Genbank Accession No. NM_005123), sterol-regulatory element binding protein (SREBP), site-1 protease (S1P), 3-hydroxy-3-methylglutaryl coenzyme-A reductase (HMG coenzyme-A reductase); and genes expressed in diabetes, such as, e.g., glucose 6-phosphatase (see, e.g., Forman et al., *Cell,* 81:687 (1995); Seol et al., *Mol. Endocrinol.,* 9:72 (1995), Zavacki et al., *Proc. Natl. Acad. Sci. USA,* 94:7909 (1997); Sakai et al., *Cell,* 85:1037-1046 (1996); Duncan et al., *J. Biol. Chem.,* 272:12778-12785 (1997); Willy et al., *Genes Dev.,* 9:1033-1045 (1995); Lehmann et al., *J. Biol. Chem.,* 272:3137-3140 (1997); Janowski et al., *Nature,* 383:728-731 (1996); and Peet et al., *Cell,* 93:693-704 (1998)).

One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder. Non-limiting examples of siRNA molecules targeting the APOB gene include those described in U.S. Patent Publication Nos. 20060134189 and 20060105976, and PCT Publication No. WO 04/091515, the disclosures of which are herein incorporated by reference in their entirety for all purposes. Non-limiting examples of siRNA molecules targeting the PCSK9 gene include those described in U.S. Patent Publication Nos. 20070173473, 20080113930, and 20080306015, the disclosures of which are herein incorporated by reference in their entirety for all purposes. Exemplary siRNA molecules targeting the DGAT1 gene may be designed using the antisense compounds described in U.S. Patent Publication No. 20040185559, the disclosure of which is herein incorporated by reference in its entirety for all purposes. Exemplary siRNA molecules targeting the DGAT2 gene may be designed using the antisense compounds described in U.S. Patent Publication No. 20050043524, the disclosure of which is herein incorporated by reference in its entirety for all purposes.

In addition to its utility in silencing APOC3 gene expression for therapeutic purposes, the siRNAs described herein are also useful in research and development applications as well as diagnostic, prophylactic, prognostic, clinical, and other healthcare applications.

5. Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%-15%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof In one particular embodiment, the siRNA comprises at least one 2'OMe-guanosine nucleotide, 2'OMe-uridine nucleotide, or mixtures thereof In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence (e.g., APOC3) relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence (e.g., APOC3) relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs targeting APOC3 mRNA are administered using a carrier system such as a nucleic acid-lipid particle. In a preferred embodiment, the nucleic acid-lipid particle comprises: (a) one or more siRNA molecules targeting the APOC3 gene; (b) a cationic lipid (e.g., DLinDMA, DLenDMA, and/or DLin-K-C2-DMA); and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

B. Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-O-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

```
5'-pXXXXXXXXXXXXXXXXXXXXXXXDD-3'
3'-YXXXXXXXXXXXXXXXXXXXXXXXXXp-5'
```

wherein "X"=RNA, "p"=a phosphate group, "X"=2'OMe RNA, "Y" is an overhang domain comprised of 1, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In particular embodiments, Dicer-substrate dsRNAs targeting APOC3 mRNA are administered using a carrier system such as a nucleic acid-lipid particle. In a preferred embodiment, the nucleic acid-lipid particle comprises: (a) one or more Dicer-substrate dsRNA molecules targeting the APOC3 gene; (b) a cationic lipid (e.g., DLinDMA, DLenDMA, and/or DLin-K-C2-DMA); and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

Additional embodiments related to the Dicer-substrate dsRNAs of the invention, as well as methods of designing and synthesizing such dsRNAs, are described in U.S. Patent Publication Nos. 20050244858, 20050277610, and 20070265220, and U.S. Provisional Application No. 61/184,652, filed Jun. 5, 2009, the disclosures of which are herein incorporated by reference in their entirety for all purposes.

C. shRNA

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Suitable shRNA sequences can be identified, synthesized, and modified using any means known in the art for designing, synthesizing, and modifying siRNA sequences. In particular embodiments, shRNAs targeting APOC3 mRNA are administered using a carrier system such as a nucleic acid-lipid particle. In a preferred embodiment, the nucleic acid-lipid particle comprises: (a) one or more shRNA molecules targeting the APOC3 gene; (b) a cationic lipid (e.g., DLinDMA, DLenDMA, and/or DLin-K-C2-DMA); and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

Additional embodiments related to the shRNAs of the invention, as well as methods of designing and synthesizing such shRNAs, are described in U.S. Provisional Application No. 61/184,652, filed Jun. 5, 2009, the disclosure of which is herein incorporated by reference in its entirety for all purposes.

D. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or 20 base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein.

In particular embodiments, aiRNAs targeting APOC3 mRNA are administered using a carrier system such as a nucleic acid-lipid particle. In a preferred embodiment, the nucleic acid-lipid particle comprises: (a) one or more aiRNA molecules targeting the APOC3 gene; (b) a cationic lipid (e.g., DLinDMA, DLenDMA, and/or DLin-K-C2-DMA); and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127060, the disclosures of which are herein incorporated by reference in their entirety for all purposes.

E. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science,* 294:853-858 (2001); Lau et al., *Science,* 294:858-862 (2001); and Lee et al., *Science,* 294:862-864 (2001).

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature,* 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., *Cell,* 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In particular embodiments, miRNAs targeting APOC3 mRNA are administered using a carrier system such as a nucleic acid-lipid particle. In a preferred embodiment, the nucleic acid-lipid particle comprises: (a) one or more miRNA molecules targeting the APOC3 gene; (b) a cationic lipid (e.g., DLinDMA, DLenDMA, and/or DLin-K-C2-DMA); and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA).

In other embodiments, one or more agents that block the activity of an miRNA targeting APOC3 mRNA are administered using a lipid particle of the invention (e.g., a nucleic acid-lipid particle). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

Additional embodiments related to the miRNA molecules of the invention are described in U.S. Patent Publication No. 20090291131 and PCT Publication No. WO 09/127060, the disclosures of which are herein incorporated by reference in their entirety for all purposes.

V. Carrier Systems Containing Therapeutic Nucleic Acids

In one aspect, the present invention provides carrier systems containing one or more therapeutic nucleic acids (e.g., interfering RNA such as siRNA). In some embodiments, the carrier system is a lipid-based carrier system such as a lipid particle (e.g., SNALP), a cationic lipid or liposome nucleic acid complex (i.e., lipoplex), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a lipid particle such as a SNALP. One skilled in the art will appreciate that the therapeutic nucleic acids of the present invention can also be delivered as a naked molecule.

A. Lipid Particles

In certain aspects, the present invention provides lipid particles comprising one or more therapeutic nucleic acids (e.g., interfering RNA such as siRNA) and one or more of cationic (amino) lipids or salts thereof. In some embodiments, the lipid particles of the invention further comprise one or more non-cationic lipids. In other embodiments, the lipid particles further comprise one or more conjugated lipids capable of reducing or inhibiting particle aggregation.

The lipid particles of the invention preferably comprise a therapeutic nucleic acid such as an interfering RNA (e.g., siRNA), a cationic lipid, a non-cationic lipid, and a conjugated lipid that inhibits aggregation of particles. In some embodiments, the therapeutic nucleic acid is fully encapsulated within the lipid portion of the lipid particle such that the therapeutic nucleic acid in the lipid particle is resistant in aqueous solution to nuclease degradation. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:therapeutic agent (e.g., lipid:nucleic acid) ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., siRNA, Dicer-substrate dsRNA, shRNA, aiRNA, and/or miRNA), a cationic lipid (e.g., one or more cationic lipids of Formula I-II or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA (e.g., siRNA) molecules that target the APOC3 gene. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.,* 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

1. Cationic Lipids

Any of a variety of cationic lipids or salts thereof may be used in the lipid particles of the present invention (e.g., SNALP), either alone or in combination with one or more other cationic lipid species or non-cationic lipid species. The cationic lipids include the (R) and/or (S) enantiomers thereof.

In one aspect, cationic lipids of Formula I having the following structure are useful in the present invention:

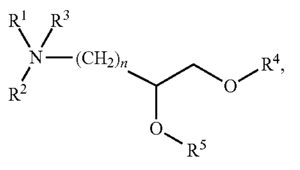

(I)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least two sites of unsaturation; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In one preferred embodiment, $R^1$ and $R^2$ are both methyl groups. In other preferred embodiments, n is 1 or 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, wherein at least one of $R^4$ and $R^5$ comprises at least two or at least three sites of unsaturation.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, an arachidonyl moiety, and a docosahexaenoyl moiety, as well as acyl derivatives thereof. In certain instances, the octadecadienyl moiety is a linoleyl moiety. In certain other instances, the octadecatrienyl moiety is a linolenyl moiety. In certain embodiments, $R^4$ and $R^5$ are both linoleyl moieties or linolenyl moieties. In particular embodiments, the cationic lipid of Formula I is 1,2-dilinoleyloxy-N,N-dimethylaminopropane (DLinDMA), 1,2-dilinolenyloxy-N,N-dimethylaminopropane (DLenDMA), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes.

In another aspect, cationic lipids of Formula II having the following structure (or salts thereof) are useful in the present invention:

(II)

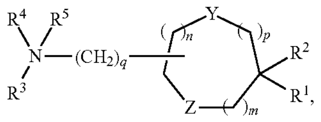

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH. In a preferred embodiment, q is 2.

In some embodiments, the cationic lipid of Formula II is 2,2-dilinoleyl-4-(2-dimethylaminoethyl)-[1,3]-dioxolane (DLin-K-C2-DMA; "XTC2" or "C2K"), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)-[1,3]-dioxolane (DLin-$K^2$-DMA), 2,2-dilinoleyl-4-methylpiperzine-[1,3]-dioxolane (D-Lin-K-N-methylpiperzine), or mixtures thereof. In preferred embodiments, the cationic lipid of Formula II is DLin-K-C2-DMA.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLin-K-DMA, as well as additional cationic lipids, is described in PCT Publication No. WO 09/086558, the disclosure of which is herein incorporated by reference in its entirety for all purposes. The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-$K^2$-DMA, and D-Lin-K-N-methylpiperzine, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes.

Examples of other cationic lipids or salts thereof which may be included in the lipid particles of the present invention include, but are not limited to, cationic lipids such as those described in U.S. Provisional Application No. 61/222,462, entitled "Improved Cationic Lipids and Methods for the Delivery of Nucleic Acids," filed Jul. 1, 2009, the disclosure of which is herein incorporated by reference in its entirety for all purposes, as well as cationic lipids such as N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3 -(N-(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), dilinoleylmethyl-3-dimethylaminopropionate (DLin-M-K-DMA; also known as DLin-M-DMA), and mixtures thereof Additional cationic lipids or salts thereof which may be included in the lipid particles of the present invention are described in U.S. Patent Publication No. 20090023673, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes. The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes. The synthesis of cationic lipids such as DO-C-DAP, DMDAP, DOTAP.Cl, DLin-M-K-DMA, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes. The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from Invitrogen); LIPOFECTAMINE® (including DOSPA and DOPE, available from Invitrogen); and TRANSFECTAM® (including DOGS, available from Promega Corp.).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol %, or from about 55 mol % to about 70 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof) of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127060, U.S. Provisional Application No. 61/184,652, filed Jun. 5, 2009, U.S. Provisional Application No. 61/222,462, filed Jul. 1, 2009, and U.S. Provisional Application No. 61/222,469, filed Jul. 1, 2009, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

2. Non-cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127060, U.S. Provisional Application No. 61/184,652, filed Jun. 5, 2009, U.S. Provisional Application No. 61/222,462, filed Jul. 1, 2009, and U.S. Provisional Application No. 61/222,469, filed Jul. 1, 2009, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be 12 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

3. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-$NH_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-$CH_2COOH$) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CC$H_2$C$H_2$C(O)—), succinamidyl (—NHC(O)C$H_2$C$H_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

(III)

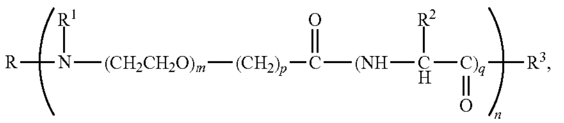

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

(IV)

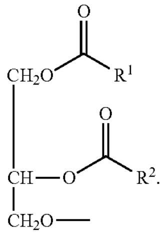

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(V)

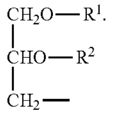

In a preferred embodiment, the PEG-lipid is a PEG-DAA conjugate having the following formula:

(VI)

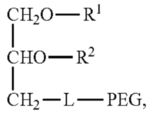

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons. The PEG can be optionally substituted with alkyl, alkoxy, acyl, or aryl groups. In certain instances, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

In addition to the foregoing components, the lipid particles (e.g., SNALP) of the present invention can further comprise cationic poly(ethylene glycol) (PEG) lipids or CPLs (see, e.g., Chen et al., *Bioconj. Chem.,* 11:433-437 (2000); U.S. Pat. No. 6,852,334; PCT Publication No. WO 00/62813, the disclosures of which are herein incorporated by reference in their entirety for all purposes).

(PEG-C-DMA)

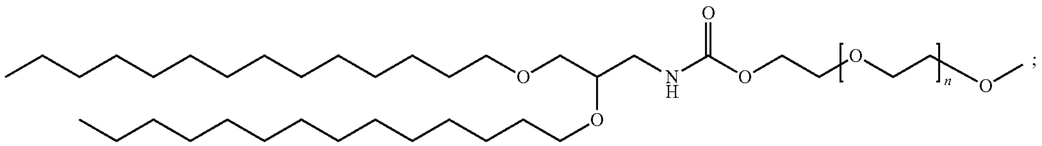

; and (PEG-C-DOMG)

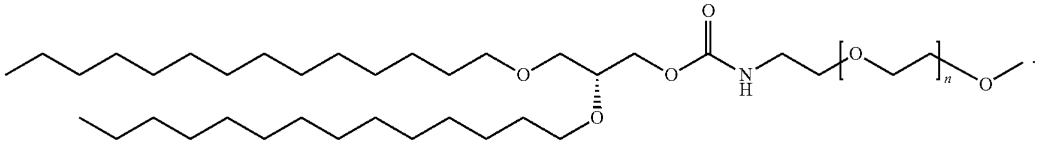

.

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

Suitable CPLs include compounds of Formula VII:

A-W-Y (VII), wherein A, W, and Y are as described below.

With reference to Formula VII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N-N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1 mol % to about 15 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, from about 4 mol % to about 10 mol %, or about 2 mol % (or any fraction thereof or range therein) of the total lipid present in the particle.

Additional percentages and ranges of lipid conjugates suitable for use in the lipid particles of the present invention are described in PCT Publication No. WO 09/127060, U.S. Provisional Application No. 61/184,652, filed Jun. 5, 2009, U.S. Provisional Application No. 61/222,462, filed Jul. 1, 2009, and U.S. Provisional Application No. 61/222,469, filed Jul. 1, 2009, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

B. Additional Carrier Systems

Non-limiting examples of additional lipid-based carrier systems suitable for use in the present invention include lipoplexes (see, e.g., U.S. Patent Publication No. 20030203865; and Zhang et al., *J. Control Release,* 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., interfering RNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., interfering RNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., *J. Am. Chem. Soc.,* 123:8155-8156 (2001)), chitosan, polyamidoamine (PAMAM) dendrimers (see, e.g., Kukowska-Latallo et al., *Proc. Natl. Acad. Sci. USA,* 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release,* 100:165-180 (2004); and Tiera et al., *Curr. Gene Ther.,* 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the interfering RNA may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the interfering RNA may be complexed with a peptide or polypeptide. An example of a protein-based carrier system includes, but is not limited to, the cationic oligopeptide-nucleic acid complex described in PCT Publication No. WO95/21931.

VI. Preparation of Lipid Particles

The lipid particles of the present invention, e.g., SNALP, in which a nucleic acid such as an interfering RNA (e.g., siRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise lipids of Formula I and II or salts thereof, alone or in combination with other cationic lipids. In other embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23

(23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

The SNALP formulations of the present invention can be tailored to preferentially target particular tissues or organs of interest. Preferential targeting of SNALP may be carried out by controlling the composition of the SNALP itself. For instance, it has been found that the 1:57 SNALP formulation can be used to preferentially target the liver. In particular embodiments, the kits of the invention comprise these lipid particles, wherein the particles are present in a container as a suspension or in dehydrated form. Such kits are particularly advantageous for use in providing effective treatment of a lipid disorder such as dyslipidemia or atherosclerosis.

In certain instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VIII. Administration of Lipid Particles

Once formed, the lipid particles of the invention (e.g., SNALP) are particularly useful for the introduction of nucleic acids (e.g., interfering RNA such as siRNA) into cells. Accordingly, the present invention also provides methods for introducing a nucleic acid (e.g., interfering RNA) into a cell. In particular embodiments, the nucleic acid (e.g., interfering RNA) is introduced into an APOC3-expressing cell such as a hepatocyte or other liver cell. The methods described herein may be carried out in vitro or in vivo by first forming the lipid particles as described above and then contacting the particles with the cells for a period of time sufficient for delivery of the nucleic acid to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid (e.g., interfering RNA) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for the treatment of APOC3-mediated diseases and disorders in a mammal (e.g., a rodent such as a mouse or a primate such as a human, chimpanzee, or monkey) by downregulating or silencing the transcription and/or translation of APOC3, alone or in combination with one or more additional target nucleic acid sequences or genes of interest. As a non-limiting example, the methods of the present invention are useful for the in vivo delivery of interfering RNA (e.g., siRNA) to the liver cells (e.g., hepatocytes) of a mammal such as a human for the treatment of a lipid disorder such as dyslipidemia or atherosclerosis. In certain embodiments, the APOC3-mediated disease or disorder is associated with expression and/or overexpression of APOC3 and expression or overexpression of the gene is reduced by the interfering RNA (e.g., siRNA). In certain other embodiments, a therapeutically effective amount of the lipid particle may be administered to the mammal. In some instances, one, two, three, or more interfering RNA molecules (e.g., siRNA molecules targeting different regions of the APOC3 gene) are formulated into a SNALP, and the particles are administered to patients requiring such treatment. In other instances, cells are removed from a patient, the interfering RNA is delivered in vitro (e.g., using a SNALP described herein), and the cells are reinjected into the patient.

A. In vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., US Patent Publication No. 20050118253). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a therapeutic nucleic acid such as an interfering RNA molecule (e.g., siRNA) is detectable in cells (e.g., liver cells) at about 8, 12, 24, 36, 48, 60, 72 or 96 hours after administration. In other embodiments, downregulation of expression of a target sequence, such as an APOC3 sequence, by an interfering RNA (e.g., siRNA) is detectable at about 8, 12, 24, 36, 48, 60, 72 or 96 hours after administration. In yet other embodiments, downregulation of expression of a target sequence, such as an APOC3 sequence, by an interfering RNA (e.g., siRNA) occurs preferentially in liver cells. In further embodiments, the presence or effect of an interfering RNA (e.g., siRNA) in cells at a site proximal or distal to the site of administration is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic nucleic acid (e.g., interfering RNA) suspended in diluents such as water, saline, or PEG 400; (b) capsules, sachets, or tablets, each containing a predetermined amount of a therapeutic nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic nucleic acid (e.g., interfering RNA) in a flavor, e.g., sucrose, as well as pastilles comprising the therapeutic nucleic acid in an inert base, such as gelatin and glycerin or sucrose and acacia emulsions, gels, and the like containing, in addition to the therapeutic nucleic acid, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic nucleic acid (e.g., interfering RNA) to lipid, the particular therapeutic nucleic acid used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In vitro Administration

For in vitro applications, the delivery of therapeutic nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 μg/ml, more preferably about 0.1 μg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are particularly well suited for treating any of a variety of APOC3-mediated diseases and disorders by targeting APOC3 gene expression in vivo. The present invention can be practiced on a wide variety of cell types from any vertebrate species, including mammals, such as, e.g, canines, felines, equines, bovines, ovines, caprines, rodents (e.g., mice, rats, and guinea pigs), lagomorphs, swine, and primates (e.g. monkeys, chimpanzees, and humans). Suitable cells include, but are not limited to, liver cells such as hepatocytes, hematopoietic precursor (stem) cells, fibroblasts, keratinocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells (e.g., intestinal epithelial cells), bone cells, and the like. In preferred embodiments, an interfering RNA (e.g., siRNA) is delivered to hepatocytes.

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), detection of a compound modulated by apoC-III (e.g., serum triglycerides or cholesterol), or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^{3}H$, $^{125}I$, $^{35}S$, $^{14}C$, $^{32}P$, $^{33}P$, etc.; enzymes such as horseradish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In Molecular Cloning: A Laboratory Manual, Cold Spring Harbor Laboratory Press (2000); and Ausubel et al., Short Protocols in Molecular Biology, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; The *Journal Of NIH Research,* 3:81 (1991); Kwoh et al., *Proc. Natl. Acad. Sci. USA,* 86:1173 (1989); Guatelli et al., *Proc. Natl. Acad. Sci. USA,* 87:1874 (1990); Lomeli et al., *J. Clin. Chem.,* 35:1826 (1989); Landegren et al., *Science,* 241:1077 (1988); Van Brunt, *Biotechnology,* 8:291 (1990); Wu and Wallace, *Gene,* 4:560 (1989); Barringer et al., *Gene,* 89:117 (1990); and Sooknanan and Malek, *Biotechnology,* 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.,* 22:1859 1862 (1981), e.g., using an automated synthesizer, as described in Needham VanDevanter et al., *Nucleic Acids Res.,* 12:6159 (1984). Purification of polynucleotides, where necessary, is typically performed by either native acrylamide gel electrophoresis or by anion exchange HPLC as described in Pearson et al., *J. Chrom.,* 255:137 149 (1983). The sequence of the synthetic polynucleotides can be verified using the chemical degradation method of Maxam and Gilbert (1980) in Grossman and Moldave (eds.) Academic Press, New York, Methods in *Enzymology,* 65:499.

An alternative means for determining the level of transcription is in situ hybridization. In situ hybridization assays are well-known and are generally described in Angerer et al., *Methods Enzymol.,* 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

IX. Combination Therapy

In some embodiments, the present invention provides methods for treating a lipid disorder associated with elevated triglycerides, cholesterol, and/or glucose by administering a therapeutic nucleic acid that targets the APOC3 gene (e.g., APOC3 interfering RNA such as APOC3 siRNA) in combination with one or more therapeutic nucleic acids that target other genes (e.g., APOB siRNA). In one particular embodiment, the present invention provides methods for preventing and/or ameliorating hepatic steatosis (e.g., fatty liver or triglyceride accumulation) induced by silencing APOB gene expression by co-administering an APOC3 siRNA together with an APOB siRNA. In a preferred embodiment, the combination of therapeutic nucleic acids is delivered to a liver cell in a mammal such as a human.

In other embodiments, the present invention provides methods for treating a lipid disorder associated with elevated triglycerides, cholesterol, and/or glucose by administering a therapeutic nucleic acid that targets the APOC3 gene (e.g., APOC3 interfering RNA such as APOC3 siRNA) in combination with a lipid-lowering agent. Non-limiting examples of lipid-lowering agents include, but are not limited to, statins, fibrates, ezetimibe, thiazolidinediones, niacin, beta-blockers, nitroglycerin, calcium antagonists, and fish oil. The methods can be carried out in vivo by administering the therapeutic nucleic acid and lipid-lowering agent as described herein or using any means known in the art. In one preferred embodiment, the combination of therapeutic agents is delivered to a liver cell in a mammal such as a human.

In certain aspects, a patient about to begin therapy with either a lipid-lowering agent or a therapeutic nucleic acid that targets another gene (e.g., APOB siRNA) is first pretreated with a suitable dose of one or more lipid particles (e.g., SNALP) containing a therapeutic nucleic acid that targets the APOC3 gene (e.g., APOC3 siRNA). The patient can be pretreated with a suitable dose of lipid particles targeting the APOC3 gene at any reasonable time prior to administration of the lipid-lowering agent or other therapeutic nucleic acid. As non-limiting examples, the dose of one or more lipid particles targeting APOC3 expression can be administered about 96, 84, 72, 60, 48, 36, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 hours, or any interval thereof, before administration of the lipid-lowering agent or other therapeutic nucleic acid.

Additionally, a patient about to begin therapy with either a lipid-lowering agent or a therapeutic nucleic acid that targets another gene (e.g., APOB siRNA) can be pretreated with more than one dose of lipid particles (e.g., SNALP) containing a therapeutic nucleic acid that targets the APOC3 gene (e.g., APOC3 siRNA) at different times before administration of the lipid-lowering agent or other therapeutic nucleic acid. As such, the methods of the present invention can further comprise administering a second dose of lipid particles targeting the APOC3 gene prior to administration of the lipid-lowering agent or other therapeutic nucleic acid. In certain instances, the lipid particles of the first dose are the same as the lipid particles of the second dose. In certain other instances, the lipid particles of the first dose are different from the lipid particles of the second dose. Preferably, the two pretreatment doses use the same lipid particles, e.g., SNALP containing the same therapeutic nucleic acid that targets the APOC3 gene (e.g., APOC3 siRNA). One skilled in the art will appreciate that the second dose of lipid particles can occur at any reasonable time following the first dose. As a non-limiting example, if the first dose was administered about 12 hours before administration of the lipid-lowering agent or other therapeutic nucleic acid, the second dose can be administered about 11, 10, 9, 8, 7, 6, 5, 4, 3, 2, 1, 0.9, 0.8, 0.7, 0.6, 0.5, 0.4, 0.3, 0.2, or 0.1 hours, or any interval thereof, before administration of the lipid-lowering agent or other therapeutic nucleic acid. One skilled in the art will also appreciate that the second dose of lipid particles can be the same or a different dose. In additional embodiments of the present invention, the patient can be pretreated with a third, fourth, fifth, sixth, seventh, eighth, ninth, tenth, or more dose of the same or different lipid particles targeting the APOC3 gene prior to administration of the lipid-lowering agent or other therapeutic nucleic acid.

A patient can also be treated with a suitable dose of one or more lipid particles (e.g., SNALP) containing a therapeutic nucleic acid that targets the APOC3 gene (e.g., APOC3 siRNA) at any reasonable time during administration of either a lipid-lowering agent or a therapeutic nucleic acid that targets another gene (e.g., APOB siRNA). As such, the methods of the present invention can further comprise administering a dose of lipid particles targeting the APOC3 gene during administration of the lipid-lowering agent or other therapeutic nucleic acid. One skilled in the art will appreciate that more than one dose of such lipid particles can be administered at different times during administration of the lipid-lowering agent or other therapeutic nucleic acid. As a non-limiting example, lipid particles (e.g., SNALP) containing one or more unmodified and/or modified APOC3 siRNA sequences can be administered at the beginning of administration of the lipid-lowering agent or other therapeutic nucleic acid, while administration of the lipid-lowering agent or other therapeutic nucleic acid is in progress, and/or at the end of administration of the lipid-lowering agent or other therapeutic nucleic acid. One skilled in the art will also appreciate that the pretreatment and intra-treatment (i.e., during administration of the lipid-lowering agent or other therapeutic nucleic acid)

doses of lipid particles targeting APOC3 gene expression can be the same or a different dose.

In addition, a patient can be treated with a suitable dose of one or more nucleic acid-lipid particles (e.g., SNALP) containing a therapeutic nucleic acid that targets the APOC3 gene (e.g., APOC3 siRNA) at any reasonable time following administration of either a lipid-lowering agent or a therapeutic nucleic acid that targets another gene (e.g., APOB siRNA). As such, the methods of the present invention can further comprise administering a dose of lipid particles targeting the APOC3 gene after administration of the lipid-lowering agent or other therapeutic nucleic acid. As non-limiting examples, the dose of one or more such lipid particles can be administered about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 36, 48, 60, 72, 84, 96, 108, or more hours, or any interval thereof, after administration of the lipid-lowering agent or other therapeutic nucleic acid. In certain instances, the same lipid particle targeting the APOC3 gene is used before and after administration of the lipid-lowering agent or other therapeutic nucleic acid. In certain other instances, a different lipid particle targeting the APOC3 gene is used following administration of the lipid-lowering agent or other therapeutic nucleic acid. One skilled in the art will appreciate that more than one dose of the lipid particles targeting APOC3 gene expression can be administered at different times following administration of the lipid-lowering agent or other therapeutic nucleic acid. One skilled in the art will also appreciate that the pretreatment and posttreatment (i.e., following administration of the lipid-lowering agent or other therapeutic nucleic acid) doses of lipid particles targeting the APOC3 gene can be the same or a different dose.

Lipid-lowering agents or therapeutic nucleic acid (e.g., interfering RNA) molecules that target other genes can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra joint, parenteral, intra-arteriole, intradermal, intraventricular, intracranial, intraperitoneal, intravesical, intrathecal, intralesional, intranasal, rectal, vaginal, or by inhalation. By "co-administer" it is meant that the therapeutic nucleic acid targeting APOC3 expression is administered at the same time, just prior to, or just after the administration of the lipid-lowering agent or therapeutic nucleic acid that targets another gene.

A therapeutically effective amount of a lipid-lowering agent may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages. One skilled in the art will appreciate that administered dosages of lipid-lowering agents will vary depending on a number of factors, including, but not limited to, the particular lipid-lowering agent or set of lipid-lowering agents to be administered, the mode of administration, the type of application, the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage.

As used herein, the term "unit dosage form" refers to physically discrete units suitable as unitary dosages for human subjects and other mammals, each unit containing a predetermined quantity of a lipid-lowering agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the lipid-lowering agent.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a lipid-lowering agent, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. A lipid-lowering agent can also be formulated into a suppository disposed, for example, in a polyethylene glycol (PEG) carrier.

Liquid dosage forms can be prepared by dissolving or dispersing a lipid-lowering agent and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. A lipid-lowering agent can also be formulated into a retention enema.

For topical administration, the therapeutically effective dose can be in the form of emulsions, lotions, gels, foams, creams, jellies, solutions, suspensions, ointments, and transdermal patches. For administration by inhalation, a lipid-lowering agent can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

X. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Exemplary siRNA Molecules Targeting APOC3

Table 7 provides non-limiting examples of siRNA molecules that are suitable for modulating (e.g., silencing) APOC3 gene expression. In some embodiments, the sense strand comprises or consists of one of the target APOC3 sequences set forth in Table 7. In related embodiments, the sense strand comprises at least 15 contiguous nucleotides (e.g., at least 15, 16, 17, 18, or 19 contiguous nucleotides) of one of the target APOC3 sequences set forth in Table 7. In other embodiments, the antisense strand comprises or consists of one of the antisense strand sequences set forth in Table 7. In related embodiments, the antisense strand comprises at least 15 contiguous nucleotides (e.g., at least 15, 16, 17, 18, or 19 contiguous nucleotides) of one of the antisense strand sequences set forth in Table 7. In further embodiments, the antisense strand specifically hybridizes to one of the target APOC3 sequences set forth in Table 7.

TABLE 7 siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 1 | UGCUCAGUUCAUCCCUAGA | 285 | UCUAGGGAUGAACUGAGCA | 286 |
| 2 | GCUCAGUUCAUCCCUAGAG | 287 | CUCUAGGGAUGAACUGAGC | 288 |
| 3 | CUCAGUUCAUCCCUAGAGG | 289 | CCUCUAGGGAUGAACUGAG | 290 |
| 4 | UCAGUUCAUCCCUAGAGGC | 291 | GCCUCUAGGGAUGAACUGA | 292 |
| 5 | CAGUUCAUCCCUAGAGGCA | 293 | UGCCUCUAGGGAUGAACUG | 294 |
| 6 | AGUUCAUCCCUAGAGGCAG | 295 | CUGCCUCUAGGGAUGAACU | 296 |
| 7 | GUUCAUCCCUAGAGGCAGC | 297 | GCUGCCUCUAGGGAUGAAC | 298 |
| 8 | UUCAUCCCUAGAGGCAGCU | 299 | AGCUGCCUCUAGGGAUGAA | 300 |
| 9 | UCAUCCCUAGAGGCAGCUG | 301 | CAGCUGCCUCUAGGGAUGA | 302 |
| 10 | CAUCCCUAGAGGCAGCUGC | 303 | GCAGCUGCCUCUAGGGAUG | 304 |
| 11 | AUCCCUAGAGGCAGCUGCU | 305 | AGCAGCUGCCUCUAGGGAU | 306 |
| 12 | UCCCUAGAGGCAGCUGCUC | 307 | GAGCAGCUGCCUCUAGGGA | 308 |
| 13 | CCCUAGAGGCAGCUGCUCC | 309 | GGAGCAGCUGCCUCUAGGG | 310 |
| 14 | CCUAGAGGCAGCUGCUCCA | 311 | UGGAGCAGCUGCCUCUAGG | 312 |
| 15 | CUAGAGGCAGCUGCUCCAG | 313 | CUGGAGCAGCUGCCUCUAG | 314 |
| 16 | UAGAGGCAGCUGCUCCAGG | 315 | CCUGGAGCAGCUGCCUCUA | 316 |
| 17 | AGAGGCAGCUGCUCCAGGA | 317 | UCCUGGAGCAGCUGCCUCU | 318 |
| 18 | GAGGCAGCUGCUCCAGGAA | 319 | UUCCUGGAGCAGCUGCCUC | 320 |
| 19 | AGGCAGCUGCUCCAGGAAC | 321 | GUUCCUGGAGCAGCUGCCU | 322 |
| 20 | GGCAGCUGCUCCAGGAACA | 323 | UGUUCCUGGAGCAGCUGCC | 324 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 21 | GCAGCUGCUCCAGGAACAG | 325 | CUGUUCCUGGAGCAGCUGC | 326 |
| 22 | CAGCUGCUCCAGGAACAGA | 327 | UCUGUUCCUGGAGCAGCUG | 328 |
| 23 | AGCUGCUCCAGGAACAGAG | 329 | CUCUGUUCCUGGAGCAGCU | 330 |
| 24 | GCUGCUCCAGGAACAGAGG | 331 | CCUCUGUUCCUGGAGCAGC | 332 |
| 25 | CUGCUCCAGGAACAGAGGU | 333 | ACCUCUGUUCCUGGAGCAG | 334 |
| 26 | UGCUCCAGGAACAGAGGUG | 335 | CACCUCUGUUCCUGGAGCA | 336 |
| 27 | GCUCCAGGAACAGAGGUGC | 337 | GCACCUCUGUUCCUGGAGC | 338 |
| 28 | CUCCAGGAACAGAGGUGCC | 339 | GGCACCUCUGUUCCUGGAG | 340 |
| 29 | UCCAGGAACAGAGGUGCCA | 341 | UGGCACCUCUGUUCCUGGA | 342 |
| 30 | CCAGGAACAGAGGUGCCAU | 343 | AUGGCACCUCUGUUCCUGG | 344 |
| 31 | CAGGAACAGAGGUGCCAUG | 345 | CAUGGCACCUCUGUUCCUG | 346 |
| 32 | AGGAACAGAGGUGCCAUGC | 347 | GCAUGGCACCUCUGUUCCU | 348 |
| 33 | GGAACAGAGGUGCCAUGCA | 349 | UGCAUGGCACCUCUGUUCC | 350 |
| 34 | GAACAGAGGUGCCAUGCAG | 351 | CUGCAUGGCACCUCUGUUC | 352 |
| 35 | AACAGAGGUGCCAUGCAGC | 353 | GCUGCAUGGCACCUCUGUU | 354 |
| 36 | ACAGAGGUGCCAUGCAGCC | 355 | GGCUGCAUGGCACCUCUGU | 356 |
| 37 | CAGAGGUGCCAUGCAGCCC | 357 | GGGCUGCAUGGCACCUCUG | 358 |
| 38 | AGAGGUGCCAUGCAGCCCC | 359 | GGGGCUGCAUGGCACCUCU | 360 |
| 39 | GAGGUGCCAUGCAGCCCCG | 361 | CGGGGCUGCAUGGCACCUC | 362 |
| 40 | AGGUGCCAUGCAGCCCCGG | 363 | CCGGGGCUGCAUGGCACCU | 364 |
| 41 | GGUGCCAUGCAGCCCCGGG | 365 | CCCGGGGCUGCAUGGCACC | 366 |
| 42 | GUGCCAUGCAGCCCCGGGU | 367 | ACCCGGGGCUGCAUGGCAC | 368 |
| 43 | UGCCAUGCAGCCCCGGGUA | 369 | UACCCGGGGCUGCAUGGCA | 370 |
| 44 | GCCAUGCAGCCCCGGGUAC | 371 | GUACCCGGGGCUGCAUGGC | 372 |
| 45 | CCAUGCAGCCCCGGGUACU | 373 | AGUACCCGGGGCUGCAUGG | 374 |
| 46 | CAUGCAGCCCCGGGUACUC | 375 | GAGUACCCGGGGCUGCAUG | 376 |
| 47 | AUGCAGCCCCGGGUACUCC | 377 | GGAGUACCCGGGGCUGCAU | 378 |
| 48 | UGCAGCCCCGGGUACUCCU | 379 | AGGAGUACCCGGGGCUGCA | 380 |
| 49 | GCAGCCCCGGGUACUCCUU | 381 | AAGGAGUACCCGGGGCUGC | 382 |
| 50 | CAGCCCCGGGUACUCCUUG | 383 | CAAGGAGUACCCGGGGCUG | 384 |
| 51 | AGCCCCGGGUACUCCUUGU | 385 | ACAAGGAGUACCCGGGGCU | 386 |
| 52 | GCCCCGGGUACUCCUUGUU | 387 | AACAAGGAGUACCCGGGGC | 388 |
| 53 | CCCCGGGUACUCCUUGUUG | 389 | CAACAAGGAGUACCCGGGG | 390 |
| 54 | CCCGGGUACUCCUUGUUGU | 391 | ACAACAAGGAGUACCCGGG | 392 |
| 55 | CCGGGUACUCCUUGUUGUU | 393 | AACAACAAGGAGUACCCGG | 394 |
| 56 | CGGGUACUCCUUGUUGUUG | 395 | CAACAACAAGGAGUACCCG | 396 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 57 | GGGUACUCCUUGUUGUUGC | 397 | GCAACAACAAGGAGUACCC | 398 |
| 58 | GGUACUCCUUGUUGUUGCC | 399 | GGCAACAACAAGGAGUACC | 400 |
| 59 | GUACUCCUUGUUGUUGCCC | 401 | GGGCAACAACAAGGAGUAC | 402 |
| 60 | UACUCCUUGUUGUUGCCCU | 403 | AGGGCAACAACAAGGAGUA | 404 |
| 61 | ACUCCUUGUUGUUGCCCUC | 405 | GAGGGCAACAACAAGGAGU | 406 |
| 62 | CUCCUUGUUGUUGCCCUCC | 407 | GGAGGGCAACAACAAGGAG | 408 |
| 63 | UCCUUGUUGUUGCCCUCCU | 409 | AGGAGGGCAACAACAAGGA | 410 |
| 64 | CCUUGUUGUUGCCCUCCUG | 411 | CAGGAGGGCAACAACAAGG | 412 |
| 65 | CUUGUUGUUGCCCUCCUGG | 413 | CCAGGAGGGCAACAACAAG | 414 |
| 66 | UUGUUGUUGCCCUCCUGGC | 415 | GCCAGGAGGGCAACAACAA | 416 |
| 67 | UGUUGUUGCCCUCCUGGCG | 417 | CGCCAGGAGGGCAACAACA | 418 |
| 68 | GUUGUUGCCCUCCUGGCGC | 419 | GCGCCAGGAGGGCAACAAC | 420 |
| 69 | UUGUUGCCCUCCUGGCGCU | 421 | AGCGCCAGGAGGGCAACAA | 422 |
| 70 | UGUUGCCCUCCUGGCGCUC | 423 | GAGCGCCAGGAGGGCAACA | 424 |
| 71 | GUUGCCCUCCUGGCGCUCC | 425 | GGAGCGCCAGGAGGGCAAC | 426 |
| 72 | UUGCCCUCCUGGCGCUCCU | 427 | AGGAGCGCCAGGAGGGCAA | 428 |
| 73 | UGCCCUCCUGGCGCUCCUG | 429 | CAGGAGCGCCAGGAGGGCA | 430 |
| 74 | GCCCUCCUGGCGCUCCUGG | 431 | CCAGGAGCGCCAGGAGGGC | 432 |
| 75 | CCCUCCUGGCGCUCCUGGC | 433 | GCCAGGAGCGCCAGGAGGG | 434 |
| 76 | CCUCCUGGCGCUCCUGGCC | 435 | GGCCAGGAGCGCCAGGAGG | 436 |
| 77 | CUCCUGGCGCUCCUGGCCU | 437 | AGGCCAGGAGCGCCAGGAG | 438 |
| 78 | UCCUGGCGCUCCUGGCCUC | 439 | GAGGCCAGGAGCGCCAGGA | 440 |
| 79 | CCUGGCGCUCCUGGCCUCU | 441 | AGAGGCCAGGAGCGCCAGG | 442 |
| 80 | CUGGCGCUCCUGGCCUCUG | 443 | CAGAGGCCAGGAGCGCCAG | 444 |
| 81 | UGGCGCUCCUGGCCUCUGC | 445 | GCAGAGGCCAGGAGCGCCA | 446 |
| 82 | GGCGCUCCUGGCCUCUGCC | 447 | GGCAGAGGCCAGGAGCGCC | 448 |
| 83 | GCGCUCCUGGCCUCUGCCC | 449 | GGGCAGAGGCCAGGAGCGC | 450 |
| 84 | CGCUCCUGGCCUCUGCCCG | 451 | CGGGCAGAGGCCAGGAGCG | 452 |
| 85 | GCUCCUGGCCUCUGCCCGA | 453 | UCGGGCAGAGGCCAGGAGC | 454 |
| 86 | CUCCUGGCCUCUGCCCGAG | 455 | CUCGGGCAGAGGCCAGGAG | 456 |
| 87 | UCCUGGCCUCUGCCCGAGC | 457 | GCUCGGGCAGAGGCCAGGA | 458 |
| 88 | CCUGGCCUCUGCCCGAGCU | 459 | AGCUCGGGCAGAGGCCAGG | 460 |
| 89 | CUGGCCUCUGCCCGAGCUU | 461 | AAGCUCGGGCAGAGGCCAG | 462 |
| 90 | UGGCCUCUGCCCGAGCUUC | 463 | GAAGCUCGGGCAGAGGCCA | 464 |
| 91 | GGCCUCUGCCCGAGCUUCA | 465 | UGAAGCUCGGGCAGAGGCC | 466 |
| 92 | GCCUCUGCCCGAGCUUCAG | 467 | CUGAAGCUCGGGCAGAGGC | 468 |
| 93 | CCUCUGCCCGAGCUUCAGA | 469 | UCUGAAGCUCGGGCAGAGG | 470 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 94 | CUCUGCCCGAGCUUCAGAG | 471 | CUCUGAAGCUCGGGCAGAG | 472 |
| 95 | UCUGCCCGAGCUUCAGAGG | 473 | CCUCUGAAGCUCGGGCAGA | 474 |
| 96 | CUGCCCGAGCUUCAGAGGC | 475 | GCCUCUGAAGCUCGGGCAG | 476 |
| 97 | UGCCCGAGCUUCAGAGGCC | 477 | GGCCUCUGAAGCUCGGGCA | 478 |
| 98 | GCCCGAGCUUCAGAGGCCG | 479 | CGGCCUCUGAAGCUCGGGC | 480 |
| 99 | CCCGAGCUUCAGAGGCCGA | 481 | UCGGCCUCUGAAGCUCGGG | 482 |
| 100 | CCGAGCUUCAGAGGCCGAG | 483 | CUCGGCCUCUGAAGCUCGG | 484 |
| 101 | CGAGCUUCAGAGGCCGAGG | 485 | CCUCGGCCUCUGAAGCUCG | 486 |
| 102 | GAGCUUCAGAGGCCGAGGA | 487 | UCCUCGGCCUCUGAAGCUC | 488 |
| 103 | AGCUUCAGAGGCCGAGGAU | 489 | AUCCUCGGCCUCUGAAGCU | 490 |
| 104 | GCUUCAGAGGCCGAGGAUG | 491 | CAUCCUCGGCCUCUGAAGC | 492 |
| 105 | CUUCAGAGGCCGAGGAUGC | 493 | GCAUCCUCGGCCUCUGAAG | 494 |
| 106 | UUCAGAGGCCGAGGAUGCC | 495 | GGCAUCCUCGGCCUCUGAA | 496 |
| 107 | UCAGAGGCCGAGGAUGCCU | 497 | AGGCAUCCUCGGCCUCUGA | 498 |
| 108 | CAGAGGCCGAGGAUGCCUC | 499 | GAGGCAUCCUCGGCCUCUG | 500 |
| 109 | AGAGGCCGAGGAUGCCUCC | 501 | GGAGGCAUCCUCGGCCUCU | 502 |
| 110 | GAGGCCGAGGAUGCCUCCC | 503 | GGGAGGCAUCCUCGGCCUC | 504 |
| 111 | AGGCCGAGGAUGCCUCCCU | 505 | AGGGAGGCAUCCUCGGCCU | 506 |
| 112 | GGCCGAGGAUGCCUCCCUU | 507 | AAGGGAGGCAUCCUCGGCC | 508 |
| 113 | GCCGAGGAUGCCUCCCUUC | 509 | GAAGGGAGGCAUCCUCGGC | 510 |
| 114 | CCGAGGAUGCCUCCCUUCU | 511 | AGAAGGGAGGCAUCCUCGG | 512 |
| 115 | CGAGGAUGCCUCCCUUCUC | 513 | GAGAAGGGAGGCAUCCUCG | 514 |
| 116 | GAGGAUGCCUCCCUUCUCA | 515 | UGAGAAGGGAGGCAUCCUC | 516 |
| 117 | AGGAUGCCUCCCUUCUCAG | 517 | CUGAGAAGGGAGGCAUCCU | 518 |
| 118 | GGAUGCCUCCCUUCUCAGC | 519 | GCUGAGAAGGGAGGCAUCC | 520 |
| 119 | GAUGCCUCCCUUCUCAGCU | 521 | AGCUGAGAAGGGAGGCAUC | 522 |
| 120 | AUGCCUCCCUUCUCAGCUU | 523 | AAGCUGAGAAGGGAGGCAU | 524 |
| 121 | UGCCUCCCUUCUCAGCUUC | 525 | GAAGCUGAGAAGGGAGGCA | 526 |
| 122 | GCCUCCCUUCUCAGCUUCA | 527 | UGAAGCUGAGAAGGGAGGC | 528 |
| 123 | CCUCCCUUCUCAGCUUCAU | 529 | AUGAAGCUGAGAAGGGAGG | 530 |
| 124 | CUCCCUUCUCAGCUUCAUG | 531 | CAUGAAGCUGAGAAGGGAG | 532 |
| 125 | UCCCUUCUCAGCUUCAUGC | 533 | GCAUGAAGCUGAGAAGGGA | 534 |
| 126 | CCCUUCUCAGCUUCAUGCA | 535 | UGCAUGAAGCUGAGAAGGG | 536 |
| 127 | CCUUCUCAGCUUCAUGCAG | 537 | CUGCAUGAAGCUGAGAAGG | 538 |
| 128 | CUUCUCAGCUUCAUGCAGG | 539 | CCUGCAUGAAGCUGAGAAG | 540 |
| 129 | UUCUCAGCUUCAUGCAGGG | 541 | CCCUGCAUGAAGCUGAGAA | 542 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 130 | UCUCAGCUUCAUGCAGGGU | 543 | ACCCUGCAUGAAGCUGAGA | 544 |
| 131 | CUCAGCUUCAUGCAGGGUU | 545 | AACCCUGCAUGAAGCUGAG | 546 |
| 132 | UCAGCUUCAUGCAGGGUUA | 547 | UAACCCUGCAUGAAGCUGA | 548 |
| 133 | CAGCUUCAUGCAGGGUUAC | 549 | GUAACCCUGCAUGAAGCUG | 550 |
| 134 | AGCUUCAUGCAGGGUUACA | 551 | UGUAACCCUGCAUGAAGCU | 552 |
| 135 | GCUUCAUGCAGGGUUACAU | 553 | AUGUAACCCUGCAUGAAGC | 554 |
| 136 | CUUCAUGCAGGGUUACAUG | 555 | CAUGUAACCCUGCAUGAAG | 556 |
| 137 | UUCAUGCAGGGUUACAUGA | 557 | UCAUGUAACCCUGCAUGAA | 558 |
| 138 | UCAUGCAGGGUUACAUGAA | 559 | UUCAUGUAACCCUGCAUGA | 560 |
| 139 | CAUGCAGGGUUACAUGAAG | 561 | CUUCAUGUAACCCUGCAUG | 562 |
| 140 | AUGCAGGGUUACAUGAAGC | 563 | GCUUCAUGUAACCCUGCAU | 564 |
| 141 | UGCAGGGUUACAUGAAGCA | 565 | UGCUUCAUGUAACCCUGCA | 566 |
| 142 | GCAGGGUUACAUGAAGCAC | 567 | GUGCUUCAUGUAACCCUGC | 568 |
| 143 | CAGGGUUACAUGAAGCACG | 569 | CGUGCUUCAUGUAACCCUG | 570 |
| 144 | AGGGUUACAUGAAGCACGC | 571 | GCGUGCUUCAUGUAACCCU | 572 |
| 145 | GGGUUACAUGAAGCACGCC | 573 | GGCGUGCUUCAUGUAACCC | 574 |
| 146 | GGUUACAUGAAGCACGCCA | 575 | UGGCGUGCUUCAUGUAACC | 576 |
| 147 | GUUACAUGAAGCACGCCAC | 577 | GUGGCGUGCUUCAUGUAAC | 578 |
| 148 | UUACAUGAAGCACGCCACC | 579 | GGUGGCGUGCUUCAUGUAA | 580 |
| 149 | UACAUGAAGCACGCCACCA | 581 | UGGUGGCGUGCUUCAUGUA | 582 |
| 150 | ACAUGAAGCACGCCACCAA | 583 | UUGGUGGCGUGCUUCAUGU | 584 |
| 151 | CAUGAAGCACGCCACCAAG | 585 | CUUGGUGGCGUGCUUCAUG | 586 |
| 152 | AUGAAGCACGCCACCAAGA | 587 | UCUUGGUGGCGUGCUUCAU | 588 |
| 153 | UGAAGCACGCCACCAAGAC | 589 | GUCUUGGUGGCGUGCUUCA | 590 |
| 154 | GAAGCACGCCACCAAGACC | 591 | GGUCUUGGUGGCGUGCUUC | 592 |
| 155 | AAGCACGCCACCAAGACCG | 593 | CGGUCUUGGUGGCGUGCUU | 594 |
| 156 | AGCACGCCACCAAGACCGC | 595 | GCGGUCUUGGUGGCGUGCU | 596 |
| 157 | GCACGCCACCAAGACCGCC | 597 | GGCGGUCUUGGUGGCGUGC | 598 |
| 158 | CACGCCACCAAGACCGCCA | 599 | UGGCGGUCUUGGUGGCGUG | 600 |
| 159 | ACGCCACCAAGACCGCCAA | 601 | UUGGCGGUCUUGGUGGCGU | 602 |
| 160 | CGCCACCAAGACCGCCAAG | 603 | CUUGGCGGUCUUGGUGGCG | 604 |
| 161 | GCCACCAAGACCGCCAAGG | 605 | CCUUGGCGGUCUUGGUGGC | 606 |
| 162 | CCACCAAGACCGCCAAGGA | 607 | UCCUUGGCGGUCUUGGUGG | 608 |
| 163 | CACCAAGACCGCCAAGGAU | 609 | AUCCUUGGCGGUCUUGGUG | 610 |
| 164 | ACCAAGACCGCCAAGGAUG | 611 | CAUCCUUGGCGGUCUUGGU | 612 |
| 165 | CCAAGACCGCCAAGGAUGC | 613 | GCAUCCUUGGCGGUCUUGG | 614 |
| 166 | CAAGACCGCCAAGGAUGCA | 615 | UGCAUCCUUGGCGGUCUUG | 616 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 167 | AAGACCGCCAAGGAUGCAC | 617 | GUGCAUCCUUGGCGGUCUU | 618 |
| 168 | AGACCGCCAAGGAUGCACU | 619 | AGUGCAUCCUUGGCGGUCU | 620 |
| 169 | GACCGCCAAGGAUGCACUG | 621 | CAGUGCAUCCUUGGCGGUC | 622 |
| 170 | ACCGCCAAGGAUGCACUGA | 623 | UCAGUGCAUCCUUGGCGGU | 624 |
| 171 | CCGCCAAGGAUGCACUGAG | 625 | CUCAGUGCAUCCUUGGCGG | 626 |
| 172 | CGCCAAGGAUGCACUGAGC | 627 | GCUCAGUGCAUCCUUGGCG | 628 |
| 173 | GCCAAGGAUGCACUGAGCA | 629 | UGCUCAGUGCAUCCUUGGC | 630 |
| 174 | CCAAGGAUGCACUGAGCAG | 631 | CUGCUCAGUGCAUCCUUGG | 632 |
| 175 | CAAGGAUGCACUGAGCAGC | 633 | GCUGCUCAGUGCAUCCUUG | 634 |
| 176 | AAGGAUGCACUGAGCAGCG | 635 | CGCUGCUCAGUGCAUCCUU | 636 |
| 177 | AGGAUGCACUGAGCAGCGU | 637 | ACGCUGCUCAGUGCAUCCU | 638 |
| 178 | GGAUGCACUGAGCAGCGUG | 639 | CACGCUGCUCAGUGCAUCC | 640 |
| 179 | GAUGCACUGAGCAGCGUGC | 641 | GCACGCUGCUCAGUGCAUC | 642 |
| 180 | AUGCACUGAGCAGCGUGCA | 643 | UGCACGCUGCUCAGUGCAU | 644 |
| 181 | UGCACUGAGCAGCGUGCAG | 645 | CUGCACGCUGCUCAGUGCA | 646 |
| 182 | GCACUGAGCAGCGUGCAGG | 647 | CCUGCACGCUGCUCAGUGC | 648 |
| 183 | CACUGAGCAGCGUGCAGGA | 649 | UCCUGCACGCUGCUCAGUG | 650 |
| 184 | ACUGAGCAGCGUGCAGGAG | 651 | CUCCUGCACGCUGCUCAGU | 652 |
| 185 | CUGAGCAGCGUGCAGGAGU | 653 | ACUCCUGCACGCUGCUCAG | 654 |
| 186 | UGAGCAGCGUGCAGGAGUC | 655 | GACUCCUGCACGCUGCUCA | 656 |
| 187 | GAGCAGCGUGCAGGAGUCC | 657 | GGACUCCUGCACGCUGCUC | 658 |
| 188 | AGCAGCGUGCAGGAGUCCC | 659 | GGGACUCCUGCACGCUGCU | 660 |
| 189 | GCAGCGUGCAGGAGUCCCA | 661 | UGGGACUCCUGCACGCUGC | 662 |
| 190 | CAGCGUGCAGGAGUCCCAG | 663 | CUGGGACUCCUGCACGCUG | 664 |
| 191 | AGCGUGCAGGAGUCCCAGG | 665 | CCUGGGACUCCUGCACGCU | 666 |
| 192 | GCGUGCAGGAGUCCCAGGU | 667 | ACCUGGGACUCCUGCACGC | 668 |
| 193 | CGUGCAGGAGUCCCAGGUG | 669 | CACCUGGGACUCCUGCACG | 670 |
| 194 | GUGCAGGAGUCCCAGGUGG | 671 | CCACCUGGGACUCCUGCAC | 672 |
| 195 | UGCAGGAGUCCCAGGUGGC | 673 | GCCACCUGGGACUCCUGCA | 674 |
| 196 | GCAGGAGUCCCAGGUGGCC | 675 | GGCCACCUGGGACUCCUGC | 676 |
| 197 | CAGGAGUCCCAGGUGGCCC | 677 | GGGCCACCUGGGACUCCUG | 678 |
| 198 | AGGAGUCCCAGGUGGCCCA | 679 | UGGGCCACCUGGGACUCCU | 680 |
| 199 | GGAGUCCCAGGUGGCCCAG | 681 | CUGGGCCACCUGGGACUCC | 682 |
| 200 | GAGUCCCAGGUGGCCCAGC | 683 | GCUGGGCCACCUGGGACUC | 684 |
| 201 | AGUCCCAGGUGGCCCAGCA | 685 | UGCUGGGCCACCUGGGACU | 686 |
| 202 | GUCCCAGGUGGCCCAGCAG | 687 | CUGCUGGGCCACCUGGGAC | 688 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 203 | UCCCAGGUGGCCCAGCAGG | 689 | CCUGCUGGGCCACCUGGGA | 690 |
| 204 | CCCAGGUGGCCCAGCAGGC | 691 | GCCUGCUGGGCCACCUGGG | 692 |
| 205 | CCAGGUGGCCCAGCAGGCC | 693 | GGCCUGCUGGGCCACCUGG | 694 |
| 206 | CAGGUGGCCCAGCAGGCCA | 695 | UGGCCUGCUGGGCCACCUG | 696 |
| 207 | AGGUGGCCCAGCAGGCCAG | 697 | CUGGCCUGCUGGGCCACCU | 698 |
| 208 | GGUGGCCCAGCAGGCCAGG | 699 | CCUGGCCUGCUGGGCCACC | 700 |
| 209 | GUGGCCCAGCAGGCCAGGG | 701 | CCCUGGCCUGCUGGGCCAC | 702 |
| 210 | UGGCCCAGCAGGCCAGGGG | 703 | CCCCUGGCCUGCUGGGCCA | 704 |
| 211 | GGCCCAGCAGGCCAGGGGC | 705 | GCCCCUGGCCUGCUGGGCC | 706 |
| 212 | GCCCAGCAGGCCAGGGGCU | 707 | AGCCCCUGGCCUGCUGGGC | 708 |
| 213 | CCCAGCAGGCCAGGGGCUG | 709 | CAGCCCCUGGCCUGCUGGG | 710 |
| 214 | CCAGCAGGCCAGGGGCUGG | 711 | CCAGCCCCUGGCCUGCUGG | 712 |
| 215 | CAGCAGGCCAGGGGCUGGG | 713 | CCCAGCCCCUGGCCUGCUG | 714 |
| 216 | AGCAGGCCAGGGGCUGGGU | 715 | ACCCAGCCCCUGGCCUGCU | 716 |
| 217 | GCAGGCCAGGGGCUGGGUG | 717 | CACCCAGCCCCUGGCCUGC | 718 |
| 218 | CAGGCCAGGGGCUGGGUGA | 719 | UCACCCAGCCCCUGGCCUG | 720 |
| 219 | AGGCCAGGGGCUGGGUGAC | 721 | GUCACCCAGCCCCUGGCCU | 722 |
| 220 | GGCCAGGGGCUGGGUGACC | 723 | GGUCACCCAGCCCCUGGCC | 724 |
| 221 | GCCAGGGGCUGGGUGACCG | 725 | CGGUCACCCAGCCCCUGGC | 726 |
| 222 | CCAGGGGCUGGGUGACCGA | 727 | UCGGUCACCCAGCCCCUGG | 728 |
| 223 | CAGGGGCUGGGUGACCGAU | 729 | AUCGGUCACCCAGCCCCUG | 730 |
| 224 | AGGGGCUGGGUGACCGAUG | 731 | CAUCGGUCACCCAGCCCCU | 732 |
| 225 | GGGGCUGGGUGACCGAUGG | 733 | CCAUCGGUCACCCAGCCCC | 734 |
| 226 | GGGCUGGGUGACCGAUGGC | 735 | GCCAUCGGUCACCCAGCCC | 736 |
| 227 | GGCUGGGUGACCGAUGGCU | 737 | AGCCAUCGGUCACCCAGCC | 738 |
| 228 | GCUGGGUGACCGAUGGCUU | 739 | AAGCCAUCGGUCACCCAGC | 740 |
| 229 | CUGGGUGACCGAUGGCUUC | 741 | GAAGCCAUCGGUCACCCAG | 742 |
| 230 | UGGGUGACCGAUGGCUUCA | 743 | UGAAGCCAUCGGUCACCCA | 744 |
| 231 | GGGUGACCGAUGGCUUCAG | 745 | CUGAAGCCAUCGGUCACCC | 746 |
| 232 | GGUGACCGAUGGCUUCAGU | 747 | ACUGAAGCCAUCGGUCACC | 748 |
| 233 | GUGACCGAUGGCUUCAGUU | 749 | AACUGAAGCCAUCGGUCAC | 750 |
| 234 | UGACCGAUGGCUUCAGUUC | 751 | GAACUGAAGCCAUCGGUCA | 752 |
| 235 | GACCGAUGGCUUCAGUUCC | 753 | GGAACUGAAGCCAUCGGUC | 754 |
| 236 | ACCGAUGGCUUCAGUUCCC | 755 | GGGAACUGAAGCCAUCGGU | 756 |
| 237 | CCGAUGGCUUCAGUUCCCU | 757 | AGGGAACUGAAGCCAUCGG | 758 |
| 238 | CGAUGGCUUCAGUUCCCUG | 759 | CAGGGAACUGAAGCCAUCG | 760 |
| 239 | GAUGGCUUCAGUUCCCUGA | 761 | UCAGGGAACUGAAGCCAUC | 762 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 240 | AUGGCUUCAGUUCCCUGAA | 763 | UUCAGGGAACUGAAGCCAU | 764 |
| 241 | UGGCUUCAGUUCCCUGAAA | 765 | UUUCAGGGAACUGAAGCCA | 766 |
| 242 | GGCUUCAGUUCCCUGAAAG | 767 | CUUUCAGGGAACUGAAGCC | 768 |
| 243 | GCUUCAGUUCCCUGAAAGA | 769 | UCUUUCAGGGAACUGAAGC | 770 |
| 244 | CUUCAGUUCCCUGAAAGAC | 771 | GUCUUUCAGGGAACUGAAG | 772 |
| 245 | UUCAGUUCCCUGAAAGACU | 773 | AGUCUUUCAGGGAACUGAA | 774 |
| 246 | UCAGUUCCCUGAAAGACUA | 775 | UAGUCUUUCAGGGAACUGA | 776 |
| 247 | CAGUUCCCUGAAAGACUAC | 777 | GUAGUCUUUCAGGGAACUG | 778 |
| 248 | AGUUCCCUGAAAGACUACU | 779 | AGUAGUCUUUCAGGGAACU | 780 |
| 249 | GUUCCCUGAAAGACUACUG | 781 | CAGUAGUCUUUCAGGGAAC | 782 |
| 250 | UUCCCUGAAAGACUACUGG | 783 | CCAGUAGUCUUUCAGGGAA | 784 |
| 251 | UCCCUGAAAGACUACUGGA | 785 | UCCAGUAGUCUUUCAGGGA | 786 |
| 252 | CCCUGAAAGACUACUGGAG | 787 | CUCCAGUAGUCUUUCAGGG | 788 |
| 253 | CCUGAAAGACUACUGGAGC | 789 | GCUCCAGUAGUCUUUCAGG | 790 |
| 254 | CUGAAAGACUACUGGAGCA | 791 | UGCUCCAGUAGUCUUUCAG | 792 |
| 255 | UGAAAGACUACUGGAGCAC | 793 | GUGCUCCAGUAGUCUUUCA | 794 |
| 256 | GAAAGACUACUGGAGCACC | 795 | GGUGCUCCAGUAGUCUUUC | 796 |
| 257 | AAAGACUACUGGAGCACCG | 797 | CGGUGCUCCAGUAGUCUUU | 798 |
| 258 | AAGACUACUGGAGCACCGU | 799 | ACGGUGCUCCAGUAGUCUU | 800 |
| 259 | AGACUACUGGAGCACCGUU | 801 | AACGGUGCUCCAGUAGUCU | 802 |
| 260 | GACUACUGGAGCACCGUUA | 803 | UAACGGUGCUCCAGUAGUC | 804 |
| 261 | ACUACUGGAGCACCGUUAA | 805 | UUAACGGUGCUCCAGUAGU | 806 |
| 262 | CUACUGGAGCACCGUUAAG | 807 | CUUAACGGUGCUCCAGUAG | 808 |
| 263 | UACUGGAGCACCGUUAAGG | 809 | CCUUAACGGUGCUCCAGUA | 810 |
| 264 | ACUGGAGCACCGUUAAGGA | 811 | UCCUUAACGGUGCUCCAGU | 812 |
| 265 | CUGGAGCACCGUUAAGGAC | 813 | GUCCUUAACGGUGCUCCAG | 814 |
| 266 | UGGAGCACCGUUAAGGACA | 815 | UGUCCUUAACGGUGCUCCA | 816 |
| 267 | GGAGCACCGUUAAGGACAA | 817 | UUGUCCUUAACGGUGCUCC | 818 |
| 268 | GAGCACCGUUAAGGACAAG | 819 | CUUGUCCUUAACGGUGCUC | 820 |
| 269 | AGCACCGUUAAGGACAAGU | 821 | ACUUGUCCUUAACGGUGCU | 822 |
| 270 | GCACCGUUAAGGACAAGUU | 823 | AACUUGUCCUUAACGGUGC | 824 |
| 271 | CACCGUUAAGGACAAGUUC | 825 | GAACUUGUCCUUAACGGUG | 826 |
| 272 | ACCGUUAAGGACAAGUUCU | 827 | AGAACUUGUCCUUAACGGU | 828 |
| 273 | CCGUUAAGGACAAGUUCUC | 829 | GAGAACUUGUCCUUAACGG | 830 |
| 274 | CGUUAAGGACAAGUUCUCU | 831 | AGAGAACUUGUCCUUAACG | 832 |
| 275 | GUUAAGGACAAGUUCUCUG | 833 | CAGAGAACUUGUCCUUAAC | 834 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 276 | UUAAGGACAAGUUCUCUGA | 835 | UCAGAGAACUUGUCCUUAA | 836 |
| 277 | UAAGGACAAGUUCUCUGAG | 837 | CUCAGAGAACUUGUCCUUA | 838 |
| 278 | AAGGACAAGUUCUCUGAGU | 839 | ACUCAGAGAACUUGUCCUU | 840 |
| 279 | AGGACAAGUUCUCUGAGUU | 841 | AACUCAGAGAACUUGUCCU | 842 |
| 280 | GGACAAGUUCUCUGAGUUC | 843 | GAACUCAGAGAACUUGUCC | 844 |
| 281 | GACAAGUUCUCUGAGUUCU | 845 | AGAACUCAGAGAACUUGUC | 846 |
| 282 | ACAAGUUCUCUGAGUUCUG | 847 | CAGAACUCAGAGAACUUGU | 848 |
| 283 | CAAGUUCUCUGAGUUCUGG | 849 | CCAGAACUCAGAGAACUUG | 850 |
| 284 | AAGUUCUCUGAGUUCUGGG | 851 | CCCAGAACUCAGAGAACUU | 852 |
| 285 | AGUUCUCUGAGUUCUGGGA | 853 | UCCCAGAACUCAGAGAACU | 854 |
| 286 | GUUCUCUGAGUUCUGGGAU | 855 | AUCCCAGAACUCAGAGAAC | 856 |
| 287 | UUCUCUGAGUUCUGGGAUU | 857 | AAUCCCAGAACUCAGAGAA | 858 |
| 288 | UCUCUGAGUUCUGGGAUUU | 859 | AAAUCCCAGAACUCAGAGA | 860 |
| 289 | CUCUGAGUUCUGGGAUUUG | 861 | CAAAUCCCAGAACUCAGAG | 862 |
| 290 | UCUGAGUUCUGGGAUUUGG | 863 | CCAAAUCCCAGAACUCAGA | 864 |
| 291 | CUGAGUUCUGGGAUUUGGA | 865 | UCCAAAUCCCAGAACUCAG | 866 |
| 292 | UGAGUUCUGGGAUUUGGAC | 867 | GUCCAAAUCCCAGAACUCA | 868 |
| 293 | GAGUUCUGGGAUUUGGACC | 869 | GGUCCAAAUCCCAGAACUC | 870 |
| 294 | AGUUCUGGGAUUUGGACCC | 871 | GGGUCCAAAUCCCAGAACU | 872 |
| 295 | GUUCUGGGAUUUGGACCCU | 873 | AGGGUCCAAAUCCCAGAAC | 874 |
| 296 | UUCUGGGAUUUGGACCCUG | 875 | CAGGGUCCAAAUCCCAGAA | 876 |
| 297 | UCUGGGAUUUGGACCCUGA | 877 | UCAGGGUCCAAAUCCCAGA | 878 |
| 298 | CUGGGAUUUGGACCCUGAG | 879 | CUCAGGGUCCAAAUCCCAG | 880 |
| 299 | UGGGAUUUGGACCCUGAGG | 881 | CCUCAGGGUCCAAAUCCCA | 882 |
| 300 | GGGAUUUGGACCCUGAGGU | 883 | ACCUCAGGGUCCAAAUCCC | 884 |
| 301 | GGAUUUGGACCCUGAGGUC | 885 | GACCUCAGGGUCCAAAUCC | 886 |
| 302 | GAUUUGGACCCUGAGGUCA | 887 | UGACCUCAGGGUCCAAAUC | 888 |
| 303 | AUUUGGACCCUGAGGUCAG | 889 | CUGACCUCAGGGUCCAAAU | 890 |
| 304 | UUUGGACCCUGAGGUCAGA | 891 | UCUGACCUCAGGGUCCAAA | 892 |
| 305 | UUGGACCCUGAGGUCAGAC | 893 | GUCUGACCUCAGGGUCCAA | 894 |
| 306 | UGGACCCUGAGGUCAGACC | 895 | GGUCUGACCUCAGGGUCCA | 896 |
| 307 | GGACCCUGAGGUCAGACCA | 897 | UGGUCUGACCUCAGGGUCC | 898 |
| 308 | GACCCUGAGGUCAGACCAA | 899 | UUGGUCUGACCUCAGGGUC | 900 |
| 309 | ACCCUGAGGUCAGACCAAC | 901 | GUUGGUCUGACCUCAGGGU | 902 |
| 310 | CCCUGAGGUCAGACCAACU | 903 | AGUUGGUCUGACCUCAGGG | 904 |
| 311 | CCUGAGGUCAGACCAACUU | 905 | AAGUUGGUCUGACCUCAGG | 906 |
| 312 | CUGAGGUCAGACCAACUUC | 907 | GAAGUUGGUCUGACCUCAG | 908 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 313 | UGAGGUCAGACCAACUUCA | 909 | UGAAGUUGGUCUGACCUCA | 910 |
| 314 | GAGGUCAGACCAACUUCAG | 911 | CUGAAGUUGGUCUGACCUC | 912 |
| 315 | AGGUCAGACCAACUUCAGC | 913 | GCUGAAGUUGGUCUGACCU | 914 |
| 316 | GGUCAGACCAACUUCAGCC | 915 | GGCUGAAGUUGGUCUGACC | 916 |
| 317 | GUCAGACCAACUUCAGCCG | 917 | CGGCUGAAGUUGGUCUGAC | 918 |
| 318 | UCAGACCAACUUCAGCCGU | 919 | ACGGCUGAAGUUGGUCUGA | 920 |
| 319 | CAGACCAACUUCAGCCGUG | 921 | CACGGCUGAAGUUGGUCUG | 922 |
| 320 | AGACCAACUUCAGCCGUGG | 923 | CCACGGCUGAAGUUGGUCU | 924 |
| 321 | GACCAACUUCAGCCGUGGC | 925 | GCCACGGCUGAAGUUGGUC | 926 |
| 322 | ACCAACUUCAGCCGUGGCU | 927 | AGCCACGGCUGAAGUUGGU | 928 |
| 323 | CCAACUUCAGCCGUGGCUG | 929 | CAGCCACGGCUGAAGUUGG | 930 |
| 324 | CAACUUCAGCCGUGGCUGC | 931 | GCAGCCACGGCUGAAGUUG | 932 |
| 325 | AACUUCAGCCGUGGCUGCC | 933 | GGCAGCCACGGCUGAAGUU | 934 |
| 326 | ACUUCAGCCGUGGCUGCCU | 935 | AGGCAGCCACGGCUGAAGU | 936 |
| 327 | CUUCAGCCGUGGCUGCCUG | 937 | CAGGCAGCCACGGCUGAAG | 938 |
| 328 | UUCAGCCGUGGCUGCCUGA | 939 | UCAGGCAGCCACGGCUGAA | 940 |
| 329 | UCAGCCGUGGCUGCCUGAG | 941 | CUCAGGCAGCCACGGCUGA | 942 |
| 330 | CAGCCGUGGCUGCCUGAGA | 943 | UCUCAGGCAGCCACGGCUG | 944 |
| 331 | AGCCGUGGCUGCCUGAGAC | 945 | GUCUCAGGCAGCCACGGCU | 946 |
| 332 | GCCGUGGCUGCCUGAGACC | 947 | GGUCUCAGGCAGCCACGGC | 948 |
| 333 | CCGUGGCUGCCUGAGACCU | 949 | AGGUCUCAGGCAGCCACGG | 950 |
| 334 | CGUGGCUGCCUGAGACCUC | 951 | GAGGUCUCAGGCAGCCACG | 952 |
| 335 | GUGGCUGCCUGAGACCUCA | 953 | UGAGGUCUCAGGCAGCCAC | 954 |
| 336 | UGGCUGCCUGAGACCUCAA | 955 | UUGAGGUCUCAGGCAGCCA | 956 |
| 337 | GGCUGCCUGAGACCUCAAU | 957 | AUUGAGGUCUCAGGCAGCC | 958 |
| 338 | GCUGCCUGAGACCUCAAUA | 959 | UAUUGAGGUCUCAGGCAGC | 960 |
| 339 | CUGCCUGAGACCUCAAUAC | 961 | GUAUUGAGGUCUCAGGCAG | 962 |
| 340 | UGCCUGAGACCUCAAUACC | 963 | GGUAUUGAGGUCUCAGGCA | 964 |
| 341 | GCCUGAGACCUCAAUACCC | 965 | GGGUAUUGAGGUCUCAGGC | 966 |
| 342 | CCUGAGACCUCAAUACCCC | 967 | GGGGUAUUGAGGUCUCAGG | 968 |
| 343 | CUGAGACCUCAAUACCCCA | 969 | UGGGGUAUUGAGGUCUCAG | 970 |
| 344 | UGAGACCUCAAUACCCCAA | 971 | UUGGGGUAUUGAGGUCUCA | 972 |
| 345 | GAGACCUCAAUACCCCAAG | 973 | CUUGGGGUAUUGAGGUCUC | 974 |
| 346 | AGACCUCAAUACCCCAAGU | 975 | ACUUGGGGUAUUGAGGUCU | 976 |
| 347 | GACCUCAAUACCCCAAGUC | 977 | GACUUGGGGUAUUGAGGUC | 978 |
| 348 | ACCUCAAUACCCCAAGUCC | 979 | GGACUUGGGGUAUUGAGGU | 980 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 349 | CCUCAAUACCCCAAGUCCA | 981 | UGGACUUGGGGUAUUGAGG | 982 |
| 350 | CUCAAUACCCCAAGUCCAC | 983 | GUGGACUUGGGGUAUUGAG | 984 |
| 351 | UCAAUACCCCAAGUCCACC | 985 | GGUGGACUUGGGGUAUUGA | 986 |
| 352 | CAAUACCCCAAGUCCACCU | 987 | AGGUGGACUUGGGGUAUUG | 988 |
| 353 | AAUACCCCAAGUCCACCUG | 989 | CAGGUGGACUUGGGGUAUU | 990 |
| 354 | AUACCCCAAGUCCACCUGC | 991 | GCAGGUGGACUUGGGGUAU | 992 |
| 355 | UACCCCAAGUCCACCUGCC | 993 | GGCAGGUGGACUUGGGGUA | 994 |
| 356 | ACCCCAAGUCCACCUGCCU | 995 | AGGCAGGUGGACUUGGGGU | 996 |
| 357 | CCCCAAGUCCACCUGCCUA | 997 | UAGGCAGGUGGACUUGGGG | 998 |
| 358 | CCCAAGUCCACCUGCCUAU | 999 | AUAGGCAGGUGGACUUGGG | 1000 |
| 359 | CCAAGUCCACCUGCCUAUC | 1001 | GAUAGGCAGGUGGACUUGG | 1002 |
| 360 | CAAGUCCACCUGCCUAUCC | 1003 | GGAUAGGCAGGUGGACUUG | 1004 |
| 361 | AAGUCCACCUGCCUAUCCA | 1005 | UGGAUAGGCAGGUGGACUU | 1006 |
| 362 | AGUCCACCUGCCUAUCCAU | 1007 | AUGGAUAGGCAGGUGGACU | 1008 |
| 363 | GUCCACCUGCCUAUCCAUC | 1009 | GAUGGAUAGGCAGGUGGAC | 1010 |
| 364 | UCCACCUGCCUAUCCAUCC | 1011 | GGAUGGAUAGGCAGGUGGA | 1012 |
| 365 | CCACCUGCCUAUCCAUCCU | 1013 | AGGAUGGAUAGGCAGGUGG | 1014 |
| 366 | CACCUGCCUAUCCAUCCUG | 1015 | CAGGAUGGAUAGGCAGGUG | 1016 |
| 367 | ACCUGCCUAUCCAUCCUGC | 1017 | GCAGGAUGGAUAGGCAGGU | 1018 |
| 368 | CCUGCCUAUCCAUCCUGCG | 1019 | CGCAGGAUGGAUAGGCAGG | 1020 |
| 369 | CUGCCUAUCCAUCCUGCGA | 1021 | UCGCAGGAUGGAUAGGCAG | 1022 |
| 370 | UGCCUAUCCAUCCUGCGAG | 1023 | CUCGCAGGAUGGAUAGGCA | 1024 |
| 371 | GCCUAUCCAUCCUGCGAGC | 1025 | GCUCGCAGGAUGGAUAGGC | 1026 |
| 372 | CCUAUCCAUCCUGCGAGCU | 1027 | AGCUCGCAGGAUGGAUAGG | 1028 |
| 373 | CUAUCCAUCCUGCGAGCUC | 1029 | GAGCUCGCAGGAUGGAUAG | 1030 |
| 374 | UAUCCAUCCUGCGAGCUCC | 1031 | GGAGCUCGCAGGAUGGAUA | 1032 |
| 375 | AUCCAUCCUGCGAGCUCCU | 1033 | AGGAGCUCGCAGGAUGGAU | 1034 |
| 376 | UCCAUCCUGCGAGCUCCUU | 1035 | AAGGAGCUCGCAGGAUGGA | 1036 |
| 377 | CCAUCCUGCGAGCUCCUUG | 1037 | CAAGGAGCUCGCAGGAUGG | 1038 |
| 378 | CAUCCUGCGAGCUCCUUGG | 1039 | CCAAGGAGCUCGCAGGAUG | 1040 |
| 379 | AUCCUGCGAGCUCCUUGGG | 1041 | CCCAAGGAGCUCGCAGGAU | 1042 |
| 380 | UCCUGCGAGCUCCUUGGGU | 1043 | ACCCAAGGAGCUCGCAGGA | 1044 |
| 381 | CCUGCGAGCUCCUUGGGUC | 1045 | GACCCAAGGAGCUCGCAGG | 1046 |
| 382 | CUGCGAGCUCCUUGGGUCC | 1047 | GGACCCAAGGAGCUCGCAG | 1048 |
| 383 | UGCGAGCUCCUUGGGUCCU | 1049 | AGGACCCAAGGAGCUCGCA | 1050 |
| 384 | GCGAGCUCCUUGGGUCCUG | 1051 | CAGGACCCAAGGAGCUCGC | 1052 |
| 385 | CGAGCUCCUUGGGUCCUGC | 1053 | GCAGGACCCAAGGAGCUCG | 1054 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 386 | GAGCUCCUUGGGUCCUGCA | 1055 | UGCAGGACCCAAGGAGCUC | 1056 |
| 387 | AGCUCCUUGGGUCCUGCAA | 1057 | UUGCAGGACCCAAGGAGCU | 1058 |
| 388 | GCUCCUUGGGUCCUGCAAU | 1059 | AUUGCAGGACCCAAGGAGC | 1060 |
| 389 | CUCCUUGGGUCCUGCAAUC | 1061 | GAUUGCAGGACCCAAGGAG | 1062 |
| 390 | UCCUUGGGUCCUGCAAUCU | 1063 | AGAUUGCAGGACCCAAGGA | 1064 |
| 391 | CCUUGGGUCCUGCAAUCUC | 1065 | GAGAUUGCAGGACCCAAGG | 1066 |
| 392 | CUUGGGUCCUGCAAUCUCC | 1067 | GGAGAUUGCAGGACCCAAG | 1068 |
| 393 | UUGGGUCCUGCAAUCUCCA | 1069 | UGGAGAUUGCAGGACCCAA | 1070 |
| 394 | UGGGUCCUGCAAUCUCCAG | 1071 | CUGGAGAUUGCAGGACCCA | 1072 |
| 395 | GGGUCCUGCAAUCUCCAGG | 1073 | CCUGGAGAUUGCAGGACCC | 1074 |
| 396 | GGUCCUGCAAUCUCCAGGG | 1072 | CCCUGGAGAUUGCAGGACC | 1076 |
| 397 | GUCCUGCAAUCUCCAGGGC | 1077 | GCCCUGGAGAUUGCAGGAC | 1078 |
| 398 | UCCUGCAAUCUCCAGGGCU | 1079 | AGCCCUGGAGAUUGCAGGA | 1080 |
| 399 | CCUGCAAUCUCCAGGGCUG | 1081 | CAGCCCUGGAGAUUGCAGG | 1082 |
| 400 | CUGCAAUCUCCAGGGCUGC | 1083 | GCAGCCCUGGAGAUUGCAG | 1084 |
| 401 | UGCAAUCUCCAGGGCUGCC | 1085 | GGCAGCCCUGGAGAUUGCA | 1086 |
| 402 | GCAAUCUCCAGGGCUGCCC | 1087 | GGGCAGCCCUGGAGAUUGC | 1088 |
| 403 | CAAUCUCCAGGGCUGCCCC | 1089 | GGGGCAGCCCUGGAGAUUG | 1090 |
| 404 | AAUCUCCAGGGCUGCCCCU | 1091 | AGGGGCAGCCCUGGAGAUU | 1092 |
| 405 | AUCUCCAGGGCUGCCCCUG | 1093 | CAGGGGCAGCCCUGGAGAU | 1094 |
| 406 | UCUCCAGGGCUGCCCCUGU | 1095 | ACAGGGGCAGCCCUGGAGA | 1096 |
| 407 | CUCCAGGGCUGCCCCUGUA | 1097 | UACAGGGGCAGCCCUGGAG | 1098 |
| 408 | UCCAGGGCUGCCCCUGUAG | 1099 | CUACAGGGGCAGCCCUGGA | 1100 |
| 409 | CCAGGGCUGCCCCUGUAGG | 1101 | CCUACAGGGGCAGCCCUGG | 1102 |
| 410 | CAGGGCUGCCCCUGUAGGU | 1103 | ACCUACAGGGGCAGCCCUG | 1104 |
| 411 | AGGGCUGCCCCUGUAGGUU | 1105 | AACCUACAGGGGCAGCCCU | 1106 |
| 412 | GGGCUGCCCCUGUAGGUUG | 1107 | CAACCUACAGGGGCAGCCC | 1108 |
| 413 | GGCUGCCCCUGUAGGUUGC | 1109 | GCAACCUACAGGGGCAGCC | 1110 |
| 414 | GCUGCCCCUGUAGGUUGCU | 1111 | AGCAACCUACAGGGGCAGC | 1112 |
| 415 | CUGCCCCUGUAGGUUGCUU | 1113 | AAGCAACCUACAGGGGCAG | 1114 |
| 416 | UGCCCCUGUAGGUUGCUUA | 1115 | UAAGCAACCUACAGGGGCA | 1116 |
| 417 | GCCCCUGUAGGUUGCUUAA | 1117 | UUAAGCAACCUACAGGGGC | 1118 |
| 418 | CCCCUGUAGGUUGCUUAAA | 1119 | UUUAAGCAACCUACAGGGG | 1120 |
| 419 | CCCUGUAGGUUGCUUAAAA | 1121 | UUUUAAGCAACCUACAGGG | 1122 |
| 420 | CCUGUAGGUUGCUUAAAAG | 1123 | CUUUUAAGCAACCUACAGG | 1124 |
| 421 | CUGUAGGUUGCUUAAAAGG | 1125 | CCUUUUAAGCAACCUACAG | 1126 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 422 | UGUAGGUUGCUUAAAAGGG | 1127 | CCCUUUUAAGCAACCUACA | 1128 |
| 423 | GUAGGUUGCUUAAAAGGGA | 1129 | UCCCUUUUAAGCAACCUAC | 1130 |
| 424 | UAGGUUGCUUAAAAGGGAC | 1131 | GUCCCUUUUAAGCAACCUA | 1132 |
| 425 | AGGUUGCUUAAAAGGGACA | 1133 | UGUCCCUUUUAAGCAACCU | 1134 |
| 426 | GGUUGCUUAAAAGGGACAG | 1135 | CUGUCCCUUUUAAGCAACC | 1136 |
| 427 | GUUGCUUAAAAGGGACAGU | 1137 | ACUGUCCCUUUUAAGCAAC | 1138 |
| 428 | UUGCUUAAAAGGGACAGUA | 1139 | UACUGUCCCUUUUAAGCAA | 1140 |
| 429 | UGCUUAAAAGGGACAGUAU | 1141 | AUACUGUCCCUUUUAAGCA | 1142 |
| 430 | GCUUAAAAGGGACAGUAUU | 1143 | AAUACUGUCCCUUUUAAGC | 1144 |
| 431 | CUUAAAAGGGACAGUAUUC | 1145 | GAAUACUGUCCCUUUUAAG | 1146 |
| 432 | UUAAAAGGGACAGUAUUCU | 1147 | AGAAUACUGUCCCUUUUAA | 1148 |
| 433 | UAAAAGGGACAGUAUUCUC | 1149 | GAGAAUACUGUCCCUUUUA | 1150 |
| 434 | AAAAGGGACAGUAUUCUCA | 1151 | UGAGAAUACUGUCCCUUUU | 1152 |
| 435 | AAAGGGACAGUAUUCUCAG | 1153 | CUGAGAAUACUGUCCCUUU | 1154 |
| 436 | AAGGGACAGUAUUCUCAGU | 1155 | ACUGAGAAUACUGUCCCUU | 1156 |
| 437 | AGGGACAGUAUUCUCAGUG | 1157 | CACUGAGAAUACUGUCCCU | 1158 |
| 438 | GGGACAGUAUUCUCAGUGC | 1159 | GCACUGAGAAUACUGUCCC | 1160 |
| 439 | GGACAGUAUUCUCAGUGCU | 1161 | AGCACUGAGAAUACUGUCC | 1162 |
| 440 | GACAGUAUUCUCAGUGCUC | 1163 | GAGCACUGAGAAUACUGUC | 1164 |
| 441 | ACAGUAUUCUCAGUGCUCU | 1165 | AGAGCACUGAGAAUACUGU | 1166 |
| 442 | CAGUAUUCUCAGUGCUCUC | 1167 | GAGAGCACUGAGAAUACUG | 1168 |
| 443 | AGUAUUCUCAGUGCUCUCC | 1169 | GGAGAGCACUGAGAAUACU | 1170 |
| 444 | GUAUUCUCAGUGCUCUCCU | 1171 | AGGAGAGCACUGAGAAUAC | 1172 |
| 445 | UAUUCUCAGUGCUCUCCUA | 1173 | UAGGAGAGCACUGAGAAUA | 1174 |
| 446 | AUUCUCAGUGCUCUCCUAC | 1175 | GUAGGAGAGCACUGAGAAU | 1176 |
| 447 | UUCUCAGUGCUCUCCUACC | 1177 | GGUAGGAGAGCACUGAGAA | 1178 |
| 448 | UCUCAGUGCUCUCCUACCC | 1179 | GGGUAGGAGAGCACUGAGA | 1180 |
| 449 | CUCAGUGCUCUCCUACCCC | 1181 | GGGGUAGGAGAGCACUGAG | 1182 |
| 450 | UCAGUGCUCUCCUACCCCA | 1183 | UGGGGUAGGAGAGCACUGA | 1184 |
| 451 | CAGUGCUCUCCUACCCCAC | 1185 | GUGGGGUAGGAGAGCACUG | 1186 |
| 452 | AGUGCUCUCCUACCCCACC | 1187 | GGUGGGGUAGGAGAGCACU | 1188 |
| 453 | GUGCUCUCCUACCCCACCU | 1189 | AGGUGGGGUAGGAGAGCAC | 1190 |
| 454 | UGCUCUCCUACCCCACCUC | 1191 | GAGGUGGGGUAGGAGAGCA | 1192 |
| 455 | GCUCUCCUACCCCACCUCA | 1193 | UGAGGUGGGGUAGGAGAGC | 1194 |
| 456 | CUCUCCUACCCCACCUCAU | 1195 | AUGAGGUGGGGUAGGAGAG | 1196 |
| 457 | UCUCCUACCCCACCUCAUG | 1197 | CAUGAGGUGGGGUAGGAGA | 1198 |
| 458 | CUCCUACCCCACCUCAUGC | 1199 | GCAUGAGGUGGGGUAGGAG | 1200 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 459 | UCCUACCCCACCUCAUGCC | 1201 | GGCAUGAGGUGGGGUAGGA | 1202 |
| 460 | CCUACCCCACCUCAUGCCU | 1203 | AGGCAUGAGGUGGGGUAGG | 1204 |
| 461 | CUACCCCACCUCAUGCCUG | 1205 | CAGGCAUGAGGUGGGGUAG | 1206 |
| 462 | UACCCCACCUCAUGCCUGG | 1207 | CCAGGCAUGAGGUGGGGUA | 1208 |
| 463 | ACCCCACCUCAUGCCUGGC | 1209 | GCCAGGCAUGAGGUGGGGU | 1210 |
| 464 | CCCCACCUCAUGCCUGGCC | 1211 | GGCCAGGCAUGAGGUGGGG | 1212 |
| 465 | CCCACCUCAUGCCUGGCCC | 1213 | GGGCCAGGCAUGAGGUGGG | 1214 |
| 466 | CCACCUCAUGCCUGGCCCC | 1215 | GGGGCCAGGCAUGAGGUGG | 1216 |
| 467 | CACCUCAUGCCUGGCCCCC | 1217 | GGGGGCCAGGCAUGAGGUG | 1218 |
| 468 | ACCUCAUGCCUGGCCCCCC | 1219 | GGGGGGCCAGGCAUGAGGU | 1220 |
| 469 | CCUCAUGCCUGGCCCCCCU | 1221 | AGGGGGGCCAGGCAUGAGG | 1222 |
| 470 | CUCAUGCCUGGCCCCCCUC | 1223 | GAGGGGGGCCAGGCAUGAG | 1224 |
| 471 | UCAUGCCUGGCCCCCCUCC | 1225 | GGAGGGGGGCCAGGCAUGA | 1226 |
| 472 | CAUGCCUGGCCCCCCUCCA | 1227 | UGGAGGGGGGCCAGGCAUG | 1228 |
| 473 | AUGCCUGGCCCCCCUCCAG | 1229 | CUGGAGGGGGGCCAGGCAU | 1230 |
| 474 | UGCCUGGCCCCCCUCCAGG | 1231 | CCUGGAGGGGGGCCAGGCA | 1232 |
| 475 | GCCUGGCCCCCCUCCAGGC | 1233 | GCCUGGAGGGGGGCCAGGC | 1234 |
| 476 | CCUGGCCCCCCUCCAGGCA | 1235 | UGCCUGGAGGGGGGCCAGG | 1236 |
| 477 | CUGGCCCCCCUCCAGGCAU | 1237 | AUGCCUGGAGGGGGGCCAG | 1238 |
| 478 | UGGCCCCCCUCCAGGCAUG | 1239 | CAUGCCUGGAGGGGGGCCA | 1240 |
| 479 | GGCCCCCCUCCAGGCAUGC | 1241 | GCAUGCCUGGAGGGGGGCC | 1242 |
| 480 | GCCCCCCUCCAGGCAUGCU | 1243 | AGCAUGCCUGGAGGGGGGC | 1244 |
| 481 | CCCCCCUCCAGGCAUGCUG | 1245 | CAGCAUGCCUGGAGGGGGG | 1246 |
| 482 | CCCCCUCCAGGCAUGCUGG | 1247 | CCAGCAUGCCUGGAGGGGG | 1248 |
| 483 | CCCCUCCAGGCAUGCUGGC | 1249 | GCCAGCAUGCCUGGAGGGG | 1250 |
| 484 | CCCUCCAGGCAUGCUGGCC | 1251 | GGCCAGCAUGCCUGGAGGG | 1252 |
| 485 | CCUCCAGGCAUGCUGGCCU | 1253 | AGGCCAGCAUGCCUGGAGG | 1254 |
| 486 | CUCCAGGCAUGCUGGCCUC | 1255 | GAGGCCAGCAUGCCUGGAG | 1256 |
| 487 | UCCAGGCAUGCUGGCCUCC | 1257 | GGAGGCCAGCAUGCCUGGA | 1258 |
| 488 | CCAGGCAUGCUGGCCUCCC | 1259 | GGGAGGCCAGCAUGCCUGG | 1260 |
| 489 | CAGGCAUGCUGGCCUCCCA | 1261 | UGGGAGGCCAGCAUGCCUG | 1262 |
| 490 | AGGCAUGCUGGCCUCCCAA | 1263 | UUGGGAGGCCAGCAUGCCU | 1264 |
| 491 | GGCAUGCUGGCCUCCCAAU | 1265 | AUUGGGAGGCCAGCAUGCC | 1266 |
| 492 | GCAUGCUGGCCUCCCAAUA | 1267 | UAUUGGGAGGCCAGCAUGC | 1268 |
| 493 | CAUGCUGGCCUCCCAAUAA | 1269 | UUAUUGGGAGGCCAGCAUG | 1270 |
| 494 | AUGCUGGCCUCCCAAUAAA | 1271 | UUUAUUGGGAGGCCAGCAU | 1272 |

TABLE 7-continued siRNA sequences that target human APOC3 expression.

| siRNA | Target or Sense Strand Sequence (5'→3') | SEQ ID NO. | Antisense strand Sequence (5'→3') | SEQ ID NO. |
|---|---|---|---|---|
| 495 | UGCUGGCCUCCCAAUAAAG | 1273 | CUUUAUUGGGAGGCCAGCA | 1274 |
| 496 | GCUGGCCUCCCAAUAAAGC | 1275 | GCUUUAUUGGGAGGCCAGC | 1276 |
| 497 | CUGGCCUCCCAAUAAAGCU | 1277 | AGCUUUAUUGGGAGGCCAG | 1278 |
| 498 | UGGCCUCCCAAUAAAGCUG | 1279 | CAGCUUUAUUGGGAGGCCA | 1280 |
| 499 | GGCCUCCCAAUAAAGCUGG | 1281 | CCAGCUUUAUUGGGAGGCC | 1282 |
| 500 | GCCUCCCAAUAAAGCUGGA | 1283 | UCCAGCUUUAUUGGGAGGC | 1284 |
| 501 | CCUCCCAAUAAAGCUGGAC | 1285 | GUCCAGCUUUAUUGGGAGG | 1286 |
| 502 | CUCCCAAUAAAGCUGGACA | 1287 | UGUCCAGCUUUAUUGGGAG | 1288 |
| 503 | UCCCAAUAAAGCUGGACAA | 1289 | UUGUCCAGCUUUAUUGGGA | 1290 |
| 504 | CCCAAUAAAGCUGGACAAG | 1291 | CUUGUCCAGCUUUAUUGGG | 1292 |
| 505 | CCAAUAAAGCUGGACAAGA | 1293 | UCUUGUCCAGCUUUAUUGG | 1294 |
| 506 | CAAUAAAGCUGGACAAGAA | 1295 | UUCUUGUCCAGCUUUAUUG | 1296 |
| 507 | AAUAAAGCUGGACAAGAAG | 1297 | CUUCUUGUCCAGCUUUAUU | 1298 |
| 508 | AUAAAGCUGGACAAGAAGC | 1299 | GCUUCUUGUCCAGCUUUAU | 1300 |
| 509 | UAAAGCUGGACAAGAAGCU | 1301 | AGCUUCUUGUCCAGCUUUA | 1302 |
| 510 | AAAGCUGGACAAGAAGCUG | 1303 | CAGCUUCUUGUCCAGCUUU | 1304 |
| 511 | AAGCUGGACAAGAAGCUGC | 1305 | GCAGCUUCUUGUCCAGCUU | 1306 |
| 512 | AGCUGGACAAGAAGCUGCU | 1307 | AGCAGCUUCUUGUCCAGCU | 1308 |
| 513 | GCUGGACAAGAAGCUGCUA | 1309 | UAGCAGCUUCUUGUCCAGC | 1310 |
| 514 | CUGGACAAGAAGCUGCUAU | 1311 | AUAGCAGCUUCUUGUCCAG | 1312 |
| 515 | UGGACAAGAAGCUGCUAUG | 1313 | CAUAGCAGCUUCUUGUCCA | 1314 |

The number under "siRNA" in Table 7 refers to the nucleotide position of the 5' base of the target or sense strand sequence relative to the first nucleotide of the human APOC3 mRNA sequence (Genbank Accession No. NM_000040.1). In certain embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In particular embodiments, the sense and/or antisense strand comprises 2'OMe nucleotides in accordance with one or more of the selective modification patterns described herein. In some instances, the sense and/or antisense strand contains "dTdT" or "UU" 3' overhangs. In other instances, the sense and/or antisense strand contains 3' overhangs that have complementarity to the target sequence (3' overhang in the antisense strand) or the complementary strand thereof (3' overhang in the sense strand). In further embodiments, the 3' overhang on the sense strand, antisense strand, or both strands may comprise one, two, three, four, or more modified nucleotides such as those described herein (e.g., 2'OMe nucleotides).

Example 2

Stable Nucleic Acid-Lipid Particle-Mediated Silencing of Apolipoprotein CIII Reduces Plasma Triglycerides in Mice This example illustrates that administration of stable nucleic acid-lipid particles (SNALP) containing fully encapsulated siRNA targeting the Apoc3 gene to mice resulted in reductions in hepatic Apoc3 mRNA levels, plasma triglycerides, and plasma cholesterol levels, without an increase in hepatic triglycerides. No measurable immune response was induced with these formulations, minimizing the potential for nonspecific effects in models of chronic inflammatory disease, such as atherosclerosis.

Introduction

Apolipoprotein CIII (apoCIII) is implicated in atherogenesis through its association with hypertriglyceridemia and induction of endothelial dysfunction. This example shows that nucleic acid-lipid particles (e.g., SNALP) facilitate RNAi-mediated silencing of apoCIII and other targets thought to be "non-druggable" with conventional medicines. Studies of siRNA-based silencing of Apoc3 in mice supports further preclinical studies of apoCIII-targeting SNALP in mouse models of atherosclerosis.

Materials and Methods siRNA design. siRNA sequences targeting mouse Apoc3 (GenBank Accession No. NM_023114.3) were selected using an algorithm implemented by the Whitehead Institute for Biomedical Research (http://jura.wi.mit.edu/bioc/siRNAext/home.php) that incorporates standard siRNA design guidelines (1-3). For 17 of the siRNA sequences, the following criteria were selected: (1) NNN21 target sequences; (2) thermodynamically unstable 5' antisense end ($\Delta G > -8.3$ kcal/mol); and (3) thermodynamically less stable 5' antisense end ($\Delta G_{sense} - \Delta G_{anti\text{-}sense} < -2.1$).

All selected sequences were assessed for potential sequence-specific targeting activity against other mouse genes using the BLASTN algorithm against the mouse mRNA Reference Sequence database at the National Center for Biotechnology Information (NCBI; http://www.ncbi.nlm.nih.gov/). siRNAs were eliminated if they contained sequence complementary to a transcript other than Apoc3 at positions 4 to 18 of the antisense strand.

Five single nucleotide polymorphisms (SNPs), rs32674708, rs32674710, rs32674712, rs8254931 and rs29889677, located in the coding or UTR sequences of the mouse Apoc3 gene, were identified in the NCBI SNP database and used to evaluate the panel of siRNAs. Several siRNAs were identified that contained a nucleotide complementary to one of the SNPs, including mApoc3_146 (rs8254931), mApoc3_232 and mApoc3_245 (rs32674712), mApoc3_344 (rs32674710), mApoc3_465, mApoc3_466, mApoc3_467, and mApoc3_484 (rs32674708); however, these siRNAs were kept in the panel because they were designed based on genomic sequence from the C57B1/6 mouse strain, the same strain used for primary hepatocytes and in vivo studies.

In order to evaluate expected cross-reactivity of siRNAs, sequences from mouse Apoc3 mRNA and human (GenBank Accession No. NM_000040.1) and cynomolgus monkey (*Macaca fascicularis;* GenBank Accession No. X68359.1) APOC3 mRNA were aligned using ClustalX (4), with manual editing when necessary. This sequence alignment was also used to identify 3 siRNAs, mApoc3_92, mApoc3_258, and mApoc3_501, that did not meet the original siRNA criteria, but instead were chosen based on an antisense (AS) sequence that contains only one mismatch to the APOC3 transcript (i.e., 95% complementary) in humans and cynomolgus monkeys. Selected sequences were verified and the positions within the mouse Apoc3 target sequence were identified.

siRNA synthesis. All siRNA molecules used in this study were chemically synthesized by Integrated DNA Technologies (Coralville, Iowa). The siRNAs were desalted and annealed using standard procedures. Sequences of unmodified mouse Apoc3 siRNAs are listed in Table 8. Sequences of modified mouse Apoc3 siRNAs are listed in Table 9. Sequence numbers represent the nucleotide position of mouse Apoc3 mRNA (Genbank Accession No. NM_023114.3) that is complementary to the 3' end of the antisense strand of the siRNA.

TABLE 8

Unmodified siRNA sequences that target mouse Apoc3 expression.

| siRNA | Target Sequence (5'→3') | SEQ ID NO. | Sense Strand (5'→3') | SEQ ID NO. | Antisense Strand (5'→3') | SEQ ID NO. |
|---|---|---|---|---|---|---|
| mApoc3_92 | CCUGGCAUCU GCCCGAGCU | 1315 | CCUGGCAUCUG CCCGAGCUGA | 1316 | AGCUCGGGCAG AUGCCAGGAG | 1317 |
| mApoc3_146 | ACAGGGCUAC AUGGAACAA | 1318 | ACAGGGCUACA UGGAACAAGC | 1319 | UUGUUCCAUGU AGCCCUGUAC | 1320 |
| mApoc3_232 | GCUGGAUGGA CAAUCACUU | 1321 | GCUGGAUGGAC AAUCACUUCA | 1322 | AAGUGAUUGUC CAUCCAGCCC | 1323 |
| mApoc3_245 | UCACUUCAGA UCCCUGAAA | 1324 | UCACUUCAGAU CCCUGAAAGG | 1325 | UUUCAGGGAUC UGAAGUGAUU | 1326 |
| mApoc3_258 | CUGAAAGGCU ACUGGAGCA | 1327 | CUGAAAGGCUA CUGGAGCAAG | 1328 | UGCUCCAGUAG CCUUUCAGGG | 1329 |
| mApoc3_262 | AAGGCUACUG GAGCAAGUU | 1330 | AAGGCUACUGG AGCAAGUUUA | 1331 | AACUUGCUCCA GUAGCCUUUC | 1332 |
| mApoc3_263 | AGGCUACUGG AGCAAGUUU | 1333 | AGGCUACUGGA GCAAGUUUAC | 1334 | AAACUUGCUCC AGUAGCCUUU | 1335 |
| mApoc3_264 | GGCUACUGGA GCAAGUUUA | 1336 | GGCUACUGGAG CAAGUUUACU | 1337 | UAAACUUGCUC CAGUAGCCUU | 1338 |
| mApoc3_265 | GCUACUGGAG CAAGUUUAC | 1339 | GCUACUGGAGC AAGUUUACUG | 1340 | GUAAACUUGCU CCAGUAGCCU | 1341 |
| mApoc3_274 | GCAAGUUUAC UGACAAGUU | 1342 | GCAAGUUUACU GACAAGUUCA | 1343 | AACUUGUCAGU AAACUUGCUC | 1344 |
| mApoc3_323 | CCAACCAACU CCAGCUAUU | 1345 | CCAACCAACUC CAGCUAUUGA | 1346 | AAUAGCUGGAG UUGGUUGGUC | 1347 |
| mApoc3_324 | CAACCAACUC CAGCUAUUG | 1348 | CAACCAACUCC AGCUAUUGAG | 1349 | CAAUAGCUGGA GUUGGUUGGU | 1350 |
| mApoc3_344 | GUCGUGAGAC UUCUGUGUU | 1351 | GUCGUGAGACU UCUGUGUUGC | 1352 | AACACAGAAGU CUCACGACUC | 1353 |

TABLE 8-continued

Unmodified siRNA sequences that target mouse Apoc3 expression.

| siRNA | Target Sequence (5'→3') | SEQ ID NO. | Sense Strand (5'→3') | SEQ ID NO. | Antisense Strand (5'→3') | SEQ ID NO. |
|---|---|---|---|---|---|---|
| mApoc3_465 | UCCCUAGAUCUCACCUAAA | 1354 | UCCCUAGAUCUCACCUAAACA | 1355 | UUUAGGUGAGAUCUAGGGAGG | 1356 |
| mApoc3_466 | CCCUAGAUCUCACCUAAAC | 1357 | CCCUAGAUCUCACCUAAACAU | 1358 | GUUUAGGUGAGAUCUAGGGAG | 1359 |
| mApoc3_467 | CCUAGAUCUCACCUAAACA | 1360 | CCUAGAUCUCACCUAAACAUG | 1361 | UGUUUAGGUGAGAUCUAGGGA | 1362 |
| mApoc3_484 | CAUGCUGUCCCUAAUAAAG | 1363 | CAUGCUGUCCCUAAUAAAGCU | 1364 | CUUUAUUAGGGACAGCAUGUU | 1365 |
| mApoc3_492 | CCCUAAUAAAGCUGGAUAA | 1366 | CCCUAAUAAAGCUGGAUAAGA | 1367 | UUAUCCAGCUUUAUUAGGGAC | 1368 |
| mApoc3_493 | CCUAAUAAAGCUGGAUAAG | 1369 | CCUAAUAAAGCUGGAUAAGAA | 1370 | CUUAUCCAGCUUUAUUAGGGA | 1371 |
| mApoc3_501 | AGCUGGAUAAGAAGCUGCU | 1372 | AGCUGGAUAAGAAGCUGCUGU | 1373 | AGCAGCUUCUUAUCCAGCUUU | 1374 |

In Table 8 above, the last 2 nucleotides at the 3' ends of the sense and antisense strands correspond to the 3' overhang sequence. In other words, nucleotides 1-19 of each sense and antisense strand sequence depicted in Table 8 correspond to that portion of the sense or antisense strand that is present in the double-stranded region of the siRNA duplex. In alternative embodiments, the 3' overhang on one or both strands of the siRNA molecule may comprise 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence (3' overhang in the antisense strand) or the complementary strand thereof (3' overhang in the sense strand). In certain instances, the sense and/or antisense strand of the siRNA molecule lacks 3' overhangs (i.e., does not contain the last 2 nucleotides at the 3' ends of the sense and/or antisense strand). In some embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In particular embodiments, the sense and/or antisense strand comprises 2'OMe nucleotides in accordance with one or more of the selective modification patterns described herein.

TABLE 9

Mouse Apoc3 siRNA sequences with 2'OMe modification patterns.

| siRNA | Abbreviated name of siRNA | Sense Strand (5'→3') | SEQ ID NO. | Antisense Strand (5'→3') | SEQ ID NO. |
|---|---|---|---|---|---|
| mApoc3_465U2.1G1.1 | 465.1 | **U**CCCUA**G**AUCUCACC**U**AAACA | 1375 | UUUAGG**U**GAGAUCUA**G**GGAGG | 1376 |
| mApoc3_465U2.2G1.1C1 | 465.2 | **UC**CCUA**G**AUCUCACC**U**AAACA | 1377 | U**U**UAGG**U**GAGAUCUA**G**GGAGG | 1378 |
| mApoc3_467U3.1G0.1 | 467.1 | CCUAGA**U**CUCACC**U**AAACA**U**G | 1379 | UGUUUAG**G**UGAGAUC**U**AGGGA | 1380 |
| mApoc3_467U3.1G0.2C1 | 467.2 | C**C**UAGA**U**CUCACC**U**AAACA**U**G | 1381 | UG**U**UUAG**G**UGAGAUC**U**AGGGA | 1382 |
| mApoc3_492U3.1G0.1 | 492.1 | CCCUAA**U**AAAGC**U**GGA**U**AAGA | 1383 | UUAUCCAGCUU**U**AUUAGG**G**AC | 1384 |
| mApoc3_492U3.2G0.1C1 | 492.2 | C**C**CUAA**U**AAAGC**U**GGA**U**AAGA | 1385 | U**U**AUCCAGCUU**U**AUUAGG**G**AC | 1386 |

2'OMe nucleotides are indicated in bold and underlined.

In Table 9 above, the last 2 nucleotides at the 3' ends of the sense and antisense strands correspond to the 3' overhang sequence. In other words, nucleotides 1-19 of each sense and antisense strand sequence depicted in Table 9 correspond to that portion of the sense or antisense strand that is present in the double-stranded region of the siRNA duplex. In alternative embodiments, the 3' overhang on one or both strands of the siRNA molecule may comprise 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence (3' overhang in the antisense strand) or the complementary strand thereof (3' overhang in the sense strand). In certain instances, the sense and/or antisense strand of the siRNA molecule lacks 3' overhangs (i.e., does not contain the last 2 nucleotides at the 3' ends of the sense and/or antisense strand). In alternative embodiments, the 465.1, 467.1, or 492.1 sense strand sequence may be paired with the 465.2, 467.2, or 492.2 antisense strand sequence, respectively. In other alternative embodiments, the 465.2, 467.2, or 492.2 sense strand sequence may be paired with the 465.1, 467.1, or 492.1 antisense strand sequence, respectively.

Lipid Encapsulation of siRNA. siRNA molecules were encapsulated into nucleic acid-lipid particles composed of the following lipids: a lipid conjugate such as PEG-C-DMA (3-N-[(-Methoxy poly(ethylene glycol)2000)carbamoyl]-1,2-dimyrestyloxy-propylamine); a cationic lipid such as DLinDMA (1,2-Dilinoleyloxy-3-(N,N-dimethyl)aminopropane); a phospholipid such as DPPC (1,2-dipalmitoyl-sn-glycero-3-phosphocholine; Avanti Polar Lipids; Alabaster, Ala.); and synthetic cholesterol (Sigma-Aldrich Corp.; St. Louis, Mo.) in the molar ratio 1.4:57.1:7.1:34.3, respectively. In other words, siRNAs were encapsulated into stable nucleic acid-lipid particles ("SNALP") of the following "1:57" formulation: 1.4 mol % lipid conjugate (e.g., PEG-C-DMA); 57.1 mol % cationic lipid (e.g., DLinDMA); 7.1 mol % phospholipid (e.g., DPPC); and 34.3 mol % cholesterol. For vehicle controls, empty particles with identical lipid composition are formed in the absence of siRNA. It should be understood that the 1:57 formulation is a target formulation, and that the amount of lipid (both cationic and non-cationic) present and the amount of lipid conjugate present in the formulation may vary. Typically, in the 1:57 formulation, the amount of cationic lipid will be 57 mol % ±5 mol %, and the amount of lipid conjugate will be 1.5 mol % ±0.5 mol %, with the balance of the 1:57 formulation being made up of non-cationic lipid (e.g., phospholipid, cholesterol, or a mixture of the two).

Hepatocyte isolation and culture. Primary hepatocytes were isolated from C57B1/6J mice by standard procedures. Briefly, mice were anesthetized by intraperitoneal injection of Ketamine-Xylazine and the livers were perfused with Hanks' Buffered Salt Solution (Invitrogen) solution containing 0.5 M EDTA and 1 mg/ml insulin followed by Hanks' collagenase solution (100 U/ml). The hepatocytes were dispersed in Williams' Media E (Invitrogen) and washed two times in Hepatocyte Wash Medium (Invitrogen), then suspended in Williams' Media E containing 10% fetal bovine serum and plated on 96-well plates ($2.5\times10^4$ cells/well). For the in vitro mouse siRNA silencing activity assay, hepatocytes were transfected with 2 nM or 20 nM of SNALP-formulated Apoc3 siRNAs in 96-well plates. Apoc3 mRNA levels were evaluated 24 h after transfection by bDNA assay (Panomics).

Animals and diet. Six- to seven-week-old C57B1/6J wild-type mice and homozygous B6.129S7-Ldlr$^{tm1Her/J}$ mice were obtained from the Jackson Laboratory and subjected to at least a 1-week acclimation period prior to use. Mice received a standard laboratory rodent chow diet or Western diet (TD.88137; Harlan Teklad; Madison, Wis.). Mice were administered SNALP-formulated siRNAs in PBS via standard i.v. injection under normal pressure and low volume (0.01 mL/g) in the lateral tail vein for all experiments. For fenofibrate treatment, animals received fenofibrate (100 mg/kg body weight) daily by oral gavage for 2 days. All animal studies were performed at Tekmira Pharmaceuticals in accordance with Canadian Council on Animal Care guidelines and following protocols approval by the Institutional Animal Care and Use Committee of Tekmira Pharmaceuticals.

In vivo immune stimulation assays. SNALP-formulated siRNA were administered at 5 mg/kg to female C57B1/6J mice at 8 weeks of age. Liver was collected into RNAlater (Sigma-Aldrich) for Ifit1 mRNA analysis.

Lipid analysis. Mice were fasted for 4-6 hours prior to terminal anaesthesia, exsanguination, and collection of liver tissue. For hepatic triglyceride analysis, liver tissue was homogenized in PBS and total lipids extracted using Foldch solution (chloroform/methanol 2:1), dried under $N_2$, and resuspended in 2% Triton X-100. Plasma and liver lipid extracts were assayed for cholesterol and triglyceride concentrations by enzymatic assays with the use of commercially available reagents.

Mouse target mRNA quantitation. The QuantiGene® Reagent System (Panomics, Inc.; Fremont, Calif.) bDNA assay was used to quantify the reduction of mouse Apoc3 mRNA levels relative to the mRNA levels of the housekeeping gene Gapdh. Primary hepatocytes were lysed 24 hours post SNALP treatment by adding 100 μL of 1× Lysis Mixture (Panomics) and 50 μg/mL proteinase K into each well followed by 30 minute incubation at 50° C. Murine liver was processed to quantitate Apoc3 mRNA 48 hours after administration of SNALP. The QuantiGene® assay was performed according to the manufacturer's instructions. Relative Apoc3 mRNA levels are expressed relative to cells treated with a Luciferase control siRNA or to animals that received a saline control injection.

Measurement of Ifit1 mRNA in mouse tissues. Murine liver was processed for bDNA assay to quantitate Ifit1 mRNA. The Ifit1 probe set was specific to mouse Ifit1 mRNA (positions 4-499 of NM_008331) and the Gapdh probe set was specific to mouse Gapdh mRNA (positions 9-319 of NM_008084). Data is shown as the ratio of Ifit1 relative light units (RLU) to Gapdh RLU.

Statistics. Data are presented as means plus or minus standard deviation. Analyses were performed using the unpaired two-tailed Student's t-test. Differences were deemed significant at $P<0.05$.

Results

Apoc3 siRNAs display dose-dependent activity in vitro. A panel of 20 siRNAs targeting mouse Apoc3 was designed and screened for silencing activity in mouse primary hepatocytes. Treatment of hepatocytes with many of these siRNAs caused a dose-dependent reduction in levels of mouse Apoc3 mRNA (FIG. 1). This screen identified mApoc3_465, mApoc3_467, and mApoc3_492 as the most potent mouse siRNAs. Additional potent siRNAs include mApoc3_258, mApoc3_264, mApoc3_274, mApoc3_323, mApoc3_324, mApoc3_344, mApoc3_466, and mApoc3_493. Of these more potent siRNAs, mApoc3_258 is the most likely to be cross-reactive in primates based on an antisense (AS) sequence that contains only one mismatch to the APOC3 transcript (i.e., 95% complementary) in humans and cynomolgus monkeys.

Figure 2:
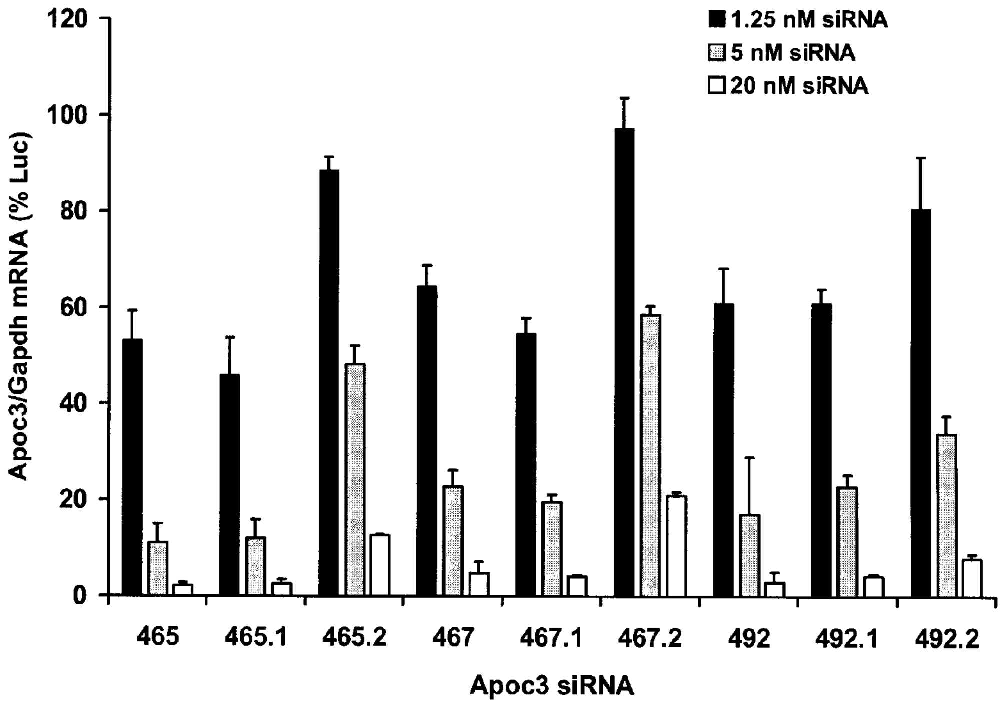
FIG. 2 illustrates data demonstrating the in vitro activity of unmodified versus 2'OMe-modified Apoc3 siRNA. Unmodified siRNA duplexes 465, 467, and 492 and 2'OMe-modified duplexes 465.1, 465.2, 467.1, 467.2, 492.1, and 492.2 were transfected into mouse primary hepatocytes and silencing activity was assessed by QuantiGene Assay 24 h post-treatment. Cells were treated with SNALP-formulated Apoc3 siRNA at 1.25 nM (black bars), 5 nM (gray bar), and 20 nM (white bars).

2'OMe-modified Apoc3 siRNAs display only modest differences in activity compared with unmodified siRNA. Prior to the assessment of synthetic siRNA in animal models, it is important to consider the potential effects of immune stimulation and take steps to reduce this risk (Judge et al., *Hum. Gene Ther.,* 19:111-24 (2008)). It has been shown that the selective incorporation of 2'-O-methyl (2'OMe) nucleotides into the constituent RNA oligonucleotides eliminates the capacity of the siRNA to activate a measurable immune response (Judge et al., *Mol. Ther.,* 13:494-505 (2006); Robbins et al., *Hum. Gene Ther.,* 19:991-9 (2008)). Therefore, 2'OMe-modified nucleotides were substituted into the native sense and AS oligonucleotides to form a panel of modified mApoc3_465, mApoc3_467, and mApoc3_492 duplexes. FIG. 2 shows that 2'OMe-modified Apoc3 siRNAs display only modest differences in silencing activity compared with the corresponding unmodified siRNA sequence.

Figure 3:
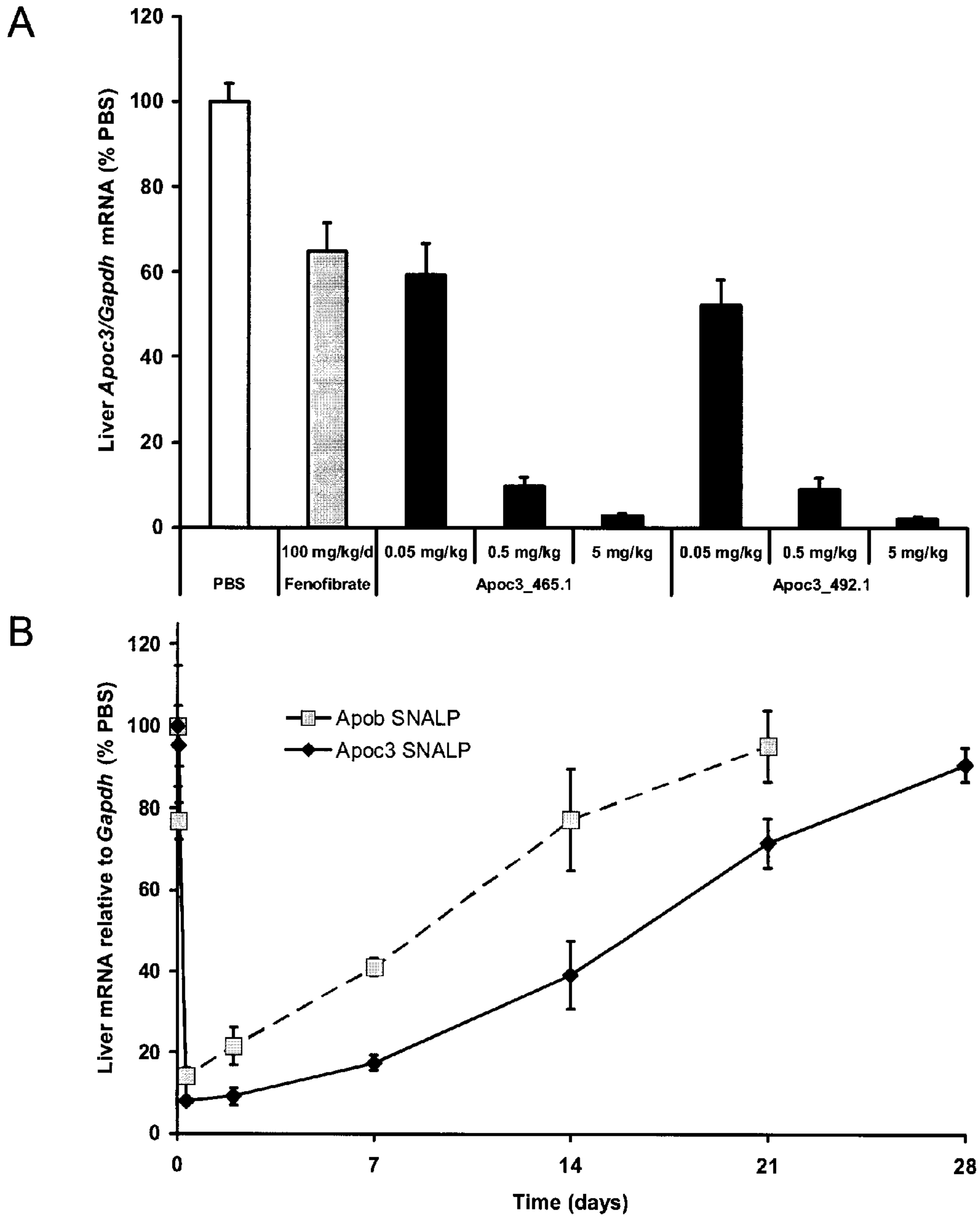
FIG. 3 illustrates data demonstrating that SNALP-mediated apoCIII silencing is potent and long-lasting. Target mRNA silencing in liver following a single dose of SNALP-formulated siRNA is shown. (A) 48 hours after siRNA administration or after initiation of 100 mg/kg/d fenofibrate delivered by oral gavage. (B) Comparison of silencing activity at various time points after administration of 0.5 mg/kg SNALP-formulated siRNA targeting apoCIII and apoB.

In vivo gene silencing efficacy. FIG. 3 shows that SNALP-mediated apoCIII silencing is potent and long-lasting. In particular, liver Apoc3 mRNA levels were reduced by more than about 90% at doses of 0.5 and 5 mg/kg, and a reduction in liver Apoc3 mRNA levels was observed for more than 21 days after a single 0.5 mg/kg treatment.

Figure 4:
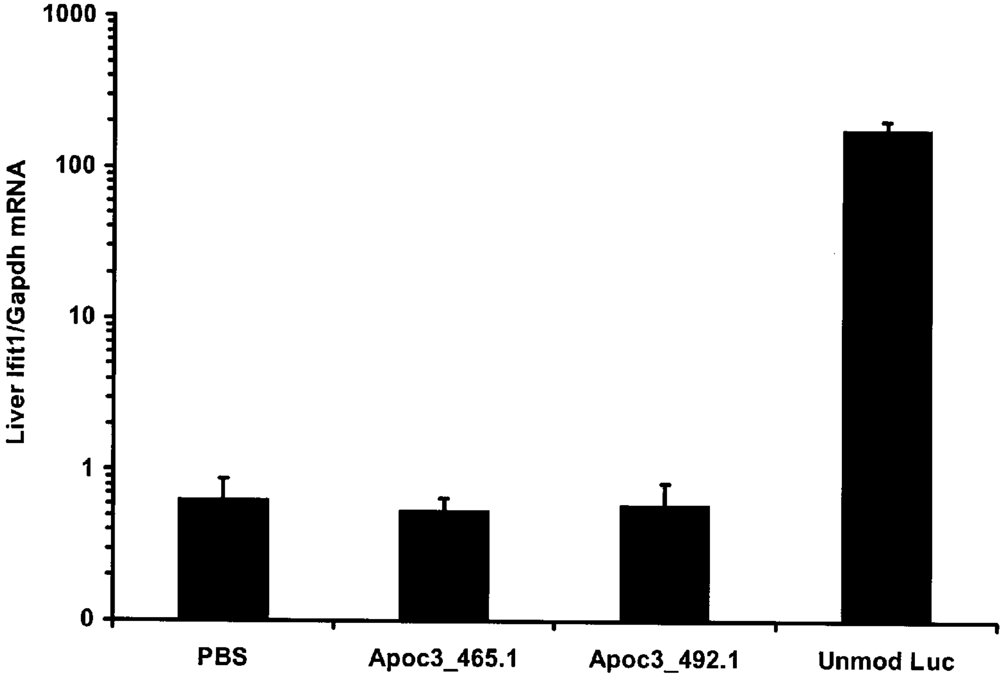
FIG. 4 illustrates data demonstrating that 2'OMe-modified Apoc3 siRNAs induce no measurable interferon response in mice. Hepatic levels of Ifit1 mRNA, a sensitive measure of low-grade immunostimulatory activity, 4 hours after IV administration of SNALP-formulated 2'OMe-modified Apoc3 siRNA and unmodified luciferase control siRNA (Unmod Luc) to C57BL/6 mice, are shown.
Figure 5:
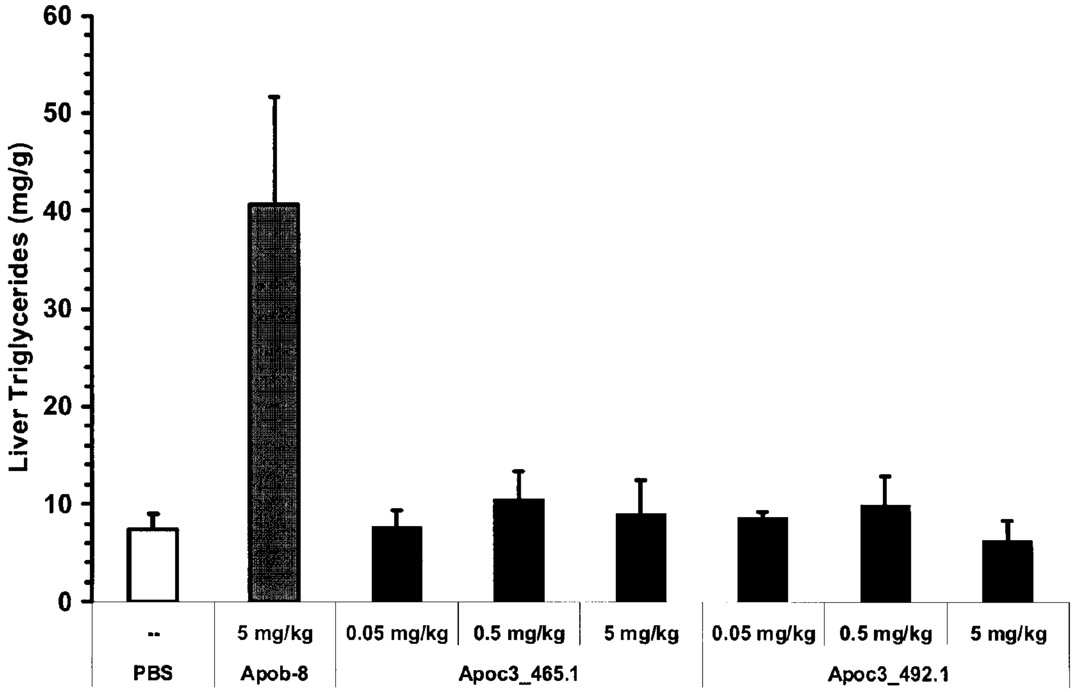
FIG. 5 illustrates data demonstrating that SNALP-mediated apoCIII silencing does not increase liver TG. Hepatic triglyceride levels, 48 hours after IV administration of SNALP-formulated Apoc3 siRNA and Apob siRNA to C57BL/6 mice, are shown.

Immune response and hepatic TG in vivo. FIG. 4 shows that 2'OMe-modified Apoc3 siRNAs induce no measurable interferon response in mice. FIG. 5 shows that SNALP-mediated apoCIII silencing does not increase liver triglyceride (TG) levels.

Figure 6:
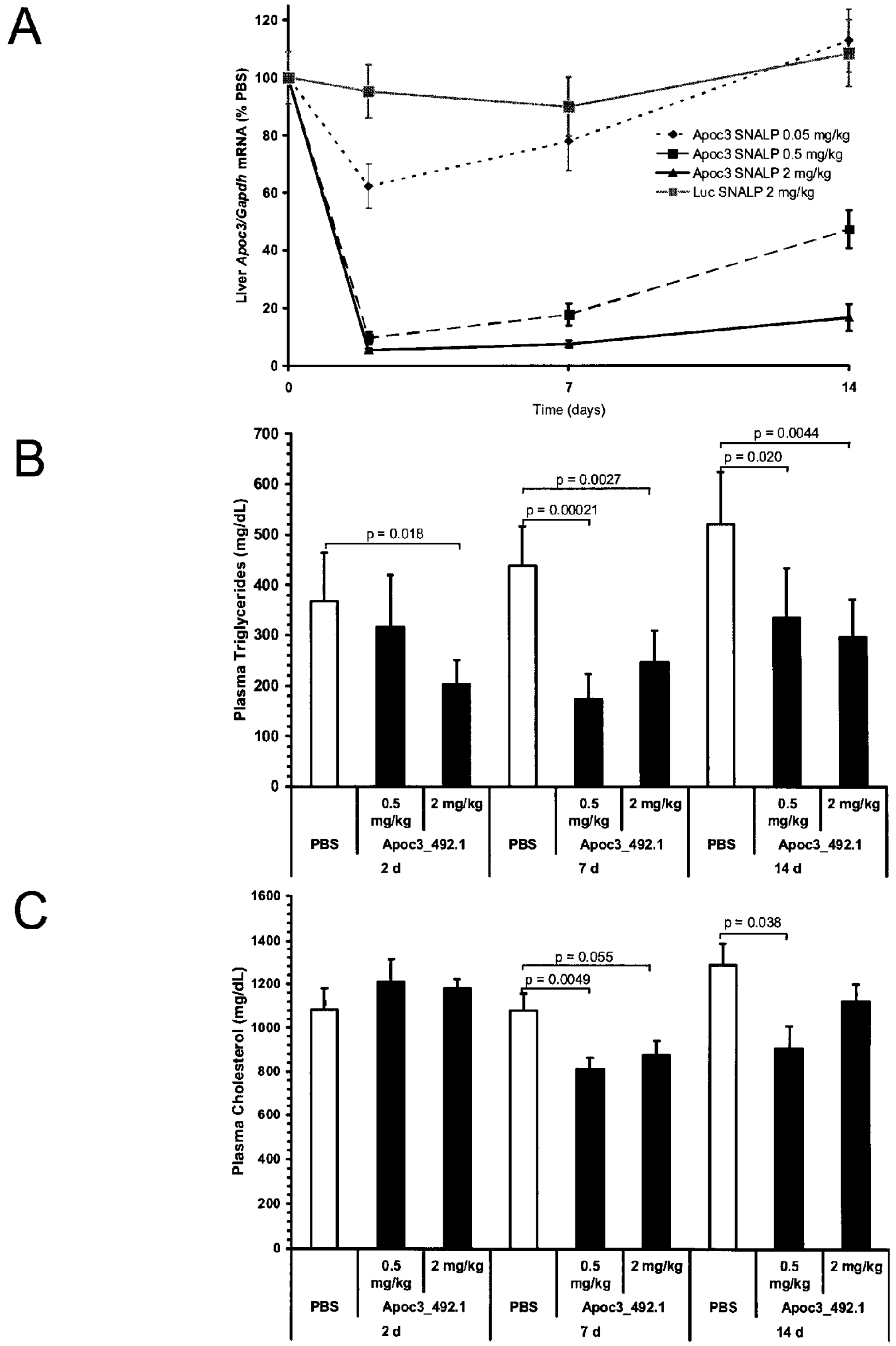
FIG. 6 illustrates data demonstrating that siRNA-based silencing of apoCIII improves plasma lipids in LDLR-deficient mice. Hepatic Apoc3 mRNA levels (A), plasma triglycerides (B), and plasma cholesterol (C) following a single IV administration of SNALP-formulated Apoc3 siRNA to LDLR-deficient mice fed a Western diet for 12 days prior to injection are shown.

Plasma lipids in a dyslipidemic model. The LDLR-deficient hyperlipidemic mouse mimics human familial hypercholesterolemia and has been used in numerous studies as a model for the disrupted lipoprotein regulation and metabolic function that leads to diabetes and atherosclerosis (Getz et al., *Arterioscler. Thromb. Vasc. Biol.,* 26:242-9 (2006)). LDLR-deficient mice develop features of the metabolic syndrome and atherosclerosis when fed a Western diet. FIG. 6 shows that siRNA-based silencing of apoCIII improves plasma lipids in LDLR-deficient mice fed a Western diet. In particular, plasma triglyceride (TG) levels were reduced by about 35-60% for 2-14 days and plasma total cholesterol (TC) levels were reduced by about 20-25% for 7-14 days following SNALP administration. As such, this study demonstrates the therapeutic reduction of hyperlipidemia by systemic administration of a SNALP formulation containing fully encapsulated siRNA targeting the Apoc3 gene.

Summary

Figure 7:
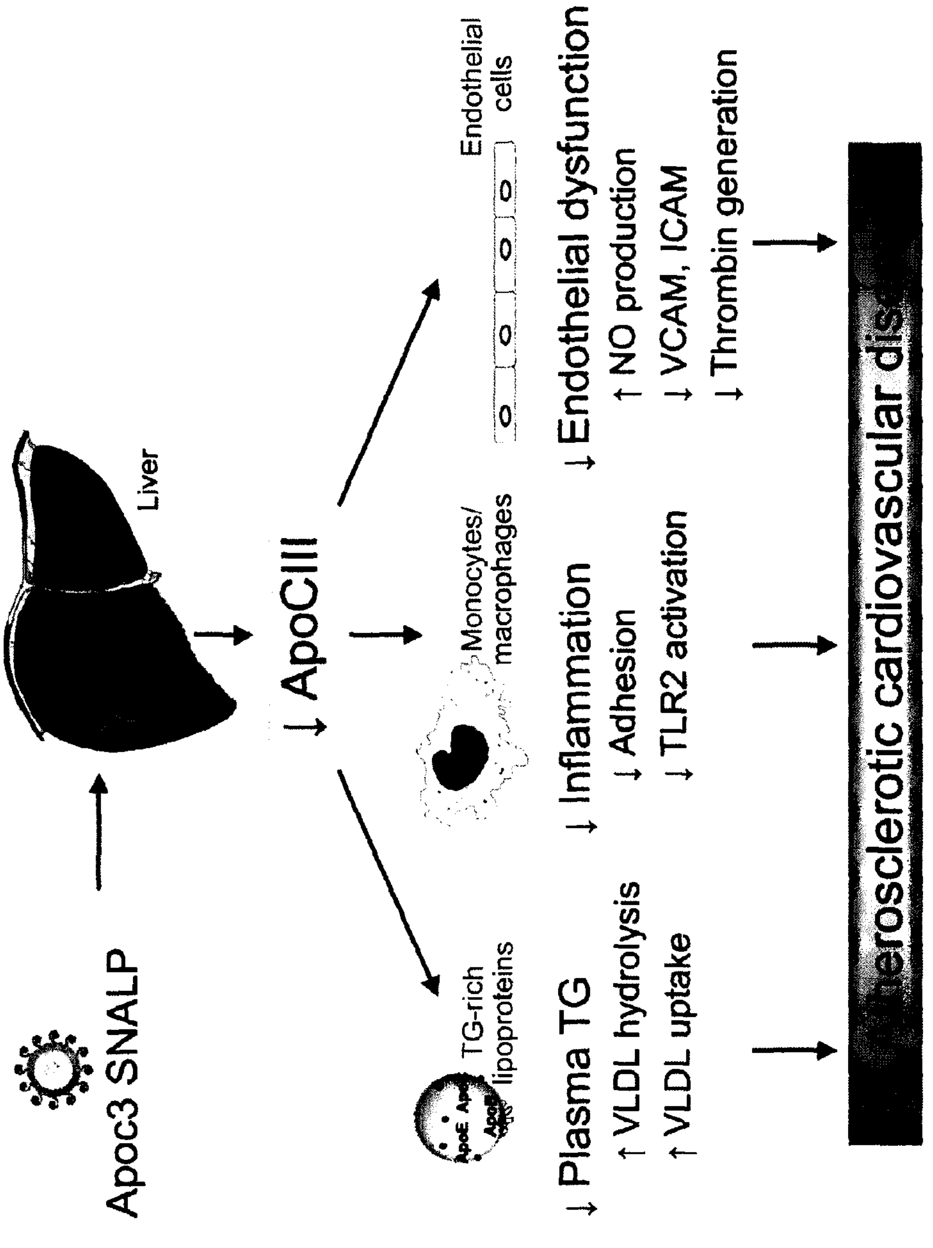
FIG. 7 is a schematic depicting the amelioration of dyslipidemia and the reduction in susceptibility to atherosclerotic cardiovascular disease associated with SNALP-mediated silencing of apoCIII.

This example demonstrates that SNALP-mediated silencing of apoCIII is potent and long-lasting. In particular, liver Apoc3 mRNA levels were reduced by more than about 90% at doses of 0.5 and 5 mg/kg. In fact, a reduction in liver Apoc3 mRNA levels was observed for more than 21 days after a single 0.5 mg/kg treatment. RACE PCR analysis also showed that Apoc3-targeting SNALP acted via a confirmed RNAi mechanism. Furthermore, this example illustrates that dyslipidemia in LDLR-deficient mice was ameliorated by siRNA-based silencing of apoCIII. In particular, plasma triglyceride (TG) levels were reduced by about 35-60% for 2-14 days and plasma total cholesterol (TC) levels were reduced by about 20-25% for 7-14 days. As such, amelioration of dyslipidemia associated with SNALP-mediated silencing of apoCIII advantageously reduces susceptibility to atherosclerosis in LDLR-deficient mice (see, FIG. 7).

References

1. Khvorova A, Reynolds A, Jayasena S D. Functional siRNAs and miRNAs exhibit strand bias. Cell. 2003 Oct. 17; 115(2):209-16.
2. Elbashir S M, Lendeckel W, Tuschl T. RNA interference is mediated by 21- and 22-nucleotide RNAs. Genes Dev. 2001 Jan. 15; 15(2):188-200.
3. Schwarz D S, Hutvagner G, Du T, Xu Z, Aronin N, Zamore P D. Asymmetry in the assembly of the RNAi enzyme complex. Cell. 2003 Oct. 17; 115(2):199-208.
4. Thompson J D, Gibson T J, Plewniak F, Jeanmougin F, Higgins D G. The CLUSTAL_X windows interface: flexible strategies for multiple sequence alignment aided by quality analysis tools. Nucleic Acids Res. 1997; 25(24): 4876-82.

Example 3

Silencing of Human APOC3 Expression Using RNA Interference

Figure 8:
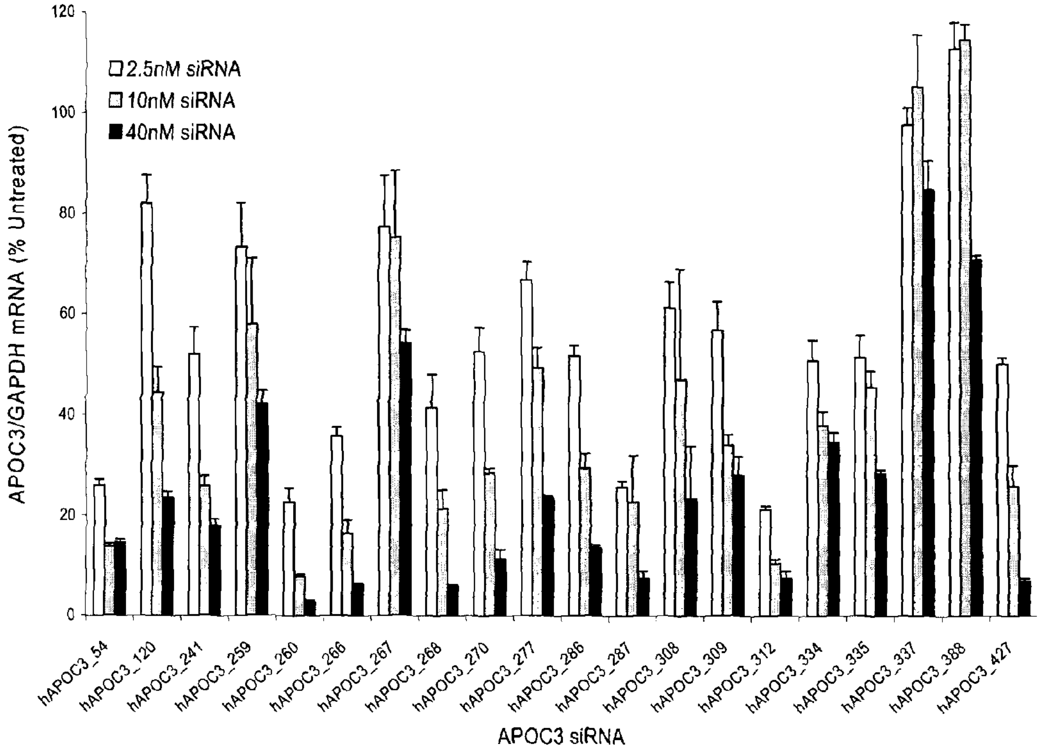
FIG. 8 illustrates data demonstrating an in vitro activity screen of APOC3 siRNA sequences. Native human APOC3 siRNA sequences targeting APOC3 mRNA were reverse transfected into HepG2 cells and silencing activity was assessed by QuantiGene Assay 48 h post-treatment. Cells were treated with SNALP formulated-APOC3 siRNA at 2.5 nM (white bar), 10 nM (grey bar), and 40 nM (black bar). Sequence numbers represent the nucleotide position of APOC3 mRNA (Genbank Accession No. NM_000040.1) that is complementary to the 3' end of the antisense strand of the siRNA.

This example provides an in vitro characterization of APOC3 siRNA activity in human cells. ApoCIII is an important regulator of lipoprotein metabolism that has been implicated in the progression of atherosclerosis (1) through its association with hypertriglyceridemia (2-5) and its direct induction of endothelial dysfunction (6-7). A panel of 20 APOC3 siRNAs were designed and screened for silencing activity in the human HepG2 hepatocellular carcinoma cell line. Treatment of HepG2 cells with many of these siRNAs caused a dose-dependent reduction in the levels of human APOC3 mRNA (FIG. 8). In particular, hAPOC3_260 was identified as the most potent human APOC3 siRNA. Additional potent APOC3 siRNAs include hAPOC3_312, hAPOC3_54, hAPOC3_266, hAPOC3_268, hAPOC3_287, and hAPOC3_427. Of these siRNAs, hAPOC3_260, hAPOC3_266, hAPOC3_268, and hAPOC3_427 are most likely to be cross-reactive in other primates based on an antisense sequence that is 100% complementary to the APOC3 transcript in cynomolgus monkeys.

Materials and Methods siRNA design. siRNA sequences targeting human APOC3 (Genbank Accession No. NM_000040.1) were selected using an algorithm implemented by the Whitehead Institute for Biomedical Research (http://jura.wi.mit.edu/bioc/siRNAext/home.php) that incorporates standard siRNA design guidelines (8-10). siRNA fulfilling the following criteria were selected: (1) NNN21 target sequences; (2) thermodynamically unstable 5' antisense end ($\Delta G > -8.2$ kcal/mol); (3) thermodynamically less stable 5' antisense end ($\Delta G_{sense} - \Delta G_{antisense} < -1.6$); (4) G/C content between 30-70%; (5) no stretches of four guanines in a row; and (6) no stretches of nine uracils or adenines in a row. Selected sequences were verified and the positions within the human APOC3 target sequence were identified.

All selected sequences were assessed for potential sequence-specific targeting activity against other human genes using the BLASTN algorithm against the human mRNA Reference Sequence database at the National Center for Biotechnology Information (NCBI; http://www.ncbi.nlm.nih.gov/). Transcripts other than APOC3 that contain a sequence that is 100% complementary to positions 2 to 15 of the antisense strand of an siRNA were evaluated for gene expression in liver and other human tissues. Gene expression analysis was performed using human gene expression data from the Genomics Institute of the Novartis Research Foundation (GNF), obtained from the human U133A+GNF1H microarray dataset and processed using the GC content adjusted robust multi-array algorithm (available at http://biogps.gnf.org) (11). EST counts from different tissue source libraries were also extracted from the NCBI UniGene database. siRNAs were eliminated if they contained sequence complementary to a transcript that is expressed ubiquitously or at moderate to high levels in liver (i.e., greater than two-fold higher than the global median over all tissues tested).

Four single nucleotide polymorphisms (SNPs), rs4225, rs4520, rs5128, and rs11540884, located in the coding or UTR sequences of the human APOC3 gene, were identified in the NCBI SNP database and used to filter the panel of siRNAs. siRNAs were eliminated if their antisense strand contained a nucleotide complementary to one of these SNPs.

In order to evaluate expected cross-reactivity of siRNAs, APOC3 sequences from human and cynomolgus monkey (*Macaca fascicularis;* Genbank Accession No. X68359.1) were aligned using ClustalX (12), with manual editing when necessary.

siRNA synthesis. All siRNA molecules used in this study were chemically synthesized by Integrated DNA Technologies (Coralville, Iowa). The siRNAs were desalted and annealed using standard procedures. Sequences of human APOC3 siRNAs are listed in Table 10. Sequence numbers represent the nucleotide position of human APOC3 mRNA (Genbank Accession No. NM_000040.1) that is complementary to the 3' end of the antisense strand of the siRNA.

Nucleotides 1-19 of the sense and antisense strand sequences of the hAPOC3_260 siRNA shown in Table 10 correspond to the sense and antisense strand sequences of APOC3 siRNA "262" shown in Table 7.

Nucleotides 1-19 of the sense and antisense strand sequences of the hAPOC3_266 siRNA shown in Table 10 correspond to the sense and antisense strand sequences of APOC3 siRNA "268" shown in Table 7.

Nucleotides 1-19 of the sense and antisense strand sequences of the hAPOC3_267 siRNA shown in Table 10 correspond to the sense and antisense strand sequences of APOC3 siRNA "269" shown in Table 7.

Nucleotides 1-19 of the sense and antisense strand sequences of the hAPOC3_268 siRNA shown in Table 10 correspond to the sense and antisense strand sequences of APOC3 siRNA "270" shown in Table 7.

Nucleotides 1-19 of the sense and antisense strand sequences of the hAPOC3_270 siRNA shown in Table 10 correspond to the sense and antisense strand sequences of APOC3 siRNA "272" shown in Table 7.

Nucleotides 1-19 of the sense and antisense strand sequences of the hAPOC3_277 siRNA shown in Table 10 correspond to the sense and antisense strand sequences of APOC3 siRNA "279" shown in Table 7.

Nucleotides 1-19 of the sense and antisense strand sequences of the hAPOC3_286 siRNA shown in Table 10

TABLE 10 siRNA sequences that target human APOC3 expression.

| siRNA | Target Sequence (5'→3') | SEQ ID NO. | Sense Strand (5'→3') | SEQ ID NO. | Antisense Strand (5'→3') | SEQ ID NO. |
|---|---|---|---|---|---|---|
| hAPOC3_54 | CGGGUACUCCUUGUUGUUG | 1387 | CGGGUACUCCUUGUUGUUGCC | 1389 | CAACAACAAGGAGUACCCGGG | 1389 |
| hAPOC3_120 | GCCUCCCUUCUCAGCUUCA | 1390 | GCCUCCCUUCUCAGCUUCAUG | 1391 | UGAAGCUGAGAAGGGAGGCAU | 1392 |
| hAPOC3_241 | GCUUCAGUUCCCUGAAAGA | 1393 | GCUUCAGUUCCCUGAAAGACU | 1394 | UCUUUCAGGGAACUGAAGCCA | 1395 |
| hAPOC3_259 | ACUACUGGAGCACCGUUAA | 1396 | ACUACUGGAGCACCGUUAAGG | 1397 | UUAACGGUGCUCCAGUAGUCU | 1398 |
| hAPOC3_260 | CUACUGGAGCACCGUUAAG | 1399 | CUACUGGAGCACCGUUAAGGA | 1400 | CUUAACGGUGCUCCAGUAGUC | 1401 |
| hAPOC3_266 | GAGCACCGUUAAGGACAAG | 1402 | GAGCACCGUUAAGGACAAGUU | 1403 | CUUGUCCUUAACGGUGCUCCA | 1404 |
| hAPOC3_267 | AGCACCGUUAAGGACAAGU | 1405 | AGCACCGUUAAGGACAAGUUC | 1406 | ACUUGUCCUUAACGGUGCUCC | 1407 |
| hAPOC3_268 | GCACCGUUAAGGACAAGUU | 1408 | GCACCGUUAAGGACAAGUUCU | 1409 | AACUUGUCCUUAACGGUGCUC | 1410 |
| hAPOC3_270 | ACCGUUAAGGACAAGUUCU | 1411 | ACCGUUAAGGACAAGUUCUCU | 1412 | AGAACUUGUCCUUAACGGUGC | 1413 |
| hAPOC3_277 | AGGACAAGUUCUCUGAGUU | 1414 | AGGACAAGUUCUCUGAGUUCU | 1415 | AACUCAGAGAACUUGUCCUUA | 1416 |
| hAPOC3_286 | UCUCUGAGUUCUGGGAUUU | 1417 | UCUCUGAGUUCUGGGAUUUGG | 1418 | AAAUCCCAGAACUCAGAGAAC | 1419 |
| hAPOC3_287 | CUCUGAGUUCUGGGAUUUG | 1420 | CUCUGAGUUCUGGGAUUUGGA | 1421 | CAAAUCCCAGAACUCAGAGAA | 1422 |
| hAPOC3_308 | CCCUGAGGUCAGACCAACU | 1423 | CCCUGAGGUCAGACCAACUUC | 1424 | AGUUGGUCUGACCUCAGGGUC | 1425 |
| hAPOC3_309 | CCUGAGGUCAGACCAACUU | 1426 | CCUGAGGUCAGACCAACUUCA | 1427 | AAGUUGGUCUGACCUCAGGGU | 1428 |
| hAPOC3_312 | GAGGUCAGACCAACUUCAG | 1429 | GAGGUCAGACCAACUUCAGCC | 1430 | CUGAAGUUGGUCUGACCUCAG | 1431 |
| hAPOC3_334 | UGGCUGCCUGAGACCUCAA | 1432 | UGGCUGCCUGAGACCUCAAUA | 1433 | UUGAGGUCUCAGGCAGCCACG | 1434 |
| hAPOC3_335 | GGCUGCCUGAGACCUCAAU | 1435 | GGCUGCCUGAGACCUCAAUAC | 1436 | AUUGAGGUCUCAGGCAGCCAC | 1437 |
| hAPOC3_337 | CUGCCUGAGACCUCAAUAC | 1438 | CUGCCUGAGACCUCAAUACCC | 1439 | GUAUUGAGGUCUCAGGCAGCC | 1440 |
| hAPOC3_388 | UCCUUGGGUCCUGCAAUCU | 1441 | UCCUUGGGUCCUGCAAUCUCC | 1442 | AGAUUGCAGGACCCAAGGAGC | 1443 |
| hAPOC3_427 | UGCUUAAAAGGGACAGUAU | 1444 | UGCUUAAAAGGGACAGUAUUC | 1445 | AUACUGUCCCUUUUAAGCAAC | 1446 |

Nucleotides 1-19 of the sense and antisense strand sequences of the hAPOC3_54 siRNA shown in Table 10 correspond to the sense and antisense strand sequences of APOC3 siRNA "56" shown in Table 7.

Nucleotides 1-19 of the sense and antisense strand sequences of the hAPOC3_120 siRNA shown in Table 10 correspond to the sense and antisense strand sequences of APOC3 siRNA "122" shown in Table 7.

Nucleotides 1-19 of the sense and antisense strand sequences of the hAPOC3_241 siRNA shown in Table 10 correspond to the sense and antisense strand sequences of APOC3 siRNA "243" shown in Table 7.

Nucleotides 1-19 of the sense and antisense strand sequences of the hAPOC3_259 siRNA shown in Table 10 correspond to the sense and antisense strand sequences of APOC3 siRNA "261" shown in Table 7.

correspond to the sense and antisense strand sequences of APOC3 siRNA "288" shown in Table 7.

Nucleotides 1-19 of the sense and antisense strand sequences of the hAPOC3_287 siRNA shown in Table 10 correspond to the sense and antisense strand sequences of APOC3 siRNA "289" shown in Table 7.

Nucleotides 1-19 of the sense and antisense strand sequences of the hAPOC3_308 siRNA shown in Table 10 correspond to the sense and antisense strand sequences of APOC3 siRNA "310" shown in Table 7.

Nucleotides 1-19 of the sense and antisense strand sequences of the hAPOC3_309 siRNA shown in Table 10 correspond to the sense and antisense strand sequences of APOC3 siRNA "311" shown in Table 7.

Nucleotides 1-19 of the sense and antisense strand sequences of the hAPOC3_312 siRNA shown in Table 10 correspond to the sense and antisense strand sequences of APOC3 siRNA "314" shown in Table 7.

Nucleotides 1-19 of the sense and antisense strand sequences of the hAPOC3_334 siRNA shown in Table 10 correspond to the sense and antisense strand sequences of APOC3 siRNA "336" shown in Table 7.

Nucleotides 1-19 of the sense and antisense strand sequences of the hAPOC3_335 siRNA shown in Table 10 correspond to the sense and antisense strand sequences of APOC3 siRNA "337" shown in Table 7.

Nucleotides 1-19 of the sense and antisense strand sequences of the hAPOC3_337 siRNA shown in Table 10 correspond to the sense and antisense strand sequences of APOC3 siRNA "339" shown in Table 7.

Nucleotides 1-19 of the sense and antisense strand sequences of the hAPOC3_388 siRNA shown in Table 10 correspond to the sense and antisense strand sequences of APOC3 siRNA "390" shown in Table 7.

Nucleotides 1-19 of the sense and antisense strand sequences of the hAPOC3_427 siRNA shown in Table 10 correspond to the sense and antisense strand sequences of APOC3 siRNA "429" shown in Table 7.

In Table 10 above, the last 2 nucleotides at the 3' ends of the sense and antisense strands correspond to the 3' overhang sequence. In other words, nucleotides 1-19 of each sense and antisense strand sequence depicted in Table 10 correspond to that portion of the sense or antisense strand that is present in the double-stranded region of the siRNA duplex. In alternative embodiments, the 3' overhang on one or both strands of the siRNA comprises 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence (3' overhang in the antisense strand) or the complementary strand thereof (3' overhang in the sense strand). In certain instances, the sense and/or antisense strand of the siRNA molecule lacks 3' overhangs (i.e., does not contain the last 2 nucleotides at the 3' ends of the sense and/or antisense strand). In some embodiments, the sense and/or antisense strand sequence shown in Table 10 comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In particular embodiments, the sense and/or antisense strand sequence shown in Table 10 comprises 2'OMe nucleotides in accordance with one or more of the selective modification patterns described herein.

Lipid Encapsulation of siRNA. siRNA molecules were encapsulated into nucleic acid-lipid particles composed of the following lipids: a lipid conjugate such as PEG-C-DMA (3-N-[(-Methoxy poly(ethylene glycol)2000)carbamoyl]-1,2-dimyrestyloxy-propylamine); a cationic lipid such as DLinDMA (1,2-Dilinoleyloxy-3-(N,N-dimethyl)aminopropane); a phospholipid such as DPPC (1,2-dipalmitoyl-sn-glycero-3-phosphocholine; Avanti Polar Lipids; Alabaster, Ala.); and synthetic cholesterol (Sigma-Aldrich Corp.; St. Louis, Mo.) in the molar ratio 1.4:57.1:7.1:34.3, respectively. In other words, siRNAs were encapsulated into stable nucleic acid-lipid particles ("SNALP") of the following "1:57" formulation: 1.4 mol % lipid conjugate (e.g., PEG-C-DMA); 57.1 mol % cationic lipid (e.g., DLinDMA); 7.1 mol % phospholipid (e.g., DPPC); and 34.3 mol % cholesterol. For vehicle controls, empty particles with identical lipid composition are formed in the absence of siRNA. It should be understood that the 1:57 formulation is a target formulation, and that the amount of lipid (both cationic and non-cationic) present and the amount of lipid conjugate present in the formulation may vary. Typically, in the 1:57 formulation, the amount of cationic lipid will be 57 mol % ±5 mol %, and the amount of lipid conjugate will be 1.5 mol % ±0.5 mol %, with the balance of the 1:57 formulation being made up of non-cationic lipid (e.g., phospholipid, cholesterol, or a mixture of the two).

Cell culture. The HepG2 cell line was obtained from ATCC and cultured in complete media (Invitrogen GibcoBRL Minimal Essential Medium, 10% heat-inactivated FBS, 200 mM L-glutamine, 10 mM MEM non-essential amino acids, 100 mM sodium pyruvate, 7.5% w/v sodium bicarbonate and 1% penicillin-streptomycin) in T175 flasks. For in vitro siRNA silencing activity assay, HepG2 cells from passage #28 were reverse transfected with 2.5 nM, 10 nM, and 40 nM of SNALP-formulated APOC3 siRNAs in 96-well plates at an initial cell confluency of 50%. After 24 hours of treatment, media was removed and fresh complete media was added.

Target mRNA Quantitation. The QuantiGene® QuantiGene 2.0 Reagent System (Panomics, Inc., Fremont, Calif.) was used to quantify the reduction of human APOC3 mRNA levels relative to the mRNA levels of the housekeeping gene GAPDH in lysates prepared from HepG2 cell cultures treated with SNALP. HepG2 Cells were lysed 48 hours post SNALP treatment by adding 100 !μL of 1× Lysis Mixture (Panomics) into each well followed by 30 minute incubation at 37° C. The assay was performed according to the manufacturer's instructions. Relative APOC3 mRNA levels are expressed relative to PBS-treated control cells.

REFERENCES

1. Pollin T I, Damcott C M, Shen H, Ott S H, Shelton J, Horenstein R B, et al. A null mutation in human APOC3 confers a favorable plasma lipid profile and apparent cardioprotection. Science. 2008; 322(5908):1702-5.
2. van der Ham R L, Alizadeh Dehnavi R, Berbee J F, Putter H, de Roos A, Romijn J A, et al. Plasma apolipoprotein CI and CIII levels are associated with increased plasma triglyceride levels and decreased fat mass in men with the metabolic syndrome. Diabetes Care. 2009 January; 32(1):184-6.
3. Carlson L A, Ballantyne D. Changing relative proportions of apolipoproteins CII and CIII of very low density lipoproteins in hypertriglyceridaemia. Atherosclerosis. 1976 May-June; 23(3):563-8.
4. Schonfeld G, George P K, Miller J, Reilly P, Witztum J. Apolipoprotein C-II and C-III levels in hyperlipoproteinemia. Metabolism. 1979 October; 28(10):1001-10.

5. Le N A, Gibson J C, Ginsberg H N. Independent regulation of plasma apolipoprotein C-II and C-III concentrations in very low density and high density lipoproteins: implications for the regulation of the catabolism of these lipoproteins. J Lipid Res. 1988 May; 29(5):669-77.
6. Kawakami A, Aikawa M, Alcaide P, Luscinskas F W, Libby P, Sacks F M. Apolipoprotein CIII induces expression of vascular cell adhesion molecule-1 in vascular endothelial cells and increases adhesion of monocytic cells. Circulation. 2006 Aug. 15; 114(7):681-7.
7. Kawakami A, Osaka M, Tani M, Azuma H, Sacks F M, Shimokado K, et al. Apolipoprotein CIII links hyperlipidemia with vascular endothelial cell dysfunction. Circulation. 2008 Aug. 12; 118(7):731-42.
8. Khvorova A, Reynolds A, Jayasena S D. Functional siRNAs and miRNAs exhibit strand bias. Cell. 2003 Oct. 17; 115(2):209-16.
9. Elbashir S M, Lendeckel W, Tuschl T. RNA interference is mediated by 21- and 22-nucleotide RNAs. Genes Dev. 2001 Jan 15; 15(2):188-200.
10. Schwarz D S, Hutvagner G, Du T, Xu Z, Aronin N, Zamore P D. Asymmetry in the assembly of the RNAi enzyme complex. Cell. 2003 Oct. 17; 115(2):199-208.
11. Su A I, Wiltshire T, Batalov S, Lapp H, Ching K A, Block D, et al. A gene atlas of the mouse and human protein-encoding transcriptomes. Proc Natl Acad Sci USA. 2004; 101(16):6062-7.
12. Thompson J D, Gibson T J, Plewniak F, Jeanmougin F, Higgins D G. The CLUSTAL_X windows interface: flexible strategies for multiple sequence alignment aided by quality analysis tools. Nucleic Acids Res. 1997; 25(24): 4876-82.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

INFORMAL SEQUENCE LISTING

SEQ ID NO: 1

*Homo sapiens* apolipoprotein C-III (APOC3) on chromosome 11, DNA.

NG_008949 REGION: 5001 . . . 8164

```
   1 tgctcagttc atccctagag gcagctgctc caggtaatgc cctctgggga ggggaaagag

  61 gaggggagga ggatgaagag gggcaagagg agctccctgc ccagcccagc cagcaagcct

 121 ggagaagcac ttgctagagc taaggaagcc tcggagctgg acgggtgccc cccacccctc

 181 atcataacct gaagaacatg gaggcccggg aggggtgtca cttgcccaaa gctacacagg

 241 gggtggggct ggaagtggct ccaagtgcag gttcccccct cattcttcag gcttagggct

 301 ggaggaagcc ttagacagcc cagtcctacc ccagacaggg aaactgaggc ctggagaggg

 361 ccagaaatca cccaaagaca cacagcatgt tggctggact ggacggagat cagtccagac

 421 cgcaggtgcc ttgatgttca gtctggtggg ttttctgctc catcccaccc acctcccttt

 481 gggcctcgat ccctcgcccc tcaccagtcc cccttctgag agcccgtatt agcagggagc

 541 cggcccctac tccttctggc agacccagct aaggttctac cttaggggcc acgccacctc

 601 cccagggagg ggtccagagg catggggacc tggggtgccc ctcacaggac acttccttgc

 661 aggaacagag gtgccatgca gccccgggta ctccttgttg ttgccctcct ggcgctcctg

 721 gcctctgccc gtaagcactt ggtgggactg ggctgggggc agggtggagg caacttgggg

 781 atcccagtcc caatgggtgg tcaagcagga gcccagggct cgtccagagg ccgatccacc

 841 ccactcagcc ctgctctttc ctcaggagct tcagaggccg aggatgcctc ccttctcagc

 901 ttcatgcagg gttacatgaa gcacgccacc aagaccgcca aggatgcact gagcagcgtg

 961 caggagtccc aggtggccca gcaggccagg tacacccgct ggcctccctc cccatccccc

1021 ctgccagctg cctccattcc cacccgcccc tgccctggtg agatcccaac aatggaatgg

1081 aggtgctcca gcctcccctg ggcctgtgcc tcttcagcct cctctttcct cacagggcct

1141 ttgtcaggct gctgcgggag agatgacaga gttgagactg cattcctccc aggtccctcc

1201 tttctccccg gagcagtcct agggcgtgcc gttttagccc tcatttccat tttcctttcc

1261 tttccctttc tttctctttc tatttctttc tttctttctt tctttctttc tttctttctt

1321 tctttctttc tttctttctt tctttctttc ctttctttct ttcctttctt tctttccttt

1381 ctttctttct ttcctttctt tctctttctt tctttctttc ctttttcttt ctttccctct
```

-continued

INFORMAL SEQUENCE LISTING 1441 cttcctttct ctctttcttt cttcttcttt tttttttaat ggagtctccc tctgtcacct 1501 aggctggagt gcagtggtgc catctcggct cactgcaacc tccgtctccc gggttcaacc 1561 cattctcctg cctcagcctc ccaagtagct gggattacag gcacgcgcca ccacacccag 1621 ctaatttttg tatttttagc agagatgggg tttcaccatg ttggccaggt tggtcttgaa 1681 ttcctgacct caggggatcc tcctgcctcg gcctcccaaa gtgctgggat tacaggcatg 1741 agccactgcg cctggcccca ttttcctttt ctgaaggtct ggctagagca gtggtcctca 1801 gcctttttgg caccagggac cagttttgtg gtggacaatt tttccatggg ccagcgggga 1861 tggttttggg atgaagctgt tccacctcag atcatcaggc attagattct cataaggagc 1921 cctccaccta gatccctggc atgtgcagtt cacaataggg ttcacactcc tatgagaatg 1981 taaggccact tgatctgaca ggaggcggag ctcaggcggt attgctcact cacccaccac 2041 tcacttcgtg ctgtgcagcc cggctcctaa cagtccatgg accagtacct atctatgact 2101 tgggggttgg ggacccctgg gctaggggtt tgccttggga ggccccacct gacccaattc 2161 aagcccgtga gtgcttctgc tttgttctaa gacctggggc cagtgtgagc agaagtgtgt 2221 ccttcctctc ccatcctgcc cctgcccatc agtactctcc tctcccctac tcccttctcc 2281 acctcaccct gactggcatt agctggcata gcagaggtgt tcataaacat tcttagtccc 2341 cagaaccggc tttggggtag gtgttatttt ctcactttgc agatgagaaa attgaggctc 2401 agagcgatta ggtgacctgc cccagatcac acaactaatc aatcctccaa tgactttcca 2461 aatgagaggc tgcctccctc tgtcctaccc tgctcagagc caccaggttg tgcaactcca 2521 ggcggtgctg tttgcacaga aaacaatgac agccttgacc tttcacatct ccccaccctg 2581 tcactttgtg cctcaggccc aggggcataa acatctgagg tgacctggag atggcagggt 2641 ttgacttgtg ctggggttcc tgcaaggata tctcttctcc cagggtggca gctgtggggg 2701 attcctgcct gaggtctcag ggctgtcgtc cagtgaagtt gagagggtgg tgtggtcctg 2761 actggtgtcg tccagtgggg acatgggtgt gggtcccatg gttgcctaca gaggagttct 2821 catgccctgc tctgttgctt cccctgactg atttaggggc tgggtgaccg atggcttcag 2881 ttccctgaaa gactactgga gcaccgttaa ggacaagttc tctgagttct gggatttgga 2941 ccctgaggtc agaccaactt cagccgtggc tgcctgagac ctcaataccc caagtccacc 3001 tgcctatcca tcctgcgagc tccttgggtc ctgcaatctc cagggctgcc cctgtaggtt 3061 gcttaaaagg gacagtattc tcagtgctct cctaccccac ctcatgcctg gcccccctcc 3121 aggcatgctg gcctcccaat aaagctggac aagaagctgc tatg SEQ ID NO: 2
*Homo sapiens* apolipoprotein C-III (APOC3), mRNA.
NM_000040.1

1 tgctcagttc atccctagag gcagctgctc caggaacaga ggtgccatgc agccccgggt 61 actccttgtt gttgccctcc tggcgctcct ggcctctgcc cgagcttcag aggccgagga 121 tgcctccctt ctcagcttca tgcagggtta catgaagcac gccaccaaga ccgccaagga 181 tgcactgagc agcgtgcagg agtcccaggt ggcccagcag gccaggggct gggtgaccga 241 tggcttcagt tccctgaaag actactggag caccgttaag gacaagttct ctgagttctg 301 ggatttggac cctgaggtca gaccaacttc agccgtggct gcctgagacc tcaatacccc -continued

| INFORMAL SEQUENCE LISTING |
| --- |
| 361 aagtccacct gcctatccat cctgcgagct ccttgggtcc tgcaatctcc agggctgccc |
| 421 ctgtaggttg cttaaaaggg acagtattct cagtgctctc ctaccccacc tcatgcctgg |
| 481 ccccctcca ggcatgctgg cctcccaata aagctggaca agaagctgct atg |

What is claimed is:

1. A composition comprising a small-interfering RNA (siRNA) that silences apolipoprotein C-III (APOC3) gene expression, wherein the siRNA comprises a sense strand and a complementary antisense strand, wherein the siRNA comprises a double-stranded region of about 19 to about 25 nucleotides in length, and wherein the antisense strand comprises a 2'OMe-modified sequence set forth in SEQ ID NOS:3-58 and/or wherein the sense strand comprises a 2'OMe-modified sequence set forth in SEQ ID NOS:59-110.

2. A nucleic acid-lipid particle comprising:

(a) an siRNA of claim 1;

(b) a cationic lipid; and (c) a non-cationic lipid.

3. The nucleic acid-lipid particle of claim 2, wherein the non-cationic lipid is a mixture of a phospholipid and cholesterol or a derivative thereof.

4. The nucleic acid-lipid particle of claim 2, further comprising a conjugated lipid that inhibits aggregation of particles.

5. A method for introducing an siRNA that silences APOC3 gene expression into a cell, the method comprising:

contacting the cell with a nucleic acid-lipid particle of claim 2.

6. A method for silencing APOC3 gene expression in a mammal in need thereof, the method comprising:

administering to the mammal a nucleic acid-lipid particle of claim 2.

7. A method for the in vivo delivery of an siRNA that silences APOC3 gene expression, the method comprising:

administering to a mammal a nucleic acid-lipid particle of claim 2.

8. A method for treating and/or ameliorating one or more symptoms associated with atherosclerosis or dyslipidemia in a mammal in need thereof, the method comprising:

administering to the mammal a therapeutically effective amount of a nucleic acid-lipid particle of claim 2.

9. A method for reducing susceptibility to atherosclerosis or dyslipidemia in a mammal in need thereof, the method comprising:

administering to the mammal a therapeutically effective amount of a nucleic acid-lipid particle of claim 2.

10. A method for preventing or delaying the onset of atherosclerosis or dyslipidemia in a mammal in need thereof, the method comprising:

administering to the mammal a therapeutically effective amount of a nucleic acid-lipid particle of claim 2.

11. A method for lowering triglyceride levels in a mammal in need thereof, the method comprising:

administering to the mammal a therapeutically effective amount of a nucleic acid-lipid particle of claim 2.

12. A method for lowering cholesterol levels in a mammal in need thereof, the method comprising:

administering to the mammal a therapeutically effective amount of a nucleic acid-lipid particle of claim 2.

* * * * *

SEQUENCE LISTING

<160> NUMBER OF SEQ ID NOS: 1446

<210> SEQ ID NO 1
<211> LENGTH: 3164
<212> TYPE: DNA
<213> ORGANISM: Homo sapiens
<220> FEATURE:
<223> OTHER INFORMATION: human apolipoprotein C-III (APOC3, apoC-III) genomic sequence

<400> SEQUENCE: 1
tgctcagttc atccctagag gcagctgctc caggtaatgc cctctgggga ggggaaagag 60
gaggggagga ggatgaagag gggcaagagg agctccctgc ccagcccagc cagcaagcct 120
ggagaagcac ttgctagagc taaggaagcc tcggagctgg acgggtgccc cccacccctc 180
atcataacct gaagaacatg gaggcccggg aggggtgtca cttgcccaaa gctacacagg 240
gggtggggct ggaagtggct ccaagtgcag gttcccccct cattcttcag gcttagggct 300
ggaggaagcc ttagacagcc cagtcctacc ccagacaggg aaactgaggc ctggagaggg 360
ccagaaatca cccaaagaca cacagcatgt tggctggact ggacggagat cagtccagac 420
cgcaggtgcc ttgatgttca gtctggtggg ttttctgctc catcccaccc acctcccttt 480
gggcctcgat ccctcgcccc tcaccagtcc ccctttctgag agcccgtatt agcagggagc 540
cggcccctac tccttctggc agacccagct aaggttctac cttaggggcc acgccacctc 600
cccagggagg ggtccagagg catggggacc tggggtgccc ctcacaggac acttccttgc 660
aggaacagag gtgccatgca gccccgggta ctccttgttg ttgccctcct ggcgctcctg 720
gcctctgccc gtaagcactt ggtgggactg ggctgggggc agggtggagg caacttgggg 780
atcccagtcc caatgggtgg tcaagcagga gcccagggct cgtccagagg ccgatccacc 840
ccactcagcc ctgctctttc ctcaggagct tcagaggccg aggatgcctc ccttctcagc 900
ttcatgcagg gttacatgaa gcacgccacc aagaccgcca aggatgcact gagcagcgtg 960
caggagtccc aggtggccca gcaggccagg tacacccgct ggcctccctc cccatccccc 1020
ctgccagctg cctccattcc cacccgcccc tgccctggtg agatcccaac aatggaatgg 1080
aggtgctcca gcctcccctg ggcctgtgcc tcttcagcct cctctttcct cacagggcct 1140
ttgtcaggct gctgcgggag agatgacaga gttgagactg cattcctccc aggtccctcc 1200
tttctccccg gagcagtcct agggcgtgcc gttttagccc tcatttccat tttcctttcc 1260
tttccctttc tttctctttc tatttctttc tttctttctt tctttctttc tttctttctt 1320
tctttctttc tttctttctt tctttctttc ctttctttct ttcctttctt tctttccttt 1380
ctttctttct ttcctttctt tctctttctt tctttctttc ctttttcttt ctttccctct 1440
cttcctttct ctctttcttt cttcttcttt tttttttaat ggagtctccc tctgtcacct 1500
aggctggagt gcagtggtgc catctcggct cactgcaacc tccgtctccc gggttcaacc 1560
cattctcctg cctcagcctc ccaagtagct gggattacag gcacgcgcca ccacacccag 1620

-continued

```
ctaatttttg tatttttagc agagatgggg tttcaccatg ttggccaggt tggtcttgaa   1680

ttcctgacct caggggatcc tcctgcctcg gcctcccaaa gtgctgggat tacaggcatg   1740

agccactgcg cctggcccca ttttcctttt ctgaaggtct ggctagagca gtggtcctca   1800

gcctttttgg caccagggac cagttttgtg gtggacaatt tttccatggg ccagcgggga   1860

tggttttggg atgaagctgt tccacctcag atcatcaggc attagattct cataaggagc   1920

cctccaccta gatccctggc atgtgcagtt cacaataggg ttcacactcc tatgagaatg   1980

taaggccact tgatctgaca ggaggcggag ctcaggcggt attgctcact cacccaccac   2040

tcacttcgtg ctgtgcagcc cggctcctaa cagtccatgg accagtacct atctatgact   2100

tgggggttgg ggacccctgg gctaggggtt tgccttggga ggccccacct gacccaattc   2160

aagcccgtga gtgcttctgc tttgttctaa gacctggggc cagtgtgagc agaagtgtgt   2220

ccttcctctc ccatcctgcc cctgcccatc agtactctcc tctcccctac tcccttctcc   2280

acctcaccct gactggcatt agctggcata gcagaggtgt tcataaacat tcttagtccc   2340

cagaaccggc tttggggtag gtgttatttt ctcactttgc agatgagaaa attgaggctc   2400

agagcgatta ggtgacctgc cccagatcac acaactaatc aatcctccaa tgactttcca   2460

aatgagaggc tgcctccctc tgtcctaccc tgctcagagc caccaggttg tgcaactcca   2520

ggcggtgctg tttgcacaga aaacaatgac agccttgacc tttcacatct ccccaccctg   2580

tcactttgtg cctcaggccc aggggcataa acatctgagg tgacctggag atggcagggt   2640

ttgacttgtg ctggggttcc tgcaaggata tctcttctcc cagggtggca gctgtggggg   2700

attcctgcct gaggtctcag ggctgtcgtc cagtgaagtt gagagggtgg tgtggtcctg   2760

actggtgtcg tccagtgggg acatgggtgt gggtcccatg gttgcctaca gaggagttct   2820

catgccctgc tctgttgctt cccctgactg atttaggggc tgggtgaccg atggcttcag   2880

ttccctgaaa gactactgga gcaccgttaa ggacaagttc tctgagttct gggatttgga   2940

ccctgaggtc agaccaactt cagccgtggc tgcctgagac ctcaataccc caagtccacc   3000

tgcctatcca tcctgcgagc tccttgggtc ctgcaatctc cagggctgcc cctgtaggtt   3060

gcttaaaagg gacagtattc tcagtgctct cctaccccac ctcatgcctg gcccccctcc   3120

aggcatgctg gcctcccaat aaagctggac aagaagctgc tatg                    3164
```

```
<210> SEQ ID NO 2
<211> LENGTH: 533
<212> TYPE: DNA
<213> ORGANISM: Homo sapiens
<220> FEATURE:
<223> OTHER INFORMATION: human apolipoprotein C-III (APOC3, apoC-III)
      cDNA
<220> FEATURE:
<221> NAME/KEY: CDS
<222> LOCATION: (47)...(346)
<223> OTHER INFORMATION: APOC3

<400> SEQUENCE: 2

tgctcagttc atccctagag gcagctgctc caggaacaga ggtgccatgc agccccgggt     60

actccttgtt gttgccctcc tggcgctcct ggcctctgcc cgagcttcag aggccgagga    120

tgcctccctt ctcagcttca tgcagggtta catgaagcac gccaccaaga ccgccaagga    180

tgcactgagc agcgtgcagg agtcccaggt ggcccagcag gccaggggct gggtgaccga    240

tggcttcagt tccctgaaag actactggag caccgttaag gacaagttct ctgagttctg    300

ggatttggac cctgaggtca gaccaacttc agccgtggct gcctgagacc tcaatacccc    360
```

aagtccacct gcctatccat cctgcgagct ccttgggtcc tgcaatctcc agggctgccc 420
ctgtaggttg cttaaaaggg acagtattct cagtgctctc ctaccccacc tcatgcctgg 480
cccccctcca ggcatgctgg cctcccaata aagctggaca agaagctgct atg 533

<210> SEQ ID NO 3
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (9)...(17)
<223> OTHER INFORMATION: n = um

<400> SEQUENCE: 3
cuuaacggng cnccagnag 19

<210> SEQ ID NO 4
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(17)
<223> OTHER INFORMATION: n = um

<400> SEQUENCE: 4
cnuaacggng cnccagnag 19

<210> SEQ ID NO 5
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(17)
<223> OTHER INFORMATION: n = um

<400> SEQUENCE: 5
cunaacggng cnccagnag 19

<210> SEQ ID NO 6
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(17)
<223> OTHER INFORMATION: n = um

<400> SEQUENCE: 6
cnnaacggng cnccagnag 19

<210> SEQ ID NO 7
<211> LENGTH: 19
<212> TYPE: RNA

<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (10)...(19)
<223> OTHER INFORMATION: n = gm

<400> SEQUENCE: 7
cuuaacggun cuccanuan 19

<210> SEQ ID NO 8
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(19)
<223> OTHER INFORMATION: n = gm

<400> SEQUENCE: 8
cuuaacngug cuccanuan 19

<210> SEQ ID NO 9
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(19)
<223> OTHER INFORMATION: n = gm

<400> SEQUENCE: 9
cuuaacngun cuccanuan 19

<210> SEQ ID NO 10
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (8)...(19)
<223> OTHER INFORMATION: n = gm

<400> SEQUENCE: 10
cuuaacgnun cuccanuan 19

<210> SEQ ID NO 11
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(19)
<223> OTHER INFORMATION: n = gm

<400> SEQUENCE: 11
cuuaacnnun cuccanuan 19

<210> SEQ ID NO 12
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(17)
<223> OTHER INFORMATION: n = um

<400> SEQUENCE: 12
cuuaacngng cnccagnag 19

<210> SEQ ID NO 13
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (9)...(19)
<223> OTHER INFORMATION: n = um

<400> SEQUENCE: 13
cuuaacggng cnccagnan 19

<210> SEQ ID NO 14
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 14
cuuaacngng cnccagnan 19

<210> SEQ ID NO 15
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 15
cnuaacngng cnccagnan 19

<210> SEQ ID NO 16
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 16
cunaacngng cnccagnan 19

<210> SEQ ID NO 17
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 17
cuuaacngng cnccannag 19

<210> SEQ ID NO 18
<211> LENGTH: 19
<212> TYPE: RNA
<213> ORGANISM: Artificial Sequence
<220> FEATURE:

```
<223> OTHER INFORMATION: synthetic 2'-OMe-modified APOC3 siRNA antisense
      strand
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 18

cuuaacngnn cnccagnan                                                    19


<210> SEQ ID NO 19
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 19

cnuaacngug cnccagnag                                                    19


<210> SEQ ID NO 20
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (2)...(3)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 20

cnnaacngug cnccagnag                                                    19


<210> SEQ ID NO 21
```

<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(3)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 21
cnnaacgnug cnccagnag 19

<210> SEQ ID NO 22
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(3)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 22
cnnaacgnug cnccagnan 19

<210> SEQ ID NO 23
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)

<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 23
cnuaacngng cnccannan 19

<210> SEQ ID NO 24
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (8)...(10)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 24
cuuaacgnun cnccagnan 19

<210> SEQ ID NO 25
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 25
cuuaacgnug cnccagnan 19

<210> SEQ ID NO 26
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (8)...(10)
<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (16)...(16)

-continued

<223> OTHER INFORMATION: n = gm
<220> FEATURE:
<221> NAME/KEY: modified_base
<222> LOCATION: (17)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 26
cuuaacgnun cnccannan 19

<210> SEQ ID NO 27
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 27
cunaacgnug cnccagnan 19

<210> SEQ ID NO 28
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(8)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 28
cuuaacnnug cnccagnan 19

<210> SEQ ID NO 29
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(10)

-continued

<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 29
cuuaacnnun cnccannag 19

<210> SEQ ID NO 30
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (7)...(10)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 30
cuuaacnnun cnccagnan 19

<210> SEQ ID NO 31
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 31
cnuaacggun cnccagnag 19

<210> SEQ ID NO 32
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(2)

<223> OTHER INFORMATION: n = um
<220> FEATURE:
<221> NAME/KEY: modified_base
<222> LOCATION: (7)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 32
cnuaacngun cnccagnag 19

<210> SEQ ID NO 33
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (7)...(10)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 33
cnuaacngun cnccagnan 19

<210> SEQ ID NO 34
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 34
cunaacggng cnccagnan 19

<210> SEQ ID NO 35
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (7)...(7)

<223> OTHER INFORMATION: n = gm
<220> FEATURE:
<221> NAME/KEY: modified_base
<222> LOCATION: (9)...(17)
<223> OTHER INFORMATION: n = um

<400> SEQUENCE: 35
cunaacngng cnccagnag 19

<210> SEQ ID NO 36
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (9)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 36
cunaacgnng cnccagnan 19

<210> SEQ ID NO 37
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (9)...(17)
<223> OTHER INFORMATION: n = um

<400> SEQUENCE: 37
cunaacgnng cnccagnag 19

<210> SEQ ID NO 38
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (10)...(10)

<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 38
cunaacggnn cnccagnan 19

<210> SEQ ID NO 39
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 39
cunaacggnn cnccagnag 19

<210> SEQ ID NO 40
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 40
cunaacngng cnccannan 19

<210> SEQ ID NO 41
<211> LENGTH: 19

<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 41
cunaacngng cnccannag 19

<210> SEQ ID NO 42
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 42
cunaacggng cnccannag 19

<210> SEQ ID NO 43
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (9)...(12)
<223> OTHER INFORMATION: n = um
<220> FEATURE:
<221> NAME/KEY: modified_base
<222> LOCATION: (16)...(16)
<223> OTHER INFORMATION: n = gm

```
<220> FEATURE:
<221> NAME/KEY: modified_base
<222> LOCATION: (17)...(17)
<223> OTHER INFORMATION: n = um

<400> SEQUENCE: 43

cunaacgnng cnccannag                                                19


<210> SEQ ID NO 44
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 44

cunaacggnn cnccannag                                                19


<210> SEQ ID NO 45
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (9)...(17)
<223> OTHER INFORMATION: n = um

<400> SEQUENCE: 45

cuuaacgnng cnccagnag                                                19


<210> SEQ ID NO 46
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (9)...(17)
<223> OTHER INFORMATION: n = um
```

```
<220> FEATURE:
<221> NAME/KEY: modified_base
<222> LOCATION: (19)...(19)
<223> OTHER INFORMATION: n = gm

<400> SEQUENCE: 46

cuuaacgnng cnccagnan                                                 19


<210> SEQ ID NO 47
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 47

cuuaacggnn cnccagnag                                                 19


<210> SEQ ID NO 48
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 48

cuuaacggnn cnccagnan                                                 19


<210> SEQ ID NO 49
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (9)...(12)
<223> OTHER INFORMATION: n = um
<220> FEATURE:
<221> NAME/KEY: modified_base
<222> LOCATION: (16)...(16)
<223> OTHER INFORMATION: n = gm
```

```
<220> FEATURE:
<221> NAME/KEY: modified_base
<222> LOCATION: (17)...(19)
<223> OTHER INFORMATION: n = um

<400> SEQUENCE: 49

cuuaacggng cnccannan                                            19


<210> SEQ ID NO 50
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 50

cuuaacngnn cnccagnan                                            19


<210> SEQ ID NO 51
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um
<220> FEATURE:
<221> NAME/KEY: modified_base
<222> LOCATION: (19)...(19)
<223> OTHER INFORMATION: n = gm
```

<400> SEQUENCE: 51
cuuaacngnn cnccannan 19

<210> SEQ ID NO 52
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (8)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 52
cuuaacgnun cnccagnag 19

<210> SEQ ID NO 53
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (8)...(10)
<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 53
cuuaacgnun cnccannag 19

<210> SEQ ID NO 54
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (8)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 54
cunaacgnun cnccagnag 19

<210> SEQ ID NO 55
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (8)...(10)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 55
cunaacgnun cnccagnan 19

<210> SEQ ID NO 56
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
strand
<220> FEATURE:
<221> NAME/KEY: modified_base
<222> LOCATION: (7)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 56
cuuaacnnun cnccagnag 19

<210> SEQ ID NO 57
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (7)...(10)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 57
cunaacnnun cnccagnag 19

<210> SEQ ID NO 58
<211> LENGTH: 19
<212> TYPE: RNA

<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (7)...(8)
<223> OTHER INFORMATION: n = gm
<220> FEATURE:
<221> NAME/KEY: modified_base
<222> LOCATION: (12)...(17)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 58
cuuaacnnug cnccagnan 19

<210> SEQ ID NO 59
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (2)...(15)
<223> OTHER INFORMATION: n = um

<400> SEQUENCE: 59
cnacnggagc accgnuaag 19

<210> SEQ ID NO 60
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (2)...(16)
<223> OTHER INFORMATION: n = um

<400> SEQUENCE: 60
cnacnggagc accgunaag 19

<210> SEQ ID NO 61
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (2)...(16)
<223> OTHER INFORMATION: n = um

<400> SEQUENCE: 61
cnacnggagc accgnnaag 19

<210> SEQ ID NO 62
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(15)
<223> OTHER INFORMATION: n = um

<400> SEQUENCE: 62
cuacnggagc accgnuaag 19

<210> SEQ ID NO 63
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(16)
<223> OTHER INFORMATION: n = um

<400> SEQUENCE: 63
cuacnggagc accgunaag 19

<210> SEQ ID NO 64
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (6)...(14)
<223> OTHER INFORMATION: n = gm

<400> SEQUENCE: 64
cuacunganc accnuuaag 19

<210> SEQ ID NO 65
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (6)...(19)
<223> OTHER INFORMATION: n = gm

<400> SEQUENCE: 65
cuacunganc accguuaan 19

<210> SEQ ID NO 66
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (7)...(14)
<223> OTHER INFORMATION: n = gm

<400> SEQUENCE: 66
cuacugnanc accnuuaag 19

<210> SEQ ID NO 67
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (7)...(19)
<223> OTHER INFORMATION: n = gm

<400> SEQUENCE: 67
cuacugnanc accguuaan 19

<210> SEQ ID NO 68
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (6)...(19)
<223> OTHER INFORMATION: n = gm

<400> SEQUENCE: 68
cuacunganc accnuuaan 19

<210> SEQ ID NO 69
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (7)...(19)
<223> OTHER INFORMATION: n = gm

<400> SEQUENCE: 69
cuacugnanc accnuuaan 19

<210> SEQ ID NO 70
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (6)...(19)
<223> OTHER INFORMATION: n = gm

<400> SEQUENCE: 70
cuacunnanc accnuuaan 19

<210> SEQ ID NO 71
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 71
cnacngnagc accgnuaag 19

<210> SEQ ID NO 72
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (15)...(15)
<223> OTHER INFORMATION: n = um

<400> SEQUENCE: 72
cnacngganc accgnuaag 19

<210> SEQ ID NO 73
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 73
cnacnggagc accgnuaan 19

<210> SEQ ID NO 74
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(15)
<223> OTHER INFORMATION: n = um

<400> SEQUENCE: 74
cnacngnanc accgnuaag 19

<210> SEQ ID NO 75
<211> LENGTH: 19

<212> TYPE: RNA
<213> ORGANISM: Artificial Sequence
<220> FEATURE:
<223> OTHER INFORMATION: synthetic 2'-OMe-modified APOC3 siRNA sense
strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 75
cnacngnagc accgnuaan 19

<210> SEQ ID NO 76
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 76
cnacngganc accgnuaan 19

<210> SEQ ID NO 77
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (15)...(16)
<223> OTHER INFORMATION: n = um
<220> FEATURE:
<221> NAME/KEY: modified_base
<222> LOCATION: (19)...(19)
<223> OTHER INFORMATION: n = gm

```
<400> SEQUENCE: 77

cnacngganc accgnnaan                                           19

<210> SEQ ID NO 78
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (6)...(9)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 78

cnacunganc accgnuaag                                           19

<210> SEQ ID NO 79
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (6)...(9)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 79

cnacunganc accgunaag                                           19

<210> SEQ ID NO 80
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 80

cnacngnagc accnunaag                                           19
```

<210> SEQ ID NO 81
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (9)...(14)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 81
cnacngganc accnunaag 19

<210> SEQ ID NO 82
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (14)...(14)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 82
cnacnggagc accnunaan 19

<210> SEQ ID NO 83
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 83
cnacngnanc accnunaag 19

<210> SEQ ID NO 84
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 84
cnacngnanc accnnuaag 19

<210> SEQ ID NO 85
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 85
cnacngnanc accgnuaan 19

<210> SEQ ID NO 86
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 86
cnacngnagc accgunaag 19

<210> SEQ ID NO 87
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 87
cnacngganc accgunaag 19

<210> SEQ ID NO 88
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 88
cnacnggagc accgunaan 19

<210> SEQ ID NO 89
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 89
cnacngnanc accgunaag 19

<210> SEQ ID NO 90
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense

```
      strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 90

cnacngnagc accgunaan                                                19


<210> SEQ ID NO 91
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 91

cnacngganc accgunaan                                                19


<210> SEQ ID NO 92
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 92

cnacngnanc accgunaan                                                19
```

<210> SEQ ID NO 93
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 93
cuacngnanc accgnuaag 19

<210> SEQ ID NO 94
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 94
cuacngnagc accgnuaan 19

<210> SEQ ID NO 95
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 95
cuacngganc accgnuaan 19

<210> SEQ ID NO 96
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 96
cuacngnanc accgnuaan 19

<210> SEQ ID NO 97
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 97
cuacngnanc accnnuaan 19

<210> SEQ ID NO 98
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(9)
<223> OTHER INFORMATION: n = gm

```
<220> FEATURE:
<221> NAME/KEY: modified_base
<222> LOCATION: (15)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 98

cuacngnanc accgnnaan                                                19


<210> SEQ ID NO 99
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (6)...(9)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 99

cuacnnganc accgnuaan                                                19


<210> SEQ ID NO 100
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 100

cuacngnanc accgunaag                                                19


<210> SEQ ID NO 101
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (5)...(5)
<223> OTHER INFORMATION: n = um
```

```
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 101

cuacngnagc accgunaan                                                19


<210> SEQ ID NO 102
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 102

cuacngganc accgunaan                                                19


<210> SEQ ID NO 103
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 103

cuacngnanc accgunaan                                                19


<210> SEQ ID NO 104
<211> LENGTH: 19
<212> TYPE: RNA
<213> ORGANISM: Artificial Sequence
```

-continued

<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (6)...(9)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 104
cnacunganc accgnuaan 19

<210> SEQ ID NO 105
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (6)...(9)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 105
cnacunganc accgunaan 19

<210> SEQ ID NO 106
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 106
cnacngnagc accnunaan 19

<210> SEQ ID NO 107
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (9)...(14)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 107
cnacngganc accnunaan 19

<210> SEQ ID NO 108
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 108
cnacngnanc accnunaan 19

<210> SEQ ID NO 109
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 109
cuacngnagc accnnuaan 19

<210> SEQ ID NO 110
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (7)...(14)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 110
cuacngnanc accnnuaag 19

<210> SEQ ID NO 111
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(11)
<223> OTHER INFORMATION: n = um

<400> SEQUENCE: 111
cngaagnugg ncugaccuc 19

<210> SEQ ID NO 112
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(11)
<223> OTHER INFORMATION: n = um

<400> SEQUENCE: 112
cngaagungg ncugaccuc 19

<210> SEQ ID NO 113
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:

-continued

<221> NAME/KEY: modified_base
<222> LOCATION: (2)...(13)
<223> OTHER INFORMATION: n = um

<400> SEQUENCE: 113
cngaagnugg ncngaccuc 19

<210> SEQ ID NO 114
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (2)...(13)
<223> OTHER INFORMATION: n = um

<400> SEQUENCE: 114
cngaagungg ncngaccuc 19

<210> SEQ ID NO 115
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (2)...(18)
<223> OTHER INFORMATION: n = um

<400> SEQUENCE: 115
cngaagnugg ncngaccnc 19

<210> SEQ ID NO 116
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (2)...(18)
<223> OTHER INFORMATION: n = um

<400> SEQUENCE: 116
cngaagungg ncngaccnc 19

<210> SEQ ID NO 117
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (2)...(18)
<223> OTHER INFORMATION: n = um

<400> SEQUENCE: 117
cngaagnngg ncngaccnc 19

<210> SEQ ID NO 118
<211> LENGTH: 19

<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (7)...(18)
<223> OTHER INFORMATION: n = um

<400> SEQUENCE: 118
cugaagnugg ncngaccnc 19

<210> SEQ ID NO 119
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (8)...(18)
<223> OTHER INFORMATION: n = um

<400> SEQUENCE: 119
cugaagungg ncngaccnc 19

<210> SEQ ID NO 120
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (7)...(18)
<223> OTHER INFORMATION: n = um

<400> SEQUENCE: 120
cugaagnngg ncngaccnc 19

<210> SEQ ID NO 121
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(9)
<223> OTHER INFORMATION: n = gm

<400> SEQUENCE: 121
cunaanuung ucugaccuc 19

<210> SEQ ID NO 122
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(10)
<223> OTHER INFORMATION: n = gm

<400> SEQUENCE: 122

-continued cunaanuugn ucugaccuc 19

<210> SEQ ID NO 123
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(14)
<223> OTHER INFORMATION: n = gm

<400> SEQUENCE: 123
cunaanuung ucunaccuc 19

<210> SEQ ID NO 124
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(14)
<223> OTHER INFORMATION: n = gm

<400> SEQUENCE: 124
cunaanuugn ucunaccuc 19

<210> SEQ ID NO 125
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(14)
<223> OTHER INFORMATION: n = gm

<400> SEQUENCE: 125
cunaanuunn ucunaccuc 19

<210> SEQ ID NO 126
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (6)...(14)
<223> OTHER INFORMATION: n = gm

<400> SEQUENCE: 126
cugaanuugn ucunaccuc 19

<210> SEQ ID NO 127
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand

```
<220> FEATURE:
<221> NAME/KEY: modified_base
<222> LOCATION: (6)...(14)
<223> OTHER INFORMATION: n = gm

<400> SEQUENCE: 127

cugaanuung ucunaccuc                                                    19


<210> SEQ ID NO 128
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
      antisense strand
<220> FEATURE:
<221> NAME/KEY: modified_base
<222> LOCATION: (2)...(7)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (11)...(11)
<223> OTHER INFORMATION: n = um

<400> SEQUENCE: 128

cngaagnung ncugaccuc                                                    19


<210> SEQ ID NO 129
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
      antisense strand
<220> FEATURE:
<221> NAME/KEY: modified_base
<222> LOCATION: (2)...(11)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 129

cngaagnugg ncunaccuc                                                    19


<210> SEQ ID NO 130
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
      antisense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (13)...(18)
<223> OTHER INFORMATION: n = um
```

<400> SEQUENCE: 130
cunaagungn ucngaccnc 19

<210> SEQ ID NO 131
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (2)...(7)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (11)...(11)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 131
cngaagnung ncunaccuc 19

<210> SEQ ID NO 132
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (7)...(18)
<223> OTHER INFORMATION: n = um

<400> SEQUENCE: 132
cunaagnugg ncngaccnc 19

<210> SEQ ID NO 133
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (7)...(7)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 133
cugaagnung ncngaccnc 19

<210> SEQ ID NO 134
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (7)...(7)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 134
cunaagnung ncngaccnc 19

<210> SEQ ID NO 135
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (7)...(7)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 135
cugaagnugn ncngaccnc 19

<210> SEQ ID NO 136
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (7)...(13)
<223> OTHER INFORMATION: n = um
<220> FEATURE:
<221> NAME/KEY: modified_base
<222> LOCATION: (14)...(14)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 136
cugaagnugg ncnnaccnc 19

<210> SEQ ID NO 137
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (7)...(7)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 137
cunaagnugn ncngaccnc 19

<210> SEQ ID NO 138
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (8)...(18)
<223> OTHER INFORMATION: n = um

<400> SEQUENCE: 138
cunaagungg ncngaccnc 19

<210> SEQ ID NO 139
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 139
cugaagunng ncngaccnc 19

<210> SEQ ID NO 140
<211> LENGTH: 19

```
<212> TYPE: RNA
<213> ORGANISM: Artificial Sequence
<220> FEATURE:
<223> OTHER INFORMATION: synthetic 2'-OMe-modified APOC3 siRNA
      antisense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 140

cunaagunng ncngaccnc                                                    19


<210> SEQ ID NO 141
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
      antisense strand
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 141

cugaagungn ncngaccnc                                                    19


<210> SEQ ID NO 142
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
      antisense strand
<220> FEATURE:
<221> NAME/KEY: modified_base
<222> LOCATION: (8)...(13)
<223> OTHER INFORMATION: n = um
<220> FEATURE:
<221> NAME/KEY: modified_base
<222> LOCATION: (14)...(14)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 142

cugaagungg ncnnaccnc                                                    19


<210> SEQ ID NO 143
<211> LENGTH: 19
```

-continued

<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (10)...(10)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 143
cunaagungn ncngaccnc 19

<210> SEQ ID NO 144
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(9)
<223> OTHER INFORMATION: n = gm
<220> FEATURE:
<221> NAME/KEY: modified_base
<222> LOCATION: (13)...(18)
<223> OTHER INFORMATION: n = um

<400> SEQUENCE: 144
cunaanuung ucngaccnc 19

<210> SEQ ID NO 145
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(9)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 145
cunaanuung ncugaccnc 19

<210> SEQ ID NO 146
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
antisense strand
<220> FEATURE:
<221> NAME/KEY: modified_base
<222> LOCATION: (3)...(9)

<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 146
cunaanuung ncngaccnc 19

<210> SEQ ID NO 147
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 147
cunaaguung ncngaccnc 19

<210> SEQ ID NO 148
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(6)
<223> OTHER INFORMATION: n = gm
<220> FEATURE:
<221> NAME/KEY: modified_base
<222> LOCATION: (11)...(18)
<223> OTHER INFORMATION: n = um

<400> SEQUENCE: 148
cunaanuugg ncngaccnc 19

<210> SEQ ID NO 149
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (11)...(18)
<223> OTHER INFORMATION: n = um

<400> SEQUENCE: 149
cugaaguugg ncngaccnc 19

<210> SEQ ID NO 150
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(10)
<223> OTHER INFORMATION: n = gm
<220> FEATURE:
<221> NAME/KEY: modified_base
<222> LOCATION: (13)...(18)
<223> OTHER INFORMATION: n = um

<400> SEQUENCE: 150
cunaanuugn ucngaccnc 19

<210> SEQ ID NO 151
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(16)
<223> OTHER INFORMATION: n = um

<400> SEQUENCE: 151
gaggncagac caacnncag 19

<210> SEQ ID NO 152
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(8)
<223> OTHER INFORMATION: n = gm

<400> SEQUENCE: 152
nangucanac caacuucag 19

<210> SEQ ID NO 153
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(8)
<223> OTHER INFORMATION: n = gm

<400> SEQUENCE: 153
nagnucanac caacuucag 19

<210> SEQ ID NO 154
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(19)
<223> OTHER INFORMATION: n = gm

<400> SEQUENCE: 154
nangucagac caacuucan 19

<210> SEQ ID NO 155
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(19)
<223> OTHER INFORMATION: n = gm

<400> SEQUENCE: 155
nagnucagac caacuucan 19

<210> SEQ ID NO 156
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(19)
<223> OTHER INFORMATION: n = gm

<400> SEQUENCE: 156
naggucanac caacuucan 19

<210> SEQ ID NO 157
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(8)
<223> OTHER INFORMATION: n = gm

<400> SEQUENCE: 157
nannucanac caacuucag 19

<210> SEQ ID NO 158
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(19)
<223> OTHER INFORMATION: n = gm

<400> SEQUENCE: 158
nannucagac caacuucan 19

<210> SEQ ID NO 159
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(19)

<223> OTHER INFORMATION: n = gm

<400> SEQUENCE: 159
nannucanac caacuucan 19

<210> SEQ ID NO 160
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 160
naggncanac caacnucag 19

<210> SEQ ID NO 161
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 161
naggncanac caacnucan 19

<210> SEQ ID NO 162
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)

-continued

<223> OTHER INFORMATION: n = gm
<220> FEATURE:
<221> NAME/KEY: modified_base
<222> LOCATION: (5)...(15)
<223> OTHER INFORMATION: n = um

<400> SEQUENCE: 162
nangncagac caacnucag 19

<210> SEQ ID NO 163
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antsense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 163
nangncanac caacnucag 19

<210> SEQ ID NO 164
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 164
nangncagac caacnucan 19

<210> SEQ ID NO 165
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(4)
<223> OTHER INFORMATION: n = gm
<220> FEATURE:
<221> NAME/KEY: modified_base
<222> LOCATION: (5)...(15)

<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 165
nagnncagac caacnucan 19

<210> SEQ ID NO 166
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(4)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 166
nagnncanac caacnucan 19

<210> SEQ ID NO 167
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 167
nangncanac caacnucan 19

<210> SEQ ID NO 168
<211> LENGTH: 19

<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 168
naggncanac caacuncag 19

<210> SEQ ID NO 169
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 169
naggncanac caacuncan 19

<210> SEQ ID NO 170
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(16)
<223> OTHER INFORMATION: n = um

<400> SEQUENCE: 170
nangncagac caacuncag 19

<210> SEQ ID NO 171
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 171
gangncagac caacnncan 19

<210> SEQ ID NO 172
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 172
nangncanac caacuncag 19

<210> SEQ ID NO 173
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 173
nangncagac caacuncan 19

<210> SEQ ID NO 174
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(4)
<223> OTHER INFORMATION: n = gm
<220> FEATURE:
<221> NAME/KEY: modified_base
<222> LOCATION: (5)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 174
nagnncagac caacuncan 19

<210> SEQ ID NO 175
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(4)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 175
nagnncanac caacuncan 19

<210> SEQ ID NO 176
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 176
nangncanac caacuncan 19

<210> SEQ ID NO 177
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 177
gaggncanac caacnucag 19

<210> SEQ ID NO 178
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 178
gaggncanac caacnucan 19

<210> SEQ ID NO 179
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(15)
<223> OTHER INFORMATION: n = um

<400> SEQUENCE: 179
gangncagac caacnucag 19

<210> SEQ ID NO 180
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 180
gangncanac caacnucag 19

<210> SEQ ID NO 181
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 181
gangncagac caacnucan 19

<210> SEQ ID NO 182
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (5)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 182
gagnncagac caacnucan 19

<210> SEQ ID NO 183
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 183
gagnncanac caacnucan 19

<210> SEQ ID NO 184
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 184
gaggncanac caacuncag 19

<210> SEQ ID NO 185
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 185
gaggncanac caacuncan 19

<210> SEQ ID NO 186
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(16)
<223> OTHER INFORMATION: n = um

<400> SEQUENCE: 186
gangncagac caacuncag 19

<210> SEQ ID NO 187
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 187
gangncanac caacuncag 19

<210> SEQ ID NO 188
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 188
gangncagac caacuncan 19

<210> SEQ ID NO 189
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (5)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 189
gagnncagac caacuncan 19

<210> SEQ ID NO 190
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 190
gagnncanac caacuncan 19

<210> SEQ ID NO 191
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense strand

```
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (5)...(16)
<223> OTHER INFORMATION: n = um

<400> SEQUENCE: 191

nangncagac caacnncag                                               19


<210> SEQ ID NO 192
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (15)...(16)
<223> OTHER INFORMATION: n = um

<400> SEQUENCE: 192

gangncanac caacnncag                                               19


<210> SEQ ID NO 193
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA
      antisense strand
<220> FEATURE:
<221> NAME/KEY: modified_base
<222> LOCATION: (2)...(15)
<223> OTHER INFORMATION: n = um

<400> SEQUENCE: 193

cnuguccnua acggngcuc                                               19


<210> SEQ ID NO 194
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
      strand
<220> FEATURE:
<221> NAME/KEY: modified_base
<222> LOCATION: (2)...(18)
<223> OTHER INFORMATION: n = um

<400> SEQUENCE: 194

cnuguccnua acggugcnc                                               19


<210> SEQ ID NO 195
<211> LENGTH: 19
```

<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(18)
<223> OTHER INFORMATION: n = um

<400> SEQUENCE: 195
cnuguccnua acggngcnc 19

<210> SEQ ID NO 196
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(15)
<223> OTHER INFORMATION: n = um

<400> SEQUENCE: 196
cunguccnua acggngcuc 19

<210> SEQ ID NO 197
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(15)
<223> OTHER INFORMATION: n = um

<400> SEQUENCE: 197
cunguccuna acggngcuc 19

<210> SEQ ID NO 198
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(18)
<223> OTHER INFORMATION: n = um

<400> SEQUENCE: 198
cunguccnua acggugcnc 19

<210> SEQ ID NO 199
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(18)
<223> OTHER INFORMATION: n = um

<400> SEQUENCE: 199
cunguccuna acggugcnc 19

<210> SEQ ID NO 200
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(18)
<223> OTHER INFORMATION: n = um

<400> SEQUENCE: 200
cunguccnua acggngcnc 19

<210> SEQ ID NO 201
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(18)
<223> OTHER INFORMATION: n = um

<400> SEQUENCE: 201
cunguccuna acggngcnc 19

<210> SEQ ID NO 202
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(15)
<223> OTHER INFORMATION: n = um

<400> SEQUENCE: 202
cunguccnna acggngcuc 19

<210> SEQ ID NO 203
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(18)
<223> OTHER INFORMATION: n = um

<400> SEQUENCE: 203
cunguccnna acggugcnc 19

<210> SEQ ID NO 204
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(18)
<223> OTHER INFORMATION: n = um

<400> SEQUENCE: 204
cunguccnna acggngcnc 19

<210> SEQ ID NO 205
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (8)...(18)
<223> OTHER INFORMATION: n = um

<400> SEQUENCE: 205
cuuguccnna acggngcnc 19

<210> SEQ ID NO 206
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (2)...(18)
<223> OTHER INFORMATION: n = um

<400> SEQUENCE: 206
cnnguccnna acggngcnc 19

<210> SEQ ID NO 207
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(16)
<223> OTHER INFORMATION: n = gm

<400> SEQUENCE: 207
cuunuccuua acnguncuc 19

<210> SEQ ID NO 208
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(16)
<223> OTHER INFORMATION: n = gm

<400> SEQUENCE: 208
cuunuccuua acgnuncuc 19

<210> SEQ ID NO 209

<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (13)...(16)
<223> OTHER INFORMATION: n = gm

<400> SEQUENCE: 209
cuuguccuua acnnuncuc 19

<210> SEQ ID NO 210
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(16)
<223> OTHER INFORMATION: n = gm

<400> SEQUENCE: 210
cuunuccuua acnnuncuc 19

<210> SEQ ID NO 211
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(8)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 211
cunguccnua acngngcuc 19

<210> SEQ ID NO 212
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 212
cunguccuna acngngcuc 19

<210> SEQ ID NO 213
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(8)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 213
cunguccnua acngugcnc 19

<210> SEQ ID NO 214
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (8)...(18)
<223> OTHER INFORMATION: n = um

<400> SEQUENCE: 214
cuunuccnua acggngcnc 19

<210> SEQ ID NO 215
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 215
cuunuccnua acngngcnc 19

-continued

<210> SEQ ID NO 216
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(8)
<223> OTHER INFORMATION: n = um
<220> FEATURE:
<221> NAME/KEY: modified_base
<222> LOCATION: (13)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 216
cunguccnua acnguncnc 19

<210> SEQ ID NO 217
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 217
cunguccuna acngugcnc 19

<210> SEQ ID NO 218
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(8)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 218
cunguccnua acngngcnc 19

<210> SEQ ID NO 219
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 219
cunguccuna acngngcnc 19

<210> SEQ ID NO 220
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (13)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 220
cunguccuna acnguncnc 19

<210> SEQ ID NO 221
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 221
cunguccnna acngngcuc 19

<210> SEQ ID NO 222
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:

<221> NAME/KEY: modified_base
<222> LOCATION: (3)...(9)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 222
cunguccnna acgguncnc 19

<210> SEQ ID NO 223
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 223
cunguccnna acngngcnc 19

<210> SEQ ID NO 224
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
strand
<220> FEATURE:
<221> NAME/KEY: modified_base
<222> LOCATION: (8)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 224
cuuguccnna acngngcnc 19

<210> SEQ ID NO 225
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense
strand
<220> FEATURE:
<221> NAME/KEY: modified_base
<222> LOCATION: (2)...(9)
<223> OTHER INFORMATION: n = um
<220> FEATURE:

<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 225
cnnguccnna acngngcnc 19

<210> SEQ ID NO 226
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (13)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 226
cunguccnna acnguncnc 19

<210> SEQ ID NO 227
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (3)...(9)
<223> OTHER INFORMATION: n = um
<220> FEATURE:
<221> NAME/KEY: modified_base
<222> LOCATION: (14)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 227
cunguccnna acgnuncnc 19

<210> SEQ ID NO 228
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (8)...(9)
<223> OTHER INFORMATION: n = um
<220> FEATURE:

<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 228
cuunuccnna acngngcnc 19

<210> SEQ ID NO 229
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(18)
<223> OTHER INFORMATION: n = um

<400> SEQUENCE: 229
cuugnccnua acggngcnc 19

<210> SEQ ID NO 230
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(8)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 230
cuugnccnua acngngcnc 19

<210> SEQ ID NO 231
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(8)
<223> OTHER INFORMATION: n = um
<220> FEATURE:
<221> NAME/KEY: modified_base
<222> LOCATION: (14)...(14)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 231
cuugnccnua acgnngcnc 19

<210> SEQ ID NO 232
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(15)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 232
cuugnccnua acggnncnc 19

<210> SEQ ID NO 233
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(18)
<223> OTHER INFORMATION: n = um

<400> SEQUENCE: 233
cuugnccnna acggngcnc 19

<210> SEQ ID NO 234
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(18)
<223> OTHER INFORMATION: n = um

<400> SEQUENCE: 234
cuugnccnna acngngcnc 19

<210> SEQ ID NO 235
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(9)
<223> OTHER INFORMATION: n = um
<220> FEATURE:
<221> NAME/KEY: modified_base
<222> LOCATION: (13)...(13)
<223> OTHER INFORMATION: n = gm
<220> FEATURE:
<221> NAME/KEY: modified_base
<222> LOCATION: (15)...(15)
<223> OTHER INFORMATION: n = um

<400> SEQUENCE: 235
cuugnccnna acngngcuc 19

<210> SEQ ID NO 236
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (5)...(9)
<223> OTHER INFORMATION: n = um
<220> FEATURE:
<221> NAME/KEY: modified_base
<222> LOCATION: (13)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 236
cuugnccnna acnguncnc 19

<210> SEQ ID NO 237
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (5)...(18)
<223> OTHER INFORMATION: n = um

<400> SEQUENCE: 237
cuunnccnua acggngcnc 19

<210> SEQ ID NO 238
<211> LENGTH: 19
<212> TYPE: RNA
<213> ORGANISM: Artificial Sequence
<220> FEATURE:
<223> OTHER INFORMATION: synthetic 2'-OMe-modified APOC3 siRNA antisense strand
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (5)...(18)
<223> OTHER INFORMATION: n = um

<400> SEQUENCE: 238
cuunnccuna acggngcnc 19

-continued

<210> SEQ ID NO 239
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (9)...(10)
<223> OTHER INFORMATION: n = um

<400> SEQUENCE: 239
gagcaccgnn aaggacaag 19

<210> SEQ ID NO 240
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(19)
<223> OTHER INFORMATION: n = gm

<400> SEQUENCE: 240
nancaccnuu aangacaan 19

<210> SEQ ID NO 241
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(19)
<223> OTHER INFORMATION: n = gm

<400> SEQUENCE: 241
nancaccnuu aagnacaan 19

<210> SEQ ID NO 242
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(19)
<223> OTHER INFORMATION: n = gm

<400> SEQUENCE: 242
gancaccnuu aangacaan 19

<210> SEQ ID NO 243
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base -continued
<222> LOCATION: (3)...(19)
<223> OTHER INFORMATION: n = gm

<400> SEQUENCE: 243
gancaccnuu aagnacaan 19

<210> SEQ ID NO 244
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(14)
<223> OTHER INFORMATION: n = gm

<400> SEQUENCE: 244
gancaccnuu aannacaag 19

<210> SEQ ID NO 245
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(14)
<223> OTHER INFORMATION: n = gm

<400> SEQUENCE: 245
nancaccnuu aannacaag 19

<210> SEQ ID NO 246
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(13)
<223> OTHER INFORMATION: n = gm

<400> SEQUENCE: 246
nancaccgnu aangacaag 19

<210> SEQ ID NO 247
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:

<221> NAME/KEY: modified_base
<222> LOCATION: (9)...(9)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 247
nancaccgnu aagnacaag 19

<210> SEQ ID NO 248
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 248
gancaccgnu aangacaan 19

<210> SEQ ID NO 249
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 249
gancaccgnu aagnacaan 19

<210> SEQ ID NO 250
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:

<221> NAME/KEY: modified_base
<222> LOCATION: (13)...(19)
<223> OTHER INFORMATION: n = gm

<400> SEQUENCE: 250
nancaccgnu aangacaan 19

<210> SEQ ID NO 251
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 251
nancaccgnu aagnacaan 19

<210> SEQ ID NO 252
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 252
nancaccgnu aannacaan 19

<210> SEQ ID NO 253
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(8)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 253
gancaccnnu aagnacaag 19

<210> SEQ ID NO 254
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(8)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 254
gancaccnnu aagnacaan 19

<210> SEQ ID NO 255
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (13)...(13)
<223> OTHER INFORMATION: n = gm

<400> SEQUENCE: 255
nancaccgnn aangacaag 19

<210> SEQ ID NO 256
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 256
nancaccgnn aagnacaag 19

<210> SEQ ID NO 257
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 257
gancaccgnn aangacaan 19

<210> SEQ ID NO 258
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 258
gancaccgnn aagnacaan 19

<210> SEQ ID NO 259
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 259
nancaccgnn aangacaan 19

<210> SEQ ID NO 260
<211> LENGTH: 19
<212> TYPE: DNA

<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 260
nancaccgnn aagnacaan 19

<210> SEQ ID NO 261
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 261
nancaccgnn aannacaan 19

<210> SEQ ID NO 262
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(13)
<223> OTHER INFORMATION: n = gm

<400> SEQUENCE: 262
nancaccgun aangacaag 19

<210> SEQ ID NO 263
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 263
nancaccgun aagnacaag 19

<210> SEQ ID NO 264
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 264
gancaccgun aangacaan 19

<210> SEQ ID NO 265
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 265
gancaccgun aagnacaan 19

<210> SEQ ID NO 266
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 266
nancaccgun aangacaan 19

<210> SEQ ID NO 267
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 267
nancaccgun aagnacaan 19

<210> SEQ ID NO 268
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 268
nancaccgun aannacaan 19

<210> SEQ ID NO 269
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (3)...(8)
<223> OTHER INFORMATION: n = gm
<220> FEATURE:
<221> NAME/KEY: modified_base
<222> LOCATION: (10)...(10)
<223> OTHER INFORMATION: n = um

```
<220> FEATURE:
<221> NAME/KEY: modified_base
<222> LOCATION: (14)...(14)
<223> OTHER INFORMATION: n = gm

<400> SEQUENCE: 269

gancaccnun aagnacaag                                              19


<210> SEQ ID NO 270
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (3)...(8)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 270

gancaccnun aagnacaan                                              19


<210> SEQ ID NO 271
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 271

nagcaccgnu aangacaan                                              19


<210> SEQ ID NO 272
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (14)...(19)
<223> OTHER INFORMATION: n = gm
```

<400> SEQUENCE: 272
nagcaccgnu aagnacaan 19

<210> SEQ ID NO 273
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(14)
<223> OTHER INFORMATION: n = gm

<400> SEQUENCE: 273
nagcaccgnu aannacaag 19

<210> SEQ ID NO 274
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 274
nagcaccgnu aannacaan 19

<210> SEQ ID NO 275
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(8)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 275
nagcaccnnu aangacaan 19

<210> SEQ ID NO 276
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (1)...(8)
<223> OTHER INFORMATION: n = gm
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 276
nagcaccnnu aagnacaan 19

<210> SEQ ID NO 277
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 277
gagcaccnun aangacaan 19

<210> SEQ ID NO 278
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 278
gagcaccnun aagnacaan 19

<210> SEQ ID NO 279
<211> LENGTH: 19

```
<212> TYPE: DNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(14)
<223> OTHER INFORMATION: n = gm

<400> SEQUENCE: 279

gagcaccnun aannacaag                                               19


<210> SEQ ID NO 280
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 280

gagcaccnun aannacaan                                               19


<210> SEQ ID NO 281
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 281

gagcaccgnn aangacaan                                               19


<210> SEQ ID NO 282
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
      strand
<220> FEATURE:
<221> NAME/KEY: modified_base
<222> LOCATION: (9)...(10)
```

<223> OTHER INFORMATION: n = um
<220> FEATURE:
<221> NAME/KEY: modified_base
<222> LOCATION: (14)...(19)
<223> OTHER INFORMATION: n = gm

<400> SEQUENCE: 282
gagcaccgnn aagnacaan 19

<210> SEQ ID NO 283
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
strand
<220> FEATURE:
<221> NAME/KEY: modified_base
<222> LOCATION: (1)...(8)
<223> OTHER INFORMATION: n = gm
<220> FEATURE:
<221> NAME/KEY: modified_base
<222> LOCATION: (9)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 283
nancaccnnn aannacaan 19

<210> SEQ ID NO 284
<211> LENGTH: 19
<212> TYPE: DNA
<213> ORGANISM: Artificial Sequence
<220> FEATURE:
<223> OTHER INFORMATION: synthetic 2'-OMe-modified APOC3 siRNA sense
strand
<220> FEATURE:
<221> NAME/KEY: modified_base
<222> LOCATION: (3)...(3)
<223> OTHER INFORMATION: n = gm
<220> FEATURE:
<221> NAME/KEY: modified_base
<222> LOCATION: (10)...(10)
<223> OTHER INFORMATION: n = um
<220> FEATURE:
<221> NAME/KEY: modified_base
<222> LOCATION: (13)...(19)
<223> OTHER INFORMATION: n = gm

<400> SEQUENCE: 284
gancaccgun aannacaan 19

<210> SEQ ID NO 285
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 285
ugcucaguuc aucccuaga 19

<210> SEQ ID NO 286
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 286
ucuagggaug aacugagca 19

<210> SEQ ID NO 287
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 287
gcucaguuca ucccuagag 19

<210> SEQ ID NO 288
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 288
cucuagggau gaacugagc 19

<210> SEQ ID NO 289
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 289
cucaguucau cccuagagg 19

<210> SEQ ID NO 290
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 290
ccucuaggga ugaacugag 19

<210> SEQ ID NO 291
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 291
ucaguucauc ccuagaggc 19

<210> SEQ ID NO 292
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 292
gccucuaggg augaacuga 19

<210> SEQ ID NO 293

<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 293
caguucaucc cuagaggca 19

<210> SEQ ID NO 294
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 294
ugccucuagg gaugaacug 19

<210> SEQ ID NO 295
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 295
aguucauccc uagaggcag 19

<210> SEQ ID NO 296
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 296
cugccucuag ggaugaacu 19

<210> SEQ ID NO 297
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 297
guucaucccu agaggcagc 19

<210> SEQ ID NO 298
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 298
gcugccucua gggaugaac 19

<210> SEQ ID NO 299
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 299
uucaucccua gaggcagcu 19

<210> SEQ ID NO 300
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 300
agcugccucu agggaugaa 19

<210> SEQ ID NO 301
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 301
ucaucccuag aggcagcug 19

<210> SEQ ID NO 302
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 302
cagcugccuc uagggauga 19

<210> SEQ ID NO 303
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 303
caucccuaga ggcagcugc 19

<210> SEQ ID NO 304
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 304
gcagcugccu cuagggaug 19

<210> SEQ ID NO 305
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 305
aucccuagag gcagcugcu 19

<210> SEQ ID NO 306
<211> LENGTH: 19
<212> TYPE: RNA

<213> ORGANISM: Artificial Sequence
<220> FEATURE:
<223> OTHER INFORMATION: synthetic APOC3 siRNA antisense strand

<400> SEQUENCE: 306
agcagcugcc ucuagggau 19

<210> SEQ ID NO 307
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 307
ucccuagagg cagcugcuc 19

<210> SEQ ID NO 308
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 308
gagcagcugc cucuaggga 19

<210> SEQ ID NO 309
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 309
cccuagaggc agcugcucc 19

<210> SEQ ID NO 310
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 310
ggagcagcug ccucuaggg 19

<210> SEQ ID NO 311
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 311
ccuagaggca gcugcucca 19

<210> SEQ ID NO 312
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 312
uggagcagcu gccucuagg 19

<210> SEQ ID NO 313
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 313
cuagaggcag cugcuccag 19

<210> SEQ ID NO 314
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 314
cuggagcagc ugccucuag 19

<210> SEQ ID NO 315
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 315
uagaggcagc ugcuccagg 19

<210> SEQ ID NO 316
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 316
ccuggagcag cugccucua 19

<210> SEQ ID NO 317
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 317
agaggcagcu gcuccagga 19

<210> SEQ ID NO 318
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 318
uccuggagca gcugccucu 19

<210> SEQ ID NO 319
<211> LENGTH: 19
<212> TYPE: RNA
<213> ORGANISM: Artificial Sequence
<220> FEATURE:

-continued

<223> OTHER INFORMATION: synthetic APOC3 siRNA target or sense strand

<400> SEQUENCE: 319
gaggcagcug cuccaggaa 19

<210> SEQ ID NO 320
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 320
uuccuggagc agcugccuc 19

<210> SEQ ID NO 321
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 321
aggcagcugc uccaggaac 19

<210> SEQ ID NO 322
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 322
guuccuggag cagcugccu 19

<210> SEQ ID NO 323
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 323
ggcagcugcu ccaggaaca 19

<210> SEQ ID NO 324
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 324
uguuccugga gcagcugcc 19

<210> SEQ ID NO 325
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 325
gcagcugcuc caggaacag 19

<210> SEQ ID NO 326
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 326
cuguuccugg agcagcugc 19

<210> SEQ ID NO 327
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 327
cagcugcucc aggaacaga 19

<210> SEQ ID NO 328
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 328
ucuguuccug gagcagcug 19

<210> SEQ ID NO 329
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 329
agcugcucca ggaacagag 19

<210> SEQ ID NO 330
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 330
cucuguuccu ggagcagcu 19

<210> SEQ ID NO 331
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 331
gcugcuccag gaacagagg 19

<210> SEQ ID NO 332
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 332
ccucuguucc uggagcagc 19

<210> SEQ ID NO 333
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 333
cugcuccagg aacagaggu 19

<210> SEQ ID NO 334
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 334
accucuguuc cuggagcag 19

<210> SEQ ID NO 335
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 335
ugcuccagga acagaggug 19

<210> SEQ ID NO 336
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 336
caccucuguu ccuggagca 19

<210> SEQ ID NO 337
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 337
gcuccaggaa cagaggugc 19

<210> SEQ ID NO 338
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 338
gcaccucugu uccuggagc 19

<210> SEQ ID NO 339
<211> LENGTH: 19

<212> TYPE: RNA
<213> ORGANISM: Artificial Sequence
<220> FEATURE:
<223> OTHER INFORMATION: synthetic APOC3 siRNA target or sense strand

<400> SEQUENCE: 339
cuccaggaac agaggugcc 19

<210> SEQ ID NO 340
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 340
ggcaccucug uuccuggag 19

<210> SEQ ID NO 341
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 341
uccaggaaca gaggugcca 19

<210> SEQ ID NO 342
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 342
uggcaccucu guuccugga 19

<210> SEQ ID NO 343
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 343
ccaggaacag aggugccau 19

<210> SEQ ID NO 344
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 344
auggcaccuc uguuccugg 19

<210> SEQ ID NO 345
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 345

-continued caggaacaga ggugccaug 19

<210> SEQ ID NO 346
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 346
cauggcaccu cuguuccug 19

<210> SEQ ID NO 347
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 347
aggaacagag gugccaugc 19

<210> SEQ ID NO 348
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 348
gcauggcacc ucuguuccu 19

<210> SEQ ID NO 349
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 349
ggaacagagg ugccaugca 19

<210> SEQ ID NO 350
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 350
ugcauggcac cucuguucc 19

<210> SEQ ID NO 351
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 351
gaacagaggu gccaugcag 19

<210> SEQ ID NO 352
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 352
cugcauggca ccucuguuc 19

<210> SEQ ID NO 353
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 353
aacagaggug ccaugcagc 19

<210> SEQ ID NO 354
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 354
gcugcauggc accucuguu 19

<210> SEQ ID NO 355
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 355
acagaggugc caugcagcc 19

<210> SEQ ID NO 356
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 356
ggcugcaugg caccucugu 19

<210> SEQ ID NO 357
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 357
cagaggugcc augcagccc 19

<210> SEQ ID NO 358
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 358
gggcugcaug gcaccucug 19

<210> SEQ ID NO 359
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 359
agaggugcca ugcagcccc 19

<210> SEQ ID NO 360
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 360
ggggcugcau ggcaccucu 19

<210> SEQ ID NO 361
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 361
gaggugccau gcagccccg 19

<210> SEQ ID NO 362
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 362
cggggcugca uggcaccuc 19

<210> SEQ ID NO 363
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 363
aggugccaug cagccccgg 19

<210> SEQ ID NO 364
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 364
ccggggcugc auggcaccu 19

<210> SEQ ID NO 365
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 365
ggugccaugc agccccggg 19

<210> SEQ ID NO 366
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 366
cccggggcug cauggcacc 19

<210> SEQ ID NO 367
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 367
gugccaugca gccccgggu 19

<210> SEQ ID NO 368
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 368
acccggggcu gcauggcac 19

<210> SEQ ID NO 369
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 369
ugccaugcag ccccgggua 19

<210> SEQ ID NO 370
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 370
uacccggggc ugcauggca 19

<210> SEQ ID NO 371
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 371
gccaugcagc cccggguac 19

<210> SEQ ID NO 372

<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 372
guacccgggg cugcauggc 19

<210> SEQ ID NO 373
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 373
ccaugcagcc ccggguacu 19

<210> SEQ ID NO 374
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 374
aguacccggg gcugcaugg 19

<210> SEQ ID NO 375
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 375
caugcagccc cggguacuc 19

<210> SEQ ID NO 376
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 376
gaguacccgg ggcugcaug 19

<210> SEQ ID NO 377
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 377
augcagcccc ggguacucc 19

<210> SEQ ID NO 378
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 378
ggaguacccg gggcugcau 19

<210> SEQ ID NO 379
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 379
ugcagccccg gguacuccu 19

<210> SEQ ID NO 380
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 380
aggaguaccc ggggcugca 19

<210> SEQ ID NO 381
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 381
gcagccccgg guacuccuu 19

<210> SEQ ID NO 382
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 382
aaggaguacc cggggcugc 19

<210> SEQ ID NO 383
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 383
cagccccggg uacuccuug 19

<210> SEQ ID NO 384
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 384
caaggaguac ccggggcug 19

<210> SEQ ID NO 385
<211> LENGTH: 19
<212> TYPE: RNA

-continued

<213> ORGANISM: Artificial Sequence
<220> FEATURE:
<223> OTHER INFORMATION: synthetic APOC3 siRNA target or sense strand

<400> SEQUENCE: 385
agccccgggu acuccuugu 19

<210> SEQ ID NO 386
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 386
acaaggagua cccggggcu 19

<210> SEQ ID NO 387
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 387
gccccgggua cuccuuguu 19

<210> SEQ ID NO 388
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 388
aacaaggagu acccggggc 19

<210> SEQ ID NO 389
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 389
ccccggguac uccuuguug 19

<210> SEQ ID NO 390
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 390
caacaaggag uacccgggg 19

<210> SEQ ID NO 391
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 391
cccggguacu ccuuguugu 19

<210> SEQ ID NO 392
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 392
acaacaagga guacccggg 19

<210> SEQ ID NO 393
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 393
ccggguacuc cuuguuguu 19

<210> SEQ ID NO 394
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 394
aacaacaagg aguacccgg 19

<210> SEQ ID NO 395
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 395
cggguacucc uuguuguug 19

<210> SEQ ID NO 396
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 396
caacaacaag gaguacccg 19

<210> SEQ ID NO 397
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 397
ggguacuccu uguuguugc 19

<210> SEQ ID NO 398
<211> LENGTH: 19
<212> TYPE: RNA
<213> ORGANISM: Artificial Sequence
<220> FEATURE:

<223> OTHER INFORMATION: synthetic APOC3 siRNA antisense strand

<400> SEQUENCE: 398
gcaacaacaa ggaguaccc 19

<210> SEQ ID NO 399
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 399
gguacuccuu guuguugcc 19

<210> SEQ ID NO 400
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 400
ggcaacaaca aggaguacc 19

<210> SEQ ID NO 401
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 401
guacuccuug uuguugccc 19

<210> SEQ ID NO 402
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 402
gggcaacaac aaggaguac 19

<210> SEQ ID NO 403
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 403
uacuccuugu uguugcccu 19

<210> SEQ ID NO 404
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 404
agggcaacaa caaggagua 19

<210> SEQ ID NO 405
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 405
acuccuuguu guugcccuc 19

<210> SEQ ID NO 406
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 406
gagggcaaca acaaggagu 19

<210> SEQ ID NO 407
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 407
cuccuuguug uugcccucc 19

<210> SEQ ID NO 408
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 408
ggagggcaac aacaaggag 19

<210> SEQ ID NO 409
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 409
uccuuguugu ugcccuccu 19

<210> SEQ ID NO 410
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 410
aggagggcaa caacaagga 19

<210> SEQ ID NO 411
<211> LENGTH: 19
<212> TYPE: RNA
<213> ORGANISM: Artificial Sequence
<220> FEATURE:
<223> OTHER INFORMATION: synthetic APOC3 siRNA target or sense strand -continued

<400> SEQUENCE: 411
ccuuguuguu gcccuccug 19

<210> SEQ ID NO 412
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 412
caggagggca acaacaagg 19

<210> SEQ ID NO 413
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 413
cuuguuguug cccuccugg 19

<210> SEQ ID NO 414
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 414
ccaggagggc aacaacaag 19

<210> SEQ ID NO 415
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 415
uuguuguugc ccuccuggc 19

<210> SEQ ID NO 416
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 416
gccaggaggg caacaacaa 19

<210> SEQ ID NO 417
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 417
uguuguugcc cuccuggcg 19

<210> SEQ ID NO 418
<211> LENGTH: 19

<212> TYPE: RNA
<213> ORGANISM: Artificial Sequence
<220> FEATURE:
<223> OTHER INFORMATION: synthetic APOC3 siRNA antisense strand

<400> SEQUENCE: 418
cgccaggagg gcaacaaca 19

<210> SEQ ID NO 419
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 419
guuguugccc uccuggcgc 19

<210> SEQ ID NO 420
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 420
gcgccaggag ggcaacaac 19

<210> SEQ ID NO 421
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 421
uuguugcccu ccuggcgcu 19

<210> SEQ ID NO 422
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 422
agcgccagga gggcaacaa 19

<210> SEQ ID NO 423
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 423
uguugcccuc cuggcgcuc 19

<210> SEQ ID NO 424
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 424
gagcgccagg agggcaaca 19

<210> SEQ ID NO 425
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 425
guugcccucc uggcgcucc 19

<210> SEQ ID NO 426
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 426
ggagcgccag gagggcaac 19

<210> SEQ ID NO 427
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 427
uugcccuccu ggcgcuccu 19

<210> SEQ ID NO 428
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 428
aggagcgcca ggagggcaa 19

<210> SEQ ID NO 429
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 429
ugcccuccug gcgcuccug 19

<210> SEQ ID NO 430
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 430
caggagcgcc aggagggca 19

<210> SEQ ID NO 431
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 431
gcccuccugg cgcuccugg 19

<210> SEQ ID NO 432
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 432
ccaggagcgc caggagggc 19

<210> SEQ ID NO 433
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 433
cccuccuggc gcuccuggc 19

<210> SEQ ID NO 434
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 434
gccaggagcg ccaggaggg 19

<210> SEQ ID NO 435
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 435
ccuccuggcg cuccuggcc 19

<210> SEQ ID NO 436
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 436
ggccaggagc gccaggagg 19

<210> SEQ ID NO 437
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 437
cuccuggcgc uccuggccu 19

<210> SEQ ID NO 438
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 438
aggccaggag cgccaggag 19

<210> SEQ ID NO 439
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 439
uccuggcgcu ccuggccuc 19

<210> SEQ ID NO 440
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 440
gaggccagga gcgccagga 19

<210> SEQ ID NO 441
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 441
ccuggcgcuc cuggccucu 19

<210> SEQ ID NO 442
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 442
agaggccagg agcgccagg 19

<210> SEQ ID NO 443
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 443
cuggcgcucc uggccucug 19

<210> SEQ ID NO 444
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 444
cagaggccag gagcgccag 19

<210> SEQ ID NO 445
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 445
uggcgcuccu ggccucugc 19

<210> SEQ ID NO 446
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 446
gcagaggcca ggagcgcca 19

<210> SEQ ID NO 447
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 447
ggcgcuccug gccucugcc 19

<210> SEQ ID NO 448
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 448
ggcagaggcc aggagcgcc 19

<210> SEQ ID NO 449
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 449
gcgcuccugg ccucugccc 19

<210> SEQ ID NO 450
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 450
gggcagaggc caggagcgc 19

<210> SEQ ID NO 451

-continued

<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 451
cgcuccuggc cucugcccg 19

<210> SEQ ID NO 452
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 452
cgggcagagg ccaggagcg 19

<210> SEQ ID NO 453
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 453
gcuccuggcc ucugcccga 19

<210> SEQ ID NO 454
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 454
ucgggcagag gccaggagc 19

<210> SEQ ID NO 455
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 455
cuccuggccu cugcccgag 19

<210> SEQ ID NO 456
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 456
cucgggcaga ggccaggag 19

<210> SEQ ID NO 457
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 457
uccuggccuc ugcccgagc 19

<210> SEQ ID NO 458
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 458
gcucgggcag aggccagga 19

<210> SEQ ID NO 459
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 459
ccuggccucu gcccgagcu 19

<210> SEQ ID NO 460
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 460
agcucgggca gaggccagg 19

<210> SEQ ID NO 461
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 461
cuggccucug cccgagcuu 19

<210> SEQ ID NO 462
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 462
aagcucgggc agaggccag 19

<210> SEQ ID NO 463
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 463
uggccucugc ccgagcuuc 19

<210> SEQ ID NO 464
<211> LENGTH: 19
<212> TYPE: RNA

<213> ORGANISM: Artificial Sequence
<220> FEATURE:
<223> OTHER INFORMATION: synthetic APOC3 siRNA antisense strand

<400> SEQUENCE: 464
gaagcucggg cagaggcca 19

<210> SEQ ID NO 465
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 465
ggccucugcc cgagcuuca 19

<210> SEQ ID NO 466
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 466
ugaagcucgg gcagaggcc 19

<210> SEQ ID NO 467
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 467
gccucugccc gagcuucag 19

<210> SEQ ID NO 468
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 468
cugaagcucg ggcagaggc 19

<210> SEQ ID NO 469
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 469
ccucugcccg agcuucaga 19

<210> SEQ ID NO 470
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 470
ucugaagcuc gggcagagg 19

<210> SEQ ID NO 471
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 471
cucugcccga gcuucagag 19

<210> SEQ ID NO 472
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 472
cucugaagcu cgggcagag 19

<210> SEQ ID NO 473
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 473
ucugcccgag cuucagagg 19

<210> SEQ ID NO 474
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 474
ccucugaagc ucgggcaga 19

<210> SEQ ID NO 475
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 475
cugcccgagc uucagaggc 19

<210> SEQ ID NO 476
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 476
gccucugaag cucgggcag 19

<210> SEQ ID NO 477
<211> LENGTH: 19
<212> TYPE: RNA
<213> ORGANISM: Artificial Sequence
<220> FEATURE:

<223> OTHER INFORMATION: synthetic APOC3 siRNA target or sense strand

<400> SEQUENCE: 477
ugcccgagcu ucagaggcc 19

<210> SEQ ID NO 478
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 478
ggccucugaa gcucgggca 19

<210> SEQ ID NO 479
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 479
gcccgagcuu cagaggccg 19

<210> SEQ ID NO 480
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 480
cggccucuga agcucgggc 19

<210> SEQ ID NO 481
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 481
cccgagcuuc agaggccga 19

<210> SEQ ID NO 482
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 482
ucggccucug aagcucggg 19

<210> SEQ ID NO 483
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 483
ccgagcuuca gaggccgag 19

<210> SEQ ID NO 484
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 484
cucggccucu gaagcucgg 19

<210> SEQ ID NO 485
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 485
cgagcuucag aggccgagg 19

<210> SEQ ID NO 486
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 486
ccucggccuc ugaagcucg 19

<210> SEQ ID NO 487
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 487
gagcuucaga ggccgagga 19

<210> SEQ ID NO 488
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 488
uccucggccu cugaagcuc 19

<210> SEQ ID NO 489
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 489
agcuucagag gccgaggau 19

<210> SEQ ID NO 490
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 490
auccucggcc ucugaagcu 19

<210> SEQ ID NO 491
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 491
gcuucagagg ccgaggaug 19

<210> SEQ ID NO 492
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 492
cauccucggc cucugaagc 19

<210> SEQ ID NO 493
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 493
cuucagaggc cgaggaugc 19

<210> SEQ ID NO 494
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 494
gcauccucgg ccucugaag 19

<210> SEQ ID NO 495
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 495
uucagaggcc gaggaugcc 19

<210> SEQ ID NO 496
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 496
ggcauccucg gccucugaa 19

<210> SEQ ID NO 497
<211> LENGTH: 19

<212> TYPE: RNA
<213> ORGANISM: Artificial Sequence
<220> FEATURE:
<223> OTHER INFORMATION: synthetic APOC3 siRNA target or sense strand

<400> SEQUENCE: 497
ucagaggccg aggaugccu 19

<210> SEQ ID NO 498
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 498
aggcauccuc ggccucuga 19

<210> SEQ ID NO 499
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 499
cagaggccga ggaugccuc 19

<210> SEQ ID NO 500
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 500
gaggcauccu cggccucug 19

<210> SEQ ID NO 501
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 501
agaggccgag gaugccucc 19

<210> SEQ ID NO 502
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 502
ggaggcaucc ucggccucu 19

<210> SEQ ID NO 503
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 503
gaggccgagg augccuccc 19

<210> SEQ ID NO 504
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 504
gggaggcauc cucggccuc 19

<210> SEQ ID NO 505
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 505
aggccgagga ugccucccu 19

<210> SEQ ID NO 506
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 506
agggaggcau ccucggccu 19

<210> SEQ ID NO 507
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 507
ggccgaggau gccucccuu 19

<210> SEQ ID NO 508
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 508
aagggaggca uccucggcc 19

<210> SEQ ID NO 509
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 509
gccgaggaug ccucccuuc 19

<210> SEQ ID NO 510
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 510
gaagggaggc auccucggc 19

<210> SEQ ID NO 511
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 511
ccgaggaugc cucccuucu 19

<210> SEQ ID NO 512
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 512
agaagggagg cauccucgg 19

<210> SEQ ID NO 513
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 513
cgaggaugcc ucccuucuc 19

<210> SEQ ID NO 514
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 514
gagaagggag gcauccucg 19

<210> SEQ ID NO 515
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 515
gaggaugccu cccuucuca 19

<210> SEQ ID NO 516
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 516
ugagaaggga ggcauccuc 19

<210> SEQ ID NO 517
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 517
aggaugccuc ccuucucag 19

<210> SEQ ID NO 518
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 518
cugagaaggg aggcauccu 19

<210> SEQ ID NO 519
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 519
ggaugccucc cuucucagc 19

<210> SEQ ID NO 520
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 520
gcugagaagg gaggcaucc 19

<210> SEQ ID NO 521
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 521
gaugccuccc uucucagcu 19

<210> SEQ ID NO 522
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 522
agcugagaag ggaggcauc 19

<210> SEQ ID NO 523
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 523
augccucccu ucucagcuu 19

<210> SEQ ID NO 524
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 524
aagcugagaa gggaggcau 19

<210> SEQ ID NO 525
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 525
ugccucccuu cucagcuuc 19

<210> SEQ ID NO 526
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 526
gaagcugaga agggaggca 19

<210> SEQ ID NO 527
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 527
gccucccuuc ucagcuuca 19

<210> SEQ ID NO 528
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 528
ugaagcugag aagggaggc 19

<210> SEQ ID NO 529
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 529
ccucccuucu cagcuucau 19

<210> SEQ ID NO 530

<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 530
augaagcuga gaagggagg 19

<210> SEQ ID NO 531
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 531
cucccuucuc agcuucaug 19

<210> SEQ ID NO 532
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 532
caugaagcug agaagggag 19

<210> SEQ ID NO 533
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 533
ucccuucuca gcuucaugc 19

<210> SEQ ID NO 534
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 534
gcaugaagcu gagaaggga 19

<210> SEQ ID NO 535
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 535
cccuucucag cuucaugca 19

<210> SEQ ID NO 536
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 536
ugcaugaagc ugagaaggg 19

<210> SEQ ID NO 537
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 537
ccuucucagc uucaugcag 19

<210> SEQ ID NO 538
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 538
cugcaugaag cugagaagg 19

<210> SEQ ID NO 539
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 539
cuucucagcu ucaugcagg 19

<210> SEQ ID NO 540
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 540
ccugcaugaa gcugagaag 19

<210> SEQ ID NO 541
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 541
uucucagcuu caugcaggg 19

<210> SEQ ID NO 542
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 542
cccugcauga agcugagaa 19

<210> SEQ ID NO 543
<211> LENGTH: 19
<212> TYPE: RNA

<213> ORGANISM: Artificial Sequence
<220> FEATURE:
<223> OTHER INFORMATION: synthetic APOC3 siRNA target or sense strand

<400> SEQUENCE: 543
ucucagcuuc augcagggu 19

<210> SEQ ID NO 544
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 544
acccugcaug aagcugaga 19

<210> SEQ ID NO 545
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 545
cucagcuuca ugcaggguu 19

<210> SEQ ID NO 546
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 546
aacccugcau gaagcugag 19

<210> SEQ ID NO 547
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 547
ucagcuucau gcaggguua 19

<210> SEQ ID NO 548
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 548
uaacccugca ugaagcuga 19

<210> SEQ ID NO 549
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 549
cagcuucaug caggguuac 19

<210> SEQ ID NO 550
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 550
guaacccugc augaagcug 19

<210> SEQ ID NO 551
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 551
agcuucaugc aggguuaca 19

<210> SEQ ID NO 552
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 552
uguaacccug caugaagcu 19

<210> SEQ ID NO 553
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 553
gcuucaugca ggguuacau 19

<210> SEQ ID NO 554
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 554
auguaacccu gcaugaagc 19

<210> SEQ ID NO 555
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 555
cuucaugcag gguuacaug 19

<210> SEQ ID NO 556
<211> LENGTH: 19
<212> TYPE: RNA
<213> ORGANISM: Artificial Sequence
<220> FEATURE:

<223> OTHER INFORMATION: synthetic APOC3 siRNA antisense strand

<400> SEQUENCE: 556
cauguaaccc ugcaugaag 19

<210> SEQ ID NO 557
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 557
uucaugcagg guuacauga 19

<210> SEQ ID NO 558
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 558
ucauguaacc cugcaugaa 19

<210> SEQ ID NO 559
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 559
ucaugcaggg uuacaugaa 19

<210> SEQ ID NO 560
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 560
uucauguaac ccugcauga 19

<210> SEQ ID NO 561
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 561
caugcagggu uacaugaag 19

<210> SEQ ID NO 562
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 562
cuucauguaa cccugcaug 19

<210> SEQ ID NO 563
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 563
augcaggguu acaugaagc 19

<210> SEQ ID NO 564
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 564
gcuucaugua acccugcau 19

<210> SEQ ID NO 565
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 565
ugcaggguua caugaagca 19

<210> SEQ ID NO 566
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 566
ugcuucaugu aacccugca 19

<210> SEQ ID NO 567
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 567
gcaggguuac augaagcac 19

<210> SEQ ID NO 568
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 568
gugcuucaug uaacccugc 19

<210> SEQ ID NO 569
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 569
caggguuaca ugaagcacg 19

<210> SEQ ID NO 570
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 570
cgugcuucau guaacccug 19

<210> SEQ ID NO 571
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 571
aggguuacau gaagcacgc 19

<210> SEQ ID NO 572
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 572
gcgugcuuca uguaacccu 19

<210> SEQ ID NO 573
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 573
ggguuacaug aagcacgcc 19

<210> SEQ ID NO 574
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 574
ggcgugcuuc auguaaccc 19

<210> SEQ ID NO 575
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 575
gguuacauga agcacgcca 19

<210> SEQ ID NO 576
<211> LENGTH: 19

<212> TYPE: RNA
<213> ORGANISM: Artificial Sequence
<220> FEATURE:
<223> OTHER INFORMATION: synthetic APOC3 siRNA antisense strand

<400> SEQUENCE: 576
uggcgugcuu cauguaacc 19

<210> SEQ ID NO 577
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 577
guuacaugaa gcacgccac 19

<210> SEQ ID NO 578
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 578
guggcgugcu ucauguaac 19

<210> SEQ ID NO 579
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 579
uuacaugaag cacgccacc 19

<210> SEQ ID NO 580
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 580
gguggcgugc uucauguaa 19

<210> SEQ ID NO 581
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 581
uacaugaagc acgccacca 19

<210> SEQ ID NO 582
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 582
ugguggcgug cuucaugua 19

<210> SEQ ID NO 583
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 583
acaugaagca cgccaccaa 19

<210> SEQ ID NO 584
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 584
uugguggcgu gcuucaugu 19

<210> SEQ ID NO 585
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 585
caugaagcac gccaccaag 19

<210> SEQ ID NO 586
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 586
cuugguggcg ugcuucaug 19

<210> SEQ ID NO 587
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 587
augaagcacg ccaccaaga 19

<210> SEQ ID NO 588
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 588
ucuugguggc gugcuucau 19

<210> SEQ ID NO 589
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 589
ugaagcacgc caccaagac 19

<210> SEQ ID NO 590
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 590
gucuuggugg cgugcuuca 19

<210> SEQ ID NO 591
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 591
gaagcacgcc accaagacc 19

<210> SEQ ID NO 592
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 592
ggucuuggug gcgugcuuc 19

<210> SEQ ID NO 593
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 593
aagcacgcca ccaagaccg 19

<210> SEQ ID NO 594
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 594
cggucuuggu ggcgugcuu 19

<210> SEQ ID NO 595
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 595
agcacgccac caagaccgc 19

<210> SEQ ID NO 596
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 596
gcggucuugg uggcgugcu 19

<210> SEQ ID NO 597
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 597
gcacgccacc aagaccgcc 19

<210> SEQ ID NO 598
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 598
ggcggucuug guggcgugc 19

<210> SEQ ID NO 599
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 599
cacgccacca agaccgcca 19

<210> SEQ ID NO 600
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 600
uggcggucuu gguggcgug 19

<210> SEQ ID NO 601
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 601
acgccaccaa gaccgccaa 19

<210> SEQ ID NO 602
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 602
uuggcggucu ugguggcgu 19

<210> SEQ ID NO 603
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 603
cgccaccaag accgccaag 19

<210> SEQ ID NO 604
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 604
cuuggcgguc uugguggcg 19

<210> SEQ ID NO 605
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 605
gccaccaaga ccgccaagg 19

<210> SEQ ID NO 606
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 606
ccuuggcggu cuugguggc 19

<210> SEQ ID NO 607
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 607
ccaccaagac cgccaagga 19

<210> SEQ ID NO 608
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 608
uccuuggcgg ucuuggugg 19

<210> SEQ ID NO 609

-continued

<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 609
caccaagacc gccaaggau 19

<210> SEQ ID NO 610
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 610
auccuuggcg gucuuggug 19

<210> SEQ ID NO 611
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 611
accaagaccg ccaaggaug 19

<210> SEQ ID NO 612
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 612
cauccuuggc ggucuuggu 19

<210> SEQ ID NO 613
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 613
ccaagaccgc caaggaugc 19

<210> SEQ ID NO 614
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 614
gcauccuugg cggucuugg 19

<210> SEQ ID NO 615
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 615
caagaccgcc aaggaugca 19

<210> SEQ ID NO 616
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 616
ugcauccuug gcggucuug 19

<210> SEQ ID NO 617
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 617
aagaccgcca aggaugcac 19

<210> SEQ ID NO 618
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 618
gugcauccuu ggcggucuu 19

<210> SEQ ID NO 619
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 619
agaccgccaa ggaugcacu 19

<210> SEQ ID NO 620
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 620
agugcauccu uggcggucu 19

<210> SEQ ID NO 621
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 621
gaccgccaag gaugcacug 19

<210> SEQ ID NO 622
<211> LENGTH: 19
<212> TYPE: RNA

<213> ORGANISM: Artificial Sequence
<220> FEATURE:
<223> OTHER INFORMATION: synthetic APOC3 siRNA antisense strand

<400> SEQUENCE: 622
cagugcaucc uuggcgguc 19

<210> SEQ ID NO 623
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 623
accgccaagg augcacuga 19

<210> SEQ ID NO 624
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 624
ucagugcauc cuuggcggu 19

<210> SEQ ID NO 625
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 625
ccgccaagga ugcacugag 19

<210> SEQ ID NO 626
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 626
cucagugcau ccuuggcgg 19

<210> SEQ ID NO 627
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 627
cgccaaggau gcacugagc 19

<210> SEQ ID NO 628
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 628
gcucagugca uccuuggcg 19

<210> SEQ ID NO 629
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 629
gccaaggaug cacugagca 19

<210> SEQ ID NO 630
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 630
ugcucagugc auccuuggc 19

<210> SEQ ID NO 631
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 631
ccaaggaugc acugagcag 19

<210> SEQ ID NO 632
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 632
cugcucagug cauccuugg 19

<210> SEQ ID NO 633
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 633
caaggaugca cugagcagc 19

<210> SEQ ID NO 634
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 634
gcugcucagu gcauccuug 19

<210> SEQ ID NO 635
<211> LENGTH: 19
<212> TYPE: RNA
<213> ORGANISM: Artificial Sequence
<220> FEATURE:

<223> OTHER INFORMATION: synthetic APOC3 siRNA target or sense strand

<400> SEQUENCE: 635
aaggaugcac ugagcagcg 19

<210> SEQ ID NO 636
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 636
cgcugcucag ugcauccuu 19

<210> SEQ ID NO 637
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 637
aggaugcacu gagcagcgu 19

<210> SEQ ID NO 638
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 638
acgcugcuca gugcauccu 19

<210> SEQ ID NO 639
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 639
ggaugcacug agcagcgug 19

<210> SEQ ID NO 640
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 640
cacgcugcuc agugcaucc 19

<210> SEQ ID NO 641
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 641
gaugcacuga gcagcgugc 19

<210> SEQ ID NO 642
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 642
gcacgcugcu cagugcauc 19

<210> SEQ ID NO 643
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 643
augcacugag cagcgugca 19

<210> SEQ ID NO 644
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 644
ugcacgcugc ucagugcau 19

<210> SEQ ID NO 645
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 645
ugcacugagc agcgugcag 19

<210> SEQ ID NO 646
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 646
cugcacgcug cucagugca 19

<210> SEQ ID NO 647
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 647
gcacugagca gcgugcagg 19

<210> SEQ ID NO 648
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 648
ccugcacgcu gcucagugc 19

<210> SEQ ID NO 649
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 649
cacugagcag cgugcagga 19

<210> SEQ ID NO 650
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 650
uccugcacgc ugcucagug 19

<210> SEQ ID NO 651
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 651
acugagcagc gugcaggag 19

<210> SEQ ID NO 652
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 652
cuccugcacg cugcucagu 19

<210> SEQ ID NO 653
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 653
cugagcagcg ugcaggagu 19

<210> SEQ ID NO 654
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 654
acuccugcac gcugcucag 19

<210> SEQ ID NO 655
<211> LENGTH: 19

<212> TYPE: RNA
<213> ORGANISM: Artificial Sequence
<220> FEATURE:
<223> OTHER INFORMATION: synthetic APOC3 siRNA target or sense strand

<400> SEQUENCE: 655
ugagcagcgu gcaggaguc 19

<210> SEQ ID NO 656
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 656
gacuccugca cgcugcuca 19

<210> SEQ ID NO 657
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 657
gagcagcgug caggagucc 19

<210> SEQ ID NO 658
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 658
ggacuccugc acgcugcuc 19

<210> SEQ ID NO 659
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 659
agcagcgugc aggaguccc 19

<210> SEQ ID NO 660
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 660
gggacuccug cacgcugcu 19

<210> SEQ ID NO 661
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 661
gcagcgugca ggaguccca                                                    19

<210> SEQ ID NO 662
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 662
ugggacuccu gcacgcugc                                                    19

<210> SEQ ID NO 663
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 663
cagcgugcag gagucccag                                                    19

<210> SEQ ID NO 664
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 664
cugggacucc ugcacgcug                                                    19

<210> SEQ ID NO 665
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 665
agcgugcagg agucccagg                                                    19

<210> SEQ ID NO 666
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 666
ccugggacuc cugcacgcu                                                    19

<210> SEQ ID NO 667
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 667
gcgugcagga gucccaggu                                                    19

<210> SEQ ID NO 668
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 668
accugggacu ccugcacgc 19

<210> SEQ ID NO 669
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 669
cgugcaggag ucccaggug 19

<210> SEQ ID NO 670
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 670
caccugggac uccugcacg 19

<210> SEQ ID NO 671
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 671
gugcaggagu cccaggugg 19

<210> SEQ ID NO 672
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 672
ccaccuggga cuccugcac 19

<210> SEQ ID NO 673
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 673
ugcaggaguc ccagguggc 19

<210> SEQ ID NO 674
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 674
gccaccuggg acuccugca 19

<210> SEQ ID NO 675
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 675
gcaggagucc cagguggcc 19

<210> SEQ ID NO 676
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 676
ggccaccugg gacuccugc 19

<210> SEQ ID NO 677
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 677
caggaguccc agguggccc 19

<210> SEQ ID NO 678
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 678
gggccaccug ggacuccug 19

<210> SEQ ID NO 679
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 679
aggaguccca gguggccca 19

<210> SEQ ID NO 680
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 680
ugggccaccu gggacuccu 19

<210> SEQ ID NO 681
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 681
ggagucccag guggcccag 19

<210> SEQ ID NO 682
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 682
cugggccacc ugggacucc 19

<210> SEQ ID NO 683
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 683
gagucccagg uggcccagc 19

<210> SEQ ID NO 684
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 684
gcugggccac cugggacuc 19

<210> SEQ ID NO 685
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 685
agucccaggu ggcccagca 19

<210> SEQ ID NO 686
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 686
ugcugggcca ccugggacu 19

<210> SEQ ID NO 687
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 687
gucccaggug gcccagcag 19

<210> SEQ ID NO 688

-continued

<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 688
cugcugggcc accugggac 19

<210> SEQ ID NO 689
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 689
ucccaggugg cccagcagg 19

<210> SEQ ID NO 690
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 690
ccugcugggc caccuggga 19

<210> SEQ ID NO 691
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 691
cccagguggc ccagcaggc 19

<210> SEQ ID NO 692
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 692
gccugcuggg ccaccuggg 19

<210> SEQ ID NO 693
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 693
ccagguggcc cagcaggcc 19

<210> SEQ ID NO 694
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 694
ggccugcugg gccaccugg 19

<210> SEQ ID NO 695
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 695
cagguggccc agcaggcca 19

<210> SEQ ID NO 696
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 696
uggccugcug ggccaccug 19

<210> SEQ ID NO 697
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 697
agguggccca gcaggccag 19

<210> SEQ ID NO 698
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 698
cuggccugcu gggccaccu 19

<210> SEQ ID NO 699
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 699
gguggcccag caggccagg 19

<210> SEQ ID NO 700
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 700
ccuggccugc ugggccacc 19

<210> SEQ ID NO 701
<211> LENGTH: 19
<212> TYPE: RNA

-continued

<213> ORGANISM: Artificial Sequence
<220> FEATURE:
<223> OTHER INFORMATION: synthetic APOC3 siRNA target or sense strand

<400> SEQUENCE: 701
guggcccagc aggccaggg 19

<210> SEQ ID NO 702
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 702
cccuggccug cugggccac 19

<210> SEQ ID NO 703
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 703
uggcccagca ggccagggg 19

<210> SEQ ID NO 704
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 704
ccccuggccu gcugggcca 19

<210> SEQ ID NO 705
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 705
ggcccagcag gccaggggc 19

<210> SEQ ID NO 706
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 706
gccccuggcc ugcugggcc 19

<210> SEQ ID NO 707
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 707
gcccagcagg ccaggggcu 19

<210> SEQ ID NO 708
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 708
agccccuggc cugcugggc 19

<210> SEQ ID NO 709
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 709
cccagcaggc caggggcug 19

<210> SEQ ID NO 710
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 710
cagccccugg ccugcuggg 19

<210> SEQ ID NO 711
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 711
ccagcaggcc aggggcugg 19

<210> SEQ ID NO 712
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 712
ccagccccug gccugcugg 19

<210> SEQ ID NO 713
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 713
cagcaggcca ggggcuggg 19

<210> SEQ ID NO 714
<211> LENGTH: 19
<212> TYPE: RNA
<213> ORGANISM: Artificial Sequence
<220> FEATURE:

<223> OTHER INFORMATION: synthetic APOC3 siRNA antisense strand

<400> SEQUENCE: 714
cccagccccu ggccugcug    19

<210> SEQ ID NO 715
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 715
agcaggccag gggcugggu    19

<210> SEQ ID NO 716
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 716
acccagcccc uggccugcu    19

<210> SEQ ID NO 717
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 717
gcaggccagg ggcugggug    19

<210> SEQ ID NO 718
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 718
cacccagccc cuggccugc    19

<210> SEQ ID NO 719
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 719
caggccaggg gcuggguga    19

<210> SEQ ID NO 720
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 720
ucacccagcc ccuggccug    19

<210> SEQ ID NO 721
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 721
aggccagggg cugggugac 19

<210> SEQ ID NO 722
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 722
gucacccagc cccuggccu 19

<210> SEQ ID NO 723
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 723
ggccaggggc ugggugacc 19

<210> SEQ ID NO 724
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 724
ggucacccag ccccuggcc 19

<210> SEQ ID NO 725
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 725
gccaggggcu gggugaccg 19

<210> SEQ ID NO 726
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 726
cggucaccca gccccuggc 19

<210> SEQ ID NO 727
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 727
ccaggggcug ggugaccga 19

<210> SEQ ID NO 728
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 728
ucggucaccc agccccugg 19

<210> SEQ ID NO 729
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 729
caggggcugg gugaccgau 19

<210> SEQ ID NO 730
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 730
aucggucacc cagccccug 19

<210> SEQ ID NO 731
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 731
aggggcuggg ugaccgaug 19

<210> SEQ ID NO 732
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 732
caucggucac ccagccccu 19

<210> SEQ ID NO 733
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 733
ggggcugggu gaccgaugg 19

<210> SEQ ID NO 734
<211> LENGTH: 19

<212> TYPE: RNA
<213> ORGANISM: Artificial Sequence
<220> FEATURE:
<223> OTHER INFORMATION: synthetic APOC3 siRNA antisense strand

<400> SEQUENCE: 734
ccaucgguca cccagcccc 19

<210> SEQ ID NO 735
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 735
gggcugggug accgauggc 19

<210> SEQ ID NO 736
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 736
gccaucgguc acccagccc 19

<210> SEQ ID NO 737
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 737
ggcuggguga ccgauggcu 19

<210> SEQ ID NO 738
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 738
agccaucggu cacccagcc 19

<210> SEQ ID NO 739
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 739
gcugggugac cgauggcuu 19

<210> SEQ ID NO 740
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 740

-continued aagccaucgg ucacccagc 19

<210> SEQ ID NO 741
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 741
cugggugacc gauggcuuc 19

<210> SEQ ID NO 742
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 742
gaagccaucg gucacccag 19

<210> SEQ ID NO 743
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 743
ugggugaccg auggcuuca 19

<210> SEQ ID NO 744
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 744
ugaagccauc ggucaccca 19

<210> SEQ ID NO 745
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 745
gggugaccga uggcuucag 19

<210> SEQ ID NO 746
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 746
cugaagccau cggucaccc 19

<210> SEQ ID NO 747
<211> LENGTH: 19
<212> TYPE: RNA
<213> ORGANISM: Artificial Sequence -continued
<220> FEATURE:
<223> OTHER INFORMATION: synthetic APOC3 siRNA target or sense strand

<400> SEQUENCE: 747
ggugaccgau ggcuucagu 19

<210> SEQ ID NO 748
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 748
acugaagcca ucggucacc 19

<210> SEQ ID NO 749
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 749
gugaccgaug gcuucaguu 19

<210> SEQ ID NO 750
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 750
aacugaagcc aucggucac 19

<210> SEQ ID NO 751
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 751
ugaccgaugg cuucaguuc 19

<210> SEQ ID NO 752
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 752
gaacugaagc caucgguca 19

<210> SEQ ID NO 753
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 753
gaccgauggc uucaguucc 19

<210> SEQ ID NO 754
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 754
ggaacugaag ccaucgguc 19

<210> SEQ ID NO 755
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 755
accgauggcu ucaguuccc 19

<210> SEQ ID NO 756
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 756
gggaacugaa gccaucggu 19

<210> SEQ ID NO 757
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 757
ccgauggcuu caguucccu 19

<210> SEQ ID NO 758
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 758
agggaacuga agccaucgg 19

<210> SEQ ID NO 759
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 759
cgauggcuuc aguucccug 19

<210> SEQ ID NO 760
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 760
cagggaacug aagccaucg 19

<210> SEQ ID NO 761
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 761
gauggcuuca guucccuga 19

<210> SEQ ID NO 762
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 762
ucagggaacu gaagccauc 19

<210> SEQ ID NO 763
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 763
auggcuucag uucccugaa 19

<210> SEQ ID NO 764
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 764
uucagggaac ugaagccau 19

<210> SEQ ID NO 765
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 765
uggcuucagu ucccugaaa 19

<210> SEQ ID NO 766
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 766
uuucagggaa cugaagcca 19

<210> SEQ ID NO 767

<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 767
ggcuucaguu cccugaaag 19

<210> SEQ ID NO 768
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 768
cuuucaggga acugaagcc 19

<210> SEQ ID NO 769
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 769
gcuucaguuc ccugaaaga 19

<210> SEQ ID NO 770
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 770
ucuuucaggg aacugaagc 19

<210> SEQ ID NO 771
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 771
cuucaguucc cugaaagac 19

<210> SEQ ID NO 772
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 772
gucuuucagg gaacugaag 19

<210> SEQ ID NO 773
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 773
uucaguuccc ugaaagacu 19

<210> SEQ ID NO 774
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 774
agucuuucag ggaacugaa 19

<210> SEQ ID NO 775
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 775
ucaguucccu gaaagacua 19

<210> SEQ ID NO 776
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 776
uagucuuuca gggaacuga 19

<210> SEQ ID NO 777
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 777
caguucccug aaagacuac 19

<210> SEQ ID NO 778
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 778
guagucuuuc agggaacug 19

<210> SEQ ID NO 779
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 779
aguucccuga aagacuacu 19

<210> SEQ ID NO 780
<211> LENGTH: 19
<212> TYPE: RNA

<213> ORGANISM: Artificial Sequence
<220> FEATURE:
<223> OTHER INFORMATION: synthetic APOC3 siRNA antisense strand

<400> SEQUENCE: 780
aguagucuuu cagggaacu 19

<210> SEQ ID NO 781
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 781
guucccugaa agacuacug 19

<210> SEQ ID NO 782
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 782
caguagucuu ucagggaac 19

<210> SEQ ID NO 783
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 783
uucccugaaa gacuacugg 19

<210> SEQ ID NO 784
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 784
ccaguagucu uucagggaa 19

<210> SEQ ID NO 785
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 785
ucccugaaag acuacugga 19

<210> SEQ ID NO 786
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 786
uccaguaguc uuucaggga 19

<210> SEQ ID NO 787
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 787
cccugaaaga cuacuggag 19

<210> SEQ ID NO 788
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 788
cuccaguagu cuuucaggg 19

<210> SEQ ID NO 789
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 789
ccugaaagac uacuggagc 19

<210> SEQ ID NO 790
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 790
gcuccaguag ucuuucagg 19

<210> SEQ ID NO 791
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 791
cugaaagacu acuggagca 19

<210> SEQ ID NO 792
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 792
ugcuccagua gucuuucag 19

<210> SEQ ID NO 793
<211> LENGTH: 19
<212> TYPE: RNA
<213> ORGANISM: Artificial Sequence
<220> FEATURE:

<223> OTHER INFORMATION: synthetic APOC3 siRNA target or sense strand

<400> SEQUENCE: 793
ugaaagacua cuggagcac 19

<210> SEQ ID NO 794
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 794
gugcuccagu agucuuuca 19

<210> SEQ ID NO 795
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 795
gaaagacuac uggagcacc 19

<210> SEQ ID NO 796
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 796
ggugcuccag uagucuuuc 19

<210> SEQ ID NO 797
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 797
aaagacuacu ggagcaccg 19

<210> SEQ ID NO 798
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 798
cggugcucca guagucuuu 19

<210> SEQ ID NO 799
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 799
aagacuacug gagcaccgu 19

-continued

<210> SEQ ID NO 800
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 800
acggugcucc aguagucuu 19

<210> SEQ ID NO 801
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 801
agacuacugg agcaccguu 19

<210> SEQ ID NO 802
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 802
aacggugcuc caguagucu 19

<210> SEQ ID NO 803
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 803
gacuacugga gcaccguua 19

<210> SEQ ID NO 804
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 804
uaacggugcu ccaguaguc 19

<210> SEQ ID NO 805
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 805
acuacuggag caccguuaa 19

<210> SEQ ID NO 806
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 806
uuaacggugc uccaguagu 19

<210> SEQ ID NO 807
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 807
cuacuggagc accguuaag 19

<210> SEQ ID NO 808
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 808
cuuaacggug cuccaguag 19

<210> SEQ ID NO 809
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 809
uacuggagca ccguuaagg 19

<210> SEQ ID NO 810
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 810
ccuuaacggu gcuccagua 19

<210> SEQ ID NO 811
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 811
acuggagcac cguuaagga 19

<210> SEQ ID NO 812
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 812
uccuuaacgg ugcuccagu 19

<210> SEQ ID NO 813
<211> LENGTH: 19

<212> TYPE: RNA
<213> ORGANISM: Artificial Sequence
<220> FEATURE:
<223> OTHER INFORMATION: synthetic APOC3 siRNA target or sense strand

<400> SEQUENCE: 813
cuggagcacc guuaaggac 19

<210> SEQ ID NO 814
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 814
guccuuaacg gugcuccag 19

<210> SEQ ID NO 815
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 815
uggagcaccg uuaaggaca 19

<210> SEQ ID NO 816
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 816
uguccuuaac ggugcucca 19

<210> SEQ ID NO 817
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 817
ggagcaccgu uaaggacaa 19

<210> SEQ ID NO 818
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 818
uuguccuuaa cggugcucc 19

<210> SEQ ID NO 819
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 819
gagcaccguu aaggacaag 19

<210> SEQ ID NO 820
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 820
cuuguccuua acggugcuc 19

<210> SEQ ID NO 821
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 821
agcaccguua aggacaagu 19

<210> SEQ ID NO 822
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 822
acuuguccuu aacggugcu 19

<210> SEQ ID NO 823
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 823
gcaccguuaa ggacaaguu 19

<210> SEQ ID NO 824
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 824
aacuuguccu uaacggugc 19

<210> SEQ ID NO 825
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 825
caccguuaag gacaaguuc 19

<210> SEQ ID NO 826
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 826
gaacuugucc uuaacggug 19

<210> SEQ ID NO 827
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 827
accguuaagg acaaguucu 19

<210> SEQ ID NO 828
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 828
agaacuuguc cuuaacggu 19

<210> SEQ ID NO 829
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 829
ccguuaagga caaguucuc 19

<210> SEQ ID NO 830
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 830
gagaacuugu ccuuaacgg 19

<210> SEQ ID NO 831
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 831
cguuaaggac aaguucucu 19

<210> SEQ ID NO 832
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 832
agagaacuug uccuuaacg 19

<210> SEQ ID NO 833
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 833
guuaaggaca aguucucug 19

<210> SEQ ID NO 834
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 834
cagagaacuu guccuuaac 19

<210> SEQ ID NO 835
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 835
uuaaggacaa guucucuga 19

<210> SEQ ID NO 836
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 836
ucagagaacu uguccuuaa 19

<210> SEQ ID NO 837
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 837
uaaggacaag uucucugag 19

<210> SEQ ID NO 838
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 838
cucagagaac uuguccuua 19

<210> SEQ ID NO 839
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 839
aaggacaagu ucucugagu 19

<210> SEQ ID NO 840
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 840
acucagagaa cuuguccuu 19

<210> SEQ ID NO 841
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 841
aggacaaguu cucugaguu 19

<210> SEQ ID NO 842
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 842
aacucagaga acuuguccu 19

<210> SEQ ID NO 843
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 843
ggacaaguuc ucugaguuc 19

<210> SEQ ID NO 844
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 844
gaacucagag aacuugucc 19

<210> SEQ ID NO 845
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 845
gacaaguucu cugaguucu 19

<210> SEQ ID NO 846

<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 846
agaacucaga gaacuuguc 19

<210> SEQ ID NO 847
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 847
acaaguucuc ugaguucug 19

<210> SEQ ID NO 848
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 848
cagaacucag agaacuugu 19

<210> SEQ ID NO 849
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 849
caaguucucu gaguucugg 19

<210> SEQ ID NO 850
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 850
ccagaacuca gagaacuug 19

<210> SEQ ID NO 851
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 851
aaguucucug aguucuggg 19

<210> SEQ ID NO 852
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 852
cccagaacuc agagaacuu 19

<210> SEQ ID NO 853
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 853
aguucucuga guucuggga 19

<210> SEQ ID NO 854
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 854
ucccagaacu cagagaacu 19

<210> SEQ ID NO 855
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 855
guucucugag uucugggau 19

<210> SEQ ID NO 856
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 856
aucccagaac ucagagaac 19

<210> SEQ ID NO 857
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 857
uucucugagu ucugggauu 19

<210> SEQ ID NO 858
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 858
aaucccagaa cucagagaa 19

<210> SEQ ID NO 859
<211> LENGTH: 19
<212> TYPE: RNA

-continued

<213> ORGANISM: Artificial Sequence
<220> FEATURE:
<223> OTHER INFORMATION: synthetic APOC3 siRNA target or sense strand

<400> SEQUENCE: 859
ucucugaguu cugggauuu 19

<210> SEQ ID NO 860
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 860
aaaucccaga acucagaga 19

<210> SEQ ID NO 861
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 861
cucugaguuc ugggauuug 19

<210> SEQ ID NO 862
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 862
caaaucccag aacucagag 19

<210> SEQ ID NO 863
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 863
ucugaguucu gggauuugg 19

<210> SEQ ID NO 864
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 864
ccaaauccca gaacucaga 19

<210> SEQ ID NO 865
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 865
cugaguucug ggauuugga 19

<210> SEQ ID NO 866
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 866
uccaaauccc agaacucag 19

<210> SEQ ID NO 867
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 867
ugaguucugg gauuuggac 19

<210> SEQ ID NO 868
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 868
guccaaaucc cagaacuca 19

<210> SEQ ID NO 869
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 869
gaguucuggg auuuggacc 19

<210> SEQ ID NO 870
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 870
gguccaaauc ccagaacuc 19

<210> SEQ ID NO 871
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 871
aguucuggga uuuggaccc 19

<210> SEQ ID NO 872
<211> LENGTH: 19
<212> TYPE: RNA
<213> ORGANISM: Artificial Sequence
<220> FEATURE:

<223> OTHER INFORMATION: synthetic APOC3 siRNA antisense strand

<400> SEQUENCE: 872
ggguccaaau cccagaacu 19

<210> SEQ ID NO 873
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 873
guucugggau uuggacccu 19

<210> SEQ ID NO 874
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 874
aggguccaaa ucccagaac 19

<210> SEQ ID NO 875
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 875
uucugggauu uggacccug 19

<210> SEQ ID NO 876
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 876 cagggucaa aucccagaa 19

<210> SEQ ID NO 877
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 877
ucugggauuu ggacccuga 19

<210> SEQ ID NO 878
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 878 ucaggg ucca aaucccaga 19

<210> SEQ ID NO 879
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 879
cugggauuug gacccugag 19

<210> SEQ ID NO 880
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 880
cucagggucc aaaucccag 19

<210> SEQ ID NO 881
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 881
ugggauuugg acccugagg 19

<210> SEQ ID NO 882
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 882
ccucaggguc caaauccca 19

<210> SEQ ID NO 883
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 883
gggauuugga cccugaggu 19

<210> SEQ ID NO 884
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 884
accucagggu ccaaauccc 19

<210> SEQ ID NO 885
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 885
ggauuuggac ccugagguc 19

<210> SEQ ID NO 886
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 886
gaccucaggg uccaaaucc 19

<210> SEQ ID NO 887
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 887
gauuuggacc cugagguca 19

<210> SEQ ID NO 888
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 888
ugaccucagg guccaaauc 19

<210> SEQ ID NO 889
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 889
auuuggaccc ugaggucag 19

<210> SEQ ID NO 890
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 890
cugaccucag gguccaaau 19

<210> SEQ ID NO 891
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 891
uuuggacccu gaggucaga 19

<210> SEQ ID NO 892
<211> LENGTH: 19

<212> TYPE: RNA
<213> ORGANISM: Artificial Sequence
<220> FEATURE:
<223> OTHER INFORMATION: synthetic APOC3 siRNA antisense strand

<400> SEQUENCE: 892
ucugaccuca ggguccaaa 19

<210> SEQ ID NO 893
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 893
uuggacccug aggucagac 19

<210> SEQ ID NO 894
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 894
gucugaccuc aggguccaa 19

<210> SEQ ID NO 895
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 895
uggacccuga ggucagacc 19

<210> SEQ ID NO 896
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 896
ggucugaccu cagggucca 19

<210> SEQ ID NO 897
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 897
ggacccugag gucagacca 19

<210> SEQ ID NO 898
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 898
uggucugacc ucagggucc 19

<210> SEQ ID NO 899
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 899
gacccugagg ucagaccaa 19

<210> SEQ ID NO 900
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 900
uuggucugac cucaggguc 19

<210> SEQ ID NO 901
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 901
acccugaggu cagaccaac 19

<210> SEQ ID NO 902
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 902
guuggucuga ccucagggu 19

<210> SEQ ID NO 903
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 903
cccugagguc agaccaacu 19

<210> SEQ ID NO 904
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 904
aguuggucug accucaggg 19

<210> SEQ ID NO 905
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 905
ccugagguca gaccaacuu 19

<210> SEQ ID NO 906
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 906
aaguuggucu gaccucagg 19

<210> SEQ ID NO 907
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 907
cugaggucag accaacuuc 19

<210> SEQ ID NO 908
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 908
gaaguugguc ugaccucag 19

<210> SEQ ID NO 909
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 909
ugaggucaga ccaacuuca 19

<210> SEQ ID NO 910
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 910
ugaaguuggu cugaccuca 19

<210> SEQ ID NO 911
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 911
gaggucagac caacuucag 19

<210> SEQ ID NO 912
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 912
cugaaguugg ucugaccuc 19

<210> SEQ ID NO 913
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 913
aggucagacc aacuucagc 19

<210> SEQ ID NO 914
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 914
gcugaaguug gucugaccu 19

<210> SEQ ID NO 915
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 915
ggucagacca acuucagcc 19

<210> SEQ ID NO 916
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 916
ggcugaaguu ggucugacc 19

<210> SEQ ID NO 917
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 917
gucagaccaa cuucagccg 19

<210> SEQ ID NO 918
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 918
cggcugaagu uggucugac 19

<210> SEQ ID NO 919
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 919
ucagaccaac uucagccgu 19

<210> SEQ ID NO 920
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 920
acggcugaag uuggucuga 19

<210> SEQ ID NO 921
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 921
cagaccaacu ucagccgug 19

<210> SEQ ID NO 922
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 922
cacggcugaa guuggucug 19

<210> SEQ ID NO 923
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 923
agaccaacuu cagccgugg 19

<210> SEQ ID NO 924
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 924
ccacggcuga aguuggucu 19

<210> SEQ ID NO 925

<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 925
gaccaacuuc agccguggc 19

<210> SEQ ID NO 926
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 926
gccacggcug aaguugguc 19

<210> SEQ ID NO 927
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 927
accaacuuca gccguggcu 19

<210> SEQ ID NO 928
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 928
agccacggcu gaaguuggu 19

<210> SEQ ID NO 929
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 929
ccaacuucag ccguggcug 19

<210> SEQ ID NO 930
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 930
cagccacggc ugaaguugg 19

<210> SEQ ID NO 931
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 931
caacuucagc cguggcugc 19

<210> SEQ ID NO 932
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 932
gcagccacgg cugaaguug 19

<210> SEQ ID NO 933
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 933
aacuucagcc guggcugcc 19

<210> SEQ ID NO 934
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 934
ggcagccacg gcugaaguu 19

<210> SEQ ID NO 935
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 935
acuucagccg uggcugccu 19

<210> SEQ ID NO 936
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 936
aggcagccac ggcugaagu 19

<210> SEQ ID NO 937
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 937
cuucagccgu ggcugccug 19

<210> SEQ ID NO 938
<211> LENGTH: 19
<212> TYPE: RNA

<213> ORGANISM: Artificial Sequence
<220> FEATURE:
<223> OTHER INFORMATION: synthetic APOC3 siRNA antisense strand

<400> SEQUENCE: 938
caggcagcca cggcugaag 19

<210> SEQ ID NO 939
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 939
uucagccgug gcugccuga 19

<210> SEQ ID NO 940
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 940
ucaggcagcc acggcugaa 19

<210> SEQ ID NO 941
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 941
ucagccgugg cugccugag 19

<210> SEQ ID NO 942
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 942
cucaggcagc cacggcuga 19

<210> SEQ ID NO 943
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 943
cagccguggc ugccugaga 19

<210> SEQ ID NO 944
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 944
ucucaggcag ccacggcug 19

-continued

<210> SEQ ID NO 945
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 945
agccguggcu gccugagac 19

<210> SEQ ID NO 946
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 946
gucucaggca gccacggcu 19

<210> SEQ ID NO 947
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 947
gccguggcug ccugagacc 19

<210> SEQ ID NO 948
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 948
ggucucaggc agccacggc 19

<210> SEQ ID NO 949
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 949
ccguggcugc cugagaccu 19

<210> SEQ ID NO 950
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 950
aggucucagg cagccacgg 19

<210> SEQ ID NO 951
<211> LENGTH: 19
<212> TYPE: RNA
<213> ORGANISM: Artificial Sequence
<220> FEATURE:

-continued

<223> OTHER INFORMATION: synthetic APOC3 siRNA target or sense strand

<400> SEQUENCE: 951
cguggcugcc ugagaccuc 19

<210> SEQ ID NO 952
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 952
gaggucucag gcagccacg 19

<210> SEQ ID NO 953
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 953
guggcugccu gagaccuca 19

<210> SEQ ID NO 954
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 954
ugaggucuca ggcagccac 19

<210> SEQ ID NO 955
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 955
uggcugccug agaccucaa 19

<210> SEQ ID NO 956
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 956
uugaggucuc aggcagcca 19

<210> SEQ ID NO 957
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 957
ggcugccuga gaccucaau 19

<210> SEQ ID NO 958
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 958
auugaggucu caggcagcc 19

<210> SEQ ID NO 959
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 959
gcugccugag accucaaua 19

<210> SEQ ID NO 960
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 960
uauugagguc ucaggcagc 19

<210> SEQ ID NO 961
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 961
cugccugaga ccucaauac 19

<210> SEQ ID NO 962
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 962
guauugaggu cucaggcag 19

<210> SEQ ID NO 963
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 963
ugccugagac cucaauacc 19

<210> SEQ ID NO 964
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 964
gguauugagg ucucaggca 19

<210> SEQ ID NO 965
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 965
gccugagacc ucaauaccc 19

<210> SEQ ID NO 966
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 966
ggguauugag gucucaggc 19

<210> SEQ ID NO 967
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 967
ccugagaccu caauacccc 19

<210> SEQ ID NO 968
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 968
gggguauuga ggucucagg 19

<210> SEQ ID NO 969
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 969
cugagaccuc aauacccca 19

<210> SEQ ID NO 970
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 970
ugggguauug aggucucag 19

<210> SEQ ID NO 971
<211> LENGTH: 19

<212> TYPE: RNA
<213> ORGANISM: Artificial Sequence
<220> FEATURE:
<223> OTHER INFORMATION: synthetic APOC3 siRNA target or sense strand

<400> SEQUENCE: 971
ugagaccuca auaccccaa 19

<210> SEQ ID NO 972
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 972 uuggguauu gaggucuca 19

<210> SEQ ID NO 973
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 973
gagaccucaa uaccccaag 19

<210> SEQ ID NO 974
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 974 cuuggguau ugaggucuc 19

<210> SEQ ID NO 975
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 975
agaccucaau accccaagu 19

<210> SEQ ID NO 976
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 976
acuuggggua uugaggucu 19

<210> SEQ ID NO 977
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 977
gaccucaaua ccccaaguc 19

<210> SEQ ID NO 978
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 978
gacuuggggu auugagguc 19

<210> SEQ ID NO 979
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 979
accucaauac cccaagucc 19

<210> SEQ ID NO 980
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 980
ggacuugggg uauugaggu 19

<210> SEQ ID NO 981
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 981
ccucaauacc ccaagucca 19

<210> SEQ ID NO 982
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 982
uggacuuggg guauugagg 19

<210> SEQ ID NO 983
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 983
cucaauaccc caaguccac 19

<210> SEQ ID NO 984
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 984
guggacuugg gguauugag 19

<210> SEQ ID NO 985
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 985
ucaauacccc aaguccacc 19

<210> SEQ ID NO 986
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 986
gguggacuug ggguauuga 19

<210> SEQ ID NO 987
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 987
caauacccca aguccaccu 19

<210> SEQ ID NO 988
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 988
agguggacuu gggguauug 19

<210> SEQ ID NO 989
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 989
aauaccccaa guccaccug 19

<210> SEQ ID NO 990
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 990
cagguggacu ugggguauu 19

<210> SEQ ID NO 991
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 991
auaccccaag uccaccugc 19

<210> SEQ ID NO 992
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 992
gcagguggac uuggggguau 19

<210> SEQ ID NO 993
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 993
uaccccaagu ccaccugcc 19

<210> SEQ ID NO 994
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 994
ggcaggugga cuuggggua 19

<210> SEQ ID NO 995
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 995
accccaaguc caccugccu 19

<210> SEQ ID NO 996
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 996
aggcaggugg acuuggggu 19

<210> SEQ ID NO 997
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 997
ccccaagucc accugccua 19

<210> SEQ ID NO 998
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 998
uaggcaggug gacuugggg 19

<210> SEQ ID NO 999
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 999
cccaagucca ccugccuau 19

<210> SEQ ID NO 1000
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1000
auaggcaggu ggacuuggg 19

<210> SEQ ID NO 1001
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1001
ccaaguccac cugccuauc 19

<210> SEQ ID NO 1002
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1002
gauaggcagg uggacuugg 19

<210> SEQ ID NO 1003
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1003
caaguccacc ugccuaucc 19

<210> SEQ ID NO 1004

<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1004
ggauaggcag guggacuug 19

<210> SEQ ID NO 1005
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1005
aaguccaccu gccuaucca 19

<210> SEQ ID NO 1006
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1006
uggauaggca gguggacuu 19

<210> SEQ ID NO 1007
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1007
aguccaccug ccuauccau 19

<210> SEQ ID NO 1008
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1008
auggauaggc agguggacu 19

<210> SEQ ID NO 1009
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1009
guccaccugc cuauccauc 19

<210> SEQ ID NO 1010
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1010
gauggauagg cagguggac 19

<210> SEQ ID NO 1011
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1011
uccaccugcc uauccaucc 19

<210> SEQ ID NO 1012
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1012
ggauggauag gcaggugga 19

<210> SEQ ID NO 1013
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1013
ccaccugccu auccauccu 19

<210> SEQ ID NO 1014
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1014
aggauggaua ggcaggugg 19

<210> SEQ ID NO 1015
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1015
caccugccua uccauccug 19

<210> SEQ ID NO 1016
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1016
caggauggau aggcaggug 19

<210> SEQ ID NO 1017
<211> LENGTH: 19
<212> TYPE: RNA

-continued

<213> ORGANISM: Artificial Sequence
<220> FEATURE:
<223> OTHER INFORMATION: synthetic APOC3 siRNA target or sense strand

<400> SEQUENCE: 1017
accugccuau ccauccugc 19

<210> SEQ ID NO 1018
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1018
gcaggaugga uaggcaggu 19

<210> SEQ ID NO 1019
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1019
ccugccuauc cauccugcg 19

<210> SEQ ID NO 1020
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1020
cgcaggaugg auaggcagg 19

<210> SEQ ID NO 1021
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1021
cugccuaucc auccugcga 19

<210> SEQ ID NO 1022
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1022
ucgcaggaug gauaggcag 19

<210> SEQ ID NO 1023
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1023
ugccuaucca uccugcgag 19

<210> SEQ ID NO 1024
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1024
cucgcaggau ggauaggca 19

<210> SEQ ID NO 1025
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1025
gccuauccau ccugcgagc 19

<210> SEQ ID NO 1026
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1026
gcucgcagga uggauaggc 19

<210> SEQ ID NO 1027
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1027
ccuauccauc cugcgagcu 19

<210> SEQ ID NO 1028
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1028
agcucgcagg auggauagg 19

<210> SEQ ID NO 1029
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1029
cuauccaucc ugcgagcuc 19

<210> SEQ ID NO 1030
<211> LENGTH: 19
<212> TYPE: RNA
<213> ORGANISM: Artificial Sequence
<220> FEATURE:

<223> OTHER INFORMATION: synthetic APOC3 siRNA antisense strand

<400> SEQUENCE: 1030
gagcucgcag gauggauag 19

<210> SEQ ID NO 1031
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1031
uauccauccu gcgagcucc 19

<210> SEQ ID NO 1032
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1032
ggagcucgca ggauggaua 19

<210> SEQ ID NO 1033
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1033
auccauccug cgagcuccu 19

<210> SEQ ID NO 1034
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1034
aggagcucgc aggauggau 19

<210> SEQ ID NO 1035
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1035
uccauccugc gagcuccuu 19

<210> SEQ ID NO 1036
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1036
aaggagcucg caggaugga 19

<210> SEQ ID NO 1037
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1037
ccauccugcg agcuccuug 19

<210> SEQ ID NO 1038
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1038
caaggagcuc gcaggaugg 19

<210> SEQ ID NO 1039
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1039
cauccugcga gcuccuugg 19

<210> SEQ ID NO 1040
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1040
ccaaggagcu cgcaggaug 19

<210> SEQ ID NO 1041
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1041
auccugcgag cuccuuggg 19

<210> SEQ ID NO 1042
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1042
cccaaggagc ucgcaggau 19

<210> SEQ ID NO 1043
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1043
uccugcgagc uccuugggu					19

<210> SEQ ID NO 1044
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1044
acccaaggag cucgcagga					19

<210> SEQ ID NO 1045
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1045
ccugcgagcu ccuuggguc					19

<210> SEQ ID NO 1046
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1046
gacccaagga gcucgcagg					19

<210> SEQ ID NO 1047
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1047
cugcgagcuc cuuggqucc					19

<210> SEQ ID NO 1048
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1048
ggacccaagg agcucgcag					19

<210> SEQ ID NO 1049
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1049
ugcgagcucc uuggguccu					19

<210> SEQ ID NO 1050
<211> LENGTH: 19

<212> TYPE: RNA
<213> ORGANISM: Artificial Sequence
<220> FEATURE:
<223> OTHER INFORMATION: synthetic APOC3 siRNA antisense strand

<400> SEQUENCE: 1050
aggacccaag gagcucgca 19

<210> SEQ ID NO 1051
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1051
gcgagcuccu uggguccug 19

<210> SEQ ID NO 1052
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1052
caggacccaa ggagcucgc 19

<210> SEQ ID NO 1053
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1053
cgagcuccuu ggguccugc 19

<210> SEQ ID NO 1054
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1054
gcaggaccca aggagcucg 19

<210> SEQ ID NO 1055
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1055
gagcuccuug gguccugca 19

<210> SEQ ID NO 1056
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1056

-continued ugcaggaccc aaggagcuc 19

<210> SEQ ID NO 1057
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1057
agcuccuugg guccugcaa 19

<210> SEQ ID NO 1058
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1058
uugcaggacc caaggagcu 19

<210> SEQ ID NO 1059
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1059
gcuccuuggg uccugcaau 19

<210> SEQ ID NO 1060
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1060
auugcaggac ccaaggagc 19

<210> SEQ ID NO 1061
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1061
cuccuugggu ccugcaauc 19

<210> SEQ ID NO 1062
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1062
gauugcagga cccaaggag 19

<210> SEQ ID NO 1063
<211> LENGTH: 19
<212> TYPE: RNA
<213> ORGANISM: Artificial Sequence

```
<220> FEATURE:
<223> OTHER INFORMATION: synthetic APOC3 siRNA target or sense strand

<400> SEQUENCE: 1063

uccuuggguc cugcaaucu                                                19

<210> SEQ ID NO 1064
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1064

agauugcagg acccaagga                                                19

<210> SEQ ID NO 1065
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1065

ccuugggucc ugcaaucuc                                                19

<210> SEQ ID NO 1066
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1066

gagauugcag gacccaagg                                                19

<210> SEQ ID NO 1067
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1067

cuuggguccu gcaaucucc                                                19

<210> SEQ ID NO 1068
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1068

ggagauugca ggacccaag                                                19

<210> SEQ ID NO 1069
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1069

uuggguccug caaucucca                                                19
```

<210> SEQ ID NO 1070
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1070
uggagauugc aggacccaa 19

<210> SEQ ID NO 1071
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1071
uggguccugc aaucuccag 19

<210> SEQ ID NO 1072
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1072
cuggagauug caggaccca 19

<210> SEQ ID NO 1073
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1073
ggguccugca aucuccagg 19

<210> SEQ ID NO 1074
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1074
ccuggagauu gcaggaccc 19

<210> SEQ ID NO 1075
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1075
gguccugcaa ucuccaggg 19

<210> SEQ ID NO 1076
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1076
cccuggagau ugcaggacc 19

<210> SEQ ID NO 1077
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1077
guccugcaau cuccagggc 19

<210> SEQ ID NO 1078
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1078
gcccuggaga uugcaggac 19

<210> SEQ ID NO 1079
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1079
uccugcaauc uccagggcu 19

<210> SEQ ID NO 1080
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1080
agcccuggag auugcagga 19

<210> SEQ ID NO 1081
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1081
ccugcaaucu ccagggcug 19

<210> SEQ ID NO 1082
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1082
cagcccugga gauugcagg 19

<210> SEQ ID NO 1083

<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1083
cugcaaucuc cagggcugc 19

<210> SEQ ID NO 1084
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1084
gcagcccugg agauugcag 19

<210> SEQ ID NO 1085
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1085
ugcaaucucc agggcugcc 19

<210> SEQ ID NO 1086
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1086
ggcagcccug gagauugca 19

<210> SEQ ID NO 1087
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1087
gcaaucucca gggcugccc 19

<210> SEQ ID NO 1088
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1088
gggcagcccu ggagauugc 19

<210> SEQ ID NO 1089
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1089
caaucuccag ggcugcccc 19

<210> SEQ ID NO 1090
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1090
ggggcagccc uggagauug 19

<210> SEQ ID NO 1091
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1091
aaucuccagg gcugccccu 19

<210> SEQ ID NO 1092
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1092
aggggcagcc cuggagauu 19

<210> SEQ ID NO 1093
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1093
aucuccaggg cugccccug 19

<210> SEQ ID NO 1094
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1094
caggggcagc ccuggagau 19

<210> SEQ ID NO 1095
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1095
ucuccagggc ugccccugu 19

<210> SEQ ID NO 1096
<211> LENGTH: 19
<212> TYPE: RNA

<213> ORGANISM: Artificial Sequence
<220> FEATURE:
<223> OTHER INFORMATION: synthetic APOC3 siRNA antisense strand

<400> SEQUENCE: 1096
acaggggcag cccuggaga 19

<210> SEQ ID NO 1097
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1097
cuccagggcu gccccugua 19

<210> SEQ ID NO 1098
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1098
uacaggggca gcccuggag 19

<210> SEQ ID NO 1099
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1099
uccagggcug ccccuguag 19

<210> SEQ ID NO 1100
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1100
cuacaggggc agcccugga 19

<210> SEQ ID NO 1101
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1101
ccagggcugc cccuguagg 19

<210> SEQ ID NO 1102
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1102
ccuacagggg cagcccugg 19

<210> SEQ ID NO 1103
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1103
cagggcugcc ccuguaggu 19

<210> SEQ ID NO 1104
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1104
accuacaggg gcagcccug 19

<210> SEQ ID NO 1105
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1105
agggcugccc cuguagguu 19

<210> SEQ ID NO 1106
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1106
aaccuacagg ggcagcccu 19

<210> SEQ ID NO 1107
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1107
gggcugcccc uguagguug 19

<210> SEQ ID NO 1108
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1108
caaccuacag gggcagccc 19

<210> SEQ ID NO 1109
<211> LENGTH: 19
<212> TYPE: RNA
<213> ORGANISM: Artificial Sequence
<220> FEATURE:

<223> OTHER INFORMATION: synthetic APOC3 siRNA target or sense strand

<400> SEQUENCE: 1109
ggcugccccu guagguugc 19

<210> SEQ ID NO 1110
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1110
gcaaccuaca ggggcagcc 19

<210> SEQ ID NO 1111
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1111
gcugccccug uagguugcu 19

<210> SEQ ID NO 1112
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1112
agcaaccuac aggggcagc 19

<210> SEQ ID NO 1113
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1113
cugccccugu agguugcuu 19

<210> SEQ ID NO 1114
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1114
aagcaaccua caggggcag 19

<210> SEQ ID NO 1115
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1115
ugccccugua gguugcuua 19

<210> SEQ ID NO 1116
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1116
uaagcaaccu acaggggca 19

<210> SEQ ID NO 1117
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1117
gccccuguag guugcuuaa 19

<210> SEQ ID NO 1118
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1118
uuaagcaacc uacaggggc 19

<210> SEQ ID NO 1119
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1119
ccccuguagg uugcuuaaa 19

<210> SEQ ID NO 1120
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1120
uuuaagcaac cuacagggg 19

<210> SEQ ID NO 1121
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1121
cccuguaggu ugcuuaaaa 19

<210> SEQ ID NO 1122
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1122
uuuuaagcaa ccuacaggg 19

<210> SEQ ID NO 1123
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1123
ccuguagguu gcuuaaaag 19

<210> SEQ ID NO 1124
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1124
cuuuuaagca accuacagg 19

<210> SEQ ID NO 1125
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1125
cuguagguug cuuaaaagg 19

<210> SEQ ID NO 1126
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1126
ccuuuuaagc aaccuacag 19

<210> SEQ ID NO 1127
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1127
uguagguugc uuaaaaggg 19

<210> SEQ ID NO 1128
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1128
cccuuuuaag caaccuaca 19

<210> SEQ ID NO 1129
<211> LENGTH: 19

-continued

<212> TYPE: RNA
<213> ORGANISM: Artificial Sequence
<220> FEATURE:
<223> OTHER INFORMATION: synthetic APOC3 siRNA target or sense strand

<400> SEQUENCE: 1129
guagguugcu uaaaaggga 19

<210> SEQ ID NO 1130
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1130
ucccuuuuaa gcaaccuac 19

<210> SEQ ID NO 1131
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1131
uagguugcuu aaaagggac 19

<210> SEQ ID NO 1132
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1132
gucccuuuua agcaaccua 19

<210> SEQ ID NO 1133
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1133
agguugcuua aaagggaca 19

<210> SEQ ID NO 1134
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1134
ugucccuuuu aagcaaccu 19

<210> SEQ ID NO 1135
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1135

-continued gguugcuuaa aagggacag 19

<210> SEQ ID NO 1136
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1136
cugucccuuu uaagcaacc 19

<210> SEQ ID NO 1137
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1137
guugcuuaaa agggacagu 19

<210> SEQ ID NO 1138
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1138
acugucccuu uuaagcaac 19

<210> SEQ ID NO 1139
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1139
uugcuuaaaa gggacagua 19

<210> SEQ ID NO 1140
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1140
uacugucccu uuuaagcaa 19

<210> SEQ ID NO 1141
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1141
ugcuuaaaag ggacaguau 19

<210> SEQ ID NO 1142
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1142
auacuguccc uuuuaagca 19

<210> SEQ ID NO 1143
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1143
gcuuaaaagg gacaguauu 19

<210> SEQ ID NO 1144
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1144
aauacugucc cuuuuaagc 19

<210> SEQ ID NO 1145
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1145
cuuaaaaggg acaguauuc 19

<210> SEQ ID NO 1146
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1146
gaauacuguc ccuuuuaag 19

<210> SEQ ID NO 1147
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1147
uuaaaaggga caguauucu 19

<210> SEQ ID NO 1148
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1148
agaauacugu cccuuuuaa 19

<210> SEQ ID NO 1149
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1149
uaaaagggac aguauucuc 19

<210> SEQ ID NO 1150
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1150
gagaauacug ucccuuuua 19

<210> SEQ ID NO 1151
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1151
aaaagggaca guauucuca 19

<210> SEQ ID NO 1152
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1152
ugagaauacu gucccuuuu 19

<210> SEQ ID NO 1153
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1153
aaagggacag uauucucag 19

<210> SEQ ID NO 1154
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1154
cugagaauac ugucccuuu 19

<210> SEQ ID NO 1155
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1155
aagggacagu auucucagu 19

<210> SEQ ID NO 1156
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1156
acugagaaua cugucccuu 19

<210> SEQ ID NO 1157
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1157
agggacagua uucucagug 19

<210> SEQ ID NO 1158
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1158
cacugagaau acugucccu 19

<210> SEQ ID NO 1159
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1159
gggacaguau ucucagugc 19

<210> SEQ ID NO 1160
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1160
gcacugagaa uacuguccc 19

<210> SEQ ID NO 1161
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1161
ggacaguauu cucagugcu 19

<210> SEQ ID NO 1162

<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1162
agcacugaga auacugucc 19

<210> SEQ ID NO 1163
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1163
gacaguauuc ucagugcuc 19

<210> SEQ ID NO 1164
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1164
gagcacugag aauacuguc 19

<210> SEQ ID NO 1165
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1165
acaguauucu cagugcucu 19

<210> SEQ ID NO 1166
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1166
agagcacuga gaauacugu 19

<210> SEQ ID NO 1167
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1167
caguauucuc agugcucuc 19

<210> SEQ ID NO 1168
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1168
gagagcacug agaauacug 19

<210> SEQ ID NO 1169
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1169
aguauucuca gugcucucc 19

<210> SEQ ID NO 1170
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1170
ggagagcacu gagaauacu 19

<210> SEQ ID NO 1171
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1171
guauucucag ugcucuccu 19

<210> SEQ ID NO 1172
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1172
aggagagcac ugagaauac 19

<210> SEQ ID NO 1173
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1173
uauucucagu gcucuccua 19

<210> SEQ ID NO 1174
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1174
uaggagagca cugagaaua 19

<210> SEQ ID NO 1175
<211> LENGTH: 19
<212> TYPE: RNA

<213> ORGANISM: Artificial Sequence
<220> FEATURE:
<223> OTHER INFORMATION: synthetic APOC3 siRNA target or sense strand

<400> SEQUENCE: 1175
auucucagug cucuccuac 19

<210> SEQ ID NO 1176
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1176
guaggagagc acugagaau 19

<210> SEQ ID NO 1177
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1177
uucucagugc ucuccuacc 19

<210> SEQ ID NO 1178
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1178
gguaggagag cacugagaa 19

<210> SEQ ID NO 1179
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1179
ucucagugcu cuccuaccc 19

<210> SEQ ID NO 1180
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1180
ggguaggaga gcacugaga 19

<210> SEQ ID NO 1181
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1181
cucagugcuc uccuacccc 19

<210> SEQ ID NO 1182
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1182
gggguaggag agcacugag 19

<210> SEQ ID NO 1183
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1183
ucagugcucu ccuacccca 19

<210> SEQ ID NO 1184
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1184
ugggguagga gagcacuga 19

<210> SEQ ID NO 1185
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1185
cagugcucuc cuaccccac 19

<210> SEQ ID NO 1186
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1186 guggguagg agagcacug 19

<210> SEQ ID NO 1187
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1187
agugcucucc uaccccacc 19

<210> SEQ ID NO 1188
<211> LENGTH: 19
<212> TYPE: RNA
<213> ORGANISM: Artificial Sequence
<220> FEATURE:

<223> OTHER INFORMATION: synthetic APOC3 siRNA antisense strand

<400> SEQUENCE: 1188
ggugggguag gagagcacu 19

<210> SEQ ID NO 1189
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1189
gugcucuccu accccaccu 19

<210> SEQ ID NO 1190
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1190 aggugggua ggagagcac 19

<210> SEQ ID NO 1191
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1191
ugcucuccua ccccaccuc 19

<210> SEQ ID NO 1192
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1192 gaggugggu aggagagca 19

<210> SEQ ID NO 1193
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1193
gcucuccuac cccaccuca 19

<210> SEQ ID NO 1194
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1194
ugaggugggg uaggagagc 19

<210> SEQ ID NO 1195
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1195
cucuccuacc ccaccucau 19

<210> SEQ ID NO 1196
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1196
augagguggg guaggagag 19

<210> SEQ ID NO 1197
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1197
ucuccuaccc caccucaug 19

<210> SEQ ID NO 1198
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1198
caugaggugg gguaggaga 19

<210> SEQ ID NO 1199
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1199
cuccuacccc accucaugc 19

<210> SEQ ID NO 1200
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1200
gcaugaggug ggguaggag 19

<210> SEQ ID NO 1201
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1201
uccuacccca ccucaugcc 19

<210> SEQ ID NO 1202
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1202
ggcaugaggu gggguagga 19

<210> SEQ ID NO 1203
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1203
ccuaccccac cucaugccu 19

<210> SEQ ID NO 1204
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1204
aggcaugagg ugggguagg 19

<210> SEQ ID NO 1205
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1205
cuaccccacc ucaugccug 19

<210> SEQ ID NO 1206
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1206
caggcaugag gugggguag 19

<210> SEQ ID NO 1207
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1207
uaccccaccu caugccugg 19

<210> SEQ ID NO 1208
<211> LENGTH: 19

<212> TYPE: RNA
<213> ORGANISM: Artificial Sequence
<220> FEATURE:
<223> OTHER INFORMATION: synthetic APOC3 siRNA antisense strand

<400> SEQUENCE: 1208
ccaggcauga gguggggua 19

<210> SEQ ID NO 1209
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1209
accccaccuc augccuggc 19

<210> SEQ ID NO 1210
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1210
gccaggcaug agguggggu 19

<210> SEQ ID NO 1211
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1211
ccccaccuca ugccuggcc 19

<210> SEQ ID NO 1212
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1212
ggccaggcau gaggugggg 19

<210> SEQ ID NO 1213
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1213
cccaccucau gccuggccc 19

<210> SEQ ID NO 1214
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1214
gggccaggca ugagguggg 19

<210> SEQ ID NO 1215
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1215
ccaccucaug ccuggcccc 19

<210> SEQ ID NO 1216
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1216
ggggccaggc augaggugg 19

<210> SEQ ID NO 1217
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1217
caccucaugc cuggccccc 19

<210> SEQ ID NO 1218
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1218
gggggccagg caugaggug 19

<210> SEQ ID NO 1219
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1219
accucaugcc uggcccccc 19

<210> SEQ ID NO 1220
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1220
ggggggccag gcaugaggu 19

<210> SEQ ID NO 1221
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1221
ccucaugccu ggcccccu 19

<210> SEQ ID NO 1222
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1222
aggggggcca ggcaugagg 19

<210> SEQ ID NO 1223
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1223
cucaugccug gccccccuc 19

<210> SEQ ID NO 1224
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1224
gaggggggcc aggcaugag 19

<210> SEQ ID NO 1225
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1225
ucaugccugg ccccccucc 19

<210> SEQ ID NO 1226
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1226
ggaggggggc caggcauga 19

<210> SEQ ID NO 1227
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1227
caugccuggc cccccucca 19

<210> SEQ ID NO 1228
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1228 uggaggggg ccaggcaug 19

<210> SEQ ID NO 1229
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1229
augccuggcc ccccuccag 19

<210> SEQ ID NO 1230
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1230
cuggaggggg gccaggcau 19

<210> SEQ ID NO 1231
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1231
ugccuggccc cccuccagg 19

<210> SEQ ID NO 1232
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1232
ccuggagggg ggccaggca 19

<210> SEQ ID NO 1233
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1233
gccuggcccc ccuccaggc 19

<210> SEQ ID NO 1234
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1234
gccuggaggg gggccaggc 19

<210> SEQ ID NO 1235
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1235
ccuggccccc cuccaggca 19

<210> SEQ ID NO 1236
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1236
ugccuggagg ggggccagg 19

<210> SEQ ID NO 1237
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1237
cuggcccccc uccaggcau 19

<210> SEQ ID NO 1238
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1238
augccuggag gggggccag 19

<210> SEQ ID NO 1239
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1239
uggccccccu ccaggcaug 19

<210> SEQ ID NO 1240
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1240
caugccugga gggggggcca 19

<210> SEQ ID NO 1241

<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1241
ggccccccuc caggcaugc 19

<210> SEQ ID NO 1242
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1242
gcaugccugg aggggggcc 19

<210> SEQ ID NO 1243
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1243
gccccccucc aggcaugcu 19

<210> SEQ ID NO 1244
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1244
agcaugccug gaggggggc 19

<210> SEQ ID NO 1245
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1245
ccccccucca ggcaugcug 19

<210> SEQ ID NO 1246
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1246
cagcaugccu ggagggggg 19

<210> SEQ ID NO 1247
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1247
cccccuccag gcaugcugg 19

<210> SEQ ID NO 1248
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1248
ccagcaugcc uggaggggg 19

<210> SEQ ID NO 1249
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1249
ccccuccagg caugcuggc 19

<210> SEQ ID NO 1250
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1250
gccagcaugc cuggagggg 19

<210> SEQ ID NO 1251
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1251
cccuccaggc augcuggcc 19

<210> SEQ ID NO 1252
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1252
ggccagcaug ccuggaggg 19

<210> SEQ ID NO 1253
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1253
ccuccaggca ugcuggccu 19

<210> SEQ ID NO 1254
<211> LENGTH: 19
<212> TYPE: RNA

<213> ORGANISM: Artificial Sequence
<220> FEATURE:
<223> OTHER INFORMATION: synthetic APOC3 siRNA antisense strand

<400> SEQUENCE: 1254
aggccagcau gccuggagg 19

<210> SEQ ID NO 1255
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1255
cuccaggcau gcuggccuc 19

<210> SEQ ID NO 1256
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1256
gaggccagca ugccuggag 19

<210> SEQ ID NO 1257
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1257
uccaggcaug cuggccucc 19

<210> SEQ ID NO 1258
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1258
ggaggccagc augccugga 19

<210> SEQ ID NO 1259
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1259
ccaggcaugc uggccuccc 19

<210> SEQ ID NO 1260
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1260
gggaggccag caugccugg 19

<210> SEQ ID NO 1261
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1261
caggcaugcu ggccuccca 19

<210> SEQ ID NO 1262
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1262
ugggaggcca gcaugccug 19

<210> SEQ ID NO 1263
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1263
aggcaugcug gccucccaa 19

<210> SEQ ID NO 1264
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1264
uugggaggcc agcaugccu 19

<210> SEQ ID NO 1265
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1265
ggcaugcugg ccucccaau 19

<210> SEQ ID NO 1266
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1266
auugggaggc cagcaugcc 19

<210> SEQ ID NO 1267
<211> LENGTH: 19
<212> TYPE: RNA
<213> ORGANISM: Artificial Sequence
<220> FEATURE:

<223> OTHER INFORMATION: synthetic APOC3 siRNA target or sense strand

<400> SEQUENCE: 1267
gcaugcuggc cucccaaua 19

<210> SEQ ID NO 1268
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1268
uauugggagg ccagcaugc 19

<210> SEQ ID NO 1269
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1269
caugcuggcc ucccaauaa 19

<210> SEQ ID NO 1270
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1270
uuauugggag gccagcaug 19

<210> SEQ ID NO 1271
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1271
augcuggccu cccaauaaa 19

<210> SEQ ID NO 1272
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1272
uuuauuggga ggccagcau 19

<210> SEQ ID NO 1273
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1273
ugcuggccuc ccaauaaag 19

<210> SEQ ID NO 1274
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1274
cuuuauuggg aggccagca 19

<210> SEQ ID NO 1275
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1275
gcuggccucc caauaaagc 19

<210> SEQ ID NO 1276
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1276
gcuuuauugg gaggccagc 19

<210> SEQ ID NO 1277
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1277
cuggccuccc aauaaagcu 19

<210> SEQ ID NO 1278
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1278
agcuuuauug ggaggccag 19

<210> SEQ ID NO 1279
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1279
uggccuccca auaaagcug 19

<210> SEQ ID NO 1280
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1280
cagcuuuauu gggaggcca 19

<210> SEQ ID NO 1281
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1281
ggccucccaa uaaagcugg 19

<210> SEQ ID NO 1282
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1282
ccagcuuuau ugggaggcc 19

<210> SEQ ID NO 1283
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1283
gccucccaau aaagcugga 19

<210> SEQ ID NO 1284
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1284
uccagcuuua uugggaggc 19

<210> SEQ ID NO 1285
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1285
ccucccaaua aagcuggac 19

<210> SEQ ID NO 1286
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1286
guccagcuuu auugggagg 19

<210> SEQ ID NO 1287
<211> LENGTH: 19

-continued

<212> TYPE: RNA
<213> ORGANISM: Artificial Sequence
<220> FEATURE:
<223> OTHER INFORMATION: synthetic APOC3 siRNA target or sense strand

<400> SEQUENCE: 1287
cucccaauaa agcuggaca 19

<210> SEQ ID NO 1288
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1288
uguccagcuu uauugggag 19

<210> SEQ ID NO 1289
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1289
ucccaauaaa gcuggacaa 19

<210> SEQ ID NO 1290
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1290
uuguccagcu uuauuggga 19

<210> SEQ ID NO 1291
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1291
cccaauaaag cuggacaag 19

<210> SEQ ID NO 1292
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1292
cuuguccagc uuuauuggg 19

<210> SEQ ID NO 1293
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1293

-continued ccaauaaagc uggacaaga 19

<210> SEQ ID NO 1294
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1294
ucuuguccag cuuuauugg 19

<210> SEQ ID NO 1295
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1295
caauaaagcu ggacaagaa 19

<210> SEQ ID NO 1296
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1296
uucuugucca gcuuuauug 19

<210> SEQ ID NO 1297
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1297
aauaaagcug gacaagaag 19

<210> SEQ ID NO 1298
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1298
cuucuugucc agcuuuauu 19

<210> SEQ ID NO 1299
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1299
auaaagcugg acaagaagc 19

<210> SEQ ID NO 1300
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1300
gcuucuuguc cagcuuuau 19

<210> SEQ ID NO 1301
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1301
uaaagcugga caagaagcu 19

<210> SEQ ID NO 1302
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1302
agcuucuugu ccagcuuua 19

<210> SEQ ID NO 1303
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1303
aaagcuggac aagaagcug 19

<210> SEQ ID NO 1304
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1304
cagcuucuug uccagcuuu 19

<210> SEQ ID NO 1305
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1305
aagcuggaca agaagcugc 19

<210> SEQ ID NO 1306
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1306
gcagcuucuu guccagcuu 19

<210> SEQ ID NO 1307
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1307
agcuggacaa gaagcugcu 19

<210> SEQ ID NO 1308
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1308
agcagcuucu uguccagcu 19

<210> SEQ ID NO 1309
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1309
gcuggacaag aagcugcua 19

<210> SEQ ID NO 1310
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1310
uagcagcuuc uuguccagc 19

<210> SEQ ID NO 1311
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1311
cuggacaaga agcugcuau 19

<210> SEQ ID NO 1312
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1312
auagcagcuu cuuguccag 19

<210> SEQ ID NO 1313
<211> LENGTH: 19
<212> TYPE: RNA
<213> ORGANISM: Artificial Sequence
<220> FEATURE:
<223> OTHER INFORMATION: synthetic APOC3 siRNA target or sense strand

<400> SEQUENCE: 1313
uggacaagaa gcugcuaug 19

<210> SEQ ID NO 1314
<211> LENGTH: 19
<212> TYPE: RNA
<213> ORGANISM: Artificial Sequence
<220> FEATURE:
<223> OTHER INFORMATION: synthetic APOC3 siRNA antisense strand

<400> SEQUENCE: 1314
cauagcagcu ucuugucca 19

<210> SEQ ID NO 1315
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1315
ccuggcaucu gcccgagcu 19

<210> SEQ ID NO 1316
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1316
ccuggcaucu gcccgagcug a 21

<210> SEQ ID NO 1317
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1317
agcucgggca gaugccagga g 21

<210> SEQ ID NO 1318
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1318
acagggcuac auggaacaa 19

<210> SEQ ID NO 1319
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1319
acagggcuac auggaacaag c 21

<210> SEQ ID NO 1320

<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1320
uuguuccaug uagcccugua c 21

<210> SEQ ID NO 1321
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1321
gcuggaugga caaucacuu 19

<210> SEQ ID NO 1322
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1322
gcuggaugga caaucacuuc a 21

<210> SEQ ID NO 1323
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1323
aagugauugu ccauccagcc c 21

<210> SEQ ID NO 1324
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1324
ucacuucaga ucccugaaa 19

<210> SEQ ID NO 1325
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1325
ucacuucaga ucccugaaag g 21

<210> SEQ ID NO 1326
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1326

-continued uuucagggau cugaagugau u 21

<210> SEQ ID NO 1327
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1327
cugaaaggcu acuggagca 19

<210> SEQ ID NO 1328
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1328
cugaaaggcu acuggagcaa g 21

<210> SEQ ID NO 1329
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1329
ugcuccagua gccuuucagg g 21

<210> SEQ ID NO 1330
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1330
aaggcuacug gagcaaguu 19

<210> SEQ ID NO 1331
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1331
aaggcuacug gagcaaguuu a 21

<210> SEQ ID NO 1332
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1332
aacuugcucc aguagccuuu c 21

<210> SEQ ID NO 1333
<211> LENGTH: 19
<212> TYPE: RNA

<213> ORGANISM: Artificial Sequence
<220> FEATURE:
<223> OTHER INFORMATION: synthetic mouse APOC3 siRNA target strand

<400> SEQUENCE: 1333
aggcuacugg agcaaguuu 19

<210> SEQ ID NO 1334
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1334
aggcuacugg agcaaguuua c 21

<210> SEQ ID NO 1335
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1335
aaacuugcuc caguagccuu u 21

<210> SEQ ID NO 1336
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1336
ggcuacugga gcaaguuua 19

<210> SEQ ID NO 1337
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1337
ggcuacugga gcaaguuuac u 21

<210> SEQ ID NO 1338
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1338
uaaacuugcu ccaguagccu u 21

<210> SEQ ID NO 1339
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1339
gcuacuggag caaguuuac 19

<210> SEQ ID NO 1340
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1340
gcuacuggag caaguuuacu g 21

<210> SEQ ID NO 1341
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1341
guaaacuugc uccaguagcc u 21

<210> SEQ ID NO 1342
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1342
gcaaguuuac ugacaaguu 19

<210> SEQ ID NO 1343
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1343
gcaaguuuac ugacaaguuc a 21

<210> SEQ ID NO 1344
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1344
aacuugucag uaaacuugcu c 21

<210> SEQ ID NO 1345
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1345
ccaaccaacu ccagcuauu 19

<210> SEQ ID NO 1346
<211> LENGTH: 21
<212> TYPE: RNA
<213> ORGANISM: Artificial Sequence
<220> FEATURE:

<223> OTHER INFORMATION: synthetic mouse APOC3 siRNA sense strand

<400> SEQUENCE: 1346
ccaaccaacu ccagcuauug a 21

<210> SEQ ID NO 1347
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1347
aauagcugga guugguuggu c 21

<210> SEQ ID NO 1348
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1348
caaccaacuc cagcuauug 19

<210> SEQ ID NO 1349
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1349
caaccaacuc cagcuauuga g 21

<210> SEQ ID NO 1350
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1350
caauagcugg aguugguugg u 21

<210> SEQ ID NO 1351
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1351
gucgugagac uucuguguu 19

<210> SEQ ID NO 1352
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1352
gucgugagac uucuguguug c 21

-continued

<210> SEQ ID NO 1353
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1353
aacacagaag ucucacgacu c 21

<210> SEQ ID NO 1354
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1354
ucccuagauc ucaccuaaa 19

<210> SEQ ID NO 1355
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1355
ucccuagauc ucaccuaaac a 21

<210> SEQ ID NO 1356
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1356
uuuaggugag aucuagggag g 21

<210> SEQ ID NO 1357
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1357
cccuagaucu caccuaaac 19

<210> SEQ ID NO 1358
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1358
cccuagaucu caccuaaaca u 21

<210> SEQ ID NO 1359
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1359
guuuagguga gaucuaggga g 21

<210> SEQ ID NO 1360
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1360
ccuagaucuc accuaaaca 19

<210> SEQ ID NO 1361
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1361
ccuagaucuc accuaaacau g 21

<210> SEQ ID NO 1362
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1362
uguuuaggug agaucuaggg a 21

<210> SEQ ID NO 1363
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1363
caugcugucc cuaauaaag 19

<210> SEQ ID NO 1364
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1364
caugcugucc cuaauaaagc u 21

<210> SEQ ID NO 1365
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1365
cuuuauuagg gacagcaugu u 21

<210> SEQ ID NO 1366
<211> LENGTH: 19

<212> TYPE: RNA
<213> ORGANISM: Artificial Sequence
<220> FEATURE:
<223> OTHER INFORMATION: synthetic mouse APOC3 siRNA target strand

<400> SEQUENCE: 1366
cccuaauaaa gcuggauaa 19

<210> SEQ ID NO 1367
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1367
cccuaauaaa gcuggauaag a 21

<210> SEQ ID NO 1368
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1368
uuauccagcu uuauuaggga c 21

<210> SEQ ID NO 1369
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1369
ccuaauaaag cuggauaag 19

<210> SEQ ID NO 1370
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1370
ccuaauaaag cuggauaaga a 21

<210> SEQ ID NO 1371
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1371
cuuauccagc uuuauuaggg a 21

<210> SEQ ID NO 1372
<211> LENGTH: 19
<212> TYPE: RNA
<213> ORGANISM: Artificial Sequence
<220> FEATURE:
<223> OTHER INFORMATION: synthetic mouse APOC3 siRNA target strand

<400> SEQUENCE: 1372
agcuggauaa gaagcugcu 19

<210> SEQ ID NO 1373
<211> LENGTH: 21
<212> TYPE: RNA
<213> ORGANISM: Artificial Sequence
<220> FEATURE:
<223> OTHER INFORMATION: synthetic mouse APOC3 siRNA sense strand

<400> SEQUENCE: 1373
agcuggauaa gaagcugcug u 21

<210> SEQ ID NO 1374
<211> LENGTH: 21
<212> TYPE: RNA
<213> ORGANISM: Artificial Sequence
<220> FEATURE:
<223> OTHER INFORMATION: synthetic mouse APOC3 siRNA antisense strand

<400> SEQUENCE: 1374
agcagcuucu uauccagcuu u 21

<210> SEQ ID NO 1375
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_465U2.1G1.1 sense strand
<220> FEATURE:
<221> NAME/KEY: modified_base
<222> LOCATION: (1)...(1)
<223> OTHER INFORMATION: n = um
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 1375
ncccuanauc ucaccnaaac a 21

<210> SEQ ID NO 1376
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_465U2.1G1.1 antisense strand
<220> FEATURE:
<221> NAME/KEY: modified_base
<222> LOCATION: (7)...(7)
<223> OTHER INFORMATION: n = um
<220> FEATURE:
<221> NAME/KEY: modified_base
<222> LOCATION: (16)...(16)
<223> OTHER INFORMATION: n = gm

<400> SEQUENCE: 1376
uuuaggngag aucuanggag g 21

<210> SEQ ID NO 1377
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA mAPoc3_465U2.2G1.1C1 sense strand
<220> FEATURE:
<221> NAME/KEY: modified_base
<222> LOCATION: (1)...(1)
<223> OTHER INFORMATION: n = um
<220> FEATURE:
<221> NAME/KEY: modified_base
<222> LOCATION: (2)...(2)
<223> OTHER INFORMATION: n = cm
<220> FEATURE:
<221> NAME/KEY: modified_base
<222> LOCATION: (7)...(7)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 1377
nnccuanauc ucaccnaaac a 21

<210> SEQ ID NO 1378
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_465U2.2G1.1C1 antisense strand
<220> FEATURE:
<221> NAME/KEY: modified_base
<222> LOCATION: (2)...(7)
<223> OTHER INFORMATION: n = um
<220> FEATURE:
<221> NAME/KEY: modified_base
<222> LOCATION: (16)...(16)
<223> OTHER INFORMATION: n = gm

<400> SEQUENCE: 1378
unuaggngag aucuanggag g 21

<210> SEQ ID NO 1379
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_467U3.1G0.1 sense strand
<220> FEATURE:
<221> NAME/KEY: modified_base
<222> LOCATION: (7)...(20)
<223> OTHER INFORMATION: n = um

<400> SEQUENCE: 1379
ccuagancuc accnaaacan g 21

<210> SEQ ID NO 1380
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_467U3.1G0.1 antisense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 1380
uguuuagnug agaucnaggg a 21

<210> SEQ ID NO 1381
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_467U3.1G0.2C1 sense strand
<220> FEATURE:
<221> NAME/KEY: modified_base
<222> LOCATION: (2)...(2)
<223> OTHER INFORMATION: n = cm
<220> FEATURE:
<221> NAME/KEY: modified_base
<222> LOCATION: (7)...(20)
<223> OTHER INFORMATION: n = um

<400> SEQUENCE: 1381
cnuagancuc accnaaacan g 21

<210> SEQ ID NO 1382
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_467U3.1G0.2C1 antisense strand
<220> FEATURE:
<221> NAME/KEY: modified_base
<222> LOCATION: (2)...(8)
<223> OTHER INFORMATION: n = gm
<220> FEATURE:
<221> NAME/KEY: modified_base
<222> LOCATION: (16)...(16)
<223> OTHER INFORMATION: n = um

<400> SEQUENCE: 1382
unuuuagnug agaucnaggg a 21

<210> SEQ ID NO 1383
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_492U3.1G0.1 sense strand
<220> FEATURE:
<221> NAME/KEY: modified_base
<222> LOCATION: (7)...(17)
<223> OTHER INFORMATION: n = um

<400> SEQUENCE: 1383
cccuaanaaa gcngganaag a 21

<210> SEQ ID NO 1384
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA
mAPoc3_492U3.1G0.1 antisense strand
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 1384
uuauccagcu unauuaggna c 21

<210> SEQ ID NO 1385
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA mAPoc3_492U3.2G0.1C1 sense strand
<220> FEATURE:
<221> NAME/KEY: modified_base
<222> LOCATION: (2)...(2)
<223> OTHER INFORMATION: n = cm
<220> FEATURE:
<221> NAME/KEY: modified_base
<222> LOCATION: (7)...(17)
<223> OTHER INFORMATION: n = um

<400> SEQUENCE: 1385
cncuaanaaa gcngganaag a 21

<210> SEQ ID NO 1386
<211> LENGTH: 21
<212> TYPE: RNA
<213> ORGANISM: Artificial Sequence
<220> FEATURE:
<223> OTHER INFORMATION: synthetic 2'-OMe-modified mouse APOC3 siRNA mAPoc3_492U3.2G0.1C1 antisense strand
<220> FEATURE:
<221> NAME/KEY: modified_base
<222> LOCATION: (2)...(12)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 1386
unauccagcu unauuaggna c 21

<210> SEQ ID NO 1387
<211> LENGTH: 19
<212> TYPE: RNA
<213> ORGANISM: Artificial Sequence
<220> FEATURE:
<223> OTHER INFORMATION: synthetic human APOC3 siRNA hAPOC3_54 target sequence

<400> SEQUENCE: 1387
cggguacucc uuguuguug 19

<210> SEQ ID NO 1388
<211> LENGTH: 21
<212> TYPE: RNA
<213> ORGANISM: Artificial Sequence
<220> FEATURE:
<223> OTHER INFORMATION: synthetic human APOC3 siRNA hAPOC3_54 sense strand

<400> SEQUENCE: 1388
cggguacucc uuguuguugc c 21

<210> SEQ ID NO 1389
<211> LENGTH: 21
<212> TYPE: RNA
<213> ORGANISM: Artificial Sequence
<220> FEATURE:
<223> OTHER INFORMATION: synthetic human APOC3 siRNA hAPOC3_54 antisense strand

<400> SEQUENCE: 1389
caacaacaag gaguacccgg g 21

<210> SEQ ID NO 1390
<211> LENGTH: 19
<212> TYPE: RNA
<213> ORGANISM: Artificial Sequence
<220> FEATURE:
<223> OTHER INFORMATION: synthetic human APOC3 siRNA hAPOC3_120 target sequence

<400> SEQUENCE: 1390
gccucccuuc ucagcuuca 19

<210> SEQ ID NO 1391
<211> LENGTH: 21
<212> TYPE: RNA
<213> ORGANISM: Artificial Sequence
<220> FEATURE:
<223> OTHER INFORMATION: synthetic human APOC3 siRNA hAPOC3_120 sense strand

<400> SEQUENCE: 1391
gccucccuuc ucagcuucau g 21

<210> SEQ ID NO 1392
<211> LENGTH: 21
<212> TYPE: RNA
<213> ORGANISM: Artificial Sequence
<220> FEATURE:
<223> OTHER INFORMATION: synthetic human APOC3 siRNA hAPOC3_120 antisense strand

<400> SEQUENCE: 1392
ugaagcugag aagggaggca u 21

<210> SEQ ID NO 1393
<211> LENGTH: 19
<212> TYPE: RNA
<213> ORGANISM: Artificial Sequence
<220> FEATURE:
<223> OTHER INFORMATION: synthetic human APOC3 siRNA hAPOC3_241 target sequence

<400> SEQUENCE: 1393
gcuucaguuc ccugaaaga 19

<210> SEQ ID NO 1394
<211> LENGTH: 21
<212> TYPE: RNA
<213> ORGANISM: Artificial Sequence
<220> FEATURE:
<223> OTHER INFORMATION: synthetic human APOC3 siRNA hAPOC3_241 sense strand

<400> SEQUENCE: 1394
gcuucaguuc ccugaaagac u 21

<210> SEQ ID NO 1395
<211> LENGTH: 21
<212> TYPE: RNA
<213> ORGANISM: Artificial Sequence
<220> FEATURE:
<223> OTHER INFORMATION: synthetic human APOC3 siRNA hAPOC3_241 antisense strand

<400> SEQUENCE: 1395
ucuuucaggg aacugaagcc a 21

<210> SEQ ID NO 1396
<211> LENGTH: 19
<212> TYPE: RNA
<213> ORGANISM: Artificial Sequence
<220> FEATURE:
<223> OTHER INFORMATION: synthetic human APOC3 siRNA hAPOC3_259 target sequence

<400> SEQUENCE: 1396
acuacuggag caccguuaa 19

<210> SEQ ID NO 1397
<211> LENGTH: 21
<212> TYPE: RNA
<213> ORGANISM: Artificial Sequence
<220> FEATURE:
<223> OTHER INFORMATION: synthetic human APOC3 siRNA hAPOC3_259 sense strand

<400> SEQUENCE: 1397
acuacuggag caccguuaag g 21

<210> SEQ ID NO 1398
<211> LENGTH: 21
<212> TYPE: RNA
<213> ORGANISM: Artificial Sequence
<220> FEATURE:
<223> OTHER INFORMATION: synthetic human APOC3 siRNA hAPOC3_259 antisense strand

<400> SEQUENCE: 1398
uuaacggugc uccaguaguc u 21

<210> SEQ ID NO 1399
<211> LENGTH: 19
<212> TYPE: RNA
<213> ORGANISM: Artificial Sequence
<220> FEATURE:
<223> OTHER INFORMATION: synthetic human APOC3 siRNA hAPOC3_260 target sequence

<400> SEQUENCE: 1399
cuacuggagc accguuaag 19

<210> SEQ ID NO 1400
<211> LENGTH: 21
<212> TYPE: RNA
<213> ORGANISM: Artificial Sequence
<220> FEATURE:
<223> OTHER INFORMATION: synthetic human APOC3 siRNA hAPOC3_260 sense strand

<400> SEQUENCE: 1400
cuacuggagc accguuaagg a 21

<210> SEQ ID NO 1401
<211> LENGTH: 21
<212> TYPE: RNA
<213> ORGANISM: Artificial Sequence
<220> FEATURE:
<223> OTHER INFORMATION: synthetic human APOC3 siRNA hAPOC3_260 antisense strand

<400> SEQUENCE: 1401
cuuaacggug cuccaguagu c 21

<210> SEQ ID NO 1402
<211> LENGTH: 19
<212> TYPE: RNA
<213> ORGANISM: Artificial Sequence
<220> FEATURE:
<223> OTHER INFORMATION: synthetic human APOC3 siRNA hAPOC3_266 target sequence

<400> SEQUENCE: 1402
gagcaccguu aaggacaag 19

<210> SEQ ID NO 1403
<211> LENGTH: 21
<212> TYPE: RNA
<213> ORGANISM: Artificial Sequence
<220> FEATURE:
<223> OTHER INFORMATION: synthetic human APOC3 siRNA hAPOC3_266 sense strand

<400> SEQUENCE: 1403
gagcaccguu aaggacaagu u 21

<210> SEQ ID NO 1404
<211> LENGTH: 21
<212> TYPE: RNA
<213> ORGANISM: Artificial Sequence
<220> FEATURE:
<223> OTHER INFORMATION: synthetic human APOC3 siRNA hAPOC3_266 antisense strand

<400> SEQUENCE: 1404
cuuguccuua acggugcucc a 21

<210> SEQ ID NO 1405
<211> LENGTH: 19
<212> TYPE: RNA
<213> ORGANISM: Artificial Sequence
<220> FEATURE:
<223> OTHER INFORMATION: synthetic human APOC3 siRNA hAPOC3_267 target sequence

<400> SEQUENCE: 1405
agcaccguua aggacaagu 19

<210> SEQ ID NO 1406
<211> LENGTH: 21
<212> TYPE: RNA
<213> ORGANISM: Artificial Sequence
<220> FEATURE:
<223> OTHER INFORMATION: synthetic human APOC3 siRNA hAPOC3_267 sense strand

<400> SEQUENCE: 1406
agcaccguua aggacaaguu c 21

<210> SEQ ID NO 1407
<211> LENGTH: 21
<212> TYPE: RNA
<213> ORGANISM: Artificial Sequence
<220> FEATURE:
<223> OTHER INFORMATION: synthetic human APOC3 siRNA hAPOC3_267 antisense strand

<400> SEQUENCE: 1407
acuuguccuu aacggugcuc c 21

<210> SEQ ID NO 1408
<211> LENGTH: 19
<212> TYPE: RNA
<213> ORGANISM: Artificial Sequence
<220> FEATURE:
<223> OTHER INFORMATION: synthetic human APOC3 siRNA hAPOC3_268 target sequence

<400> SEQUENCE: 1408
gcaccguuaa ggacaaguu 19

<210> SEQ ID NO 1409
<211> LENGTH: 21
<212> TYPE: RNA
<213> ORGANISM: Artificial Sequence
<220> FEATURE:
<223> OTHER INFORMATION: synthetic human APOC3 siRNA hAPOC3_268 sense strand

<400> SEQUENCE: 1409
gcaccguuaa ggacaaguuc u 21

<210> SEQ ID NO 1410
<211> LENGTH: 21
<212> TYPE: RNA
<213> ORGANISM: Artificial Sequence
<220> FEATURE:
<223> OTHER INFORMATION: synthetic human APOC3 siRNA hAPOC3_268 antisense strand

<400> SEQUENCE: 1410
aacuuguccu uaacggugcu c 21

<210> SEQ ID NO 1411
<211> LENGTH: 19
<212> TYPE: RNA
<213> ORGANISM: Artificial Sequence
<220> FEATURE:
<223> OTHER INFORMATION: synthetic human APOC3 siRNA hAPOC3_270 target sequence

<400> SEQUENCE: 1411
accguuaagg acaaguucu 19

<210> SEQ ID NO 1412
<211> LENGTH: 21
<212> TYPE: RNA
<213> ORGANISM: Artificial Sequence
<220> FEATURE:
<223> OTHER INFORMATION: synthetic human APOC3 siRNA hAPOC3_270 sense strand

<400> SEQUENCE: 1412
accguuaagg acaaguucuc u 21

<210> SEQ ID NO 1413
<211> LENGTH: 21
<212> TYPE: RNA
<213> ORGANISM: Artificial Sequence
<220> FEATURE:
<223> OTHER INFORMATION: synthetic human APOC3 siRNA hAPOC3_270 antisense strand

<400> SEQUENCE: 1413
agaacuuguc cuuaacggug c 21

-continued

<210> SEQ ID NO 1414
<211> LENGTH: 19
<212> TYPE: RNA
<213> ORGANISM: Artificial Sequence
<220> FEATURE:
<223> OTHER INFORMATION: synthetic human APOC3 siRNA hAPOC3_277 target sequence

<400> SEQUENCE: 1414
aggacaaguu cucugaguu 19

<210> SEQ ID NO 1415
<211> LENGTH: 21
<212> TYPE: RNA
<213> ORGANISM: Artificial Sequence
<220> FEATURE:
<223> OTHER INFORMATION: synthetic human APOC3 siRNA hAPOC3_277 sense strand

<400> SEQUENCE: 1415
aggacaaguu cucugaguuc u 21

<210> SEQ ID NO 1416
<211> LENGTH: 21
<212> TYPE: RNA
<213> ORGANISM: Artificial Sequence
<220> FEATURE:
<223> OTHER INFORMATION: synthetic human APOC3 siRNA hAPOC3_277 antisense strand

<400> SEQUENCE: 1416
aacucagaga acuuguccuu a 21

<210> SEQ ID NO 1417
<211> LENGTH: 19
<212> TYPE: RNA
<213> ORGANISM: Artificial Sequence
<220> FEATURE:
<223> OTHER INFORMATION: synthetic human APOC3 siRNA hAPOC3_286 target sequence

<400> SEQUENCE: 1417
ucucugaguu cugggauuu 19

<210> SEQ ID NO 1418
<211> LENGTH: 21
<212> TYPE: RNA
<213> ORGANISM: Artificial Sequence
<220> FEATURE:
<223> OTHER INFORMATION: synthetic human APOC3 siRNA hAPOC3_286 sense strand

<400> SEQUENCE: 1418
ucucugaguu cugggauuug g 21

<210> SEQ ID NO 1419
<211> LENGTH: 21
<212> TYPE: RNA
<213> ORGANISM: Artificial Sequence
<220> FEATURE:
<223> OTHER INFORMATION: synthetic human APOC3 siRNA hAPOC3_286 antisense strand

<400> SEQUENCE: 1419
aaaucccaga acucagagaa c 21

-continued

<210> SEQ ID NO 1420
<211> LENGTH: 19
<212> TYPE: RNA
<213> ORGANISM: Artificial Sequence
<220> FEATURE:
<223> OTHER INFORMATION: synthetic human APOC3 siRNA hAPOC3_287 target sequence

<400> SEQUENCE: 1420
cucugaguuc ugggauuug 19

<210> SEQ ID NO 1421
<211> LENGTH: 21
<212> TYPE: RNA
<213> ORGANISM: Artificial Sequence
<220> FEATURE:
<223> OTHER INFORMATION: synthetic human APOC3 siRNA hAPOC3_287 sense strand

<400> SEQUENCE: 1421
cucugaguuc ugggauuugg a 21

<210> SEQ ID NO 1422
<211> LENGTH: 21
<212> TYPE: RNA
<213> ORGANISM: Artificial Sequence
<220> FEATURE:
<223> OTHER INFORMATION: synthetic human APOC3 siRNA hAPOC3_287 antisense strand

<400> SEQUENCE: 1422
caaaucccag aacucagaga a 21

<210> SEQ ID NO 1423
<211> LENGTH: 19
<212> TYPE: RNA
<213> ORGANISM: Artificial Sequence
<220> FEATURE:
<223> OTHER INFORMATION: synthetic human APOC3 siRNA hAPOC3_308 target sequence

<400> SEQUENCE: 1423
cccugagguc agaccaacu 19

<210> SEQ ID NO 1424
<211> LENGTH: 21
<212> TYPE: RNA
<213> ORGANISM: Artificial Sequence
<220> FEATURE:
<223> OTHER INFORMATION: synthetic human APOC3 siRNA hAPOC3_308 sense strand

<400> SEQUENCE: 1424
cccugagguc agaccaacuu c 21

<210> SEQ ID NO 1425
<211> LENGTH: 21
<212> TYPE: RNA
<213> ORGANISM: Artificial Sequence
<220> FEATURE:
<223> OTHER INFORMATION: synthetic human APOC3 siRNA hAPOC3_308 antisense strand

<400> SEQUENCE: 1425
aguuggucug accucagggu c 21

<210> SEQ ID NO 1426
<211> LENGTH: 19
<212> TYPE: RNA
<213> ORGANISM: Artificial Sequence
<220> FEATURE:
<223> OTHER INFORMATION: synthetic human APOC3 siRNA hAPOC3_309 target sequence

<400> SEQUENCE: 1426
ccugagguca gaccaacuu 19

<210> SEQ ID NO 1427
<211> LENGTH: 21
<212> TYPE: RNA
<213> ORGANISM: Artificial Sequence
<220> FEATURE:
<223> OTHER INFORMATION: synthetic human APOC3 siRNA hAPOC3_309 sense strand

<400> SEQUENCE: 1427
ccugagguca gaccaacuuc a 21

<210> SEQ ID NO 1428
<211> LENGTH: 21
<212> TYPE: RNA
<213> ORGANISM: Artificial Sequence
<220> FEATURE:
<223> OTHER INFORMATION: synthetic human APOC3 siRNA hAPOC3_309 antisense strand

<400> SEQUENCE: 1428
aaguuggucu gaccucaggg u 21

<210> SEQ ID NO 1429
<211> LENGTH: 19
<212> TYPE: RNA
<213> ORGANISM: Artificial Sequence
<220> FEATURE:
<223> OTHER INFORMATION: synthetic human APOC3 siRNA hAPOC3_312 target sequence

<400> SEQUENCE: 1429
gaggucagac caacuucag 19

<210> SEQ ID NO 1430
<211> LENGTH: 21
<212> TYPE: RNA
<213> ORGANISM: Artificial Sequence
<220> FEATURE:
<223> OTHER INFORMATION: synthetic human APOC3 siRNA hAPOC3_312 sense strand

<400> SEQUENCE: 1430
gaggucagac caacuucagc c 21

<210> SEQ ID NO 1431
<211> LENGTH: 21
<212> TYPE: RNA
<213> ORGANISM: Artificial Sequence
<220> FEATURE:
<223> OTHER INFORMATION: synthetic human APOC3 siRNA hAPOC3_312 antisense strand

<400> SEQUENCE: 1431
cugaaguugg ucugaccuca g 21

<210> SEQ ID NO 1432

<211> LENGTH: 19
<212> TYPE: RNA
<213> ORGANISM: Artificial Sequence
<220> FEATURE:
<223> OTHER INFORMATION: synthetic human APOC3 siRNA hAPOC3_334 target sequence

<400> SEQUENCE: 1432
uggcugccug agaccucaa 19

<210> SEQ ID NO 1433
<211> LENGTH: 21
<212> TYPE: RNA
<213> ORGANISM: Artificial Sequence
<220> FEATURE:
<223> OTHER INFORMATION: synthetic human APOC3 siRNA hAPOC3_334 sense strand

<400> SEQUENCE: 1433
uggcugccug agaccucaau a 21

<210> SEQ ID NO 1434
<211> LENGTH: 21
<212> TYPE: RNA
<213> ORGANISM: Artificial Sequence
<220> FEATURE:
<223> OTHER INFORMATION: synthetic human APOC3 siRNA hAPOC3_334 a ntisense strand

<400> SEQUENCE: 1434
uugaggucuc aggcagccac g 21

<210> SEQ ID NO 1435
<211> LENGTH: 19
<212> TYPE: RNA
<213> ORGANISM: Artificial Sequence
<220> FEATURE:
<223> OTHER INFORMATION: synthetic human APOC3 siRNA hAPOC3_335 target sequence

<400> SEQUENCE: 1435
ggcugccuga gaccucaau 19

<210> SEQ ID NO 1436
<211> LENGTH: 21
<212> TYPE: RNA
<213> ORGANISM: Artificial Sequence
<220> FEATURE:
<223> OTHER INFORMATION: synthetic human APOC3 siRNA hAPOC3_335 sense strand

<400> SEQUENCE: 1436
ggcugccuga gaccucaaua c 21

<210> SEQ ID NO 1437
<211> LENGTH: 21
<212> TYPE: RNA
<213> ORGANISM: Artificial Sequence
<220> FEATURE:
<223> OTHER INFORMATION: synthetic human APOC3 siRNA hAPOC3_335 antisense strand

<400> SEQUENCE: 1437
auugaggucu caggcagcca c 21

<210> SEQ ID NO 1438
<211> LENGTH: 19

<212> TYPE: RNA
<213> ORGANISM: Artificial Sequence
<220> FEATURE:
<223> OTHER INFORMATION: synthetic human APOC3 siRNA hAPOC3_337 target sequence

<400> SEQUENCE: 1438
cugccugaga ccucaauac 19

<210> SEQ ID NO 1439
<211> LENGTH: 21
<212> TYPE: RNA
<213> ORGANISM: Artificial Sequence
<220> FEATURE:
<223> OTHER INFORMATION: synthetic human APOC3 siRNA hAPOC3_337 sense strand

<400> SEQUENCE: 1439
cugccugaga ccucaauacc c 21

<210> SEQ ID NO 1440
<211> LENGTH: 21
<212> TYPE: RNA
<213> ORGANISM: Artificial Sequence
<220> FEATURE:
<223> OTHER INFORMATION: synthetic human APOC3 siRNA hAPOC3_337 antisense strand

<400> SEQUENCE: 1440
guauugaggu cucaggcagc c 21

<210> SEQ ID NO 1441
<211> LENGTH: 19
<212> TYPE: RNA
<213> ORGANISM: Artificial Sequence
<220> FEATURE:
<223> OTHER INFORMATION: synthetic human APOC3 siRNA hAPOC3_388 target sequence

<400> SEQUENCE: 1441 uccuugggcuc cugcaaucu 19

<210> SEQ ID NO 1442
<211> LENGTH: 21
<212> TYPE: RNA
<213> ORGANISM: Artificial Sequence
<220> FEATURE:
<223> OTHER INFORMATION: synthetic human APOC3 siRNA hAPOC3_388 sense strand

<400> SEQUENCE: 1442 uccuugggcuc cugcaaucuc c 21

<210> SEQ ID NO 1443
<211> LENGTH: 21
<212> TYPE: RNA
<213> ORGANISM: Artificial Sequence
<220> FEATURE:
<223> OTHER INFORMATION: synthetic human APOC3 siRNA hAPOC3_388 antisense strand

<400> SEQUENCE: 1443
agauugcagg acccaaggag c 21

<210> SEQ ID NO 1444
<211> LENGTH: 19
<212> TYPE: RNA

-continued

```
<213> ORGANISM: Artificial Sequence
<220> FEATURE:
<223> OTHER INFORMATION: synthetic human APOC3 siRNA hAPOC3_427 target
      sequence

<400> SEQUENCE: 1444

ugcuuaaaag ggacaguau                                                    19


<210> SEQ ID NO 1445
<211> LENGTH: 21
<212> TYPE: RNA
<213> ORGANISM: Artificial Sequence
<220> FEATURE:
<223> OTHER INFORMATION: synthetic human APOC3 siRNA hAPOC3_427 sense
      strand

<400> SEQUENCE: 1445

ugcuuaaaag ggacaguauu c                                                 21


<210> SEQ ID NO 1446
<211> LENGTH: 21
<212> TYPE: RNA
<213> ORGANISM: Artificial Sequence
<220> FEATURE:
<223> OTHER INFORMATION: synthetic human APOC3 siRNA hAPOC3_427
      antisense strand

<400> SEQUENCE: 1446

auacuguccc uuuuaagcaa c                                                 21
```